United States Patent
Nakata et al.

(10) Patent No.: US 12,186,715 B2
(45) Date of Patent: Jan. 7, 2025

(54) PRODUCTION METHOD FOR RESIST COMPOSITION PURIFIED PRODUCT, RESIST PATTERN FORMING METHOD, AND RESIST COMPOSITION PURIFIED PRODUCT

(71) Applicant: TOKYO OHKA KOGYO CO., LTD., Kanagawa (JP)

(72) Inventors: Akihiko Nakata, Kawasaki (JP); Miku Abe, Kawasaki (JP); Hiroki Saito, Kawasaki (JP)

(73) Assignee: TOKYO OHKA KOGYO CO., LTD., Kanagawa (JP)

( * ) Notice: Subject to any disclaimer, the term of this patent is extended or adjusted under 35 U.S.C. 154(b) by 489 days.

(21) Appl. No.: 17/611,412

(22) PCT Filed: May 20, 2020

(86) PCT No.: PCT/JP2020/019998
§ 371 (c)(1),
(2) Date: Nov. 15, 2021

(87) PCT Pub. No.: WO2020/235608
PCT Pub. Date: Nov. 26, 2020

(65) Prior Publication Data
US 2022/0242821 A1 Aug. 4, 2022

(30) Foreign Application Priority Data
May 22, 2019 (JP) .................... 2019-096193

(51) Int. Cl.
*B01D 71/64* (2006.01)
*B01D 67/00* (2006.01)
(Continued)

(52) U.S. Cl.
CPC ......... *B01D 71/641* (2022.08); *B01D 67/003* (2013.01); *B01D 69/12* (2013.01);
(Continued)

(58) Field of Classification Search
CPC .... G03F 7/0382; G03F 7/0045; G03F 7/2004; G03F 7/26; G03F 7/16; G03F 7/0397;
(Continued)

(56) References Cited

U.S. PATENT DOCUMENTS

2006/0014098 A1  1/2006 Hada et al.
2007/0264592 A1  11/2007 Tachibana et al.
(Continued)

FOREIGN PATENT DOCUMENTS

CN  106552517  4/2017
EP  3 435 158  1/2019
(Continued)

OTHER PUBLICATIONS

Translated Description of JP 2017068261A (Year: 2017).*
International Search Report issued Aug. 18, 2020 in International (PCT) Application No. PCT/JP2020/019998.

*Primary Examiner* — Sean M DeGuire
*Assistant Examiner* — Andrew Preston Traywick
(74) *Attorney, Agent, or Firm* — Wenderoth, Lind & Ponack, L.L.P.

(57) ABSTRACT

There is provided a production method for a resist composition purified product, which includes a step (i) of filtering a resist composition with a filter having a porous structure in which adjacent spherical cells are connected to each other. The filter includes a porous membrane containing at least one resin selected from the group consisting of polyimide and polyamide imide. The resist composition contains a base material component (A) that exhibits changed solubility in a developing solution under action of acid, an onium salt, and
(Continued)

an organic solvent component (S), where the content of the organic solvent component (S) is 97% by mass or more.

13 Claims, 1 Drawing Sheet

(51) Int. Cl.
  *B01D 69/12* (2006.01)
  *C07C 381/12* (2006.01)
  *G03F 7/004* (2006.01)
  *G03F 7/038* (2006.01)
  *G03F 7/20* (2006.01)

(52) U.S. Cl.
  CPC .......... *C07C 381/12* (2013.01); *G03F 7/0045* (2013.01); *G03F 7/0382* (2013.01); *G03F 7/2004* (2013.01); *B01D 2325/021* (2013.01)

(58) Field of Classification Search
  CPC ........ G03F 7/0392; G03F 7/038; G03F 7/004; C07C 381/12; B01D 71/64; B01D 71/641; B01D 71/261; B01D 67/003; B01D 67/0006; B01D 69/125; B01D 69/02; B01D 2325/021; B01D 2325/30; B01D 61/145; B01D 61/58
  USPC ...................................... 430/270.1
  See application file for complete search history.

(56) References Cited

U.S. PATENT DOCUMENTS

| | | | |
|---|---|---|---|
| 2013/0108957 A1 | 5/2013 | Iwabuchi et al. | |
| 2016/0314991 A1 | 10/2016 | Ogihara et al. | |
| 2017/0090293 A1* | 3/2017 | Nakata .................... | G03F 7/322 |
| 2018/0364568 A1 | 12/2018 | Tsubaki et al. | |
| 2019/0011827 A1 | 1/2019 | Shimizu et al. | |
| 2019/0310552 A1 | 10/2019 | Asano et al. | |
| 2020/0050106 A1 | 2/2020 | Shirakawa et al. | |

FOREIGN PATENT DOCUMENTS

| | | | | |
|---|---|---|---|---|
| JP | 2002-099076 | 4/2002 | | |
| JP | 2005-70423 | 3/2005 | | |
| JP | 2007-302809 | 11/2007 | | |
| JP | 4637476 | 2/2011 | | |
| JP | 2013-092643 | 5/2013 | | |
| JP | 2014-118466 | 6/2014 | | |
| JP | 2016-206500 | 12/2016 | | |
| JP | 2017-64711 | 4/2017 | | |
| JP | 2017-068261 | 4/2017 | | |
| JP | 2017-068262 | 4/2017 | | |
| JP | 2017068261 A * | 4/2017 | ............ | B01D 61/00 |
| JP | 2018-128477 | 8/2018 | | |
| TW | 201807505 | 3/2018 | | |
| WO | 2017/163922 | 9/2017 | | |
| WO | 2017/170428 | 10/2017 | | |
| WO | 2018/123388 | 7/2018 | | |
| WO | 2018/193954 | 10/2018 | | |

* cited by examiner

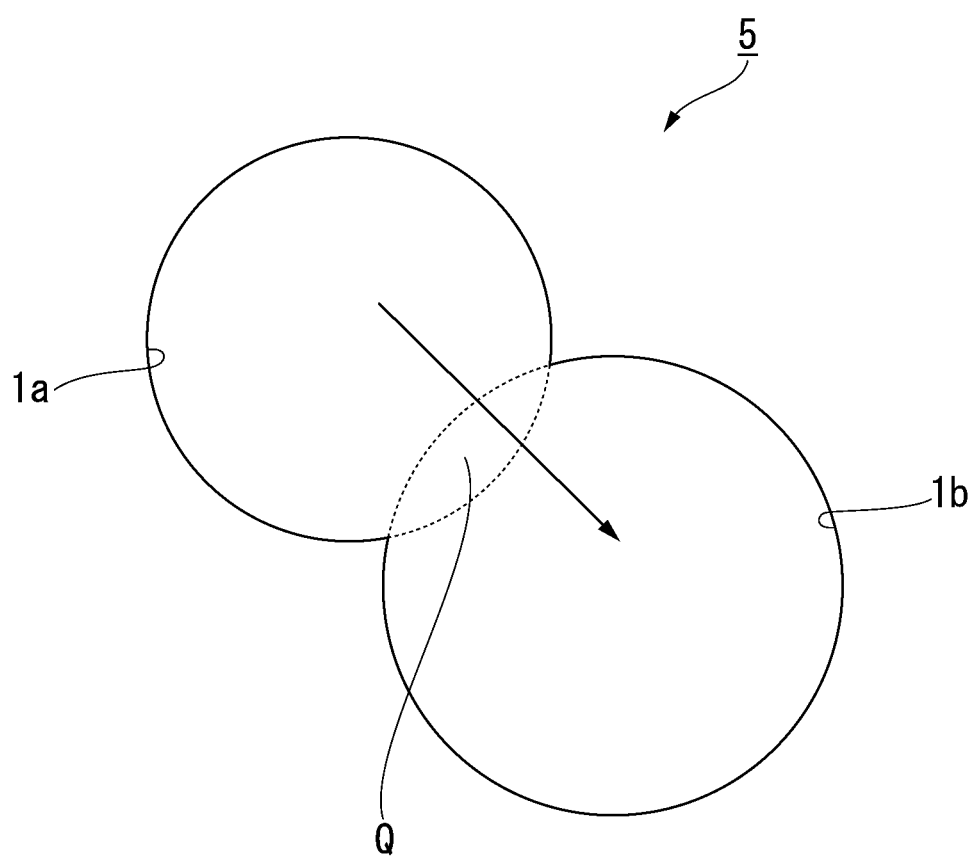

PRODUCTION METHOD FOR RESIST COMPOSITION PURIFIED PRODUCT, RESIST PATTERN FORMING METHOD, AND RESIST COMPOSITION PURIFIED PRODUCT

TECHNICAL FIELD

The present invention relates to a production method for a resist composition purified product, a resist pattern forming method, and a resist composition purified product.

Priority is claimed on Japanese Patent Application No. 2019-096193, filed May 22, 2019, the content of which is incorporated herein by reference.

BACKGROUND ART

In lithography techniques, for example, a resist film formed of a resist material is formed on a substrate, and the resist film is subjected to selective exposure, followed by a developing treatment, thereby forming a resist pattern having a predetermined shape on the resist film. A resist material in which exposed portions of the resist film become soluble in a developing solution is called positive-tone, and a resist material in which exposed portions of the resist film becomes insoluble in a developing solution is called negative-tone.

In recent years, in the production of semiconductor elements and liquid crystal display elements, advances in lithography techniques have led to a rapid progress in pattern fining. Typically, the pattern fining technique is carried out by shortening the wavelength (increasing the energy) of the light source for exposure. Specifically, ultraviolet radiation typified by g-line and i-line radiation has been used in the related art, but nowadays KrF excimer lasers and ArF excimer lasers are used in the mass production of semiconductor elements. Furthermore, research is also being carried out into lithography techniques that use an exposure light source having a wavelength shorter (having energy higher) than these excimer lasers, such as an electron beam (EB), an extreme ultraviolet ray (EUV), or an X ray.

Resist materials for use with these types of light sources for exposure require lithography characteristics such as a high resolution capable of reproducing a fine-sized pattern, and a high level of sensitivity to these types of light sources for exposure.

As a resist material that satisfies these requirements, a chemically amplified resist composition that contains a base material component that exhibits changed solubility in a developing solution under action of acid, and an acid generator component that generates acid upon exposure has been conventionally used in the related art.

As the pattern fining progresses further, the resist material is required to improve various lithography characteristics and suppress the occurrence of defects (surface defects).

Here, "defects" refers to all defects detected in a case where a resist pattern after development is observed from just above the surface by, for example, a surface defect observation device (product name "KLA") manufactured by KLA Corporation. These defects refer to, for example, a defect due to adhesion of foreign substances or precipitates on the surface of the resist pattern after development, such as scum (a resist residue), bubbles, and dust, a bridge between line patterns, a defect related to a pattern shape such as filling of pores in the contact hole pattern, and uneven color of the pattern.

In addition, in the resist material, there is also a problem of temporal characteristics (one of storage stability) of foreign substances, which means that foreign substances having a fine grain shape is generated during storage of a resist solution (a resist composition in a solution state), and this is also desired to be ameliorated.

In the related art, in the production of a resist composition, purification is generally carried out by passing a resist composition through a filter in order to remove foreign substances. However, the method of passing a resist composition through a membrane filter or a depth filter, which has been used in the related art, has been insufficient to suppress the occurrence of defects of the resist pattern after development.

In response to the requirements for the suppression of the occurrence of defects of the resist pattern and the temporal characteristics of foreign substances of the resist material described above, a production method for a resist composition, including both a step of passing a resist composition through a filter made of nylon and a step of passing a resist composition through a filter made of a polyolefin resin or a fluororesin, has been proposed (see Patent Document 1).

In addition to the resist composition, various chemical liquids for lithography such as a resin solution containing a resin, a developing solution, a resist solvent, and a pre-wetting solvent are used in the formation of the resist pattern. As a method for removing foreign substances (impurities) such as grains mixed in these chemical liquids, a method using a filter has been adopted in the related art.

As the pattern fining progresses, the influence of impurities present in these chemical liquids also appears in the pattern formation.

CITATION LIST

Patent Document

[Patent Document 1]
Japanese Patent No. 4637476

SUMMARY OF INVENTION

Technical Problem

With the further progress of lithography technology and the resist pattern fining, in a case of forming a resist pattern having a size of tens to hundreds of nanometers, defects such as the generation of scum or microbridge after development become a remarkable problem. As a result, more than ever, there is a need for a technique capable of suppressing the occurrence of defects in the resist pattern after development.

On the other hand, as the resist pattern fining progress, the formulation of the resist composition may change before and after the step of passing through the filter, which causes problems such as a change in pattern size and a pattern collapse.

The present invention has been made in consideration of the above circumstances, and an object of the present invention is to provide a production method for a resist composition purified product in which impurities are further reduced and problems such as pattern collapse hardly occur, a resist composition purified product produced by the production method, and a method of forming a resist pattern formed by the resist composition purified product.

Solution to Problem

In order to achieve the above-described object, the present invention employs the following configurations.

A first aspect of the present invention is a production method for a resist composition purified product, characterized by including a step (i) of filtering a resist composition with a filter having a porous structure in which adjacent spherical cells are connected to each other, in which the filter has a porous membrane containing at least one resin selected from the group consisting of polyimide and polyamide imide, and the resist composition contains a base material component (A) that exhibits changed solubility in a developing solution under action of acid, an onium salt, and an organic solvent component (S), where a content of the organic solvent component (S) is 97% by mass or more.

A second aspect of the present invention is a resist pattern forming method characterized by including a step of obtaining a resist composition purified product, by the production method for a resist composition purified product according to the first aspect, a step of forming a resist film on a support using the resist composition purified product, a step of exposing the resist film, and a step of developing the exposed resist film to form a resist pattern.

A third aspect of the present invention is a resist composition purified product characterized by containing a base material component (A) that exhibits changed solubility in a developing solution under action of acid, an onium salt, and an organic solvent component (S), in which the number of counting target objects having a size of 0.135 µm or more is less than 1 piece/mL, where the counting target objects are counted by a light scattering-type liquid-borne grain counter.

A fourth aspect of the present invention is a resist composition purified product characterized by containing a base material component (A) that exhibits changed solubility in a developing solution under action of acid, an onium salt, and an organic solvent component (S), in which a content of a metal component (M) is less than 1.1 ppb, where the metal component (M) is selected from the group consisting of Li, Na, Mg, Al, K, Ca, Ti, V, Cr, Mn, Fe, Co, Ni, Cu, Zn, As, Ag, Cd, Sn, Ba, W, Au, and Pb.

A fifth aspect of the present invention is a resist pattern forming method characterized by including a step of forming a resist film on a support using the resist composition purified product according to the third aspect or the fourth aspect, a step of exposing the resist film, and a step of developing the exposed resist film to form a resist pattern.

Advantageous Effects of Invention

According to the present invention, it is possible to provide a production method for a resist composition purified product in which impurities are further reduced and problems such as pattern collapse hardly occur, a resist composition purified product produced by the production method, and a method of forming a resist pattern formed by the resist composition purified product.

BRIEF DESCRIPTION OF DRAWINGS

FIG. 1 is a diagram schematically showing an embodiment of an interconnection pore constituting a polyimide-based resin porous membrane.

DESCRIPTION OF EMBODIMENTS

In the present specification and the scope of the present claims, the "aliphatic" is a relative concept used with respect to the "aromatic" and defines a group or compound that has no aromaticity.

The "alkyl group" includes linear, branched, and cyclic monovalent saturated hydrocarbon groups, unless otherwise specified. The same applies to the alkyl group in an alkoxy group.

The "alkylene group" includes linear, branched, and cyclic divalent saturated hydrocarbon groups, unless otherwise specified.

The "halogenated alkyl group" is a group obtained by substituting part or all hydrogen atoms of an alkyl group with a halogen atom. Examples of the halogen atom include a fluorine atom, a chlorine atom, a bromine atom, and an iodine atom.

The "fluorinated alkyl group" or a "fluorinated alkylene group" is a group obtained by substituting part or all hydrogen atoms of an alkyl group or an alkylene group with a fluorine atom.

The "constitutional unit" indicates a monomer unit that constitutes the formation of a polymeric compound (a resin, a polymer, or a copolymer).

The description of "may have a substituent" means that a case where a hydrogen atom (—H) is substituted with a monovalent group or a case where a methylene (—$CH_2$—) group is substituted with a divalent group.

The "exposure" is used as a general concept that includes irradiation with any form of radiation.

The "constitutional unit derived from acrylic acid ester" indicates a constitutional unit that is formed by the cleavage of the ethylenic double bond of acrylic acid ester.

The "acrylic acid ester" indicates a compound in which the terminal hydrogen atom of the carboxy group of acrylic acid ($CH_2$=CH—COOH) has been substituted with an organic group.

In the "acrylic acid ester", the hydrogen atom bonded to the carbon atom at the α-position may be substituted with a substituent. The substituent ($R^{\alpha 0}$) that is substituted for the hydrogen atom bonded to the carbon atom at the α-position is an atom other than a hydrogen atom or a group, and examples thereof include an alkyl group having 1 to 5 carbon atoms and a halogenated alkyl group having 1 to 5 carbon atoms. Further, an itaconic acid diester in which the substituent ($R^{\alpha 0}$) is substituted with a substituent having an ester bond and an α-hydroxyacryl ester in which the substituent ($R^{\alpha 0}$) is substituted with a hydroxyalkyl group or a group obtained by modifying a hydroxyl group of the hydroxyalkyl group are also included in the acrylic acid ester. The carbon atom at the α-position of acrylic acid ester indicates the carbon atom bonded to the carbonyl group of acrylic acid unless otherwise specified.

Hereinafter, the acrylic acid ester obtained by substituting a hydrogen atom bonded to the carbon atom at the α-position with a substituent is also referred to as an α-substituted acrylic acid ester. In addition, an acrylic acid ester and an α-substituted acrylic acid ester may be collectively referred to as an "(α-substituted) acrylic acid ester".

The "constitutional unit derived from acrylamide" indicates a constitutional unit that is formed by the cleavage of the ethylenic double bond of acrylamide.

In acrylamide, the hydrogen atom bonded to the carbon atom at the α-position may be substituted with a substituent, and one or both of hydrogen atoms on the amino group of the acrylamide may be substituted with a substituent. The carbon atom at the α-position of acrylamide indicates the carbon atom bonded to the carbonyl group of acrylamide, unless otherwise specified.

Examples of the substituent that is substituted for the hydrogen atom bonded to the carbon atom at the α-position of acrylamide include the same one as that (the substituent ($R^{\alpha 0}$)) described above as the substituent for the α-position in the α-substituted acrylic acid ester.

The "constitutional unit derived from hydroxystyrene" indicates a constitutional unit that is formed by the cleavage of an ethylenic double bond of hydroxystyrene. The "constitutional unit derived from a hydroxystyrene derivative" indicates a constitutional unit formed by the cleavage of an ethylenic double bond of a hydroxystyrene derivative.

The "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxyl group has been substituted with an organic group and may have the hydrogen atom at the α-position substituted with a substituent; and hydroxystyrene which has a substituent other than a hydroxyl group bonded to the benzene ring and may have the hydrogen atom at the α-position substituted with a substituent. Here, the α-position (carbon atom at the α-position) indicates the carbon atom having the benzene ring bonded thereto, unless otherwise specified.

Examples of the substituent that is substituted for the hydrogen atom at the α-position of hydroxystyrene include the same ones as those described above as the substituent for the α-position in the α-substituted acrylic acid ester.

The "constitutional unit derived from vinylbenzoic acid or a vinylbenzoic acid derivative" indicates a constitutional unit that is formed by the cleavage of the ethylenic double bond of vinylbenzoic acid or a vinylbenzoic acid derivative.

The "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include vinylbenzoic acid in which the hydrogen atom of the carboxy group has been substituted with an organic group and may have the hydrogen atom at the α-position substituted with a substituent; and vinylbenzoic acid which has a substituent other than a hydroxyl group and a carboxy group bonded to the benzene ring and may have the hydrogen atom at the α-position substituted with a substituent. Here, the α-position (carbon atom at the α-position) indicates the carbon atom having the benzene ring bonded thereto, unless otherwise specified.

The "styrene derivative" includes a compound obtained by substituting a hydrogen atom at the α-position of styrene with another substituent such as an alkyl group or a halogenated alkyl group; and a derivative thereof. Examples of the derivatives thereof include those obtained by bonding a substituent to a benzene ring of hydroxystyrene in which a hydrogen atom at the α-position may be substituted with a substituent. Here, the α-position (carbon atom at the α-position) indicates the carbon atom having the benzene ring bonded thereto, unless otherwise specified.

The "constitutional unit derived from styrene" or the "constitutional unit derived from a styrene derivative" indicates a constitutional unit formed by cleavage of an ethylenic double bond of styrene or a styrene derivative.

The alkyl group as a substituent at the α-position is preferably a linear or branched alkyl group, and specific examples thereof include an alkyl group having 1 to 5 carbon atoms, such as a methyl group, an ethyl group, a propyl group, an isopropyl group, an n-butyl group, an isobutyl group, a tort-butyl group, a pentyl group, an isopentyl group, and a neopentyl group.

Specific examples of the halogenated alkyl group as the substituent at the α-position include a group obtained by substituting part or all hydrogen atoms of the above-described "alkyl group as the substituent at the α-position" with a halogen atom. Examples of the halogen atom include a fluorine atom, a chlorine atom, a bromine atom and, an iodine atom, and a fluorine atom is particularly preferable.

Specific examples of the hydroxyalkyl group as the substituent at the α-position include groups in which some or all hydrogen atoms of the above-described "alkyl group as the substituent at the α-position" are substituted with a hydroxyl group. The number of hydroxyl groups in the hydroxyalkyl group is preferably in a range of 1 to 5, and most preferably 1.

The "polyimide-based resin" means one or both of polyimide and polyamide imide. The polyimide and the polyamide imide may each have at least one functional group selected from the group consisting of a carboxy group, a salt-type carboxy group, and an —NH— bond.

A porous membrane containing at least one of polyimide and polyamide imide may be referred to as a "polyimide-based resin porous membrane". A porous membrane containing polyimide may be referred to as a "polyimide porous membrane". A porous membrane containing polyamideimide may be referred to as a "polyamide imide porous membrane".

In the present specification and the scope of the present claims, asymmetric carbon atoms may be present, and thus enantiomers or diastereomers may be present depending on the structures represented by the chemical formula. In that case, these isomers are represented by one chemical formula. These isomers may be used alone or in the form of a mixture.

(Production Method for Resist Composition Purified Product)

A production method for a resist composition purified product according to the first aspect of the present invention includes a step (i) of filtering a resist composition with a filter having a porous structure in which adjacent spherical cells are connected to each other. The filter has a porous membrane containing at least one resin selected from the group consisting of polyimide and polyamide imide. The resist composition contains a base material component (A) that exhibits changed solubility in a developing solution under action of acid, an onium salt, and an organic solvent component (S), where the content of the organic solvent component (S) is 97% by mass or more.

According to the step (i), impurities such as grains are removed from the resist composition, and a high-purity resist composition purified product is obtained.

According to such a production method, in particular, by using a filter having a porous membrane that has a porous structure in which adjacent spherical cells are connected to each other and contains at least one resin selected from the group consisting of polyimide and polyamide imide, highly polar components and polymers, which have been difficult to be removed in the related art, are sufficiently removed from the resist composition, and among them, the highly polar polymer is specifically removed.

In addition, in the step (i), a metal component as an impurity is also sufficiently removed from the resist composition. This metal component may be originally contained in the component constituting the resist composition; however, it may also be mixed from a resist composition transfer path such as a pipe or a joint of a producing device. In the step (i), it is possible to effectively remove, for example, iron, nickel, zinc, chromium, and the like, which are easily mixed from a producing device or the like.

<Step (i)>

The step (i) is a step of filtering the resist composition with a filter having a porous structure in which adjacent spherical cells are connected to each other.

«Filter»

The filter that is used in the present step has a porous structure in which adjacent spherical cells are connected to each other.

For example, such a filter may be made of a single substance of a porous membrane in which adjacent spherical cells are connected to each other, or may be a filter in which another filter medium is used together with the porous membrane.

Examples of other filter media include a nylon membrane, a polytetrafluoroethylene membrane, a tetrafluoroethylene/perfluoroalkyl vinyl ether copolymer (PFA) membrane, and a membrane obtained by modifying these membranes.

In such a filter, regions of the porous membrane before and after a liquid is allowed to pass are preferably sealed so that a supply liquid and a filtrate of the resist composition are separated without being mixed. Examples of the method for this sealing include a method of processing the porous membrane by adhesion with light (UV) curing, adhesion with heat (including adhesion by an anchoring effect (heat welding or the like)), adhesion using an adhesive, or the like, and a method of carrying out processing by adhering the porous membrane and another filter medium by an assembling method or the like. Examples of such a filter include those in which such a porous membrane described above is provided in an outer container made of a thermoplastic resin (polyethylene, polypropylene, PFA, polyether sulfone (PES), polyimide, polyamide imide, or the like).

In such a filter, examples of the form of the porous membrane include a planar shape and a pipe shape in which opposite sides of a porous membrane are merged. The surface of the pipe-shaped porous membrane is preferably pleated from the viewpoint of increasing the area that comes into contact with the supply liquid.

• In Regard to "Porous Membrane in which Adjacent Spherical Cells are Connected to Each Other"

The "porous membrane in which adjacent spherical cells are connected to each other" provided in such a filter has an interconnection pore in which adjacent spherical cells are connected to each other.

The interconnection pore is formed from individual pores (cells) that impart porosity to the porous membrane. Such a pore includes a pore in which almost the entire inner surface of the pore is a curved surface, and may include a pore having a shape other than this shape.

In the present specification, a pore in which almost the entire inner surface of the pore is a curved surface is referred to as a "spherical cell" or a "substantially spherical pore". In the spherical cell (the substantially spherical pore), the inner surface of the pore forms a substantially spherical space. The spherical cell is easily formed in a case where fine grains that are used in the production method for a polyimide-based resin porous membrane described later are substantially spherical.

"Substantially spherical" is a concept including a true sphere. However, it is not necessarily limited to the true sphere and is a concept including a substantially spherical one. "Substantially spherical" means that a sphericity defined by a ratio of a major axis to a minor axis, which is represented by a value obtained by dividing the major axis by the minor axis of the grain, is within $1\pm0.3$. Here, in the spherical cell, such a sphericity is preferably within $1\pm0.1$ and more preferably within $1\pm0.05$. In the porous membrane in which adjacent spherical cells are connected to each other, the adjacent spherical cells form at least a part of the interconnection pore.

FIG. 1 is a diagram schematically showing an embodiment of an interconnection pore constituting a porous membrane.

In each of a spherical cell $1a$ and a spherical cell $1b$ in the porous membrane according to the present embodiment, almost the entire inner surface is curved surface, and a substantially spherical space is formed.

The spherical cell $1a$ and the spherical cell $1b$ are adjacent to each other, and an interconnection pore 5 in which an overlapping portion Q of the spherical cell $1a$ and the spherical cell $1b$ adjacent to each other penetrates between the cells is formed. A filtration target flows through the interconnection pore 5, for example, in the direction (the arrow direction) from the spherical cell $1a$ toward the spherical cell $1b$.

As described above, in the porous membrane having a structure in which adjacent spherical cells are connected to each other, it is preferable that a plurality of pores (spherical cells or interconnection pores) are connected to form a flow path of a filtration target as a whole.

The "flow path" is generally formed by the individual "pores" and/or "interconnection pores" that are connected to each other. The individual pores are formed, for example, by removing individual fine grains present in a polyimide-based resin-fine grain composite membrane in a subsequent step in the production method for a polyimide-based resin porous membrane described later. In addition, the interconnection pore is pores adjacent to each other, which are formed in a portion where individual fine grains have been in contact with each other, where the portion is present in the polyimide-based resin-fine grain composite membrane, by removing the fine grains in a subsequent step in the production method for a polyimide-based resin porous membrane described later.

In the porous membrane, a spherical cell and an interconnection pore in which adjacent spherical cells are connected to each other are formed, and thus the degree of porosity is increased. Further, in the porous membrane, a spherical cell or an interconnection pore opens on a surface of the porous membrane, and an interconnection pore that opens on one surface is connected to the inside of the porous membrane and opens on the other (on the back side) surface, and thus a flow path in which a fluid can pass through the inside of the porous membrane is formed. As a result, according to the porous membrane, in a case where a filtration target flows through the flow path, foreign substances contained in a filtration target are removed from the filtration target before filtration.

Since the porous membrane has a flow path obtained by causing interconnection pores formed by spherical cells having a curved surface on the inner surface thereof to be continuous, the surface area of the inner surface of the spherical cells is large. As a result, not only a filtration target can pass through the inside of the porous membrane but also the frequency of contacting with the inner surface of the spherical cell increases in a case where the filtration target passes while coming into contact with the curved surfaces of the individual spherical cells, and thus foreign substances that are present in the filtration target are adsorbed by the inner surface of the spherical cell, and the foreign substances are easily removed from the filtration target.

The porous membrane preferably has a structure in which spherical cells having an average sphere diameter of 10 to 500 nm are connected to each other. The average sphere diameter of the spherical cells is more preferably 30 to 500 nm and still more preferably 50 to 400 nm.

The average sphere diameter of the spherical cells means an average value of the diameters of the interconnection pores formed from the two adjacent spherical cells. The average sphere diameter of the spherical cells is a value obtained by measuring diameters of pores based on a bubble point method using a palm porometer (for example, manufactured by Porous Materials Inc.). Specifically, it can be determined by the same method as the method for the average pore diameter in the porous membrane described later.

The flow path included in the inside of the "porous membrane in which adjacent spherical cells are connected to each other" may have, in addition to the above-described spherical cells and the interconnection pores between the spherical cells, pores having other shapes or interconnection pores including these pores.

In addition, the spherical cell may further have a recessed part on the inner surface thereof. For example, a pore having a pore diameter smaller than that of the spherical cell may be formed in the recessed part, where the pore opens on the inner surface of the spherical cell.

Examples of the "porous membrane in which adjacent spherical cells are connected to each other" include those containing a resin, which may be substantially made of only a resin, and includes those in which the resin in the entire porous membrane is preferably 95% by mass or more, more preferably 98% by mass or more, and still more preferably 99% by mass or more.

The porous membrane contains a polyimide-based resin. A porous membrane containing a polyimide-based resin is excellent in foreign substances removing property and strength, and stability of lithography characteristics before and after filtration. The porous membrane contains at least one of polyimide and polyamideimide as a resin and preferably contains at least polyimide. The porous membrane may contain only polyimide as a resin or may contain only polyamide imide; however, it preferably contains only polyimide.

It is particularly preferable that in the "porous membrane in which adjacent spherical cells are connected to each other", 95% by mass or more of the entire porous membrane is at least one of polyimide and polyamide imide.

Hereinafter, a porous membrane (a polyimide-based resin porous membrane) in which adjacent spherical cells are connected to each other, which contains a polyimide-based resin as the resin, will be described.

•• Polyimide-Based Resin Porous Membrane

The polyimide-based resin may have at least one functional group selected from the group consisting of a carboxy group, a salt-type carboxy group, and an —NH— bond.

The polyimide-based resin preferably has the above functional group in a moiety other than the terminal of the main chain. Preferred examples having the above functional group in a moiety other than the terminal of the main chain include a polyamic acid.

In the present specification, the "salt-type carboxy group" means a group obtained by substituting a hydrogen atom in a carboxy group with a cation component. The "cation component" may be a cation itself in a state of being completely ionized, may be a cation constitutional element in a state of being ionically bonded to —COO⁻ and virtually uncharged, and may be a partially charged cation constitutional element having a partial charge in a state of being an intermediate state between the two above.

In a case where the "cation component" is an M ion component consisting of an n-valent metal M, the cation itself is represented by $M^{n+}$, and the cation constitutional element is an element represented by "$M_{1/n}$" in "—COOM$_{1/n}$".

Examples of the "cation component" include a cation in a case where a compound mentioned as a compound contained in an etching liquid described later is ion-dissociated. Representative examples thereof include an ionic component and an organic alkali ionic component. For example, in a case where the alkali metal ion component is a sodium ion component, the cation itself is a sodium ion (Nat), and the cation constitutional element is an element represented by "Na" in "—COONa". The partially charged cation constitutional element is $Na^{\delta+}$.

The cation component is not particularly limited, and examples thereof include an inorganic component of $NH_4^+$ and an organic component such as $N(CH_3)_4^+$. Examples of the inorganic component include alkali metals such as Li, Na, and K; and metal elements such as alkaline earth metals such as Mg and Ca. Examples of the organic component include an organic alkali ionic component. Examples of the organic alkali ionic component include quaternary ammonium cations represented by $NH_4^+$, for example, $NR_4^+$ (all four R's represent organic groups and may be the same or different from each other). The organic group as R is preferably an alkyl group and more preferably an alkyl group having 1 to 6 carbon atoms. Examples of the quaternary ammonium cation include $N(CH_3)_4^+$.

The state of the cation component in the salt-type carboxy group is not particularly limited, and generally depends on the environment in which the polyimide-based resin is present, for example, an environment in an aqueous solution, an environment in an organic solvent, and a dry environment. In a case where the cation component is a sodium ion component, for example, there is a possibility that —COO— and Na are dissociated in a case of being in an aqueous solution, and there is a high possibility that —COONa is not dissociated in a case of being in an organic solvent or in a dry environment.

The polyimide-based resin may have at least one functional group selected from the group consisting of a carboxy group, a salt-type carboxy group, and an —NH— bond; however, in a case of having at least one of these, it generally has both a carboxy group and/or a salt-type carboxy group and a —NH— bond. The polyimide-based resin may have only a carboxy group, may have only a salt-type carboxy group, or may have both a carboxy group and a salt-type carboxy group, in a case where the carboxy group and/or the salt-type carboxy group is concerned. The ratio between the carboxy group and the salt-type carboxy group contained in the polyimide-based resin may vary, for example, depending on the environment in which the polyimide-based resin is present, even in a case where the polyimide-based resin is the same, and it is also affected by the concentration of the cation component.

In the case of polyimide, the total of the number of moles of the carboxy group and the salt-type carboxy group contained in the polyimide-based resin is generally equimolar to that of the —NH— bond.

In particular, in the production method for a polyimide porous membrane described later, in a case where a carboxy group and/or a salt-type carboxy group is formed from part of imide bonds in the polyimide, an —NH— bond is also formed substantially at the same time. The total of the numbers of moles of the carboxy group to be formed and the salt-type carboxy group to be formed is equimolar to that of the —NH-bond formed.

In the case of the production method for a porous polyamideimide membrane, the total of the number of moles of the carboxy group and the salt-type carboxy group in the polyamideimide is not necessarily equimolar to that of the —NH— bond, and it depends on the conditions for chemical etching or the like in the etching (decyclization of the imide bond) step described later.

The polyimide-based resin preferably has, for example, at least one constitutional unit selected from the group consisting of constitutional units each represented by General Formulae (1) to (4).

In the case of polyimide, it is preferable to contain at least one constitutional unit selected from the group consisting of a constitutional unit represented by General Formula (1) and a constitutional unit represented by General Formula (2).

In the case of polyamide imide, it is preferable to contain at least one constitutional unit selected from the group consisting of a constitutional unit represented by General Formula (3) and a constitutional unit represented by General Formula (4).

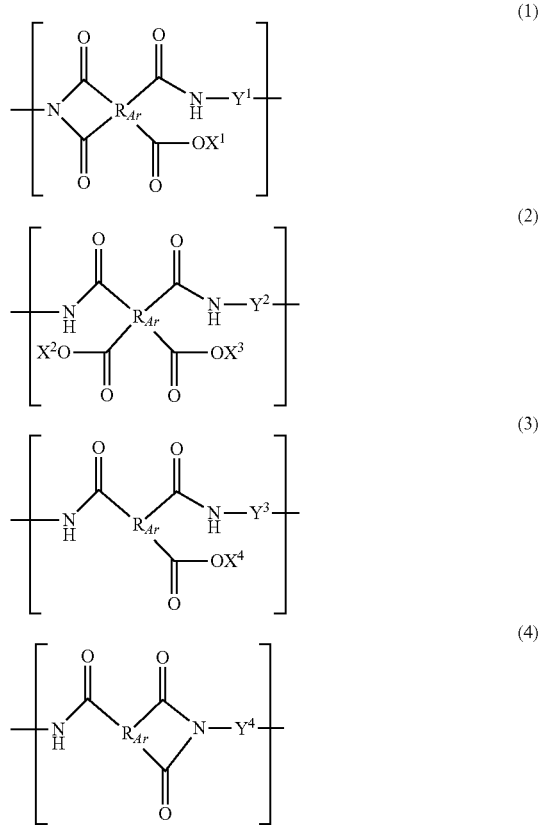

In General Formulae (1) to (3) shown above, $X^1$ to $X^4$ may be the same or different from each other and are a hydrogen atom or a cation component.

$R_{Ar}$ represents an aryl group, and examples thereof include the same one as the aryl group represented by $R_{Ar}$, to which a carbonyl group is bonded, in each of a constitutional unit represented by General Formula (5) constituting a polyamic acid described later or a constitutional unit represented by General Formula (6) constituting am aromatic polyimide.

$Y^1$ to $Y^4$ each independently represents a divalent residue excluding the amino group of the diamine compound, and examples thereof include the same one as the arylene group represented by $R'_{Ar}$, to which N is bonded, in each of a constitutional unit represented by General Formula (5) constituting a polyamic acid described later or a constitutional unit represented by General Formula (6) constituting am aromatic polyimide.

The polyimide-based resin may be one obtained by decyclizing part of imide bonds (—N[—C(=O)]$_2$) of a general polyimide or polyamide imide, thereby having each of the constitutional unit represented by General Formula (1) or General Formula (2) in the case of polyimide and the constitutional unit represented by General Formula (3) in the case of polyamide imide.

The polyimide-based resin porous membrane may contain a polyimide-based resin obtained by decyclizing part of imide bonds, thereby having at least one functional group selected from the group consisting of a carboxy group, a salt-type carboxy group, and an —NH— bond.

The non-change rate in a case where part of imide bonds are decyclized is determined by the following procedures (1) to (3).

Procedure (1): For a polyimide-based resin porous membrane that does not undergo the etching (the decyclization of imide bond) step described later (however, in case where a varnish for producing the porous membrane contains a polyamic acid, it is assumed that the imidization reaction has been substantially completed in the step of sintering an unsintered composite membrane), an area of a peak that represents the imide bond, measured by a Fourier transform infrared spectroscopy (FT-IR) apparatus, is divided by an area of a peak that represents benzene, also measured by the Fourier transform infrared spectroscopy (FT-IR) apparatus, to determine a value represented by a value (X01).

Procedure (2): For a polyimide-based resin porous membrane obtained by using the same polymer (the varnish) as that of the porous membrane from which the above value (X01) has been determined, where the polyimide-based resin porous membrane has undergone the etching (the decyclization of imide bond) step described later, an area of a peak that represents the imide bond, measured by a Fourier transform infrared spectroscopy (FT-IR) apparatus, is divided by an area of a peak that represents benzene, also measured by the Fourier transform infrared spectroscopy (FT-IR) apparatus, to determine a value represented by a value (X02).

Procedure (3): the non-change rate is calculated according to the following expression.

Non-change rate (%)=(X02)/(X01)×100

The non-change rate in the polyimide-based resin porous membrane is preferably in a range of 60% or more, more preferably in a range of 70% to 99.5%, and still more preferably in a range of 80% to 99%. In the case of a porous membrane containing polyimide imide, the non-change rate may be 100% since a —NH— bond is contained.

In the case of a polyimide porous membrane, an area of a peak that represents the imide bond, measured by an FT-IR apparatus, is divided by an area of a peak that represents benzene, also measured by the FT-IR apparatus, to determine a value that is denoted by the "imidization rate".

The imidization rate regarding the value (X02) determined in the above procedure (2) is preferably 1.2 or more, more preferably in a range of 1.2 to 2, and still more preferably in a range of 1.3 to 1.6, particularly preferably in a range of 1.30 to 1.55, and most preferably 1.35 or more and less than 1.5. In addition, the imidization rate regarding the value (X01) determined in the above procedure (1) is preferably 1.5 or more.

As the numerical value of such an imidization rate becomes relatively larger, it means that the number of imide bonds becomes larger, that is, the number of decyclized imide bonds described above becomes smaller

•• Production Method for Polyimide-Based Resin Porous Membrane

The polyimide-based resin porous membrane can be produced by a method including a step (hereinafter, referred to as an "etching step") of forming a carboxy group and/or a salt-type carboxy group from part of imide bonds in polyimide and/or polyamideimide.

In the etching step, in a case where a carboxy group and/or a salt-type carboxy group is formed from part of imide bonds in the polyimide, an —NH— bond theoretically equimolar to these groups is also formed substantially at the same time.

In a case where the resin contained in the polyimide-based resin porous membrane is substantially made of polyamide imide, the porous membrane already has a —NH— bond even without undergoing the etching step and exhibits good adsorption power to foreign substances in the filtration target. In such a case, the etching step is not always necessary since it is not needed to slow down the flow rate of the filtration target; however, it is preferable to provide the etching step from the viewpoint of more effectively achieving the object of the present invention.

In the production method for a polyimide-based resin porous membrane, it is preferable to carry out the etching step after preparing a molding membrane containing polyimide and/or polyamideimide as a main component (hereinafter, may be abbreviated as a "polyimide-based resin molded membrane").

The polyimide-based resin molded membrane to be subjected to the etching step may be porous or may be non-porous.

In addition, the form of the polyimide-based resin molded membrane is not particularly limited; however, it preferably has a thin shape such as a membrane, and it is more preferably porous and has a thin shape such as a membrane from the viewpoint that the degree of porosity in the polyimide-based resin porous membrane to be obtained can be increased.

As described above, the polyimide-based resin molded membrane may be non-porous in a case where the etching step is carried out; however, in that case, it is preferable to make the polyimide-based resin molded membrane porous after the etching step.

The method for making the polyimide-based resin molded membrane porous before or after the etching step is preferably a method including a [fine grain removal] step of removing fine grains from a composite membrane (hereinafter, referred to as a "polyimide-based resin-fine grain composite membrane") of polyimide and/or polyamideimide and fine grains, to make the composite membrane porous.

Examples of the production method for a polyimide-based resin porous membrane include the following production method (a) and production method (b).

The production method (a): a method of etching a composite membrane of polyimide and/or polyamideimide and fine grains before a [fine grain removal] step.

The production method (b): a method of carrying out an etching step, after a [fine grain removal] step, on a polyimide-based resin molded membrane made porous by the [fine grain removal] step.

Among these, the latter production method (b) is preferable from the viewpoint that the degree of porosity in the polyimide-based resin porous membrane to be obtained can be further increased.

An example of the production method for a polyimide-based resin porous membrane will be described below.

[Preparation of Varnish]

A fine grain dispersion liquid in which fine grains are dispersed in an organic solvent in advance is mixed with polyamic acid, or polyimide or polyamideimide at any ratio or tetracarboxylic acid dianhydride and a diamine are polymerized in the above fine grain dispersion liquid, or further, the above polyamic acid is imidized to be polyimide, whereby a varnish is prepared.

The viscosity of the varnish is preferably in a range of 300 to 2,000 cP (0.3 to 2 Pa·s) and more preferably in a range of 400 to 1,800 cP (0.4 to 1.8 Pa·s). In a case where the viscosity of the varnish is within the above range, a membrane can be formed more uniformly.

The viscosity of the varnish can be measured with an E-type rotational viscometer under a temperature condition of 25° C.

Resin fine grains are mixed with polyamic acid, or polyimide or polyamideimide in the varnish so that the ratio of the fine grains/the polyimide-based resin is preferably in a range of 1 to 4 (mass ratio) and more preferably in a range of 1.1 to 3.5 (mass ratio) when sintered (dried in a case where sintering is optional) to form a polyimide-based resin-fine grain composite membrane.

In addition, fine grains are mixed with polyamic acid, or polyimide or polyamideimide so that the volume fraction of the fine grains/the polyimide-based resin is preferably in a range of 1.1 to 5 and more preferably in a range of 1.1 to 4.5 when made to form a polyimide-based resin-fine grain composite membrane. In a case where the mass ratio or the volume fraction is equal to or larger than the preferred lower limit value of the above range, pores having a suitable density as a porous membrane can be easily obtained, and in a case where it is equal to or smaller than the preferred upper limit value of the above range, problems such as the increase in viscosity and the cracking in the membrane hardly occur, and membrane formation can be stably achieved.

In addition, in the present specification, the volume fraction indicates a value obtained at 25° C.

••• Fine Grain

As the fine grain material, any material can be used without particular limitation as long as it is insoluble in an organic solvent that is used for the varnish and can be selectively removed after the membrane formation.

Examples of the fine grain material include metal oxides such as silica (silicon dioxide), titanium oxide, alumina ($Al_2O_3$), and calcium carbonate as the inorganic material. Examples of organic materials include organic polymers such as a high molecular weight olefin (polypropylene, polyethylene, or the like), polystyrene, an acrylic resin (methyl methacrylate, isobutyl methacrylate, polymethyl methacrylate (PMMA), or the like), an epoxy resin, cellulose, polyvinyl alcohol, polyvinyl butyral, polyester, polyether, and polyethylene.

Among the above, the inorganic material is preferably silica such as colloidal silica since micropores having a curved surface on the inner surface are easily be formed in the porous membrane. The organic material is preferably an acrylic resin such as PMMA.

The resin fine grains can be selected from, for example, typical linear polymers and known depolymerizable polymers without particular limitation depending on the intended purpose. The typical linear polymer is a polymer in which the molecular chains of the polymer are randomly cleaved during thermal decomposition. The depolymerizable polymer is a polymer that decomposes into monomers during thermal decomposition. Any polymer can be removed from the polyimide-based resin membrane by being decomposed into monomers, low molecular weight substances, or $CO_2$ when being heated.

Among the depolymerizable polymers, from the viewpoint of handling at the time of pore formation, a polymer of methyl methacrylate or isobutyl methacrylate alone (a polymethyl methacrylate or a polyisobutyl methacrylate), which has a low thermal decomposition temperature, or a copolymerization polymer containing this as a main component is preferable.

The decomposition temperature of the resin fine grains is preferably in a range of 200° C. to 320° C. and more preferably in a range of 230° C. to 260° C. In a case where the decomposition temperature is 200° C. or higher, membrane formation can be carried out even in a case where a high boiling point solvent is used for the varnish, and the range of selection of sintering conditions for the polyimide-based resin becomes wider. In a case where the decomposition temperature is 320° C. or lower, only the resin fine grains can be easily eliminated without causing thermal damage to the polyimide-based resin.

The fine grains preferably have a high true sphere ratio since they tend to have a curved surface on the inner surface of the pore in the formed porous membrane. The grain diameter (the average diameter) of the fine grains to be used is, for example, preferably in a range of 50 to 2,000 nm and more preferably in a range of 200 to 1,000 nm.

In a case where the average diameter of the fine grains is within the above range, a filtration target can be brought into uniform contact with the inner surface of the pores in the porous membrane in a case where the filtration target is allowed to pass through the polyimide-based resin porous membrane obtained by removing the fine grains, and thus foreign substances contained in the filtration target can be efficiently adsorbed.

The grain diameter distribution index (d25/d75) of the fine grains is preferably in a range of 1 to 6 and more preferably in a range of 1.6 to 5, and still more preferably in a range of 2 to 4.

In a case where the grain diameter distribution index is set equal to or larger than the preferred lower limit value or more of the above range, the porous membrane can be efficiently filled with fine grains, and thus a flow path is easily formed and the flow rate is improved. In addition, pores having different sizes are easily formed, different convections are generated, and thus the adsorption rate of foreign substances is further improved.

It is noted that d25 and d75 are values of grain diameters in which the cumulative frequencies of the grain diameter distribution are each 25% and 75%, and d25 is the value having the larger grain diameter in the present specification.

Further, in a case of forming an unsintered composite membrane in a two-layer shape in [Membrane formation of unsintered composite membrane] described later, as a fine grain (B1) that is used for a first varnish and a fine grain (B2) that is used for a second varnish, the same one may be used or those different from each other may be used. In order to make the pores on the side in contact with the base material more dense, it is preferable that the fine grain (B1) has a small or the same grain diameter distribution index as compared with the fine grain (B2). Alternatively, it is preferable that the fine grain (B1) has a small or the same true sphere ratio as compared with the fine grain (B2). In addition, the fine grain (B1) preferably has a smaller grain diameter (average diameter) than the fine grain (B2), and in particular, it is preferable that the fine grain (B1) in a range of 100 to 1,000 nm (more preferably in a range of 100 to 600 nm) and the fine grain (B2) in a range of 500 to 2,000 nm (more preferably in a range of 700 to 2,000 nm) are each used. In a case where fine grain (B1) having a grain diameter smaller than that of the fine grains (B2) is used, the opening proportion of the pores on the surface of the polyimide-based resin porous membrane to be obtained can be increased, and the diameters thereof can be made uniform, and the strength of the porous membrane can be increased as compared with a case where the entire polyimide-based resin porous membrane is made of the fine grain (B1) alone.

In the present embodiment, a dispersant may be further added to the varnish together with the fine grains for the intended purpose of uniformly dispersing the fine grains. In a case of further adding a dispersant, it is possible to more uniformly mix polyamic acid, or polyimide or polyamide-imide with fine grains, and thus it is possible to more uniformly distribute the fine grains in the unsintered composite membrane. As a result of the above, it is possible to efficiently form an interconnection pore that is allowed to be connected to the front and back surfaces of the polyimide-based resin porous membrane, so that dense openings are provided on the surface of the polyimide-based resin porous membrane to be finally obtained and the air permeability of the polyimide-based resin porous membrane is improved.

As the dispersant, a known one can be used without particular limitation. Examples of the dispersant include anionic surfactants such as a palm fatty acid salt, a castor sulfate oil salt, a lauryl sulfate salt, a polyoxyalkylene allylphenyl ether sulfate salt, an alkylbenzene sulfonic acid, an alkylbenzene sulfonic acid salt, an alkyldiphenyl ether disulfonic acid salt, an alkylnaphthalene sulfonic acid salt, a dialkyl sulfosuccinate salt, isopropyl phosphate, a polyoxyethylene alkyl ether phosphate salt, and a polyoxyethylene allylphenyl ether phosphate salt; cationic surfactants such as an oleylamine acetic acid salt, laurylpyridinium chloride, cetylpyridinium chloride, lauryltrimethylammonium chloride, stearyltrimethylammonium chloride, behenyltrimethylammonium chloride, and didecyldimethylammonium chloride; amphoteric surfactants such as a palm alkyldimethylamine oxide, a fatty acid amide propyldimethylamine oxide, an alkylpolyaminoethylglycine hydrochloric acid salt, an amide betaine-type activator, an alanine-type activator, and lauryliminodipropionic acid; polyoxyalkylene primary alkyl ether-based or polyoxyalkylene secondary alkyl ether-based nonionic surfactants such as a polyoxyethylene octyl ether, a polyoxyethylene decyl ether, a polyoxyethylene lauryl ether, a polyoxyethylene laurylamine, a polyoxyethylene oleylamine, a polyoxyethylene polystyrylphenyl ether, and a polyoxyalkylene polystyrylphenyl ether, and polyoxyalkylene-based nonionic surfactants such as a polyoxyethylene dilaurate, a polyoxyethylene laurate, a polyoxyethylene hydrogenated castor oil, a polyoxyethylene hydrogenated castor oil, a sorbitan lauric acid ester, a polyoxyethylene sorbitan lauric acid ester, and a fatty acid diethanolamide; fatty acid alkyl esters such as octyl stearate and trimethylolpropane tridecanoate; and polyether polyols such as a polyoxyalkylene butyl ether, a polyoxyalkylene oleyl ether, and triinethylolpropane tris(polyoxyalkylene) ether. The above dispersants can be used alone, or a mixture of two or more thereof can be used.

•••  Polyamic Acid

Examples of the polyamic acid that can be used in the present embodiment include those obtained by polymerizing any tetracarboxylic acid dianhydride with a diamine.

••••  Tetracarboxylic Acid Dianhydride

The tetracarboxylic acid dianhydride can be appropriately selected from the tetracarboxylic acid dianhydrides that are used as raw materials for synthesizing polyamic acids in the related art.

The tetracarboxylic acid dianhydride may be an aromatic tetracarboxylic acid dianhydride or may be an aliphatic tetracarboxylic acid dianhydride.

Examples of the aromatic tetracarboxylic acid dianhydride include pyromellitic acid dianhydride, 1,1-bis(2,3-dicarboxyphenyl)ethane dianhydride, bis(2,3-dicarboxyphenyl)methane dianhydride, bis(3,4-dicarboxyphenyl)methane dianhydride, 3,3',4,4'-biphenyltetracarboxylic acid dianhydride, 2,3,3',4'-biphenyltetracarboxylic acid dianhydride, 2,2,6,6-biphenyltetracarboxylic acid dianhydride, 2,2-bis(3,4-dicarboxyphenyl)propane dianhydride, 2,2-bis(2,3-dicarboxyphenyl)propane dianhydride, 2,2-bis(3,4-dicarboxyphenyl)-1,1,1,3,3,3-hexafluoropropane dianhydride, 2,2-bis(2,3-dicarboxyphenyl)-1,1,1,3,3,3-hexafluoropropane dianhydride, 3,3',4,4'-benzophenonetetracarboxylic acid dianhydride, bis(3,4-dicarboxyphenyl)ether dianhydride, bis(2,3-dicarboxyphenyl)ether dianhydride, 2,2',3,3'-benzophenonetetracarboxylic acid dianhydride, 4,4-(p-phenylenedioxy)diphthalic acid dianhydride, 4,4-(m-phenylenedioxy)diphthalic acid dianhydride, 1,2,5,6-naphthalenetetracarboxylic acid dianhydride, 1,4,5,8-naphthalenetetracarboxylic acid dianhydride, 2,3,6,7-naphthalenetetracarboxylic acid dianhydride, 1,2,3,4-benzenetetracarboxylic acid dianhydride, 3,4,9,10-perylenetetracarboxylic acid dianhydride, 2,3,6,7-anthracenetetracarboxylic acid dianhydride, 1,2,7,8-phenanthrenetetracarboxylic acid dianhydride, 9,9-bisphthalic acid anhydride fluorene, and 3,3',4,4'-diphenylsulfonetetracarboxylic acid dianhydride.

Examples of the aliphatic tetracarboxylic acid dianhydride include ethylenetetracarboxylic acid dianhydride, butanetetracarboxylic acid dianhydride, cyclopentanetetracarboxylic acid dianhydride, cyclohexanetetracarboxylic acid dianhydride, 1,2,4,5-cyclohexanetetracarboxylic acid dianhydride, and 1,2,3,4-cyclohexanetetracarboxylic acid dianhydride.

Among the above, an aromatic tetracarboxylic acid dianhydride is preferable from the viewpoint of heat resistance of the polyimide resin to be obtained. Among them, 3,3',4,4'-biphenyltetracarboxylic acid dianhydride or pyromellitic acid dianhydride is preferable from the viewpoint of price, availability, and the like.

The tetracarboxylic acid dianhydride may be used alone, or a mixture of two or more thereof can be used.

••••  Diamine

A diamine can be appropriately selected from the diamines that are used as raw materials for synthesizing polyamic acids in the related art. This diamine may be an aromatic diamine or an aliphatic diamine; however, an aromatic diamine is preferable from the viewpoint of heat resistance of the polyimide resin to be obtained. The diamine can be used alone, or a mixture of two or more thereof can be used.

Examples of the aromatic diamine include a diamino compound obtained by bonding one phenyl group or about 2 to 10 phenyl groups. Specific examples of the aromatic diamine include a phenylenediamine or a derivative thereof, a diaminobiphenyl compound or a derivative thereof, a diaminodiphenyl compound or a derivative thereof, a diaminotriphenyl compound or a derivative thereof, a diaminonaphthalene or a derivative thereof, an aminophenyl aminoindane or a derivative thereof, a diaminotetraphenyl compound or a derivative thereof, a diaminohexaphenyl compound or a derivative thereof, and a cardo-type fluorinamine derivative.

The phenylenediamine is preferably m-phenylenediamine or p-phenylenediamine. Examples of the phenylenediamine derivative include diamines to which an alkyl group such as a methyl group or an ethyl group is bonded, such as, for example, 2,4-diaminotoluene and 2,4-triphenylenediamine.

The diaminobiphenyl compound is a compound in which two aminophenyl groups are bonded to each other. Examples of the diaminobiphenyl compound include 4,4'-diaminobiphenyl, and 4,4'-diamino-2,2'-bis(trifluoromethyl)biphenyl.

The diaminodiphenyl compound is a compound obtained by bonding phenyl groups of two aminophenyl groups to each other through another group. Examples of the other group include an ether bond, a sulfonyl bond, a thioether bond, an alkylene group or a derivative group thereof, an imino bond, an azo bond, a phosphine oxide bond, an amide bond, and a ureylene bond. The alkylene group preferably has about 1 to 6 carbon atoms, and the derivative group thereof is one in which one or more hydrogen atoms of an alkylene group are substituted with a halogen atom or the like.

Examples of the diaminodiphenyl compound include 3,3'-diaminodiphenyl ether, 3,4'-diaminodiphenyl ether, 4,4'-diaminodiphenyl ether, 3,3'-diaminodiphenyl sulfone, 3,4'-diaminodiphenyl sulfone, 4,4'-diaminodiphenylsulfone, 3,3'-diaminodiphenylmethane, 3,4'-diaminodiphenylmethane, 4,4'-diaminodiphenylmethane, 4,4'-diaminodiphenylsulfide, 3,3'-diaminodiphenylketone, 3,4'-diaminodiphenylketone, 2,2-bis(p-aminophenyl)propane, 2,2'-bis(p-aminophenyl)hexafluoropropane, 4-methyl-2,4-bis(p-aminophenyl)-1-pentene, 4-methyl-2,4-bis(p-aminophenyl)-2-pentene, iminodianiline, 4-methyl-2,4-bis(p-aminophenyl)pentane, bis(p-aminophenyl)phosphine oxide, 4,4'-diaminoazobenzene, 4,4'-diaminodiphenylurea, 4,4'-diaminodiphenylamide, 1,4-bis(4-aminophenoxy)benzene, 1,3-bis(4-aminophenoxy)benzene, 1,3-bis(3-aminophenoxy)benzene, 4,4'-bis(4-aminophenoxy)biphenyl, bis[4-(4-aminophenoxy)phenyl]sulphone, bis[4-(3-aminophenoxy)phenyl]sulfone, 2,2-bis[4-(4-aminophenoxy)phenyl]propane, and 2,2-bis[4-(4-aminophenoxy)phenyl]hexafluoropropane.

The diaminotriphenyl compound is a compound obtained by bonding each of two aminophenyl groups and one phenylene group through another group. Examples of the other group include the same one as the other group in diaminodiphenyl compound.

Examples of the diaminotriphenyl compound include 1,3-bis(m-aminophenoxy)benzene, 1,3-bis(p-aminophenoxy)benzene, and 1,4-bis(p-aminophenoxy)benzene.

Examples of diaminonaphthalene include 1,5-diaminonaphthalene and 2,6-diaminonaphthalene.

Examples of aminophenyl aminoindane include 5- or 6-amino-1-(p-aminophenyl)-1,3,3-trimethylindane.

Examples of the diaminotetraphenyl compound include 4,4'-bis(p-aminophenoxy)biphenyl, 2,2'-bis[p-(p'-aminophenoxy)phenyl]propane, 2,2'-bis[p-(p'-aminophenoxy)biphenyl]propane, and 2,2'-bis[p-(m-aminophenoxy)phenyl]benzophenone.

Examples of the cardo-type fluorene amine derivative include 9,9-bisaniline fluorene.

The aliphatic diamine preferably has, for example, about 2 to 15 carbon atoms, and specific examples thereof include pentamethylenediamine, hexamethylenediamine, and heptamethylenediamine.

Here, the diamine may be a compound in which a hydrogen atom is substituted with at least one substituent selected from the group consisting of a halogen atom, a methyl group, a methoxy group, a cyano group, and a phenyl group.

Among the above, the diamine is preferably a phenylenediamine, a phenylenediamine derivative, or a diaminodiphenyl compound. Among them, p-phenylenediamine, m-phenylenediamine, 2,4-diaminotoluene, or 4,4'-diaminodiphenyl ether is particularly preferable from the viewpoint of price, availability, and the like.

The production method for a polyamic acid is not particularly limited, and a known technique such as a method of reacting any tetracarboxylic acid dianhydride with a diamine in an organic solvent is used.

The reaction of tetracarboxylic acid dianhydride with a diamine is generally carried out in an organic solvent. The organic solvent used here is not particularly limited as long as it can dissolve each of tetracarboxylic acid dianhydride and a diamine and does not react with tetracarboxylic acid dianhydride and a diamine. The organic solvent can be used alone, or a mixture of two or more thereof can be used.

Examples of the organic solvent that is used for the reaction between tetracarboxylic acid dianhydride and a diamine include nitrogen-containing polar solvents such as N-methyl-2-pyrrolidone, N,N-dimethylacetamide, N,N-diethylacetamide, N,N-dimethylformamide, N,N-diethylformamide, N-methylcaprolactam, N,N,N',N'-tetramethylurea; lactone-based polar solvents such as β-propiolactone, γ-butyrolactone, γ-valerolactone, δ-valerolactone, γ-caprolactone, and ε-caprolactone; dimethylsulfoxide; acetonitrile; fatty acid esters such as ethyl lactate and butyl lactate; ethers such as diethylene glycol dimethyl ether, diethylene glycol diethyl ether, dioxane, tetrahydrofuran, methyl cellosolve acetate, and ethyl cellosolve acetate; and phenol-based solvents such as cresols.

Among these, as the organic solvent here, it is preferable to use a nitrogen-containing polar solvent from the viewpoint of the solubility of the polyamic acid to be generated.

Further, from the viewpoint of membrane formation property and the like, it is preferable to use a mixed solvent containing a lactone-based polar solvent. In this case, the content of the lactone-based polar solvent is preferably in a range of 1% to 20% by mass and more preferably in a range of 5% to 15% by mass with respect to the entire organic solvent (100% by mass).

As the organic solvent here, it is preferable to use one or more selected from the group consisting of a nitrogen-containing polar solvent and a lactone-based polar solvent, and it is more preferable to use a mixed solvent of a nitrogen-containing polar solvent and a lactone-based polar solvent.

The using amount of the organic solvent is not particularly limited; however, it is preferably such an amount that the content of the generated polyamic acid in the reaction solution after the reaction is in a range of 5% to 50% by mass.

The using amount of each of tetracarboxylic acid dianhydride and a diamine used is not particularly limited; however, it is preferable to use an amount in a range of 0.50 to 1.50 mol, more preferable to use an amount in a range of 0.60 to 1.30 mol, and particularly preferable to use an amount in a range of 0.70 to 1.20 mol, with respect to the 1 mol of tetracarboxylic acid dianhydride.

The reaction (polymerization) temperature is generally in a range of −10° C. to 120° C. and preferably in a range of 5° C. to 30° C. The reaction (polymerization) time varies depending on the raw material composition to be used; however, it is generally in a range of 3 to 24 (hours).

The intrinsic viscosity of the polyamic acid solution obtained under such conditions is preferably in a range of 1,000 to 100,000 centipores (cP) (1 to 100 Pa·s) and more preferably 5,000 to 70,000 cP (5 to 70 Pa·s).

The intrinsic viscosity of the polyamic acid solution can be measured with an E-type rotational viscometer under a temperature condition of 25° C.

••• Polyimide

As the polyimide that can be used in the present embodiment, any known polyimide can be used as long as it can be dissolved in an organic solvent that is used for the varnish, without being limited by the structure and the molecular weight thereof.

The polyimide may have, in the side chain, a condensable functional group such as a carboxy group or a functional group that promotes a crosslinking reaction or the like during sintering.

In order to obtain polyimide that is soluble in an organic solvent that is used for the varnish, it is effective to use a monomer for introducing a flexible bent structure into the main chain.

Examples of this monomer include aliphatic diamines such as ethylenediamine, hexamethylenediamine, 1,4-diaminocyclohexane, 1,3-diaminocyclohexane, and 4,4'-diaminodicyclohexylmethane; aromatic diamines such as 2-methyl-1,4-phenylene, o-tolidine, m-tolidine, 3,3'-dimethoxybenzidine, 4,4'-diaminobenzanilide; polyoxyalkylenediamines such as polyoxyethylenediamine, polyoxypropylenediamine, and polyoxybutylenediamine; polysiloxanediamine; and 2,3,3',4'-oxydiphthalic acid anhydride, 3,4,3',4'-oxydiphthalic acid anhydride, and 2,2-bis(4-hydroxyphenyl)propanedibenzoate-3,3',4,4'-tetracarboxylic acid dianhydride.

In addition, it is also effective to use a monomer having a functional group that improves the solubility in such an organic solvent. Examples of the monomer having such a functional group include fluorinated diamines such as 2,2'-bis(trifluoromethyl)-4,4'-diaminobiphenyl and 2-trifluoromethyl-1,4-phenylenediamine.

Further, in addition to the monomer having such a functional group, the monomer exemplified in the above description of the polyamic acid can be used in combination as long as the solubility is not impaired.

The production method for polyimide is not particularly limited, and examples thereof include known technique such as a method in which polyamic acid is chemically imidized or thermally imidized to be dissolved in an organic solvent.

Examples of the polyimide that can be used in the present embodiment include an aliphatic polyimide (a full-aliphatic polyimide) and an aromatic polyimide, and among them, an aromatic polyimide is preferable.

The aromatic polyimide may be one obtained by subjecting a polyamic acid having a constitutional unit represented by General Formula (5) to thermal or chemical ring closure reaction or may be one obtained by dissolving a polyamic acid having a constitutional unit represented by General Formula (6) in a solvent.

In the formula, $R_{Ar}$ represents an aryl group, and $R'_{Ar}$ represents an arylene group.

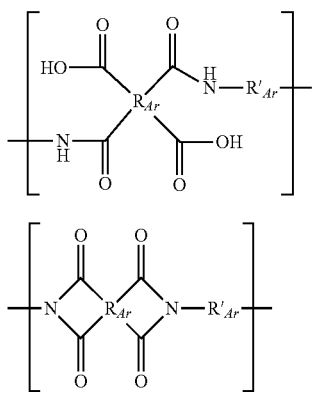

In the above formula, $R_{Ar}$ is not particularly limited as long as it is a cyclic conjugated system having (4n+2) π electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon ring with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring. Among them, $R_{Ar}$ is preferably an aromatic hydrocarbon ring, more preferably benzene or naphthalene, and particularly preferably benzene.

In the above formula, examples of $R'_{Ar}$ include the group obtained by removing two hydrogen atoms from the aromatic ring $R_{Ar}$ described above. Among them, $R'_{Ar}$ is preferably a group obtained by removing two hydrogen atoms from an aromatic hydrocarbon ring, more preferably a group obtained by removing two hydrogen atoms from benzene or naphthalene, and particularly preferably a phenylene group obtained by removing two hydrogen atoms from benzene.

The aryl group in $R_{Ar}$ and the arylene group in $R'_{Ar}$ may each have a substituent.

••• Polyamide Imide

As the polyamideimide that can be used in the present embodiment, any known polyimide can be used as long as it can be dissolved in an organic solvent that is used for the varnish, without being limited by the structure and the molecular weight thereof.

The polyamideimide may have, in the side chain, a condensable functional group such as a carboxy group or a functional group that promotes a crosslinking reaction or the like during sintering.

As such a polyamide imide, it is possible to use, without particular limitation, one obtained by reacting any trimellitic acid anhydride with a diisocyanate or one obtained by imidizing a precursor polymer that is obtained by reacting a reactive derivative of any trimellitic acid anhydride with a diamine.

Examples of the reactive derivative of any trimellitic acid anhydride include a halogenated trimellitic acid anhydride such as trimellitic anhydride chloride and a trimellitic acid anhydride ester.

Examples of the diisocyanate include metaphenylene diisocyanate, p-phenylene diisocyanate, o-tolidine diisocyanate, p-phenylene diisocyanate, m-phenylene diisocyanate, 4,4'-oxybis(phenyl isocyanate), 4,4'-diisocyanate diphenylmethane, bis[4-(4-isocyanoxidephenoxy)phenyl]sulfone, 2,2'-bis[4-(4-isocyanoxidephenoxy)phenyl]propane, 2,4-tolylene diisocyanate, 2,6-tolylene diisocyanate, 4,4'-diphenylmethane diisocyanate, 3,3'-dimethyldiphenyl-4,4'-diisocyanate, 3,3'-diethyldiphenyl-4,4'-diisocyanate, isophorone diisocyanate, hexamethylene diisocyanate, 4,4'-dicyclohexylmethane diisocyanate, m-xylene diisocyanate, p-xylene diisocyanate, and naphthalene diisocyanate.

Examples of the diamine include the same ones as the diamines provided as exemplary examples in the description of the polyamic acid described above.

••• Organic Solvent

The organic solvent that can be used for preparing the varnish is not particularly limited as long as it can dissolve the polyamic acid and/or the polyimide-based resin and does not dissolve fine grains, and examples thereof include the same one as the organic solvent that is used in the reaction between tetracarboxylic acid dianhydride and a diamine. The organic solvent can be used alone, or a mixture of two or more thereof can be used.

The content of the organic solvent in the varnish is preferably in a range of 50% to 95% by mass and more preferably in a range of 60% to 85% by mass. The solid content concentration in the varnish is preferably in a range of 5% to 50% by mass and more preferably in a range of 15% to 40% by mass.

Further, in a case of forming an unsintered composite membrane in a two-layer shape in the [Membrane formation of unsintered composite membrane] described later, the volume fraction of polyamic acid or polyimide, or a polyamideimide (A1) to a fine grain (B1) in the first varnish is preferably set in a range of 19:81 to 45:55. In a case where the total volume is assumed to be 100, grains are uniformly dispersed in a case where the volume occupied by the fine grain (B1) is 55 or more, and grains are easily dispersed without being aggregated in a case where it is 81 or less. This makes it possible to uniformly form pores on the surface side of the base material of the polyimide-based resin molded membrane.

Further, the volume fraction of polyamic acid or polyimide, or a polyamideimide (A2) to a fine grain (B2) in the second varnish is preferably set in a range of 20:80 to 50:50. In a case where the total volume is assumed to be 100, grains are easily dispersed singly and uniformly in a case where the volume occupied by the fine grain (B2) is 50 or more, and grains not aggregated and surface cracking or the like hardly occurs in a case where it is 80 or less. As a result, a polyimide-based resin porous membrane having good mechanical characteristics such as stress and breaking elongation is easily formed.

Regarding the above volume fraction, it is preferable that the second varnish has a lower fine grain content rate than the first varnish. In a case where the above conditions are satisfied, the strength and flexibility of the unsintered composite membrane, the polyimide-based resin-fine grain composite membrane, and the polyimide-based resin porous membrane are ensured even in a case where polyamic acid or polyimide, or polyamideimide is filled with fine grains in a high degree. Further, in a case where a layer having a low fine grain content rate is provided, the production cost can be reduced.

When preparing a varnish, in addition to the above-described components, it is possible to blend, as necessary, known components such as an antistatic agent, a flame retardant, a chemical imidizing agent, a condensing agent, a mold releasing agent, and a surface conditioner for the intended purpose of prevention of static charge, flame retardancy impartment, low temperature sintering, mold releaseability, coatability, and the like.

[Membrane Formation of Unsintered Composite Membrane]

The membrane formation of the unsintered composite membrane containing polyamic acid or polyimide, or polyamideimide and containing fine grains is carried out, for example, by coating a base material with the above varnish and drying under the conditions of normal pressure or vacuum at a temperature in a range of 0° C. to 120° C. (preferably 0° C. to 100° C.) and more preferably under the conditions of normal pressure at a temperature in a range of 60° C. to 95° C. (still more preferably 65° C. to 90° C.). The coating film thickness is, for example, preferably 1 to 500 μm and more preferably 5 to 50 μm.

Here, a mold releasing layer may be provided on the base material as necessary. Further, in the membrane formation of the unsintered composite membrane, each of a dipping step of carrying out dipping in a solvent containing water, a drying step, and a pressing step may be provided as optional steps before [Sintering of unsintered composite membrane] described later.

The mold releasing layer can be prepared by applying a mold releasing agent on the base material and carrying out drying or baking. As the mold releasing agent used here, a known mold releasing agent such as an alkyl phosphate ammonium salt-based mold releasing agent, a fluorine-based mold releasing agent, or a silicone-based mold releasing agent can be used without particular limitation. In a case where the unsintered composite membrane after drying is peeled from the base material, a small amount of the mold releasing agent remains on the peeled surface of the unsintered composite membrane. Since the remaining mold releasing agent may affect the wettability of the surface of the polyimide-based resin porous membrane and the mixing of impurities, it is preferable to remove the remaining mold releasing agent.

As a result, it is preferable to wash the unsintered composite membrane peeled from the base material with an organic solvent or the like. Examples of the washing method include known technique such as a method of dipping an unsintered composite membrane in a washing liquid and then taking it out and a method of shower washing.

In order to dry the unsintered composite membrane after washing, for example, the unsintered composite membrane after washing is air-dried at room temperature or heated to a suitable set temperature in a constant temperature bath. At that time, for example, it is possible to adopt a method in which an end part of the unsintered composite membrane is fixed to a mold made of SUS or the like to prevent deformation.

On the other hand, in a case where the base material is used as it is without providing a mold releasing layer in the membrane formation of the unsintered composite membrane, the step of forming the mold releasing layer and the step of washing the unsintered composite membrane can be omitted.

In addition, in a case where the unsintered composite membrane is formed into a membrane in a two-layer shape, first, the formation of a first unsintered composite membrane having a membrane thickness in a range of 1 to 5 μm is carried out by directly coating a base material such as glass with the above varnish and then drying under the conditions of normal pressure or vacuum at a temperature in a range of 0° C. to 120° C. (preferably 0° C. to 90° C.) and more preferably under the conditions of normal pressure at a temperature in a range of 10° C. to 100° C. (still more preferably 10° C. to 90° C.).

Subsequently, the first unsintered composite membrane is coated with the above second varnish, and drying is carried out in the same manner under the conditions of a temperature in a range of 0° C. to 80° C. (preferably 0° C. to 50° C.) and more preferably under the conditions of normal pressure at a temperature in a range of 10° C. to 80° C. (still more preferably 10° C. to 30° C.) to form a second unsintered composite membrane having a membrane thickness in a range of 5 to 50 μm, whereby unsintered composite membrane having a two-layer shape can be formed into a membrane.

[Sintering of Unsintered Composite Membrane]

After [Membrane formation of unsintered composite membrane] described above, the unsintered composite membrane is subjected to heat treatment (sintering) to form a composite membrane (a polyimide-based resin-fine grain composite membrane) composed of a polyimide-based resin and fine grains.

In a case where the varnish contains polyamic acid, it is preferable to complete the imidization by [Sintering of unsintered composite membrane] of the present step.

The temperature (the sintering temperature) of the heat treatment varies depending on the structure of the polyamic acid, or polyimide or polyamideimide contained in the unsintered composite membrane and the presence or absence of the condensing agent; however, it is preferably in a range of 120° C. to 400° C. and more preferably in a range of 150° C. to 375° C.

For carrying out sintering, it is not always necessary to clearly separate the operation from the drying in the previous step. For example, in a case of sintering at 375° C., it is also possible to use a method in which the temperature is raised from room temperature to 375° C. over 3 hours and then held at 375° C. for 20 minutes or a stepwise drying-thermal imidization method in which, for example, the temperature is gradually raised from room temperature to 375° C. in 50° C. increments (held for 20 minutes in each increment) and finally held at 375° C. for 20 minutes. At that time, a method in which an end part of the unsintered composite membrane is fixed to a mold made of SUS or the like may be adopted to prevent deformation.

The thickness of the polyimide-based resin-fine grain composite membrane after the heat treatment (sintering) is, for example, preferably 1 μm or more, more preferably in a range of 5 to 500 μm, and still more preferably in a range of 8 to 100 μm.

The thickness of the polyimide-based resin-fine grain composite membrane can be determined by measuring thicknesses of a plurality of positions using a micrometer and averaging the measured thicknesses.

The present step is an optional step. The present step may not be carried out, particularly in a case where polyimide or polyamideimide is used for the varnish.

[Removal of Fine Grains]

After [Sintering of unsintered composite membrane] described above, the fine grains are removed from the polyimide-based resin-fine grain composite membrane, whereby a polyimide-based resin porous membrane is produced.

For example, in a case where silica is used as the fine grain, the polyimide-based resin-fine grain composite membrane is brought into contact with a low-concentration hydrogen fluoride (HF) water to dissolve and remove the silica, whereby a porous membrane is obtained. In addition, in a case where the fine grains are resin fine grains, the resin fine grains are decomposed and removed by heating to a temperature equal to or higher than the thermal decomposition temperature of the resin fine grains and lower than the thermal decomposition temperature of the polyimide-based resin, whereby a porous membrane is obtained.

[Etching (Decyclization of Imide Bond)]

The etching step can be carried out by a chemical etching method or a physical removal method, or a method in which these methods are combined.

• In Regard to Chemical Etching Method

A known technique in the related art can be used as the chemical etching method.

The chemical etching method is not particularly limited, and examples thereof include a treatment with an etching liquid such as an inorganic alkaline solution or an organic alkaline solution. Among the above, a treatment with an inorganic alkaline solution is preferable.

Examples of the inorganic alkaline solution include a hydrazine solution containing hydrazine hydrate and ethylenediamine; a solution of an alkali metal hydroxide such as potassium hydroxide, sodium hydroxide, sodium carbonate, sodium silicate, or sodium metasilicate; an ammonia solution; and an etching liquid containing alkali hydroxide, hydrazine, and 1,3-dimethyl-2-imidazolidinone as main components.

Examples of the organic alkaline solution include primary amines such as ethylamine and n-propylamine; secondary amines such as diethylamine and di-n-butylamine; tertiary amines such as triethylamine and methyldiethylamine; alcohol amines such as dimethylethanolamine and triethanolamine; quaternary ammonium salts such as tetramethylammonium hydroxide and tetraethylammonium hydroxide; and alkaline etching liquids such as cyclic amines such as pyrrole and piperidine. The alkali concentration in the etching liquid is, for example, in a range of 0.01% to 20% by mass.

Pure water or alcohols can be appropriately selected as the solvent for each of the above etching liquids, and those to which a suitable amount of a surfactant is added can also be used.

• In Regard to Physical Removal Method

As the physical removal method, for example, a dry etching method using plasma (oxygen, argon, or the like), corona discharge, or the like can be used.

The above-described chemical etching method or physical removal method can be applied before [Removal of fine grains] described above or can be applied after [Removal of fine grains] described above.

Among the above, it is preferable to be applied after [Removal of fine grains] described above since the interconnection pores inside the polyimide-based resin porous membrane are more easily formed and the foreign substances removing property is enhanced.

In a case where the chemical etching method is carried out in the etching step, a step of washing the polyimide-based resin porous membrane may be provided after the present step in order to remove excess etching liquid.

The washing after the chemical etching may be carried out by washing with water alone; however, it is preferable to combine washing with acid and washing with water.

Further, after the etching step, the polyimide-based resin porous membrane may be subjected to heat treatment (re-sintering) in order to improve the wettability of the polyimide-based resin porous membrane surface to an organic solvent and remove residual organic substances. The conditions of this heating are the same as the conditions in [Sintering of unsintered composite membrane] described above.

For example, in the polyimide-based resin porous membrane produced by the above-described production method, spherical cells and an interconnection pore in which adjacent spherical cells are connected to each other are formed. The polyimide-based resin porous membrane preferably has an interconnection pore so that an interconnection pore that opens on one outer surface is connected to the inside of the porous membrane and opens up to the other (on the back side) outer surface, and thus a flow path in which a fluid can pass through the porous membrane is ensured.

The Garley air permeability of the "porous membrane in which adjacent spherical cells are connected to each other" is, for example, preferably 30 seconds or more from the viewpoint of efficiently removing foreign substances while maintaining a certain degree of high flow rate of a filtration target that passes through the porous membrane. The Garley air permeability of the porous membrane is more preferably in a range of 30 to 1,000 seconds, still more preferably in a range of 30 to 600 seconds, particularly preferably in a range of 30 to 500 seconds, and most preferably in a range of 30 to 300 seconds. In a case where the Garley air permeability is equal to or smaller than the preferred upper limit value of the above range, the degree of porosity (the presence ratio of the interconnection pore and the like) is sufficiently high, and thus the effect of removing foreign substances can be more easily obtained.

The Garley air permeability of the porous membrane can be measured according to JIS P 8117.

The "porous membrane in which adjacent spherical cells are connected to each other" preferably contains interconnection pores having a pore diameter in a range of 1 to 200 nm, more preferably in a range of 3 to 180 nm, still more preferably in a range of 5 to 150 nm, and particularly preferably in a range of 10 to 130 nm.

The pore diameter of the interconnection pore means the diameter of the interconnection pore. However, for example, in a case where a direction in which two pores constituting an interconnection pore are adjacent to each other is denoted by a longitudinal direction, a direction perpendicular to the longitudinal direction is included in the above diameter since one interconnection pore is generally formed from two adjacent grains by the above-described production method.

In a case where the above-described etching (decyclization of imide bond) step is not provided, the pore diameter of the interconnection pore tends to be small.

The average pore diameter of the "porous membrane in which adjacent spherical cells are connected to each other" is preferably in a range of 100 to 2,000 nm, more preferably in a range of 200 to 1,000 nm, and still more preferably in a range of 300 to 900 nm.

Regarding the porous membrane (for example, the polyimide porous membrane) subjected to the above-described chemical etching, the average pore diameter of the porous membrane is a value obtained by measuring diameters of interconnection pores based on a bubble point method using a palm porometer (for example, manufactured by Porous Materials Inc.). Regarding a porous membrane (for example, a porous polyamideimide membrane) not subjected to chemical etching, the average grain diameter of the fine grains that are used in the production of the porous membrane is adopted as the average pore diameter.

As described above, the "porous membrane in which adjacent spherical cells are connected to each other" is preferably a porous membrane containing pores having an average pore diameter of several hundred nanometers. As a result, for example, even minute substances in the nanometer unit can be adsorbed or captured in the pores and/or the interconnection pores in the porous membrane.

Regarding the pore diameter of the interconnection pore, in a case where the distribution of the pore diameters of the individual pores that impart porosity to the "porous membrane in which adjacent spherical cells are connected to each other" is broader, the pore diameter of the interconnection pore that is formed by pores adjacent to each other tends to be smaller.

From the viewpoint of reducing the pore diameter of the interconnection pore, the void ratio of the "porous membrane in which adjacent spherical cells are connected to each other" is, for example, preferably 50% by mass or more, more preferably in a range of 60% to 90% by mass, still more preferably in a range of 60% to 80% by mass, and particularly preferably about 70% by mass. In a case where the void ratio is equal to or larger than the preferred lower limit value of the above range, the effect of removing foreign substances can be more easily obtained. In a case where it is equal to or smaller than the preferred upper limit value of the above range, the strength of the porous membrane is further increased.

The void ratio of the porous membrane is determined by calculating the proportion of the mass of the fine grains with respect to the total mass of the resin and the like that are used in the production of the porous membrane, and the fine grains.

Further, the "porous membrane in which adjacent spherical cells are connected to each other" preferably contains interconnection pores having an average pore diameter in a range of 0.01 to 50 nm and more preferably contains interconnection pores having an average pore diameter in a range of 0.05 to 10 nm, where the average pore diameter is determined by the BET method. The average pore diameter of the interconnection pores is more preferably in a range of 0.1 to 40 nm, still more preferably in a range of 1 to 30 nm, and particularly preferably in a range of 1 to 20 nm.

In a case where interconnection pores having an average pore diameter in the above range are used, where the average pore diameter is determined by the BET method, it is possible to effectively reduce high molecular weight substances (for example, molecules having a molecular weight of 30,000 or more in the molecular weight distribution) which may cause defects in a resist pattern, in a resin that is used in the semiconductor manufacturing process.

The BET method is a method in which an adsorption isotherm is measured by adsorbing and desorbing an adsorbing molecule (for example, nitrogen) on a porous body, and the measured data is analyzed based on BET Expression represented by the following expression (Be 1). A specific surface area A and a total micropore volume V can be calculated based on this method, and further, the average pore diameter can be calculated from an expression [4V/A] based on the obtained specific surface area A and total micropore volume V. Here, the specific surface area determined by the BET method is preferably 15 m$^2$/g or more, more preferably 20 m$^2$/g or more and 200 m$^2$/g or less, and still more preferably 25 m$^2$/g or more and 100 m$^2$/g or less.

Specifically, first, the adsorption isotherm is obtained by adsorbing and desorbing an adsorbing molecule on the porous body. Then, $[P/\{V_a(P_0-P)\}]$ is calculated from the obtained adsorption isotherm based on Expression (B1) below, and plotted with respect to the equilibrium relative pressure (P/P0). Next, this plot is regarded as a straight line, and the slope s $(=[(C-1)/(Vm\times C)])$ and the intercept i $(=[1/(Vm\times C)])$ are calculated based on the least squares method. Then, Vm and C are calculated from the obtained slope s and intercept i based on Expression (Be2-1) and Expression (B2-2). Furthermore, the specific surface area A can be calculated from Viii based on Expression (Be3). Further, the adsorption data of the obtained adsorption isotherm is linearly interpolated to determine the adsorption amount at the relative pressure set from the micropore volume calculation relative pressure. The total micropore volume V can be calculated from this adsorption amount. This BET method is a measurement method based on JIS R1626-1996 "Measurement method of specific surface area by gas adsorption BET method for fine ceramic powder". The measuring device by the BET method is not particularly limited; however, examples thereof include Micromeritics (manufactured by Shimadzu Corporation).

$$[P/\{V_a(P_0-P)\}]=[1/(Vm\times C)]+[(C-1)/(Vm\times C)](P/P0) \quad (1)$$

$$Vm=1/(s+i) \quad (2\text{-}1)$$

$$C=(s/i)+1 \quad (2\text{-}2)$$

$$A=(Vm\times L\cdot\sigma)/22,414 \quad (3)$$

Va: Adsorption amount
Vm: Adsorption amount of unimolecular layer
P: Equilibrium pressure of adsorbing molecule
P0: Saturated vapor pressure of adsorbing molecule
L: Avogadro's number
σ: Adsorption cross-sectional area of adsorbing molecule Further, the "porous membrane in which adjacent spherical cells are connected to each other" preferably has an average pore diameter in a range of 100 nm or less and more preferably has an average pore diameter of 90 nm or less, where the average pore diameter is determined by a porometer. The maximum value of the micropore diameter distribution (%) determined by the porometer is preferably 40% or more, more preferably 45% or more, still more preferably 50% or more. In addition, the pore diameter (hereinafter, the pore diameter A), at which the micropore diameter distribution (%) is maximal, is preferably 100 nm or less and more preferably 90 nm or less. Further, the ratio (the maximum pore diameter/the pore diameter A) of the maximum pore diameter in the pore diameter distribution width relative to the pore diameter A determined by the porometer is preferably 1.4 or less, more preferably 1.3 or less, and still more preferably 1.2 or less.

The "porous membrane in which adjacent spherical cells are connected to each other" is excellent in mechanical characteristics such as stress and breaking elongation.

The stress of the "porous membrane in which adjacent spherical cells are connected to each other" provided in the filter is, for example, preferably 10 MPa or more, more preferably 15 MPa or more, and still more preferably in a range of 15 to 50 MPa.

The stress of the porous membrane is a value measured by preparing a sample having a size of 4 mm×30 mm and subjecting the sample to the measurement using a testing machine under the measuring condition of 5 mm/min.

Further, the breaking elongation of the "porous membrane in which adjacent spherical cells are connected to each other" is, for example, preferably 10% GL or more and more preferably 15% GL or more. The upper limit of the breaking elongation is, for example, preferably 50% GL or less, more preferably 45% GL or less, and still more preferably 40%

GL or less. In a case where the void ratio of the polyimide-based resin porous membrane decreases, breaking elongation tends to increase.

The breaking elongation of the porous membrane is a value measured by preparing a sample having a size of 4 mm×30 mm and subjecting the sample to the measurement using a testing machine under the measuring condition of 5 mm/min.

The thermal decomposition temperature of the "porous membrane in which adjacent spherical cells are connected to each other" is preferably 200° C. or higher, more preferably 320° C. or higher, and still more preferably 350° C. or higher.

The thermal decomposition temperature of the porous membrane can be measured by raising the temperature to 1,000° C. at a temperature rising rate of 10° C./min in an air atmosphere.

The filter in the present embodiment is not limited to the one that includes a porous membrane in which the interconnection pores 5 in which the adjacent spherical cell 1$a$ and the spherical cell 1$b$ are connected to each other as shown in FIG. 1 is formed, and may include a porous membrane in which, in addition to the interconnection pores 5, a cell or interconnection pore having another form is formed. Examples of the cell (hereinafter, referred to as "another cell") having another form include a cell that differs in shape or pore diameter, and examples thereof include an elliptical cell, a polyhedral cell, a spherical cell having a different pore diameter. Examples of the above-described "interconnection pore having another form" include an interconnection pore in which a spherical cell and another cell are connected to each other.

The shape or pore diameter of another cell may be appropriately determined depending on the kinds of impurities to be removed. The interconnection pore in which a spherical cell and another cell are connected to each other can be formed by the selection of material of the fine grain material described above, the shape control of the fine grains, and the like.

According to the filter including a porous membrane in which, in addition to the interconnection pore in which adjacent spherical cells are connected to each other, a cell or interconnection pore having another form is formed, it is possible to efficiently remove various foreign substances from a filtration target.

Further, the filter in the present embodiment replaces a filter cartridge or the like for removing impurities having a fine grain shape, which has been installed in the related art, in the supply lines of various chemical liquids or the point of use (POU) in the semiconductor manufacturing process or can be used in combination with these. As a result, various foreign substances can be efficiently removed from a filtration target (a chemical liquid for lithography) using the same device and operation as those in the related art, and a high-purity resist composition purified product can be prepared.

《Filtration of Resist Composition》

Filtration of a resist composition using a filter having a porous structure in which adjacent spherical cells are connected to each other may be carried out in a state where differential pressure is not provided (that is, a resist composition may be allowed to pass through the filter only by gravity) or may be carried out in a state where differential pressure is provided. Among the above, the latter is preferable, and it is preferable to carry out an operation of allowing a resist composition to pass through the filter by differential pressure.

The "state where differential pressure is provided" means that a pressure difference is present between one side and the other side of the polyimide-based resin porous membrane provided in the filter.

For example, pressurization (positive pressure) that applies pressure to one side (the resist composition supply side) of the polyimide-based resin porous membrane, and decompression (negative pressure) that causes one side (the filtrate side) of the polyimide-based resin porous membrane to be negative pressure. In the filtration step according to the present embodiment, the former pressurization is preferable.

The pressurization is an operation to apply pressure to the supply liquid side of the polyimide-based resin porous membrane, where a resist composition (hereinafter, may be referred to as a "supply liquid") before being allowed to pass through the polyimide-based resin porous membrane is present on the supply liquid side.

For example, it is preferable to apply pressure to the supply liquid side by using the liquid flow pressure generated by the circulation or liquid feeding of the supply liquid or by using the positive pressure of the gas.

The liquid flow pressure can be generated, for example, by an active liquid flow pressure applying method with a pump (a feeding pump, a circulation pump, or the like). Examples of the pump include a rotary pump, a diaphragm pump, a metering pump, a chemical pump, a plunger pump, a bellows pump, a gear pump, a vacuum pump, an air pump, and a liquid pump.

In a case where the supply liquid is circulated or fed by the pump, the pump is generally arranged between the supply liquid bath (or the circulation bath) and the polyimide-based resin porous membrane.

For example, in a case where a supply liquid is allowed to pass through the polyimide-based resin porous membrane only by gravity, the liquid flow pressure may be the pressure that is applied to the polyimide-based resin porous membrane by the supply liquid; however, it is preferably the pressure that is applied by the active liquid flow pressure applying method.

The gas that is used for pressurization is preferably a gas that is inert or non-reactive to the supply liquid, and specific examples thereof include nitrogen and a rare gas such as helium and argon.

Regarding a method of applying pressure to the supply liquid side, it is preferable to use the positive pressure of the gas. At that time, the filtrate side where the filtrate has passed through the polyimide-based resin porous membrane may be at atmospheric pressure without being decompressed.

Further, the pressurization may utilize both the liquid flow pressure and the positive pressure of the gas. Further, the differential pressure may be a combination of pressurization and decompression, and for example, one that utilizes both liquid flow pressure and decompression, one that utilizes both positive pressure and decompression of the gas, or one that utilizes liquid flow pressure, and positive pressure and decompression of the gas may be used. In a case where the method of providing differential pressure is combined, a combination of liquid flow pressure and positive pressure of the gas or a combination of liquid flow pressure and decompression is preferable from the viewpoint of simplification of production.

In the present embodiment, as the method of providing differential pressure, for example, even one method using positive pressure by gas or the like is excellent in foreign substances removing property since the polyimide-based resin porous membrane is used.

The decompression is an operation to decompress the filtrate side where the filtrate has passed through the polyimide-based resin porous membrane. For example, the decompression may be decompression by a pump; however, it is preferable to reduce pressure to form a vacuum.

In a case where the operation of allowing the resist composition to pass through the filter is carried out in a state where differential pressure is provided, the pressure difference is appropriately set in consideration of the membrane thickness, void ratio, or average pore diameter of the polyimide-based resin porous membrane to be used, or the desired degree of purification, the flow amount, the flow rate, or the concentration or viscosity of the supply liquid, or the like. For example, in a case of the so-called cross-flow method (the supply liquid is allowed to flow in parallel with the polyimide-based resin porous membrane), the pressure difference is preferably, for example, 0.3 MPa or less.

In a case of the so-called dead-end method (the supply liquid is allowed to flow to intersect the polyimide-based resin porous membrane), the pressure difference is, for example, preferably 1 MPa or less and more preferably 0.3 MPa or less. The lower limit value of each of the pressure differences is preferably 0.01 MPa or more and more preferably 0.05 MPa or more.

In the step (i), the operation of allowing the resist composition to pass through the filter having the polyimide-based resin porous membrane described above can be carried out while maintaining a high flow rate of the resist composition (the supply liquid).

The flow rate in this case is not particularly limited; however, for example, the flow rate of pure water in a case of being pressurized at 0.08 MPa at room temperature (20° C.) is preferably 1 mL/min or more, more preferably 3 mL/min or more, still more preferably 5 mL/min or more, and particularly preferably 10 mL/min or more. The upper limit value of the flow rate is not particularly limited, and it is, for example, 50 mL/min or less.

In the present embodiment, since the filter having the polyimide-based resin porous membrane described above is used, filtration can be carried out while maintaining a high flow rate in this manner, and the removal rate of foreign substances contained in the resist composition can be increased.

In addition, in the step (i), the operation of allowing the resist composition to pass through the filter is preferably carried out by setting the temperature of the resist composition in a range of to 0° C. to 30° C. and preferably carried out by setting in a range of 5° C. to 25° C.

Further, in the step (i), the resist composition may be allowed to pass through the filter having the polyimide-based resin porous membrane a plurality of times (may be subjected recirculation filtration a plurality of times) or may be allowed to pass through a plurality of filters including at least a filter having the polyimide-based resin porous membrane.

Further, before allowing the supply liquid to pass through the polyimide-based resin porous membrane, a solution such as alcohol such as methanol, ethanol, or isopropyl alcohol, a ketone such as acetone or methyl ethyl ketone, water, or a solvent contained in the supply liquid or a mixture thereof may be brought into contact with the polyimide-based resin porous membrane to be allowed to pass, for washing the polyimide-based resin porous membrane, improving the wettability with respect to the supply liquid, or adjusting the surface energy between the polyimide-based resin porous membrane and the supply liquid. In order to bring the above solution into contact with the polyimide-based resin porous membrane, the polyimide-based resin porous membrane may be impregnated or dipped in the above solution. In a case where the above solution is brought into contact with the polyimide-based resin porous membrane, for example, the solution can be permeated into the pores inside the polyimide-based resin porous membrane. The bringing of the solution into contact with the polyimide-based resin porous membrane may be carried out in a state where the differential pressure described above is provided and is preferably carried out under pressure particularly in a case where the solution is allowed to permeate into the pores inside the polyimide-based resin porous membrane.

<Other Steps>

The production method according to the present embodiment may include other steps in addition to the step (i). Examples of the other steps include a step of carrying out filtering with a filter other than the filter having a polyimide-based resin porous membrane. The filter other than the filter having a polyimide-based resin porous membrane is not particularly limited; however, examples thereof include a filter having a porous membrane of a thermoplastic resin, such as a nylon membrane, a polyethylene membrane, a polypropylene membrane, a polytetrafluoroethylene (PTFE) membrane, a tetrafluoroethylene/perfluoroalkyl vinyl ether copolymer (PFA) membrane, or a membrane obtained by modifying these membranes. Among the above, as the other filter, a filter having a porous membrane containing a polyethylene resin is preferable since it is excellent in foreign substances removing property.

«Step (ii)»

The production method according to the present embodiment preferably further includes a step (ii) of filtering the resist composition after the step (i) with a filter having a porous membrane containing a polyethylene resin. A porous membrane (hereinafter, also referred to as a "polyethylene resin porous membrane") containing a polyethylene resin may be composed of only a polyethylene resin or may contain a polyethylene resin and another resin; however, it is preferably composed of only a polyethylene resin.

The polyethylene resin porous membrane is not particularly limited, and a known one can be used. Since the polyethylene resin porous membrane is excellent in impact resistance, abrasion resistance, and chemical resistance, it is preferable to use a porous membrane of an ultrahigh molecular weight polyethylene (UPE).

The average pore diameter of such a polyethylene resin porous membrane is not particularly limited; however, it is preferably in a range of 0.1 to 100 nm, more preferably in a range of 0.3 to 50 nm, and still more preferably in a range of 0.5 to 10 nm, from the viewpoint of removing fine foreign substances.

Examples of such a filter having a polyethylene resin porous membrane include those in which a polyethylene resin porous membrane is provided in an outer container made of a thermoplastic resin (polyethylene, polypropylene, PFA, polyether sulfone (PES), polyimide, polyamide imide, or the like).

The step (ii) is preferably carried out after the step (i), and in this case, the average pore diameter of the polyethylene resin porous membrane is preferably smaller than the average pore diameter of the interconnection pores of the polyimide-based porous membrane.

In the production method according to the present embodiment, the step (ii) may be repeated after the step (i). In this case, the resist composition (the supply liquid) is allowed to pass through a filter having a polyimide-based resin porous membrane and a filter having a polyethylene resin porous membrane, while being circulated at all times. In a case of performing circulation-type filtration as described above, it is preferable that both filters are arranged so that the resist composition passes through the filter having a polyimide-based resin porous membrane and then passes through the filter having a polyethylene resin porous membrane in the circulation path.

In a case where the step (ii) is carried out, before allowing the supply liquid to pass through the polyethylene resin porous membrane, a solution such as alcohol such as methanol, ethanol, or isopropyl alcohol, a ketone such as acetone or methyl ethyl ketone, water, or a solvent contained in the supply liquid or a mixture thereof may be brought into contact with the polyethylene resin porous membrane to be allowed to pass in the same manner as described in the step (i), for washing the polyethylene resin porous membrane, improving the wettability with respect to the supply liquid, or adjusting the surface energy between the polyethylene resin porous membrane and the supply liquid.

<Resist Composition>

The resist composition which is a filtration target contains a base material component (A) (hereinafter, also referred to as a "component (A)" that exhibits changed solubility in a developing solution under action of acid, an onium salt, and an organic solvent component (S). The content of the organic solvent component (S) in the resist composition is 97% by mass or more.

In a case where a resist film is formed using the resist composition and the formed resist film is subjected to selective exposure, an acid is generated at exposed portions of the resist film, and the generated acid acts on the component (A) to change the solubility of the component (A) in a developing solution, whereas the solubility of the component (A) in a developing solution is not changed at unexposed portions of the resist film, which generates the difference in solubility in the developing solution between exposed portions and unexposed portions of the resist film. Therefore, by subjecting the resist film to development, exposed portions of the resist film are dissolved and removed to form a positive-tone resist pattern in a case where the resist composition is a positive-tone type, whereas unexposed portions of the resist film are dissolved and removed to form a negative-tone resist pattern in a case where the resist composition is a negative-tone type.

In the present specification, a resist composition which forms a positive-tone resist pattern by dissolving and removing the exposed portions of the resist film is called a positive-tone resist composition, and a resist composition which forms a negative-tone resist pattern by dissolving and removing the unexposed portions of the resist film is called a negative-tone resist composition.

The resist composition may be a positive-tone resist composition or a negative-tone resist composition.

Further, in the formation of a resist pattern, the resist composition may be applied to an alkali developing process using an alkali developing solution in the developing treatment, or a solvent developing process using a developing solution (an organic developing solution) containing an organic solvent in the developing treatment.

That is, the resist composition is a "positive-tone resist composition for an alkali developing process" that forms a positive-tone resist pattern in an alkali developing process and is a "negative-tone resist composition for a solvent developing process" that forms a negative-tone resist pattern in a solvent developing process.

The resist composition has a function of generating acid upon exposure, the component (A) may generate an acid upon exposure, and an additive component that is separately blended from the component (A) may generate an acid upon exposure.

Specifically, the resist composition may (1) contain an acid generator component (B) (hereinafter, referred to as "component (B)") that generates an acid upon exposure; (2) have a component (A) that generates an acid upon exposure; and (3) have a component (A) that generates an acid upon exposure and further contains component (B).

That is, in a case of (2) or (3) described above, the component (A) becomes a "base material component that generates acid upon exposure and exhibits changed solubility in a developing solution under action of acid". In a case where the component (A) is a base material component that generates acid upon exposure and exhibits changed solubility in a developing solution under action of acid, it is preferable that the component (A1) described below is a polymeric compound that generates acid upon exposure and exhibits changed solubility in a developing solution under action of acid. As such a polymeric compound, a copolymer having a constitutional unit that generates acid upon exposure can be used. Examples of the constitutional units that generate acid upon exposure include, for example, known constitutional units.

The resist composition is particularly preferably the case of the above (1).

In addition, the resist composition may contain a base component (hereinafter, also referred to as a component (D)) that traps (that is, controls the acid diffusion) acid generated from the component (B) upon exposure.

The onium salt contained in the resist composition which is a filtration target may be contained in the component (B), may be contained in the component (D), or may be contained in the component (A). In a case where the onium salt is contained in the component (A), the component (A) is a component that generates acid upon exposure.

«In Regard to Component (A)»

In the resist composition, the component (A) is a base material component that exhibits changed solubility in a developing solution under action of acid.

In the present invention, the "base material component" is an organic compound having a film forming ability, and an organic compound having a molecular weight of 500 or more is preferably used. In a case where the molecular weight of the organic compound is 500 or more, the film forming ability is improved, and in addition, a nano-level resist pattern is easily formed.

The organic compounds used as the base material component are roughly classified into a non-polymer and a polymer.

As the non-polymer, those having a molecular weight of 500 or more and less than 4,000 are generally used. Hereinafter, a "low molecular weight compound" refers to a non-polymer having a molecular weight of 500 or more and less than 4,000. As the polymer, those having a molecular weight of 1,000 or more are generally used. Hereinafter, a "resin", a "polymeric compound", or a "polymer" refers to a polymer having a molecular weight of 1,000 or more. As the molecular weight of the polymer, a polystyrene-equivalent mass average molecular weight determined by gel permeation chromatography (GPC) is used.

That is, in a case where the resist composition is a "negative-tone resist composition for an alkali developing process" that forms a negative-tone resist pattern in an alkali developing process or a "positive-tone resist composition for a solvent developing process" that forms a positive-tone resist pattern in a solvent developing process, a base material component (A-2) soluble in an alkali developing solution (hereinafter, referred to as "component (A-2)") is preferably used as the component (A), and a crosslinking agent component is further added. In the resist composition, in a case where acid is generated from the component (B) upon exposure, the acid acts to cause crosslinking between the component (A-2) and a crosslinking agent component, and as a result, the solubility in an alkali developing solution is decreased (the solubility in an organic developing solution is increased). Therefore, in the formation of a resist pattern, by conducting selective exposure of a resist film formed by applying the resist composition to a support, the exposed portions of the resist film change to an insoluble state in an alkali developing solution (a soluble state in an organic developing solution), whereas the unexposed portions of the resist film remain soluble in an alkali developing solution (an insoluble state in an organic developing solution), and thus a negative-tone resist pattern is formed by the alkali developing solution. Further, in this case, a positive-tone resist pattern is formed by development with the organic developing solution.

As the component (A-2), a resin soluble in an alkali developing solution (hereinafter, referred to as "alkali-soluble resin") is preferably used.

From the viewpoint that a good resist pattern with less swelling can be formed, the alkali-soluble resins is preferably, for example, a resin having a constitutional unit derived from at least one selected from an α-(hydroxyalkyl) acrylic acid or an alkyl ester of an α-(hydroxyalkyl) acrylic acid (preferably an alkyl ester having 1 to 5 carbon atoms) disclosed in Japanese Unexamined Patent Application, First Publication No. 2000-206694; an acrylic resin or polycycloolefin resin in which a hydrogen atom bonded to a carbon atom at an α-position having a sulfonamide group may be substituted with a substituent disclosed in U.S. Pat. No. 6,949,325; an acrylic resin containing a fluorinated alcohol, in which a hydrogen atom bonded to a carbon atom at an α-position may be substituted with a substituent disclosed in U.S. Pat. No. 6,949,325, Japanese Unexamined Patent Application, First Publication No. 2005-336452, and Japanese Unexamined Patent Application, First Publication No. 2006-317803; or a polycycloolefin resin containing a fluorinated alcohol disclosed in Japanese Unexamined Patent Application, First Publication No. 2006-259582.

The α-(hydroxyalkyl) acrylic acid refers to one or both of an acrylic acid in which a hydrogen atom is bonded to the carbon atom at the α-position to which a carboxy group is bonded or an α-hydroxyalkyl acrylic acid in which a hydroxyalkyl group (preferably a hydroxyalkyl group having 1 to 5 carbon atoms) is bonded to the carbon atom the α-position, among acrylic acids in which a hydrogen atom bonded to the carbon atom at the α-position may be substituted with a substituent.

As the crosslinking agent component, for example, an amine-based crosslinking agent such as a glycoluril having a methylol group or an alkoxymethyl group, or a melamine-based crosslinking agent is preferably used since a good resist pattern with less swelling is easily formed. The blending amount of the crosslinking agent component is preferably 1 to 50 parts by mass with respect to 100 parts by mass of the alkali-soluble resin.

That is, in a case where the resist composition is a "positive-tone resist composition for an alkali developing process" that forms a positive-tone resist pattern in an alkali developing process or a "negative-tone resist composition for a solvent developing process" that forms a negative-tone resist pattern in a solvent developing process, a base material component (A-1) (hereinafter, referred to as a "component (A-1)") having polarity that is increased under action of acid is preferably used as the component (A). In the alkali developing process and the solvent developing process, since the polarity of the base material component before and after the exposure is changed by using the component (A-1), an excellent development contrast between exposed portions and unexposed portions can be obtained.

In a case of applying an alkali developing process, the component (A-1) is insoluble in an alkali developing solution prior to exposure; however, it has a polarity that is increased under action of acid and then exhibits increased solubility in an alkali developing solution, for example, in a case where acid is generated from the component (B) upon exposure. Therefore, in the formation of a resist pattern, in a case where a resist film formed by applying the resist composition onto a support is subjected to the selective exposure, exposed portions of the resist film change from an insoluble state to a soluble state in an alkali developing solution, whereas unexposed portions of the resist film remain insoluble in an alkali developing solution, and thus, a positive-tone resist pattern is formed by alkali developing.

On the other hand, in a case of applying a solvent developing process, the component (A-1) has a high solubility in an organic developing solution prior to exposure; however, it has an increased polarity under action of acid and then exhibits decreased solubility in an organic developing solution in a case where acid is generated from the component (B) upon exposure. Therefore, in the formation of a resist pattern, in a case where a resist film formed by applying the resist composition onto a support is subjected to the selective exposure, exposed portions of the resist film change from a soluble state to an insoluble state in an organic developing solution, whereas unexposed portions of the resist film remain soluble and do not change, thereby a contrast between exposed portions and unexposed portions can be obtained, and thus a negative-tone resist pattern is formed by development in the organic developing solution.

In the resist composition, the component (A) may be used alone or a combination of two or more kinds thereof may be used.

In the resist composition, the component (A) is preferably the component (A-1). That is, the resist composition is preferably a "positive-tone resist composition for an alkali developing process" that forms a positive-tone resist pattern in an alkali developing process or a "negative-tone resist composition for a solvent developing process" that forms a negative-tone resist pattern in a solvent developing process. As the component (A), at least one of a polymeric compound and a low molecular weight compound can be used.

In a case where the component (A) is the component (A-1), the component (A-1) preferably contains a resin component (A1) (hereinafter, also referred to as "component (A1)").

• In Regard to Component (A1)

The component (A1) is a resin component and is preferably a polymeric compound having a constitutional unit (a1) that contains an acid decomposable group having a polarity that is increased under action of acid.

The component (A1) is preferably a component having a constitutional unit (a10) further containing a hydroxystyrene skeleton in addition to the constitutional unit (a1).

In addition, the component (A1) may further have, in addition to the constitutional unit (a1), a constitutional unit (a2) containing a lactone-containing cyclic group, a —$SO_2$-containing cyclic group, or a carbonate-containing cyclic group, a constitutional unit (a3) (provided that a constitutional unit corresponding to the constitutional unit (a1) or a constitutional unit (a2) is excluded) containing a polar group-containing aliphatic hydrocarbon group, or a constitutional unit (a6) that generates acid upon exposure.

Further, the component (A1) may have a constitutional unit other than the constitutional unit (a1), the constitutional unit (a2), the constitutional unit (a3), the constitutional unit (a10), and the constitutional unit (a6).

[Constitutional Unit (a1)]

The constitutional unit (a1) is a constitutional unit that contains an acid decomposable group having polarity that is increased under action of acid.

The term "acid decomposable group" indicates a group in which at least part of bonds in the structure of the acid decomposable group can be cleaved under action of acid.

Examples of the acid decomposable group having a polarity that is increased under action of acid include groups which are decomposed under action of acid to generate a polar group.

Examples of the polar group include a carboxy group, a hydroxyl group, an amino group, and a sulfo group ($-SO_3H$). Among these, a polar group containing $-OH$ in the structure thereof (hereinafter, also referred to as an "OH-containing polar group") is preferable, a carboxy group or a hydroxyl group is more preferable, and a carboxy group is particularly preferable.

More specific examples of the acid decomposable group include a group (for example, a group obtained by protecting a hydrogen atom of the OH-containing polar group with an acid dissociable group) obtained by protecting the above-described polar group with an acid dissociable group.

Here, the "acid dissociable group" indicates any one of (i) a group in which a bond between the acid dissociable group and an atom adjacent to the acid dissociable group can be cleaved under action of acid; and (ii) a group in which part of bonds are cleaved under action of acid, and then a decarboxylation reaction occurs, thereby cleaving the bond between the acid dissociable group and the atom adjacent to the acid dissociable group.

It is necessary that the acid dissociable group that constitutes the acid decomposable group is a group that exhibits a lower polarity than the polar group generated by the dissociation of the acid dissociable group. Thus, in a case where the acid dissociable group is dissociated under action of acid, a polar group exhibiting a higher polarity than the acid dissociable group is generated, whereby the polarity increases. As a result of the above, the polarity of the entire component (A1) is increased. By the increase in the polarity, the solubility in a developing solution relatively changes. The solubility in a developing solution is increased in a case where the developing solution is an alkali developing solution, whereas the solubility in a developing solution is decreased in a case where the developing solution is an organic developing solution.

Examples of the acid dissociable group are the same as those which have been proposed so far as acid dissociable groups for the base resin for a chemically amplified resist composition.

Specific examples of acid dissociable groups of the base resin proposed for a chemically amplified resist composition contains an "acetal-type acid dissociable group", a "tertiary alkyl ester-type acid dissociable group", and a "tertiary alkyloxycarbonyl acid dissociable group" described below.

Acetal-Type Acid Dissociable Group:

Examples of the acid dissociable group for protecting a carboxy group or a hydroxyl group as a polar group include the acid dissociable group represented by General Formula (a1-r-1) shown below (hereinafter, also referred to as an "acetal-type acid dissociable group").

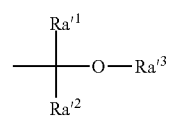

(a1-r-1)

[In the formula, $Ra'^1$ and $Ra'^2$ represent a hydrogen atom or an alkyl group. $Ra'^3$ represents a hydrocarbon group, and $Ra'^3$ may be bonded to any one of $Ra'^1$ or $Ra'^2$ to form a ring.]

In General Formula (a1-r-1), it is preferable that at least one of $Ra'^1$ and $Ra'^2$ represents a hydrogen atom and more preferable that both $Ra'^1$ and $Ra'^2$ represent a hydrogen atom.

In a case where $Ra'^1$ or $Ra'^2$ represents an alkyl group, examples of the alkyl group include the same one as the alkyl group described as the substituent which may be bonded to the carbon atom at the α-position in the description on the α-substituted acrylic acid ester, and the alkyl group preferably has 1 to 5 carbon atoms. Specific examples thereof preferably include a linear or branched alkyl group. More specific examples thereof include a methyl group, an ethyl group, a propyl group, an isopropyl group, an n-butyl group, an isobutyl group, a tert-butyl group, a pentyl group, an isopentyl group, and a neopentyl group. Among these, a methyl group or an ethyl group is preferable, and a methyl group is particularly preferable.

In General Formula (a1-r-1), examples of the hydrocarbon group as $Ra'^3$ include a linear or branched alkyl group and a cyclic hydrocarbon group.

The linear alkyl group has preferably 1 to 5 carbon atoms, more preferably 1 to 4 carbon atoms, and still more preferably 1 or 2 carbon atoms. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The branched alkyl group has preferably 3 to 10 carbon atoms and more preferably 3 to 5 carbon atoms. Specific examples thereof include an isopropyl group, an isobutyl group, a tert-butyl group, an isopentyl group, a neopentyl group a 1,1-diethylpropyl group, and a 2,2-dimethylbutyl group, and an isopropyl group is preferable.

In a case where $Ra'^3$ represents a cyclic hydrocarbon group, the hydrocarbon group may be an aliphatic hydrocarbon group or an aromatic hydrocarbon group and may be a polycyclic group or a monocyclic group.

The aliphatic hydrocarbon group which is a monocyclic group is preferably a group obtained by removing one hydrogen atom from a monocycloalkane. The monocycloalkane preferably has 3 to 6 carbon atoms, and specific examples thereof include cyclopentane and cyclohexane.

The aliphatic hydrocarbon group which is a polycyclic group is preferably a group obtained by removing one hydrogen atom from a polycycloalkane. The polycycloalkane preferably has 7 to 12 carbon atoms, and specific examples thereof include adamantane, norbornane, isobornane, tricyclodecane, and tetracyclododecane.

In a case where the cyclic hydrocarbon group as $Ra'^3$ is an aromatic hydrocarbon group, the aromatic hydrocarbon group is a hydrocarbon group having at least one aromatic ring.

The aromatic ring is not particularly limited as long as it is a cyclic conjugated system having (4n+2) π electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon ring with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Specific examples of the aromatic hydrocarbon group as $Ra'^3$ include a group obtained by removing one hydrogen atom from the above-described aromatic hydrocarbon ring or aromatic heterocyclic ring (an aryl group or a heteroaryl group); a group obtained by removing one hydrogen atom from an aromatic compound having two or more aromatic rings (biphenyl, fluorene or the like); and a group obtained by substituting one hydrogen atom of the above-described aromatic hydrocarbon ring or aromatic heterocyclic ring with an alkylene group (an arylalkyl group such as a benzyl group, a phenethyl group, a 1-naphthylmethyl group, a 2-naphthylmethyl group, a 1-naphthylethyl group, or a 2-naphthylethyl group). The number of carbon atoms in the alkylene group bonded to the aromatic hydrocarbon ring or aromatic heterocyclic ring is preferably in a range of 1 to 4, more preferably 1 or 2, and particularly preferably 1.

The cyclic hydrocarbon group as $Ra'^3$ may have a substituent. Examples of the substituent include, $-R^{P1}$, $-R^{P2}-O-R^{P1}$, $-R^{P2}-CO-R^{P1}$, $-R^{P2}-CO-OR^{P1}$, $-R^{P2}-O-CO-R^{P1}$, $-R^{P2}-OH$, $-R^{P2}-CN$, and $-R^{P2}-COOH$ (hereinafter, these substituents are also collectively referred to as "$Ra^{05}$").

Here, $R^{P1}$ represents a monovalent chain-like saturated hydrocarbon group having 1 to 10 carbon atoms, a monovalent aliphatic cyclic saturated hydrocarbon group having 3 to 20 carbon atoms, or a monovalent aromatic hydrocarbon group having 6 to 30 carbon atoms. In addition, $R^{P2}$ represents a single bond, a divalent chain-like saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms. However, part or all hydrogen atoms contained in the chain-like saturated hydrocarbon group, the aliphatic cyclic saturated hydrocarbon group, and the aromatic hydrocarbon group of $R^{P1}$ and $R^{P2}$ may be substituted with a fluorine atom. In the aliphatic cyclic hydrocarbon group, one or more of the above-described substituents may be included as a single kind, or one or more of the above-described substituents may be included as a plurality of kinds.

Examples of the monovalent chain-like saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include monocyclic aliphatic saturated hydrocarbon groups such as a cyclopropyl group, a cyclobutyl group, a cyclopentyl group, a cyclohexyl group, a cycloheptyl group, a cyclooctyl group, a cyclodecyl group, and cyclododecyl group; and polycyclic aliphatic saturated hydrocarbon groups such as a bicyclo[2.2.2]octanyl group, a tricyclo[5.2.1.0²,⁶]decanyl group, a tricyclo[3.3.1.1³,⁷]decanyl group, a tetracyclo[6.2.1.1³,⁶.0²,⁷]dodecanyl group, and an adamantyl group.

Examples of the monovalent aromatic hydrocarbon group having 6 to 30 carbon atoms include groups obtained by removing one hydrogen atom from an aromatic hydrocarbon ring such as benzene, biphenyl, fluorene, naphthalene, anthracene, and phenanthrene.

In a case where $Ra'^3$ is bonded to any one of $Ra'^1$ or $Ra'^2$ to form a ring, the cyclic group is preferably a 4-membered to 7-membered ring, and more preferably a 4-membered to 6-membered ring. Specific examples of the cyclic group include a tetrahydropyranyl group and a tetrahydrofuranyl group.

Tertiary Alkyl Ester-Type Acid Dissociable Group:

Among the above polar groups, examples of the acid dissociable group for protecting the carboxy group include the acid dissociable group represented by General Formula (a1-r-2) shown below.

Among the acid dissociable groups represented by General Formula (a1-r-2), for convenience, a group which is constituted of alkyl groups is referred to as a "tertiary alkyl ester-type acid dissociable group".

(a1-r-2)

[In the formula, $Ra'^4$ to $Ra'^6$ each represent a hydrocarbon group, and $Ra'^5$ and $Ra'^6$ may be bonded to each other to form a ring.]

Examples of the hydrocarbon group as $Ra'^4$ include a linear or branched alkyl group, a chain-like or cyclic alkenyl group, and a cyclic hydrocarbon group.

Examples of the linear or branched alkyl group and the cyclic hydrocarbon group (the aliphatic hydrocarbon group which is a monocyclic group, the aliphatic hydrocarbon group which is a polycyclic group, or the aromatic hydrocarbon group) as $Ra'^4$ include the same one as $Ra'^3$ described above.

The chain-like or cyclic alkenyl group as $Ra'^4$ is preferably an alkenyl group having 2 to 10 carbon atoms.

Examples of the hydrocarbon group as $Ra'^5$ and $Ra'^6$ include the same ones as those mentioned above as $Ra'^3$.

In a case where $Ra'^5$ to $Ra'^6$ are bonded to each other to form a ring, suitable examples thereof include groups represented by General Formula (a1-r2-1), General Formula (a1-r2-2), and General Formula (a1-r2-3).

On the other hand, in a case where $Ra'^4$ to $Ra'^6$ are not bonded to each other and represent an independent hydrocarbon group, suitable examples thereof include a group represented by General Formula (a1-r2-4).

(a1-r2-1)

-continued

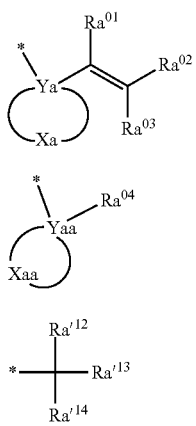

(a1-r2-2)

(a1-r2-3)

(a1-r2-4)

[In General Formula (a1-r2-1), $Ra'^{10}$ represents an alkyl group having 1 to 10 carbon atoms or a group represented by General Formula (a1-r2-r1). $Ra'^{11}$ represents a group that forms an aliphatic cyclic group together with a carbon atom to which $Ra'^{10}$ is bonded. In General Formula (a1-r2-2), Ya represents a carbon atom. Xa is a group that forms a cyclic hydrocarbon group together with Ya. Part or all hydrogen atoms contained in the cyclic hydrocarbon group may be substituted. $Ra^{01}$ to $Ra^{03}$ each independently represent a hydrogen atom, a monovalent chain-like saturated hydrocarbon group having 1 to 10 carbon atoms, or a monovalent aliphatic cyclic saturated hydrocarbon group having 3 to 20 carbon atoms. Part or all hydrogen atoms contained in the chain-like saturated hydrocarbon group and the aliphatic cyclic saturated hydrocarbon group may be substituted. Two or more of $Ra^{01}$ to $Ra^{03}$ may be bonded with each other to form a cyclic structure. In General Formula (a1-r2-3), Yaa represents a carbon atom. Xaa is a group that forms an aliphatic cyclic group together with Yaa. $Ra^{04}$ represents an aromatic hydrocarbon group which may have a substituent. In General Formula (a1-r2-4), $Ra'^{12}$ and $Ra'^{13}$ each independently represent a monovalent chain-like saturated hydrocarbon group having 1 to 10 carbon atoms or a hydrogen atom. Part or all hydrogen atoms contained in the chain-like saturated hydrocarbon group may be substituted. $Ra'^{14}$ represents a hydrocarbon group which may have a substituent. * represents a bonding site (the same applies hereinafter).]

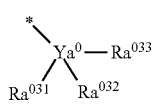

(a1-r2-r1)

In the formula, $Ya^0$ represents a quaternary carbon atom. [$Ra^{031}$, $Ra^{032}$, and $Ra^{033}$ each independently represent a hydrocarbon group which may have a substituent. Here, one or more of $Ra^{031}$, $Ra^{032}$, and $Ra^{033}$ are hydrocarbon groups having at least one polar group.]

In Formula (a1-r2-1) show above, as the alkyl group having 1 to 10 carbon atoms as $Ra'^{10}$, the groups mentioned as the linear or branched alkyl group as $Ra'^3$ in Formula (a1-r-1) are preferable. $Ra'^{10}$ is preferably an alkyl group having 1 to 5 carbon atoms.

In Formula (a1-r2-r1), $Ya^0$ represents a quaternary carbon atom. That is, there are four adjacent carbon atoms bonded to $Ya^0$ (carbon atom).

[In General Formula (a1-r2-r1), $Ra^{031}$, $Ra^{032}$, and $Ra^{033}$ each independently represent a hydrocarbon group which may have a substituent. The hydrocarbon groups as $Ra^{031}$, $Ra^{032}$, and $Ra^{033}$ each independently include a linear or branched alkyl group, a chain-like or cyclic alkenyl group, and a cyclic hydrocarbon group.

The linear alkyl groups as $Ra^{031}$, $Ra^{032}$, and $Ra^{033}$ have preferably 1 to 5 carbon atoms, more preferably 1 to 4 carbon atoms, and still more preferably 1 or 2 carbon atoms. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The branched alkyl groups as $Ra^{031}$, $Ra^{032}$, and $Ra^{033}$ have preferably 3 to 10 carbon atoms and more preferably 3 to 5 carbon atoms. Specific examples thereof include an isopropyl group, an isobutyl group, a tert-butyl group, an isopentyl group, a neopentyl group a 1,1-diethylpropyl group, and a 2,2-dimethylbutyl group, and an isopropyl group is preferable.

The chain-like or cyclic alkenyl groups as $Ra^{031}$, $Ra^{032}$, and $Ra^{033}$ are preferably an alkenyl group having 2 to 10 carbon atoms.

The cyclic hydrocarbon group as $Ra^{031}$, $Ra^{032}$, and $Ra^{031}$ may be an aliphatic hydrocarbon group or an aromatic hydrocarbon group and may be a polycyclic group or a monocyclic group.

The aliphatic hydrocarbon group which is a monocyclic group is preferably a group obtained by removing one hydrogen atom from a monocycloalkane. The monocycloalkane preferably has 3 to 6 carbon atoms, and specific examples thereof include cyclopentane and cyclohexane.

The aliphatic hydrocarbon group which is a polycyclic group is preferably a group obtained by removing one hydrogen atom from a polycycloalkane. The polycycloalkane preferably has 7 to 12 carbon atoms, and specific examples thereof include adamantane, norbornane, isobornane, tricyclodecane, and tetracyclododecane.

The aromatic hydrocarbon groups as $Ra^{031}$, $Ra^{032}$, and $Ra^{033}$ are a hydrocarbon group having at least one aromatic ring. The aromatic ring is not particularly limited as long as it is a cyclic conjugated system having (4n+2) π electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon ring with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring. Specific examples of the aromatic hydrocarbon group include a group obtained by removing one hydrogen atom from the above-described aromatic hydrocarbon ring or aromatic heterocyclic ring (an aryl group or a heteroaryl group); a group obtained by removing one hydrogen atom from an aromatic compound having two or more aromatic rings (biphenyl, fluorene or the like); and a group obtained by substituting one hydrogen atom of the above-described aromatic hydrocarbon ring or aromatic heterocyclic ring with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aromatic hydrocarbon ring or aromatic heterocyclic ring preferably has 1 to 4 carbon atoms, more preferably 1 or 2 carbon atoms, and particularly preferably 1 carbon atom.

In a case where the hydrocarbon groups represented by $Ra^{031}$, $Ra^{032}$, and $Ra^{033}$ are substituted, examples of the substituent include a hydroxy group, a carboxy group, a halogen atom (a fluorine atom, a chlorine atom, a bromine atom, and the like), an alkoxy group (a methoxy group, an ethoxy group, a propoxy group, a butoxy group, and the like), and an alkyloxycarbonyl group.

Among the above examples, as $Ra^{031}$, $Ra^{032}$, and $Ra^{033}$, the hydrocarbon group which may have a substituent is preferably a linear or branched alkyl group which may have a substituent and more preferably a linear alkyl group.

Here, one or more of $Ra^{031}$, $Ra^{032}$, and $Ra^{033}$ are hydrocarbon groups having at least a polar group.]

The "hydrocarbon group having a polar group" includes any one of a hydrocarbon group in which a methylene group (—$CH_2$—) constituting the hydrocarbon group is substituted with a polar group and a hydrocarbon group in which at least one hydrogen atom constituting the hydrocarbon group is substituted with a polar group.

As such a "hydrocarbon group having a polar group", a functional group represented by General Formula (a1-p1) is preferable.

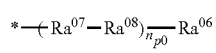
(a1-p1)

[In the formula, $Ra^{07}$ represents a divalent hydrocarbon group having 2 to 12 carbon atoms. $Ra^{08}$ represents a divalent linking group including a hetero atom. $Ra^{06}$ represents a monovalent hydrocarbon group having 1 to 12 carbon atoms. $n_{p0}$ represents an integer in a range of 1 to 6.]

In Formula (a1-p1), $Ra^{07}$ represents a divalent hydrocarbon group having 2 to 12 carbon atoms. $Ra^{07}$ has 2 to 12 carbon atoms, has preferably 2 to 8 carbon atoms, more preferably 2 to 6 carbon atoms, still more preferably 2 to 4 carbon atoms, and particularly preferably 2 carbon atoms.

The hydrocarbon group as $Ra^{07}$ is preferably a chain-like or cyclic aliphatic hydrocarbon group and more preferably a chain-like hydrocarbon group.

Examples of $Ra^{07}$ include: linear alkanediyl groups such an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, and a dodecane-1,12-diyl group; branched alkanediyl groups such as a propane-1,2-diyl group, a 1-methylbutane-1,3-diyl group, a 2-methylpropane-1,3-diyl group, a pentane-1,4-diyl group, and a 2-methylbutane-1,4-diyl group; cycloalkanediyl groups such as a cyclobutane-1,3-diyl group, a cyclopentane-1,3-diyl group, a cyclohexane-1,4-diyl group, a cyclooctane-1,5-diyl group; and polycyclic divalent alicyclic hydrocarbon groups such as a norbornane-1,4-diyl group, a norbornane-2,5-diyl group, an adamantane-1,5-diyl group, and an adamantane-2,6-diyl group.

Among them, an alkanediyl group is preferable, and a linear alkanediyl group is more preferable.

In Formula (a1-p1), $Ra^{08}$ represents a divalent linking group including a hetero atom.

Examples of $Ra^{08}$ include —O—, —C(=O)—O—, —C(=O)—, —C(=O)—NH—, —NH—, —NH—C(=NH)— (H may be substituted with a substituent such as an alkyl group and an acyl group), —S—, —S(=O)$_2$—, and —S(=O)$_2$—O—.

Among these, —O—, —C(=O)—O—, —C(=O)—, or —O—C(=O)—O— is preferable, and —O— or —C(=O)— is particularly preferable, from the viewpoint of the solubility in a developing solution.

In Formula (a1-p1), $Ra^{06}$ represents a monovalent hydrocarbon group having 1 to 12 carbon atoms. $Ra^{06}$ has 1 to 12 carbon atoms and has preferably 1 to 8 carbon atoms, more preferably 1 to 5 carbon atoms, still more preferably 1 to 3 carbon atoms, particularly preferably 1 or 2 carbon atoms, and most preferably 1 carbon atom, from the viewpoint of the solubility in a developing solution.

Examples of the hydrocarbon group as $Ra^{06}$ include a chain-like hydrocarbon group or a cyclic hydrocarbon group, or a hydrocarbon group obtained by combining a chain-like hydrocarbon group or a cyclic hydrocarbon group.

Examples of the chain-like hydrocarbon group include a methyl group, an ethyl group, an n-propyl group, an isopropyl group, an n-butyl group, a sec-butyl group, a tert-butyl group, an n-pentyl group, an n-hexyl group, an n-heptyl group, a 2-ethylhexyl group, an n-octyl group, an n-nonyl group, an n-decyl group, an n-undecyl group, and an n-dodecyl group.

The cyclic hydrocarbon group may be an alicyclic hydrocarbon group or an aromatic hydrocarbon group.

Examples of the alicyclic hydrocarbon group may be either monocyclic or polycyclic, and examples of the monocyclic alicyclic hydrocarbon group include cycloalkyl groups such as a cyclopropyl group, a cyclobutyl group, a cyclopentyl group, a cyclohexyl group, a methylcyclohexyl group, a dimethylcyclohexyl group, a cycloheptyl group, a cyclooctyl group, a cycloheptyl group, and a cyclodecyl group. Examples of the polycyclic alicyclic hydrocarbon group include a decahydronaphthyl group, an adamantyl group, a 2-alkyladamantan-2-yl group, a 1-(adamantan-1-yl)alkane-1-yl group, a norbornyl group, a methylnorbornyl group, and an isobornyl group.

Examples of the aromatic hydrocarbon group include a phenyl group, a naphthyl group, an anthryl group, a p-methylphenyl group, a p-tert-butylphenyl group, a p-adamantylphenyl group, a tolyl group, a xylyl group, a cumenyl group, a mesityl group, a biphenyl group, a phenanthryl group, a 2,6-diethylphenyl group, and a 2-methyl-6-ethylphenyl group.

From the viewpoint of solubility in a developing solution, $Ra^{06}$ is preferably a chain-like hydrocarbon group, more preferably an alkyl group, and still more preferably a linear alkyl group.

In Formula (a1-p1) $n_{p0}$ represents an integer of 1 to 6, is preferably an integer of 1 to 3, more preferably an integer of 1 or 2, and still more preferably 1.

Specific examples of the hydrocarbon group having at least a polar group are described below.

In the following formulae, is a bonding site that is bonded to the quaternary carbon atom ($Ya^0$).

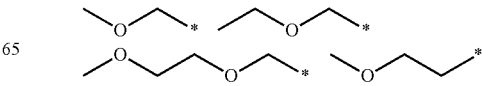

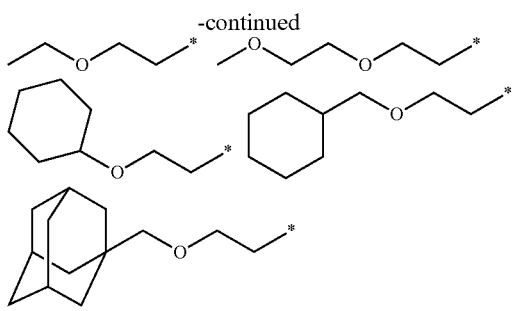

In General Formula (a1-r2-r1), the number of hydrocarbon groups having at least a polar group among $Ra^{o31}$, $Ra^{o32}$, and $Ra^{o33}$ is one or more. The number of hydrocarbon groups may be appropriately determined in consideration of the solubility in a developing solution at the time of forming a resist pattern, for example, one or two are preferable, and one is particularly preferable among $Ra^{o31}$, $Ra^{o32}$, and $Ra^{o33}$.

The hydrocarbon group having at least a polar group may have a substituent other than the polar group. Examples of the substituent include a halogen atom (a fluorine atom, a chlorine atom, a bromine atom, or the like) and a halogenated alkyl group having 1 to 5 carbon atoms.

In General Formula (a1-r2-1), $Ra^{t11}$ (an aliphatic cyclic group that is formed together with the carbon atom to which $Ra^{t10}$ is bonded) is preferably the group mentioned as the aliphatic hydrocarbon group which is a monocyclic group or a polycyclic group as $Ra^{t3}$ in General Formula (a1-r-1).

In General Formula (a1-r2-2), examples of the cyclic hydrocarbon group formed by Xa together with Ya include a group in which one or more hydrogen atoms are further removed from a cyclic monovalent hydrocarbon group (an aliphatic hydrocarbon group) as $Ra^{t3}$ in General Formula (a1-r-1).

The cyclic hydrocarbon group that is formed by Xa together with Ya may have a substituent. Examples of this substituent include the same one as the substituent which may be contained in the cyclic hydrocarbon group as $Ra^{t3}$.

In Formula (a1-r2-2), as $Ra^{o1}$ to $Ra^{o3}$, examples of the monovalent chain-like saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms, as $Ra^{o1}$ to $Ra^{o3}$, include monocyclic aliphatic saturated hydrocarbon groups such as a cyclopropyl group, a cyclobutyl group, a cyclopentyl group, a cyclohexyl group, a cycloheptyl group, a cyclooctyl group, a cyclodecyl group, and cyclododecyl group; and polycyclic aliphatic saturated hydrocarbon groups such as a bicyclo[2.2.2]octanyl group, a tricyclo[5.2.1.0²,⁶]decanyl group, a tricyclo[3.3.1.1³,⁷]decanyl group, a tetracyclo[6.2.1.1³,⁶.0²,⁷]dodecanyl group, and an adamantyl group.

Among them, $Ra^{o1}$ to $Ra^{o3}$ are preferably a hydrogen atom or a monovalent chain-like saturated hydrocarbon group having 1 to 10 carbon atoms, from the viewpoint of the easy synthesis of a monomer compound from which the constitutional unit (a1) is derived, among them, a hydrogen atom, a methyl group, and an ethyl group are more preferable, and a hydrogen atom is particularly preferable.

Examples of the substituent contained in the chain-like saturated hydrocarbon group represented by $Ra^{o1}$ to $Ra^{o3}$ or the aliphatic cyclic saturated hydrocarbon group include the same group as $Ra^{o5}$ described above.

Examples of the group containing a carbon-carbon double bond generated by forming a cyclic structure, which is obtained by bonding two or more of $Ra^{o1}$ to $Ra^{o3}$ to each other, include a cyclopentenyl group, a cyclohexenyl group, a methylcyclopentenyl group, a methylcyclohexenyl group, a cyclopentylideneethenyl group, and a cyclohexylideneethenyl group. Among these, a cyclopentenyl group, a cyclohexenyl group, and a cyclopentylideneethenyl group are preferable from the viewpoint of easy synthesis of a monomer compound from which the constitutional unit (a1) is derived.

In General Formula (a1-r2-3), an aliphatic cyclic group that is formed by Xaa together with Yaa is preferably the group mentioned as the aliphatic hydrocarbon group which is a monocyclic group or a polycyclic group as $Ra^{t3}$ in General Formula (a1-r-1).

In Formula (a1-r2-3), Examples of the aromatic hydrocarbon group as $Ra^{o4}$ include a group obtained by removing one or more hydrogen atoms from an aromatic hydrocarbon ring having 5 to 30 carbon atoms. Among them, $Ra^{o4}$ is preferably a group obtained by removing one or more hydrogen atoms from an aromatic hydrocarbon ring having 6 to 15 carbon atoms, more preferably a group obtained by removing one or more hydrogen atoms from benzene, naphthalene, anthracene, or phenanthrene, still more preferably a group obtained by removing one or more hydrogen atoms from benzene, naphthalene, or anthracene, particularly preferably a group obtained by removing one or more hydrogen atoms from benzene or naphthalene, and most preferably a group obtained by removing one or more hydrogen atoms from benzene.

Examples of the substituent which may be contained in $Ra^{o4}$ in General Formula (a1-r2-3) include a methyl group, an ethyl group, a propyl group, a hydroxyl group, a carboxyl group, a halogen atom (a fluorine atom, a chlorine atom, a bromine atom, and the like), an alkoxy group (a methoxy group, an ethoxy group, a propoxy group, a butoxy group, and the like), and an alkyloxycarbonyl group.

In General Formula (a1-r2-4), $Ra^{t12}$ and $Ra^{t13}$ each independently represent a monovalent chain-like saturated hydrocarbon group having 1 to 10 carbon atoms or a hydrogen atom. Examples of the monovalent chain-like saturated hydrocarbon group having 1 to 10 carbon atoms as $Ra^{t12}$ and $Ra^{t13}$ include the same one as the monovalent chain-like saturated hydrocarbon group having 1 to 10 carbon atoms as $Ra^{o1}$ to $Ra^{o3}$ as described above. Part or all hydrogen atoms contained in the chain-like saturated hydrocarbon group may be substituted.

Among the above, $Ra^{t12}$ and $Ra^{t13}$ are preferably a hydrogen atom or an alkyl group having 1 to 5 carbon atoms, more preferably an alkyl group having 1 to 5 carbon atoms, still more preferably a methyl group or an ethyl group, and particularly preferably a methyl group.

In a case where the chain-like saturated hydrocarbon groups represented by $Ra^{t12}$ and $Ra^{t13}$ are substituted, examples of the substituent include the same group as $Ra^{o5}$ described above.

In General Formula (a1-r2-4), $Ra^{t14}$ represents a hydrocarbon group which may have a substituent. Examples of the hydrocarbon group as $Ra^{t14}$ include a linear or branched alkyl group and a cyclic hydrocarbon group.

The linear alkyl group as $Ra^{t14}$ has preferably 1 to 5 carbon atoms, more preferably 1 to 4 carbon atoms, and still more preferably 1 or 2 carbon atoms. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The branched alkyl group as $Ra^{t14}$ preferably has 3 to 10 carbon atoms and more preferably 3 to 5 carbon atoms. Specific examples thereof include an isopropyl group, an isobutyl group, a tert-butyl group, an isopentyl group, a neopentyl group a 1,1-diethylpropyl group, and a 2,2-dimethylbutyl group, and an isopropyl group is preferable.

In a case where $Ra^{t14}$ represents a cyclic hydrocarbon group, the hydrocarbon group may be an aliphatic hydrocarbon group or an aromatic hydrocarbon group and may be a polycyclic group or a monocyclic group.

The aliphatic hydrocarbon group which is a monocyclic group is preferably a group obtained by removing one hydrogen atom from a monocycloalkane. The monocycloalkane preferably has 3 to 6 carbon atoms, and specific examples thereof include cyclopentane and cyclohexane.

The aliphatic hydrocarbon group which is a polycyclic group is preferably a group obtained by removing one hydrogen atom from a polycycloalkane. The polycycloalkane preferably has 7 to 12 carbon atoms, and specific examples thereof include adamantane, norbornane, isobornane, tricyclodecane, and tetracyclododecane.

Examples of the aromatic hydrocarbon group as $Ra^{t14}$ include the same one as the aromatic hydrocarbon group as $Ra^{o4}$. Among them, $Ra^{t14}$ is preferably a group in which one or more hydrogen atoms have been removed from an aromatic hydrocarbon ring having 6 to 15 carbon atoms, more preferably a group in which one or more hydrogen atoms have been removed from benzene, naphthalene, anthracene, or phenanthrene, still more preferably a group in which one or more hydrogen atoms have been removed from benzene, naphthalene, or anthracene, particularly preferably a group in which one or more hydrogen atoms have been removed from naphthalene or anthracene, and most preferably a group in which one or more hydrogen atoms have been removed from naphthalene.

Examples of the substituent which may be contained in $Ra^{t14}$ include the same one as the substituent which may be contained in $Ra^{o4}$.

In a case where $Ra^{t14}$ in General Formula (a1-r2-4) is a naphthyl group, the position at which the tertiary carbon atom in General Formula (a1-r2-4) is bonded may be any of the 1-position and the 2-position of the naphthyl group.

In a case where $Ra^{t14}$ in General Formula (a1-r2-4) is an anthryl group, the position at which the tertiary carbon atom in General Formula (a1-r2-4) is bonded may be any of the 1-position, the 2-position, and 9-position of the anthryl group.

Specific examples of the group represented by General Formula (a1-r2-1) are shown below.

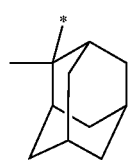

(r-pr-m1)

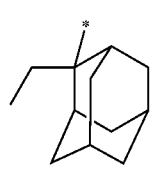

(r-pr-m2)

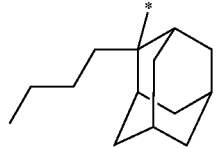

(r-pr-m3)

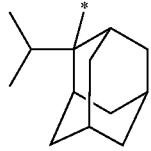

(r-pr-m4)

(r-pr-m5)

(r-pr-m6)

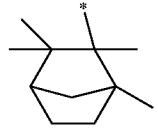

(r-pr-m7)

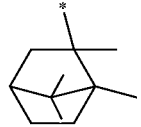

(r-pr-m8)

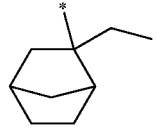

(r-pr-m9)

(r-pr-m10)

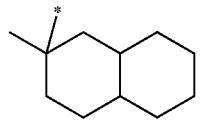

(r-pr-m11)

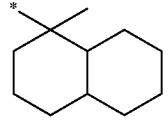

(r-pr-m12)

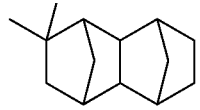

(r-pr-m13)

-continued
(r-pr-m14)
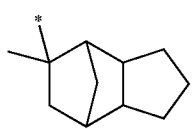
(r-pr-m15)
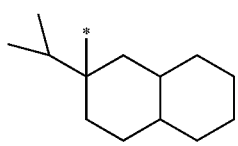
(r-pr-m16)
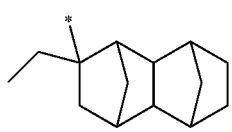
(r-pr-m17)
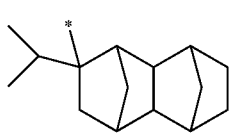
(r-pr-s1)
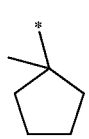
(r-pr-s2)
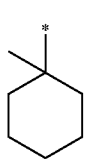
(r-pr-s3)
(r-pr-s4)
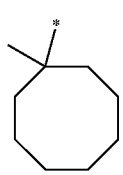
(r-pr-s5)
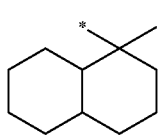
(r-pr-s6)
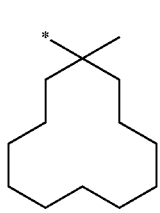
-continued
(r-pr-s7)
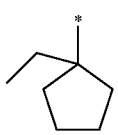
(r-pr-s8)
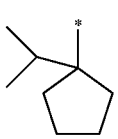
(r-pr-s9)
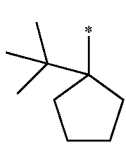
(r-pr-s10)
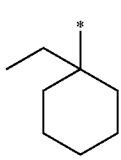
(r-pr-s11)
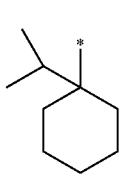
(r-pr-s12)
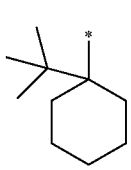
(r-pr-s13)
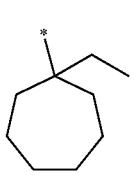
(r-pr-s14)
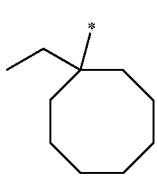
(r-pr-s15)
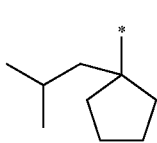
(r-pr-s16)
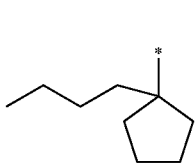

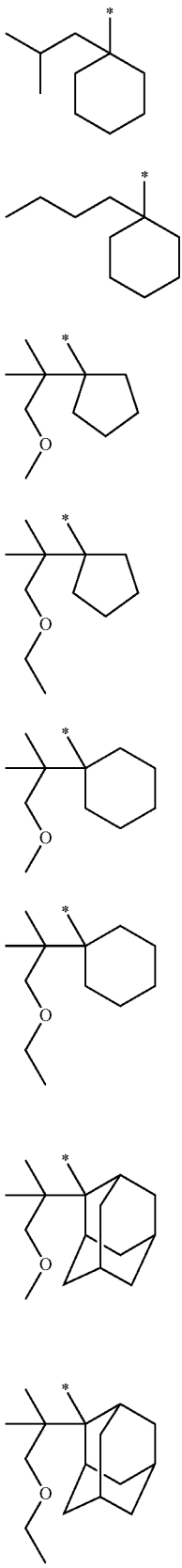
Specific examples of the group represented by General Formula (a1-r2-2) are shown below.
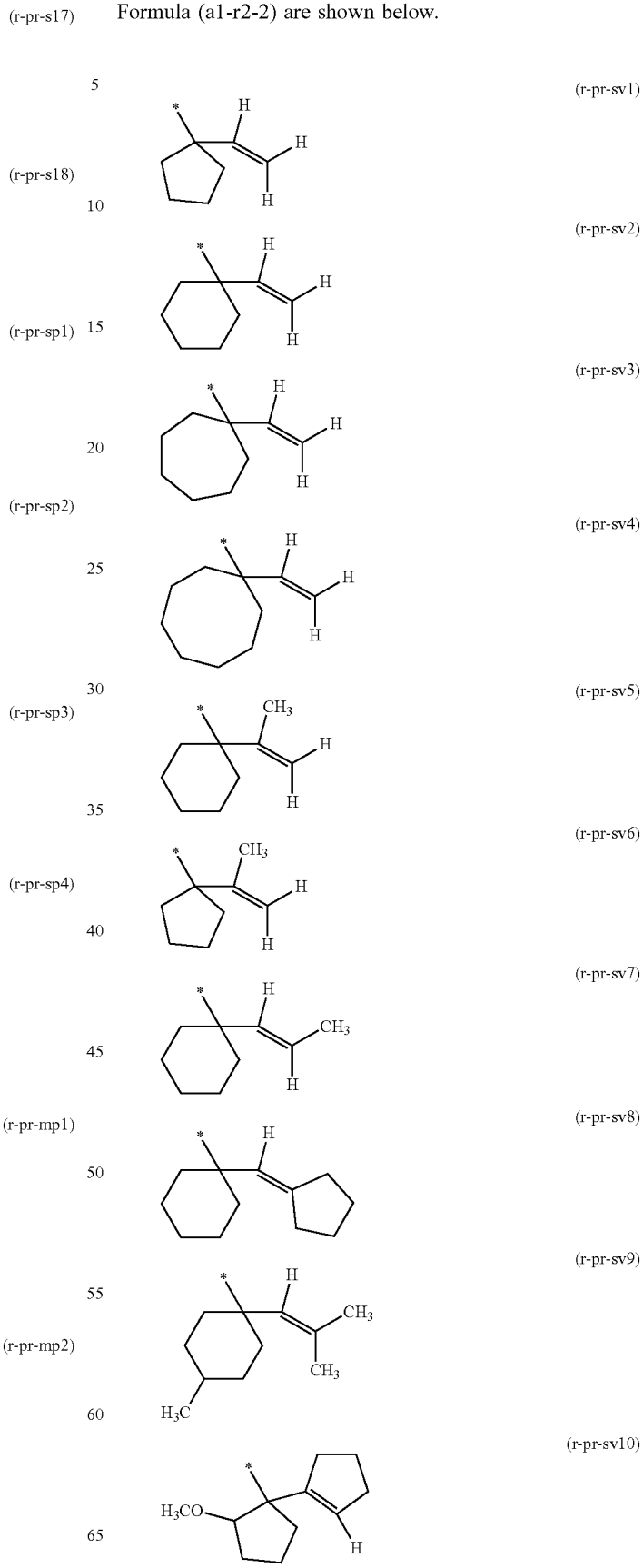

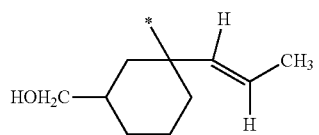 (r-pr-sv11)
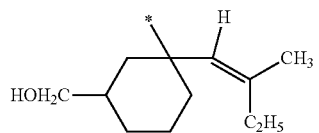 (r-pr-sv12)
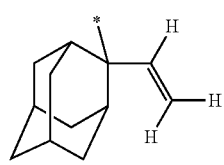 (r-pr-mv1)
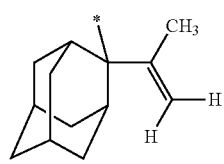 (r-pr-mv2)
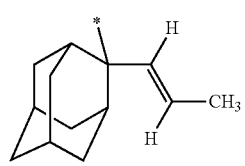 (r-pr-mv3)
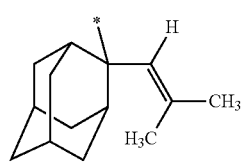 (r-pr-mv4)
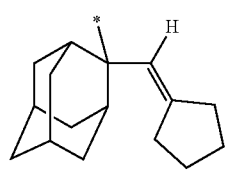 (r-pr-mv5)
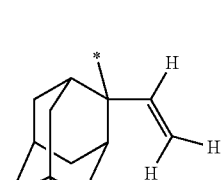 (r-pr-mv6)
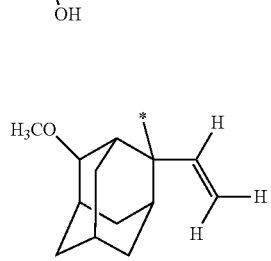 (r-pr-mv7)
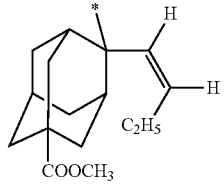 (r-pr-mv8)
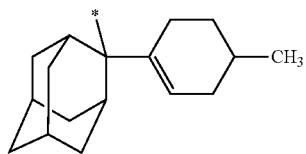 (r-pr-mv9)
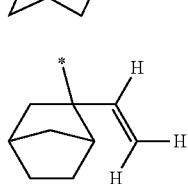 (r-pr-mv10)
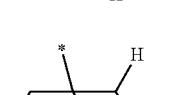 (r-pr-mv11)
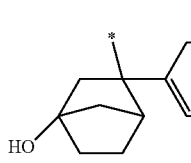 (r-pr-mv12)
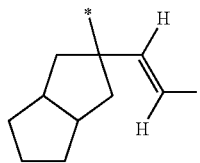 (r-pr-mv13)
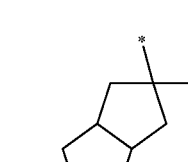 (r-pr-mv14)
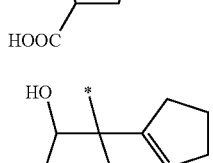 (r-pr-mv15)
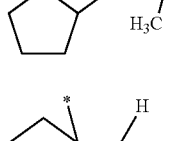 (r-pr-mv16)

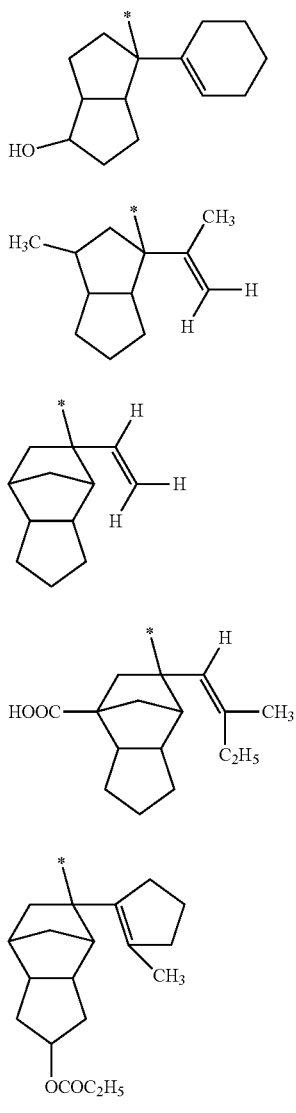
Specific examples of the group represented by General Formula (a1-r2-3) are shown below.
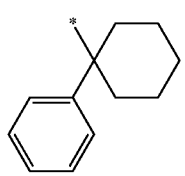
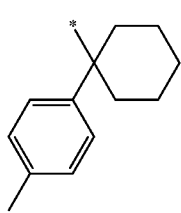
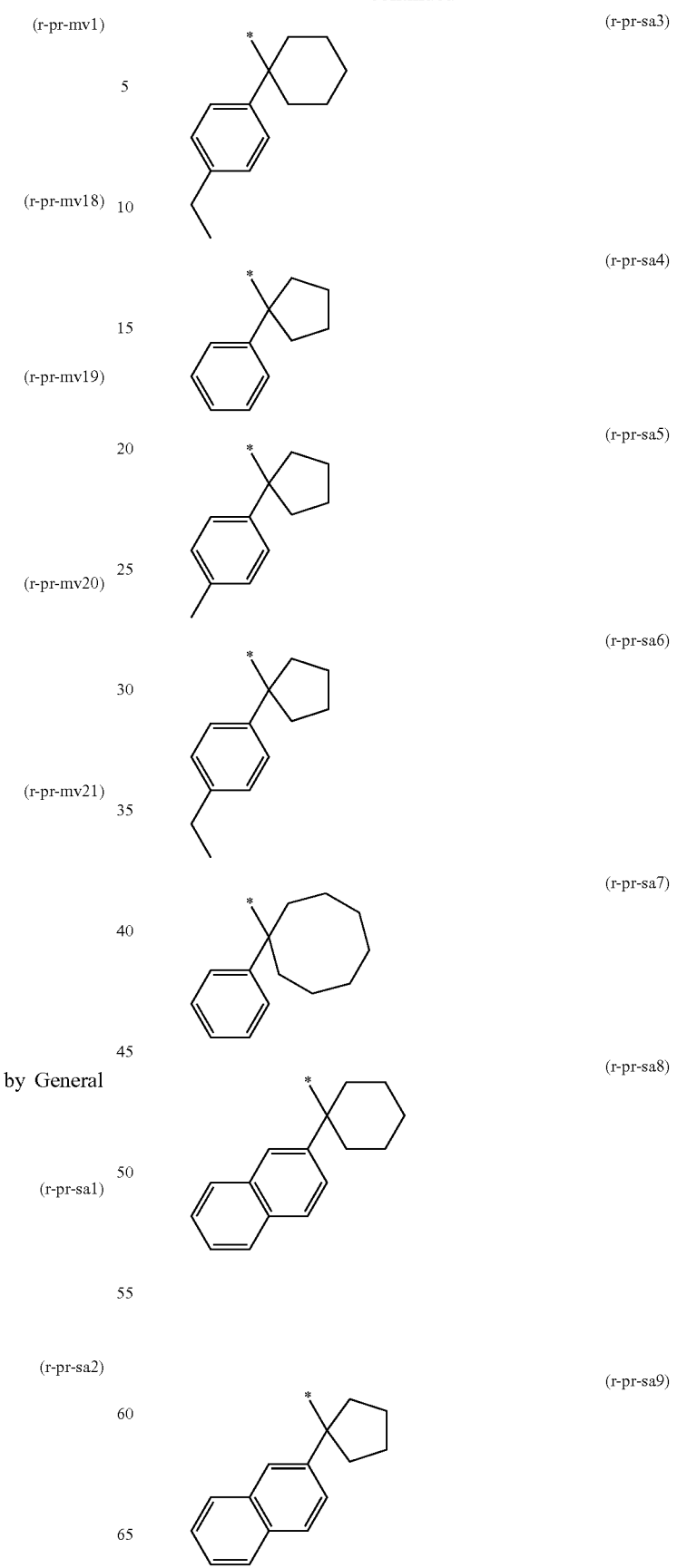

(r-pr-ma1)
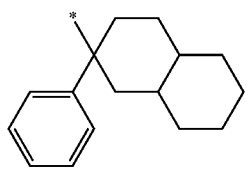
(r-pr-ma2)
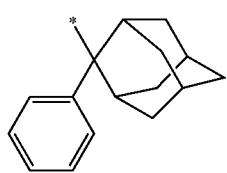
Specific examples of the group represented by General Formula (a1-r2-4) are shown below.
(r-pr-cm1)
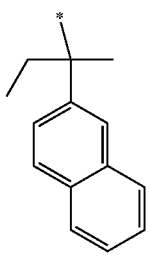
(r-pr-cm2)
(r-pr-cm3)
(r-pr-cm4)
(r-pr-cm5)
(r-pr-cm6)
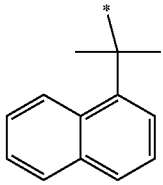
(r-pr-cm7)
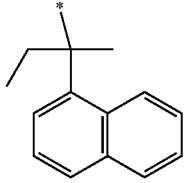
(r-pr-cm8)
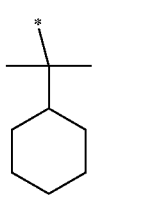
(r-pr-cs1)
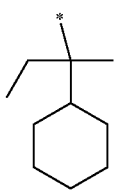
(r-pr-cs2)
(r-pr-cs3)
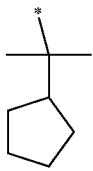
(r-pr-cs4)
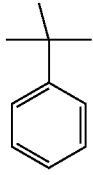
(r-pr-cs5)
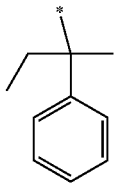

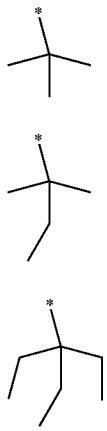

(r-pr-c1)

(r-pr-c2)

(r-pr-c3)

Tertiary Alkyloxycarbonyl Acid Dissociable Group:

Among the polar groups, examples of the acid dissociable group for protecting a hydroxyl group include an acid dissociable group (hereinafter, for convenience, also referred to as a "tertiary alkyloxycarbonyl acid dissociable group") represented by General Formula (a1-r-3) shown below.

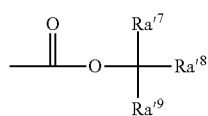

(a1-r-3)

[In the formula, Ra'$^7$ to Ra'$^9$ each represent an alkyl group.]

In General Formula (a1-r-3), Ra'$^7$ to Ra'$^9$ are each preferably an alkyl group having 1 to 5 carbon atoms and more preferably an alkyl group having 1 to 3 carbon atoms.

Further, the total number of carbon atoms in each of the alkyl groups is preferably in a range of 3 to 7, more preferably in a range of 3 to 5, and most preferably 3 or 4.

Examples of the constitutional unit (a1) include a constitutional unit derived from acrylic acid ester in which the hydrogen atom bonded to the carbon atom at the α-position may be substituted with a substituent; a constitutional unit derived from acrylamide; a constitutional unit in which at least part of hydrogen atoms in a hydroxyl group of a constitutional unit derived from hydroxystyrene or a hydroxystyrene derivative are protected by a substituent including an acid decomposable group; and a constitutional unit in which at least part of hydrogen atoms in —C(=O)—OH of a constitutional unit derived from vinylbenzoic acid or a vinylbenzoic acid derivative are protected by the substituent including an acid decomposable group.

Among the above, the constitutional unit (a1) is preferably a constitutional unit derived from acrylic acid ester in which the hydrogen atom bonded to the carbon atom at the α-position may be substituted with a substituent. Preferred specific examples of such a constitutional unit (a1) include constitutional units represented by General Formula (a1-1) or (a1-2).

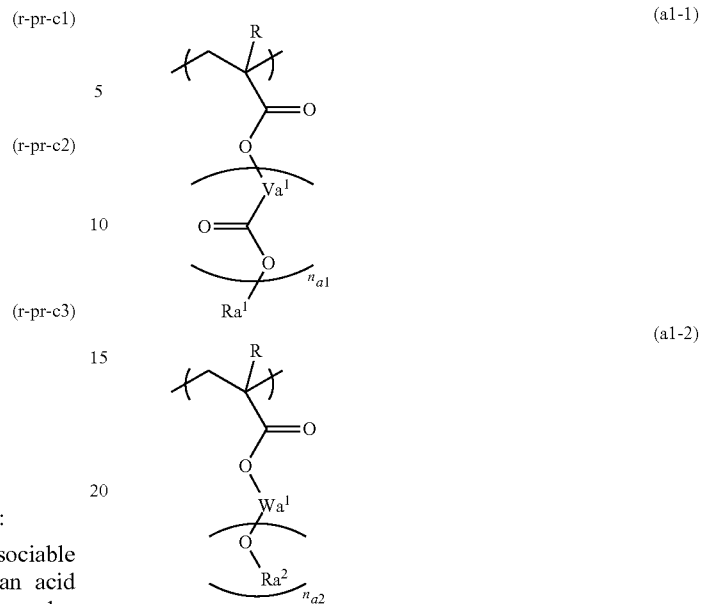

[In the formula, R represents a hydrogen atom, an alkyl group having 1 to 5 carbon atoms, or a halogenated alkyl group having 1 to 5 carbon atoms. Va$^1$ represents a divalent hydrocarbon group which may have an ether bond. $n_{a1}$ represents an integer in a range of 0 to 2. Ra$^1$ is an acid dissociable group represented by General Formula (a1-r-1) or (a1-r-2). Wa$^1$ represents an ($n_{a2}$+1)-valent hydrocarbon group, $n_{a2}$ represents an integer in a range of 1 to 3, and Ra$^2$ represents an acid dissociable group represented by General Formula (a1-r-1) or (a1-r-3).]

In General Formula (a1-1), the alkyl group having 1 to 5 carbon atoms as R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group obtained by substituting part or all hydrogen atoms in the alkyl group having 1 to 5 carbon atoms with a halogen atom. Examples of the halogen atom include a fluorine atom, a chlorine atom, a bromine atom and, an iodine atom, and a fluorine atom is particularly preferable.

R is preferably a hydrogen atom, an alkyl group having 1 to 5 carbon atoms, or a fluorinated alkyl group having 1 to 5 carbon atoms, and most preferably a hydrogen atom or a methyl group in terms of industrial availability.

In General Formula (a1-1), the divalent hydrocarbon group as Va$^1$ may be an aliphatic hydrocarbon group or an aromatic hydrocarbon group.

The aliphatic hydrocarbon group as the divalent hydrocarbon group represented by Va$^1$ may be saturated or unsaturated. In general, it is preferable that the aliphatic hydrocarbon group is saturated.

Specific examples of the aliphatic hydrocarbon group include a linear or branched aliphatic hydrocarbon group, and an aliphatic hydrocarbon group containing a ring in the structure thereof.

The linear aliphatic hydrocarbon group preferably has 1 to 10 carbon atoms, more preferably 1 to 6 carbon atoms, still more preferably 1 to 4 carbon atoms, and most preferably 1 to 3 carbon atoms. The linear aliphatic hydrocarbon group is preferably a linear alkylene group, and specific examples thereof include a methylene group [—CH$_2$—], an ethylene group [—(CH$_2$)$_2$—], a trimethylene group [—(CH$_2$)$_3$—], a tetramethylene group [—(CH$_2$)$_4$—], and a pentamethylene group [—(CH$_2$)$_5$—].

The branched aliphatic hydrocarbon group has preferably 2 to 10 carbon atoms, more preferably 3 to 6 carbon atoms, still more preferably 3 or 4 carbon atoms, and most preferably 3 carbon atoms. The branched aliphatic hydrocarbon group is preferably a branched alkylene group, and specific examples thereof include alkylalkylene groups, for example, alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. The alkyl group in the alkylalkylene group is preferably a linear alkyl group having 1 to 5 carbon atoms.

Examples of the aliphatic hydrocarbon group containing a ring in the structure thereof include an alicyclic hydrocarbon group (a group obtained by removing two hydrogen atoms from an aliphatic hydrocarbon ring), a group obtained by bonding the alicyclic hydrocarbon group to the terminal of a linear or branched aliphatic hydrocarbon group, and a group obtained by interposing the alicyclic hydrocarbon group is in a linear or branched aliphatic hydrocarbon group. Examples of the linear or branched aliphatic hydrocarbon group include the same one as the above-described linear aliphatic hydrocarbon group or the above-described branched aliphatic hydrocarbon group.

The alicyclic hydrocarbon group preferably has 3 to 20 carbon atoms and more preferably 3 to 12 carbon atoms.

The alicyclic hydrocarbon group may be monocyclic or polycyclic. The monocyclic alicyclic hydrocarbon group is preferably a group obtained by removing two hydrogen atoms from a monocycloalkane. The monocycloalkane preferably has 3 to 6 carbon atoms, and specific examples thereof include cyclopentane and cyclohexane. The polycyclic alicyclic hydrocarbon group is preferably a group obtained by removing two hydrogen atoms from a polycycloalkane, and the polycycloalkane is preferably a group having 7 to 12 carbon atoms. Specific examples thereof include adamantane, norbornane, isobornane, tricyclodecane, and tetracyclododecane.

The aromatic hydrocarbon group as the divalent hydrocarbon group represented by Va$^1$ is a hydrocarbon group having an aromatic ring.

The aromatic hydrocarbon group preferably has 3 to 30 carbon atoms, more preferably 5 to 30 carbon atoms, still more preferably 5 to 20 carbon atoms, particularly preferably 6 to 15 carbon atoms, and most preferably 6 to 12 carbon atoms. Here, the number of carbon atoms in a substituent is not included in the number of carbon atoms. Specific examples of the aromatic ring contained in the aromatic hydrocarbon group include aromatic hydrocarbon rings such as benzene, biphenyl, fluorene, naphthalene, anthracene, and phenanthrene; and an aromatic heterocyclic ring obtained by substituting part of carbon atoms constituting the above-described aromatic hydrocarbon rings with a hetero atom. Examples of the hetero atom in the aromatic heterocyclic rings include an oxygen atom, a sulfur atom, and a nitrogen atom.

Specific examples of the aromatic hydrocarbon group include a group obtained by removing two hydrogen atoms from the above-described aromatic hydrocarbon ring (an arylene group); and a group obtained by substituting one hydrogen atom of a group (an aryl group) obtained by removing one hydrogen atom from the aromatic hydrocarbon ring with an alkylene group (for example, a group obtained by removing one hydrogen atom from an aryl group in an arylalkyl group such as a benzyl group, a phenethyl group, a 1-naphthylmethyl group, a 2-naphthylmethyl group, a 1-naphthylethyl group, or a 2-naphthylethyl group). The alkylene group (an alkyl chain in the arylalkyl group) preferably has 1 to 4 carbon atoms, more preferably 1 or 2 carbon atoms, and particularly preferably 1 carbon atom.

In General Formula (a1-1), Ra$^1$ is an acid dissociable group represented by General Formula (a1-r-1) or (a1-r-2).

In General Formula (a1-2), the ($n_{a2}$+1)-valent hydrocarbon group as Wa$^1$ may be an aliphatic hydrocarbon group or an aromatic hydrocarbon group. The aliphatic hydrocarbon group indicates a hydrocarbon group that has no aromaticity and may be saturated or unsaturated. In general, it is preferable that the aliphatic hydrocarbon group is saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. The valency of ($n_{a2}$+1) is preferably divalent, trivalent, or tetravalent, and more preferably divalent or trivalent.

In General Formula (a1-2), Ra$^2$ is an acid dissociable group represented by General Formula (a1-r-1) or (a1-r-3).

Specific examples of the constitutional unit represented by General Formula (a1-1) are shown below. In each of the formulae shown below, IV represents a hydrogen atom, a methyl group, or a trifluoromethyl group.

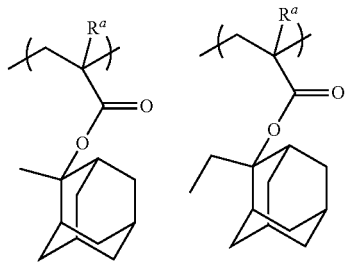

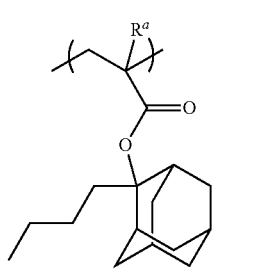

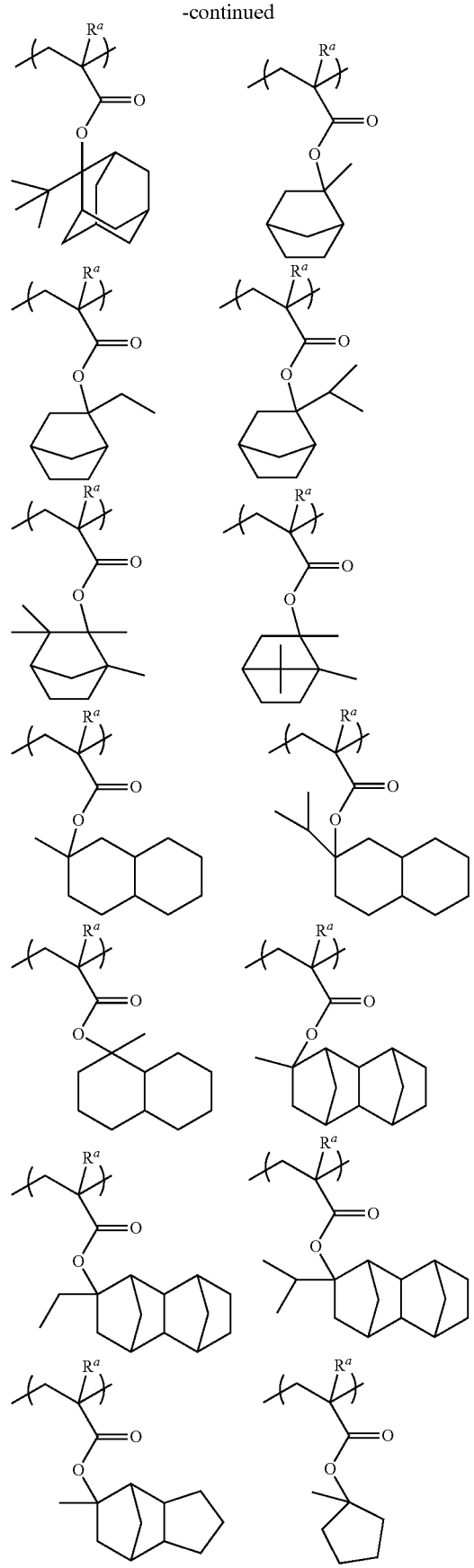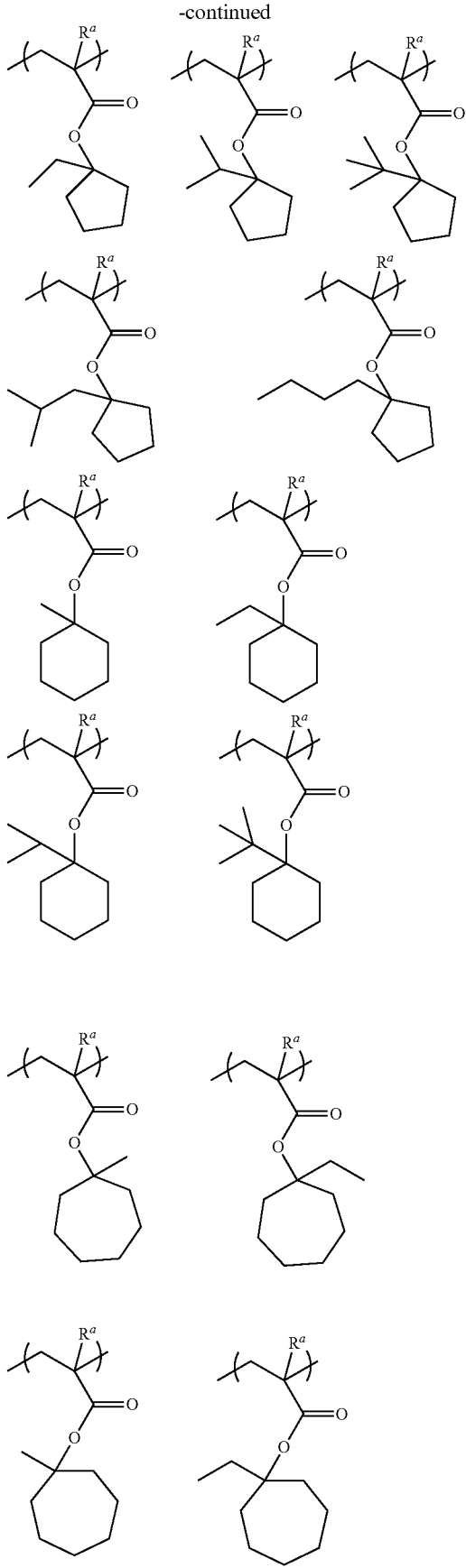

-continued
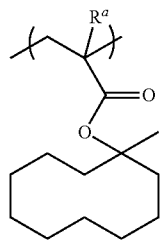 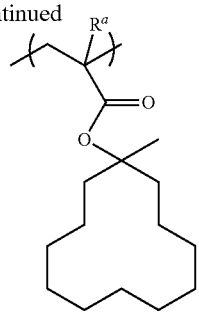
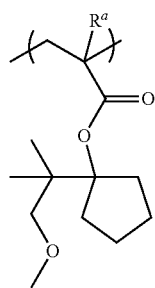 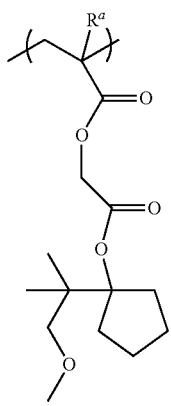
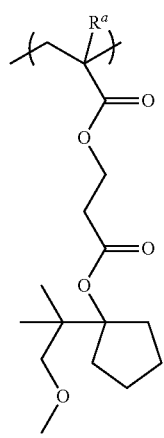
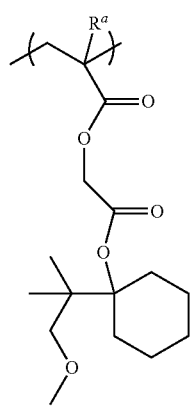 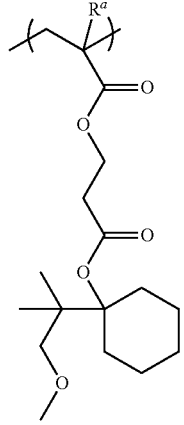
-continued
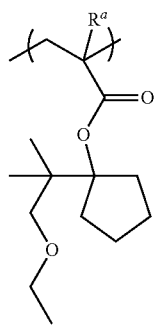 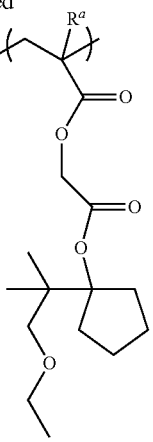
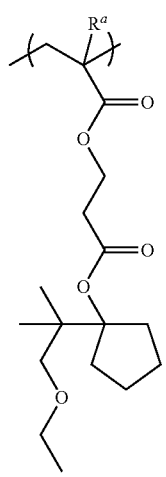 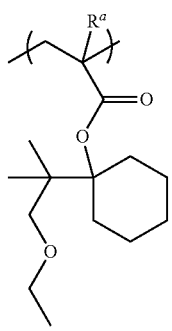
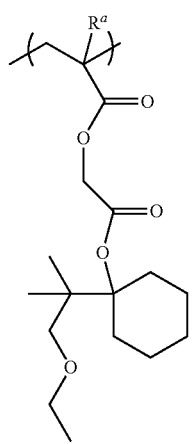 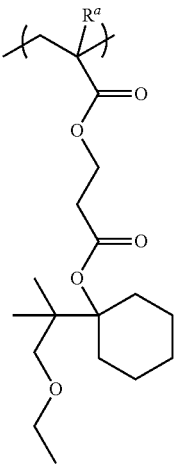

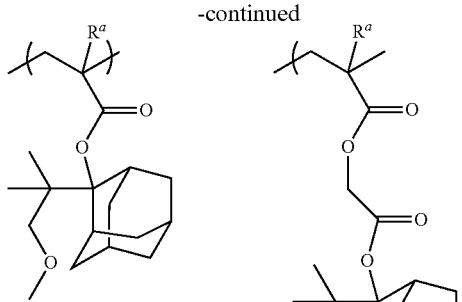
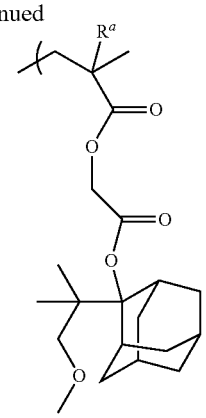
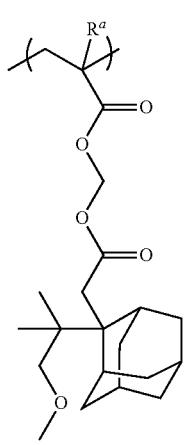
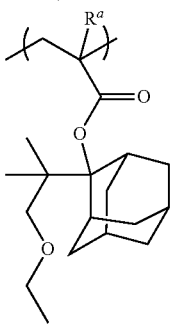
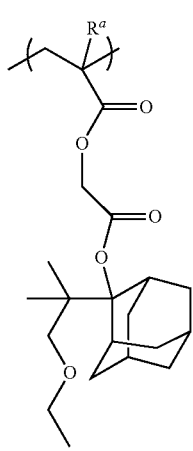
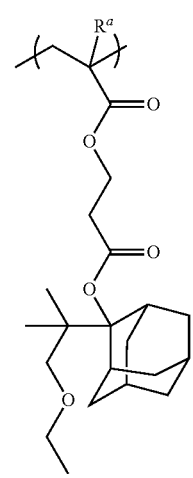
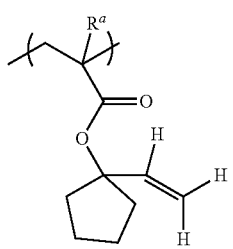
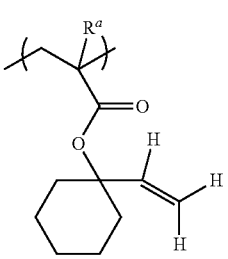
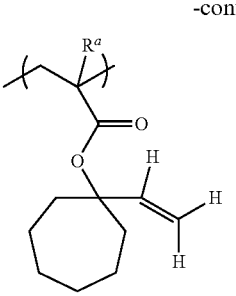
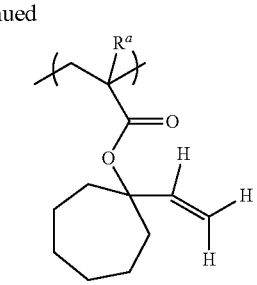
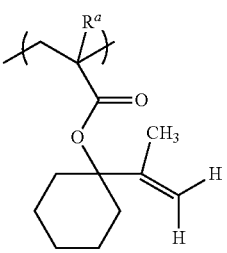
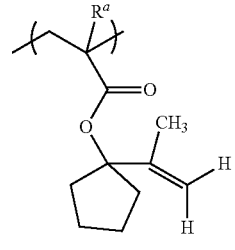
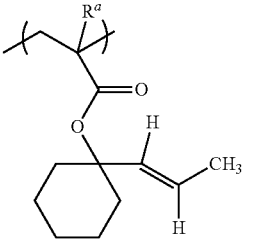
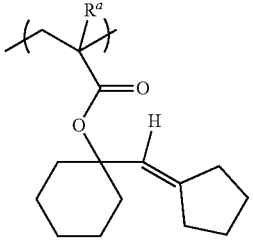
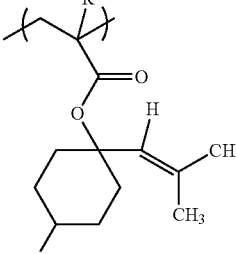
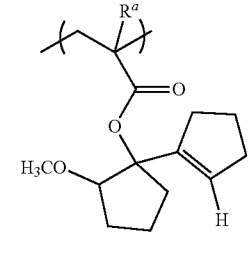
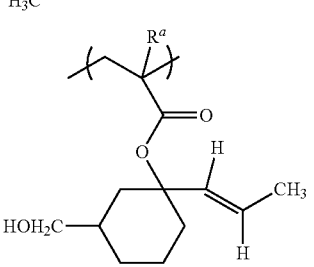

-continued
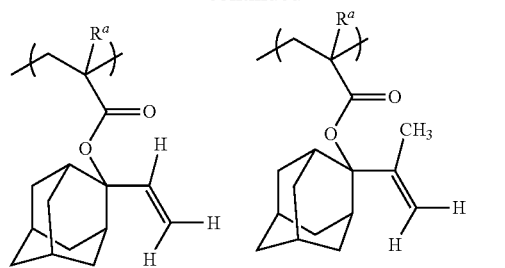
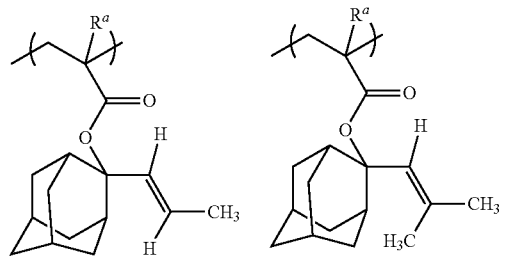
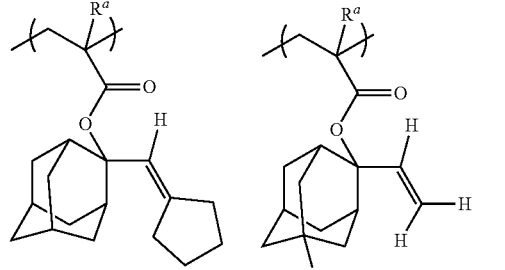
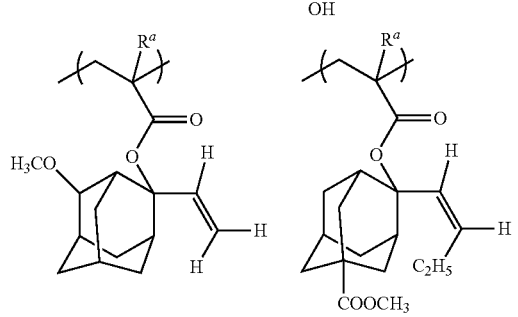
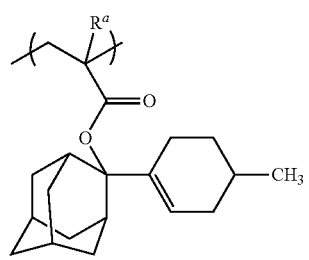
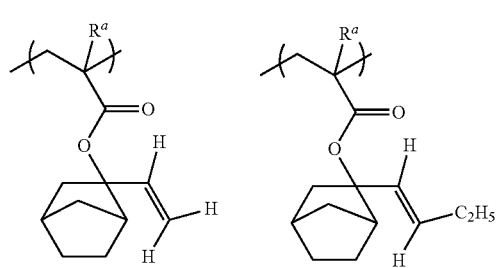
-continued
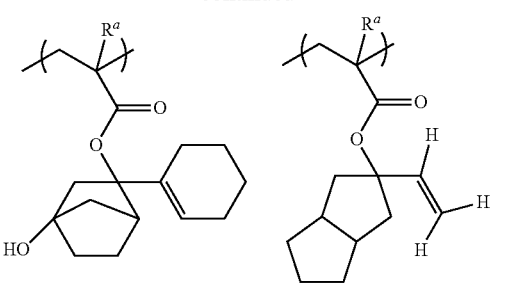
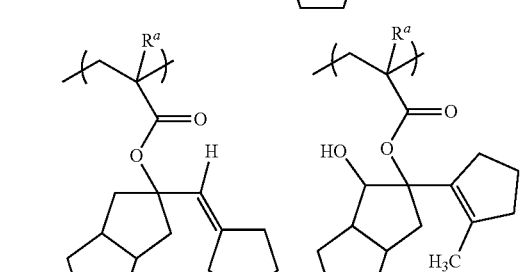
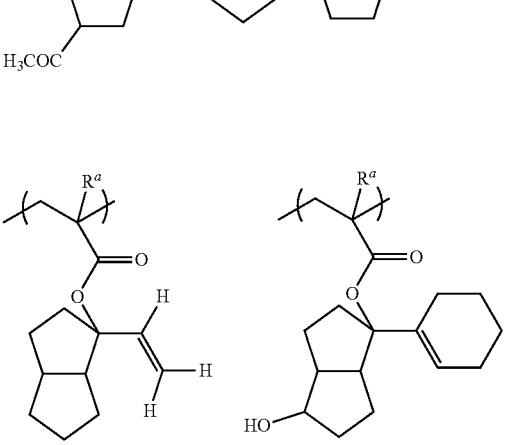
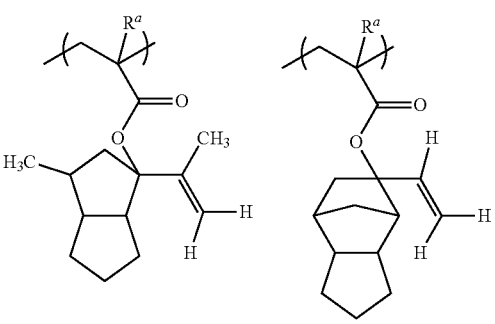
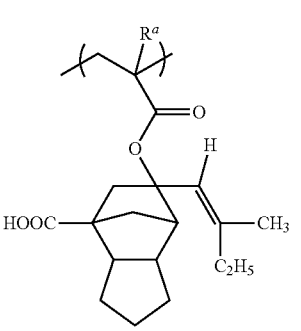

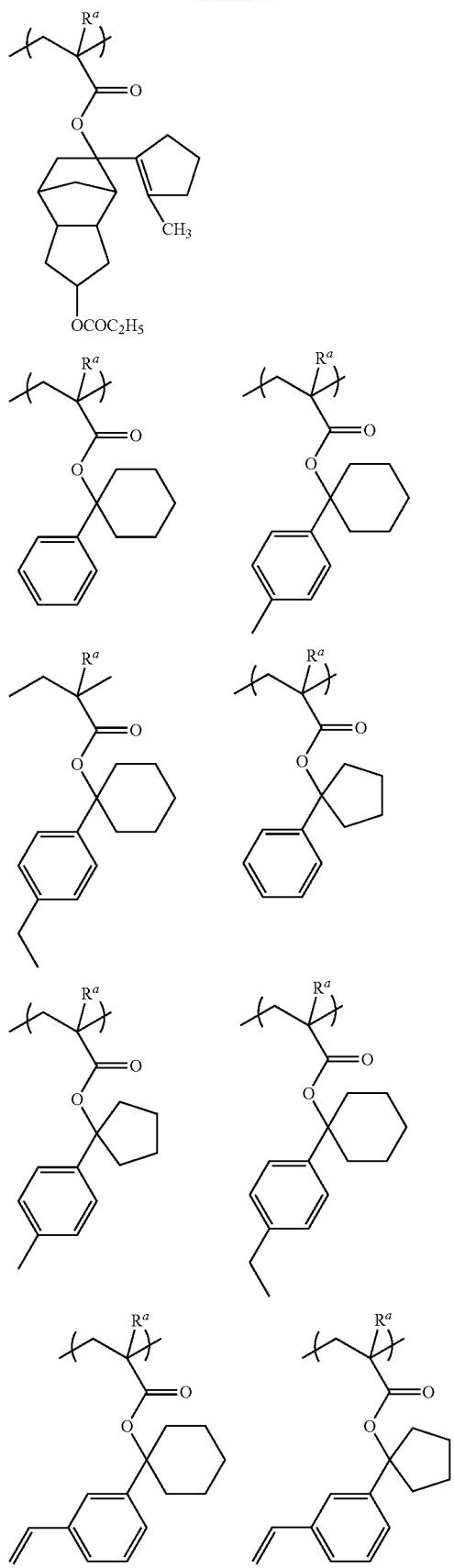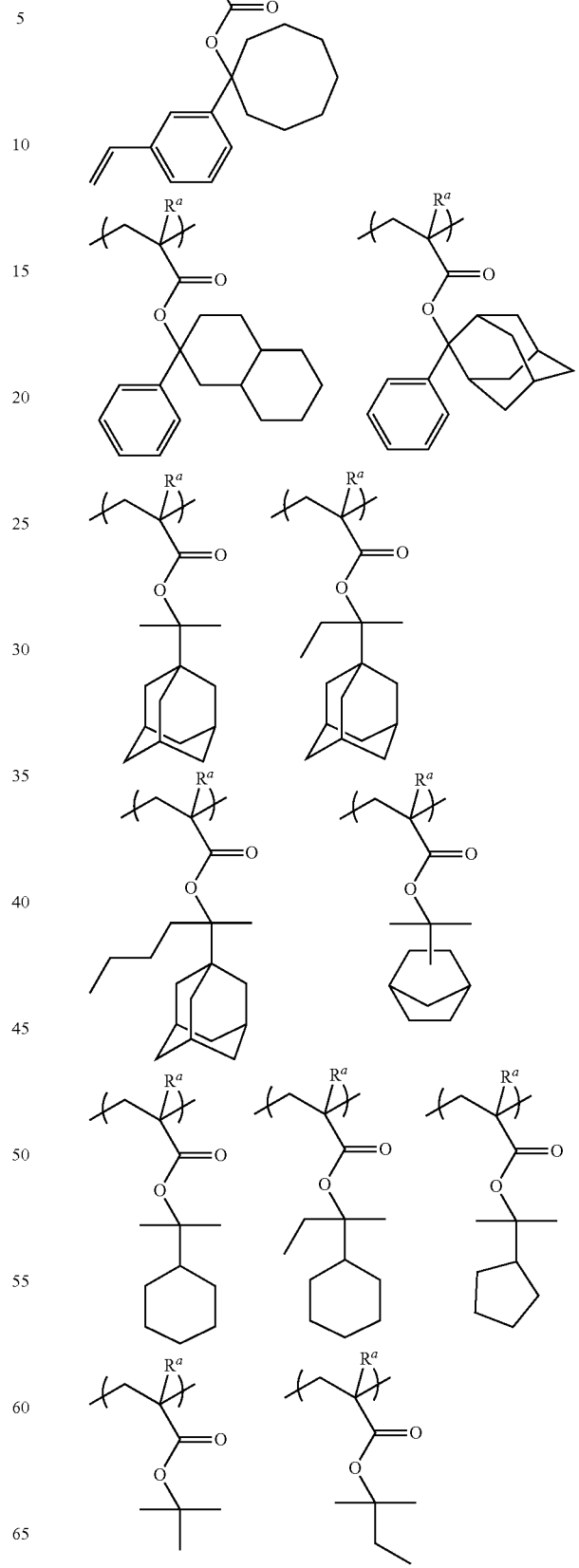

-continued
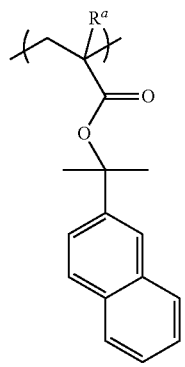 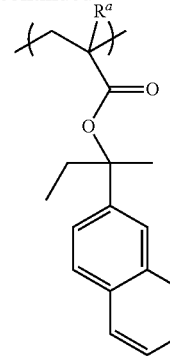 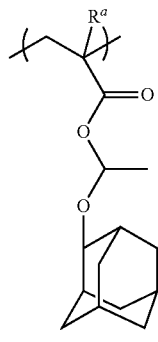 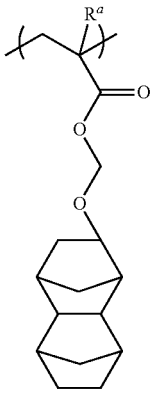
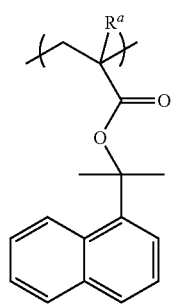 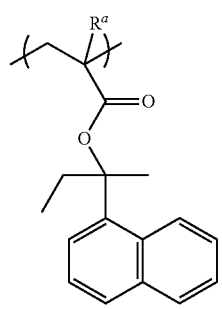 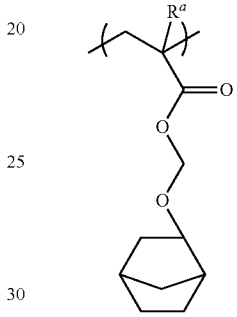 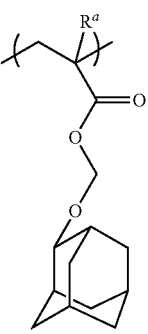
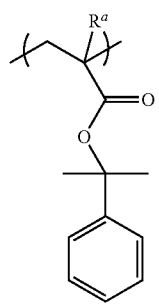 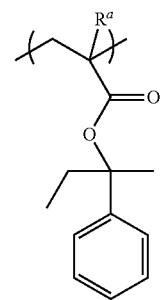 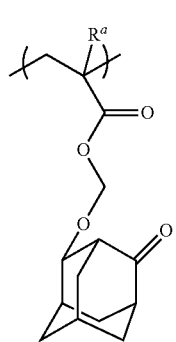 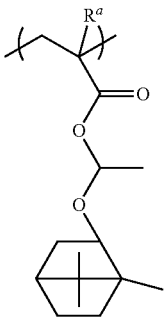
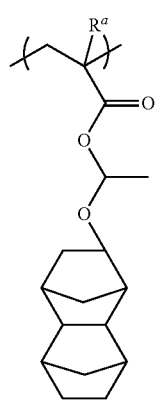 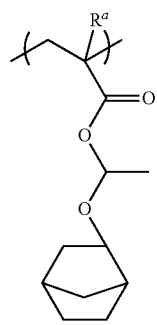 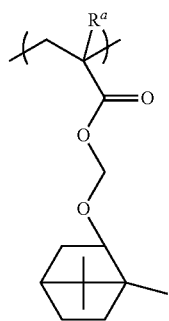 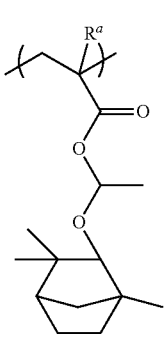

-continued
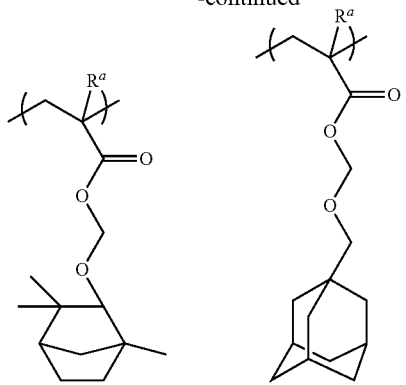
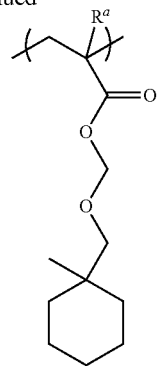
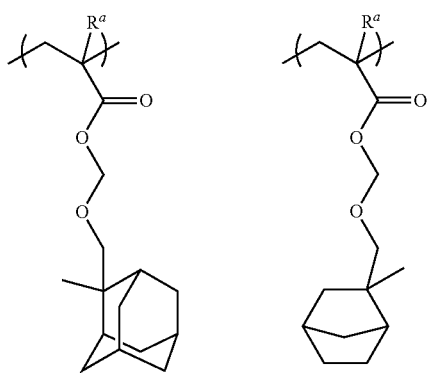
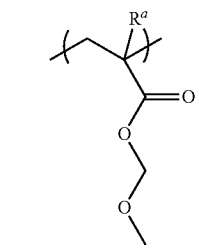
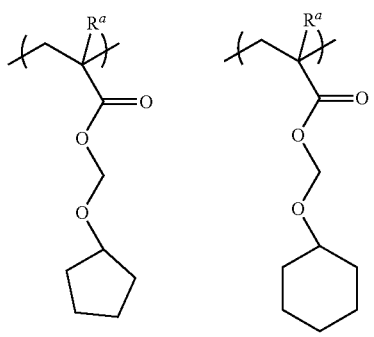
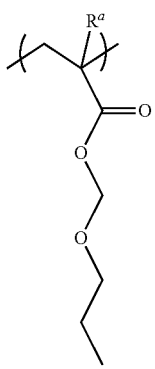
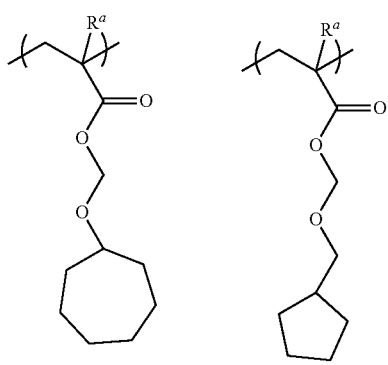
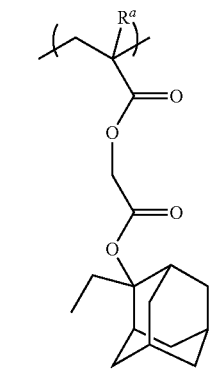

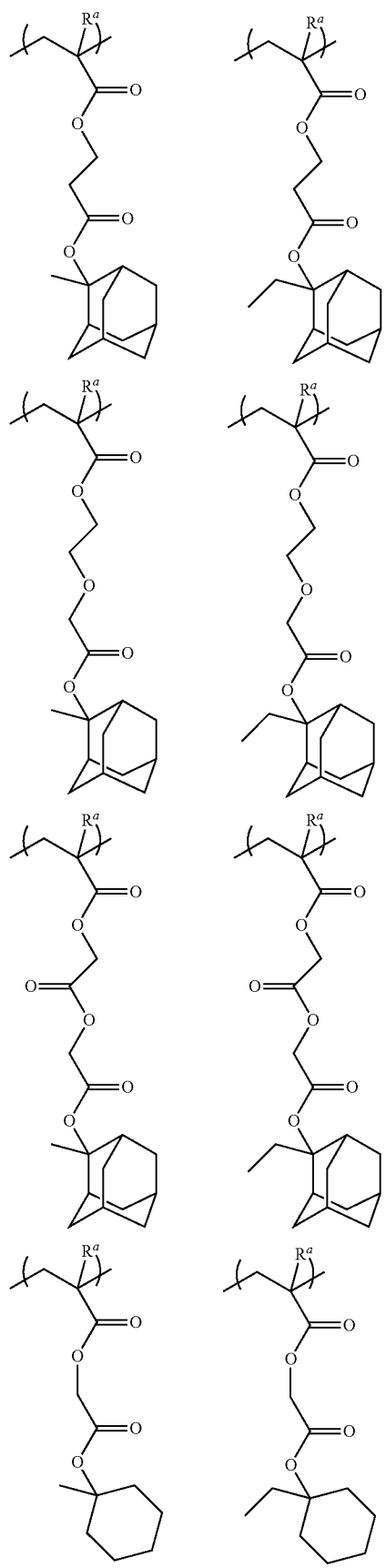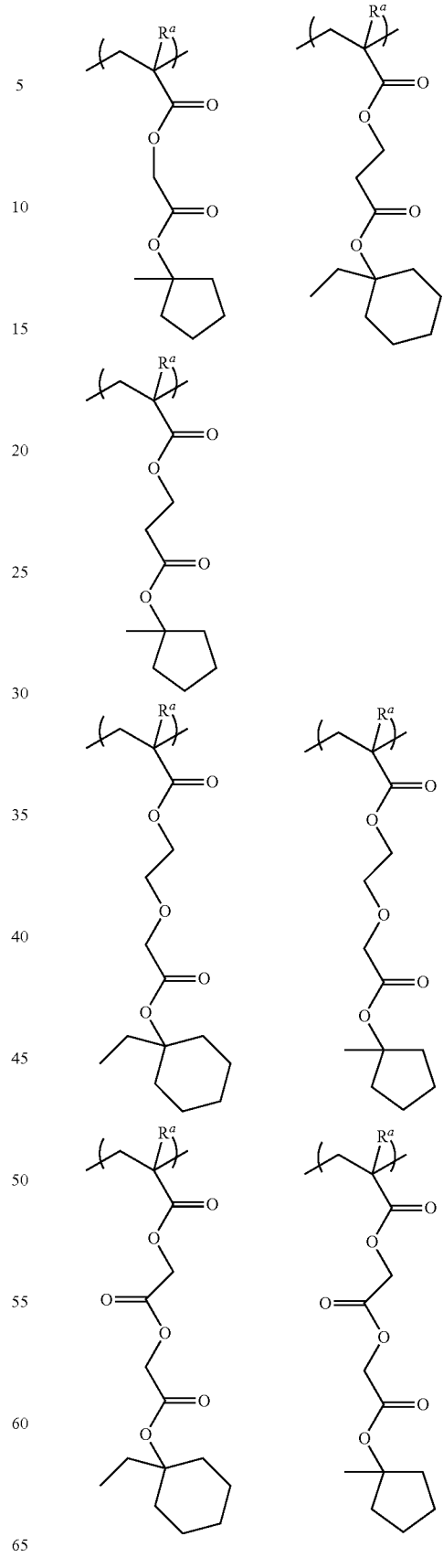

Specific examples of the constitutional unit represented by General Formula (a1-2) are shown below.

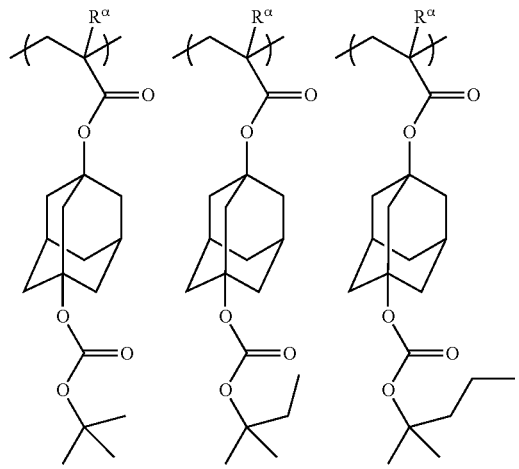
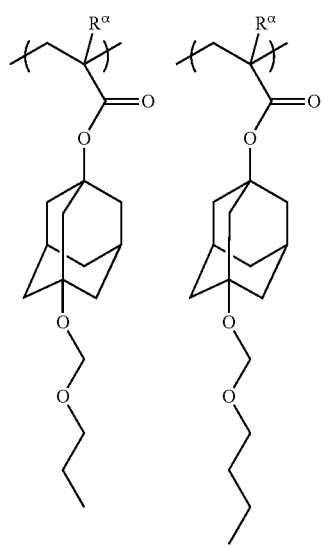
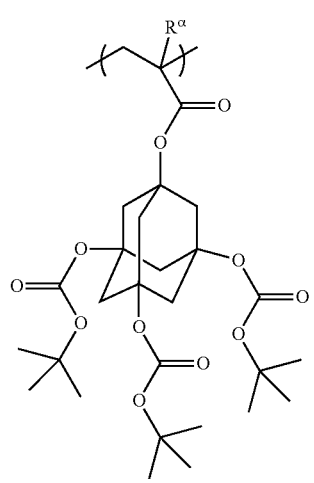
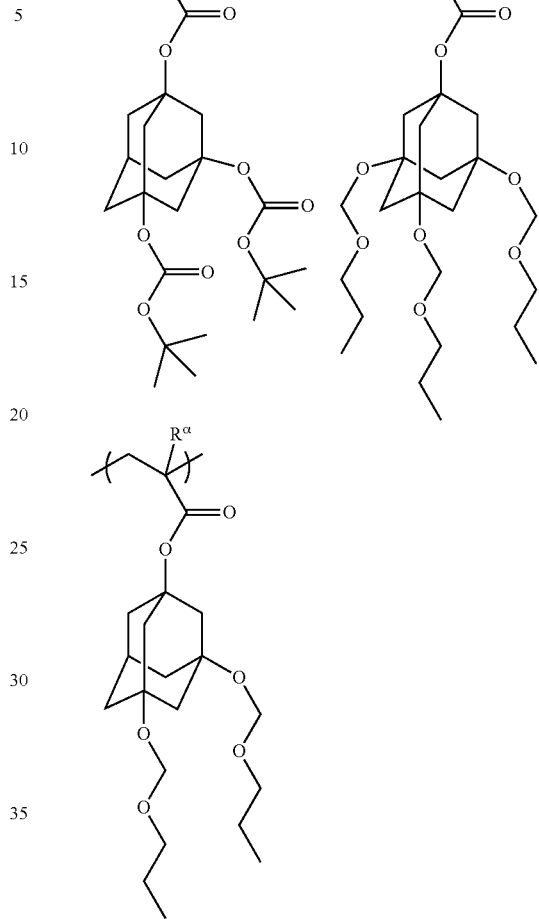

The constitutional unit (a1) contained in the component (A1) may be one kind or may be two or more kinds.

The constitutional unit (a1) is more preferably a constitutional unit represented by General Formula (a1-1) since lithography characteristics (sensitivity, shape, and the like) in lithography depending on an electron beam or EUV can be more easily increased.

Among these, the constitutional unit (a1) particularly preferably includes a constitutional unit represented by General Formula (a1-1-1) shown below.

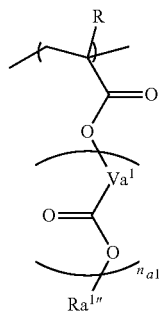

(a1-1-1)

-continued

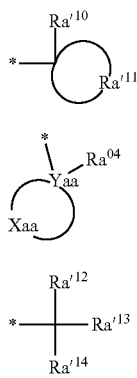

(a1-r2-1)

(a1-r2-3)

(a1-r2-4)

[In the formula, $Ra^{1'''}$ is an acid dissociable group represented by General Formula (a1-r2-1), (a1-r2-3), or (a1-r2-4).]

In General Formula (a1-1-1), R, $Va^1$, and $n_{a1}$ are each the same as R, $Va^1$, and $n_{a1}$ in General Formula (a1-1).

The description for the acid dissociable group represented by General Formula (a1-r2-1), (a1-r2-3), or (a1-r2-4) is as described above.

The proportion of the constitutional unit (a1) in the component (A1) is preferably in a range of 5% to 80% by mole, more preferably in a range of 10% to 75% by mole, and still more preferably in a range of 30% to 70% by mole, with respect to the total (100% by mole) of all constitutional units constituting the component (A1), from the viewpoint of further improving the effects of the present invention.

[Constitutional Unit Containing Hydroxystyrene Skeleton (a10)]

The component (A1) is preferably a component having a constitutional unit (a10) further containing a hydroxystyrene skeleton in addition to the constitutional unit (a1).

Suitable examples of the constitutional unit (a10) include a constitutional unit represented by General Formula (a10-1).

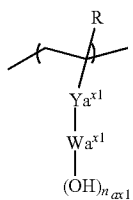

(a10-1)

[In the formula, R represents a hydrogen atom, an alkyl group having 1 to 5 carbon atoms, or a halogenated alkyl group having 1 to 5 carbon atoms. $Ya^{x1}$ represents a single bond or a divalent linking group. $Wa^{x1}$ represents an ($n_{ax1}$+1)-valent aromatic hydrocarbon group. $n_{ax1}$ represents an integer in a range of 1 to 3.]

In General Formula (a10-1), R represents a hydrogen atom, an alkyl group having 1 to 5 carbon atoms, or a halogenated alkyl group having 1 to 5 carbon atoms.

The alkyl group having 1 to 5 carbon atoms as R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms as R is a group obtained by substituting part or all hydrogen atoms in the alkyl group having 1 to 5 carbon atoms with a halogen atom. Examples of the halogen atom include a fluorine atom, a chlorine atom, a bromine atom and, an iodine atom, and a fluorine atom is particularly preferable.

R is preferably a hydrogen atom, an alkyl group having 1 to 5 carbon atoms, or a fluorinated alkyl group having 1 to 5 carbon atoms, and most preferably a hydrogen atom or a methyl group in terms of industrial availability.

In General Formula (a10-1), $Ya^{x1}$ represents a single bond or a divalent linking group.

Suitable examples of the divalent linking group as $Ya^{x1}$ include a divalent hydrocarbon group which may have a substituent and a divalent linking group having a hetero atom.

• Divalent Hydrocarbon Group which May have Substituent:

In a case where ye' represents a divalent hydrocarbon group which may have a substituent, the hydrocarbon group may be an aliphatic hydrocarbon group or an aromatic hydrocarbon group.

•• Aliphatic Hydrocarbon Group as $Ya^{x1}$

The aliphatic hydrocarbon group indicates a hydrocarbon group that has no aromaticity. The aliphatic hydrocarbon group may be saturated or unsaturated. In general, it is preferable that the aliphatic hydrocarbon group is saturated. Examples of the aliphatic hydrocarbon group include a linear or branched aliphatic hydrocarbon group, and an aliphatic hydrocarbon group containing a ring in the structure thereof.

••• Linear or Branched Aliphatic Hydrocarbon Group

The linear aliphatic hydrocarbon group preferably has 1 to 10 carbon atoms, more preferably 1 to 6 carbon atoms, still more preferably 1 to 4 carbon atoms, and most preferably 1 to 3 carbon atoms.

The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group has preferably 2 to 10 carbon atoms, more preferably 3 to 6 carbon atoms, still more preferably 3 or 4 carbon atoms, and most preferably 3 carbon atoms.

The branched aliphatic hydrocarbon group is preferably a branched alkylene group, and specific examples thereof include alkyl alkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. The alkyl group in the alkylalkylene group is preferably a linear alkyl group having 1 to 5 carbon atoms.

The linear or branched aliphatic hydrocarbon group may have or may not have a substituent. Examples of the substituent include a fluorine atom, a fluorinated alkyl group having 1 to 5 carbon atoms, which has been substituted with a fluorine atom, and a carbonyl group.

••• Aliphatic Hydrocarbon Group Containing Ring in Structure Thereof

Examples of the aliphatic hydrocarbon group containing a ring in the structure thereof include a cyclic aliphatic hydrocarbon group which may have a substituent containing a hetero atom in the ring structure thereof (a group obtained by removing two hydrogen atoms from an aliphatic hydrocarbon ring), a group obtained by bonding the cyclic aliphatic hydrocarbon group to the terminal of a linear or branched aliphatic hydrocarbon group, and a group obtained by interposing the cyclic aliphatic hydrocarbon group in a linear or branched aliphatic hydrocarbon group. Examples of the linear or branched aliphatic hydrocarbon group include the same ones as those described above.

The cyclic aliphatic hydrocarbon group preferably has 3 to 20 carbon atoms and more preferably 3 to 12 carbon atoms.

The cyclic aliphatic hydrocarbon group may be a polycyclic group or a monocyclic group. The monocyclic alicyclic hydrocarbon group is preferably a group obtained by removing two hydrogen atoms from a monocycloalkane. The monocycloalkane preferably has 3 to 6 carbon atoms, and specific examples thereof include cyclopentane and cyclohexane. The polycyclic alicyclic hydrocarbon group is preferably a group obtained by removing two hydrogen atoms from a polycycloalkane, and the polycycloalkane is preferably a group having 7 to 12 carbon atoms. Specific examples thereof include adamantane, norbornane, isobornane, tricyclodecane, and tetracyclododecane.

The cyclic aliphatic hydrocarbon group may have or may not have a substituent. Examples of the substituent include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and most preferably a methyl group, an ethyl group, a propyl group, an n-butyl group, or a tert-butyl group.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom for the substituent include a fluorine atom, a chlorine atom, a bromine atom, and an iodine atom, and a fluorine atom is preferable.

Examples of the halogenated alkyl group as the substituent include a group obtained by substituting part or all hydrogen atoms in the above-described alkyl groups with the above-described halogen atoms.

In the cyclic aliphatic hydrocarbon group, part of carbon atoms constituting the ring structure thereof may be substituted with a substituent containing a hetero atom. The substituent containing a hetero atom is preferably —O—, —C(=O)—O—, —S—, —S(=O)$_2$—, or —S(=O)$_2$—O—.

•• Aromatic Hydrocarbon Group as Ya$^{x1}$

The aromatic hydrocarbon group is a hydrocarbon group having at least one aromatic ring.

The aromatic ring is not particularly limited as long as it is a cyclic conjugated system having (4n+2) π electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Here, the number of carbon atoms in a substituent is not included in the number of carbon atoms. Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon ring with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Specific examples of the aromatic hydrocarbon group include a group (an arylene group or a heteroarylene group) obtained by removing two hydrogen atoms from the above-described aromatic hydrocarbon ring or the above-described aromatic heterocyclic ring; a group obtained by removing two hydrogen atoms from an aromatic compound (for example, biphenyl or fluorene) having two or more aromatic rings; and a group (for example, a group obtained by further removing one hydrogen atom from an aryl group in the arylalkyl group such as a benzyl group, a phenethyl group, a 1-naphthylmethyl group, a 2-naphthylmethyl group, a 1-naphthylethyl group, or a 2-naphthylethyl group) obtained by substituting one hydrogen atom of a group (an aryl group or a heteroaryl group) obtained by removing one hydrogen atom from the above aromatic hydrocarbon ring or the above aromatic heterocyclic ring, with an alkylene group. The alkylene group bonded to the aryl group or the heteroaryl group preferably has 1 to 4 carbon atoms, more preferably 1 or 2 carbon atoms, and particularly preferably 1 carbon atom.

With respect to the aromatic hydrocarbon group, the hydrogen atom contained in the aromatic hydrocarbon group may be substituted with a substituent. For example, the hydrogen atom bonded to the aromatic ring in the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group having 1 to 5 carbon atoms, and most preferably a methyl group, an ethyl group, a propyl group, an n-butyl group, or a tert-butyl group.

Examples of the alkoxy group, the halogen atom, and the halogenated alkyl group, as the substituent, include the same groups as those exemplified as the substituent that is substituted for a hydrogen atom contained in the cyclic aliphatic hydrocarbon group.

• Divalent Linking Group Containing Hetero Atom:

In a case where Ya$^{x1}$ represents a divalent linking group containing a hetero atom, preferred examples of the linking group include —O—, —C(=O)—O—, —C(=O)—, —O—C(=O)—O—, —C(=O)—NH—, —NH—, —NH—C(=NH)—(H may be substituted with a substituent such as an alkyl group, an acyl group, or the like), —S—, —S(=O)$_2$—, —S(=O)$_2$—O—, and a group represented by General Formula Y C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$— or —Y$^{21}$—S(=O)$_2$—O—Y$^{22}$— [in the formulae, Y$^{21}$ and Y$^{22}$ each independently represent a divalent hydrocarbon group which may have a substituent, 0 represents an oxygen atom, and m" represents an integer in a range of 0 to 3].

In a case where the divalent linking group containing a hetero atom is —C(=O)—NH—, —C(=O)—NH—C(=O)—, —NH—, or —NH—C(=NH)—, H may be substituted with a substituent such as an alkyl group, an acyl group, or the like. The substituent (an alkyl group, an acyl group, or the like) preferably has 1 to 10 carbon atoms, more preferably 1 to 8 carbon atoms, and particularly preferably 1 to 5 carbon atoms.

In General Formulae —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$—, and —$Y^{21}$—S(=O)$_2$—O—$Y^{22}$—, $Y^{21}$, and $Y^{22}$ each independently represent a divalent hydrocarbon group which may have a substituent. Examples of the divalent hydrocarbon group include the same one as the divalent hydrocarbon groups which may have a substituent, mentioned in the explanation of the above-described divalent linking group.

$Y^{21}$ is preferably a linear aliphatic hydrocarbon group, more preferably a linear alkylene group, still more preferably a linear alkylene group having 1 to 5 carbon atoms, and particularly preferably a methylene group or an ethylene group.

$Y^{22}$ is preferably a linear or branched aliphatic hydrocarbon group and more preferably a methylene group, an ethylene group, or an alkylmethylene group. The alkyl group in the alkylmethylene group is preferably a linear alkyl group having 1 to 5 carbon atoms, more preferably a linear alkyl group having 1 to 3 carbon atoms, and most preferably a methyl group.

In the group represented by General Formula —[$Y^{21}$—C(=O)—O]$_{m''}$—$Y^{22}$—, m" represents an integer in a range of 0 to 3, preferably an integer in a range of 0 to 2, more preferably 0 or 1, and particularly preferably 1. In other words, it is particularly preferable that the group represented by General Formula —[$Y^{21}$—C(=O)—O]$_{m''}$—$Y^{22}$— represents a group represented by General Formula —$Y^{21}$—C(=O)—O—$Y^{22}$—. Among them, a group represented by Formula —(CH$_2$)$_{a'}$—C(=O)—O—(CH$_2$)$_{b'}$— is preferable. In the formula, a' represents an integer in a range of 1 to 10, preferably an integer in a range of 1 to 8, more preferably an integer in a range of 1 to 5, still more preferably 1 or 2, and most preferably 1. b' represents an integer in a range of 1 to 10, preferably an integer in a range of 1 to 8, more preferably an integer in a range of 1 to 5, still more preferably 1 or 2, and most preferably 1.

As Ya$^{x1}$, a single bond, an ester bond [—C(=O)—O—], an ether bond (—O—), —C(=O)—NH—, a linear or branched alkylene group, or a combination of these is preferable, and a single bond is particularly more preferable among these.

In General Formula (a10-1), Wa$^{x1}$ represents an ($n_{ax1}$+1)-valent aromatic hydrocarbon group.

Examples of the aromatic hydrocarbon group as Wa$^{x1}$ include a group obtained by removing ($n_{ax1}$+1) hydrogen atoms from an aromatic ring. Here, the aromatic ring is not particularly limited as long as it is a cyclic conjugated system having (4n+2) π electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Specific examples of the aromatic ring include aromatic hydrocarbon rings such as benzene, naphthalene, anthracene, and phenanthrene; and an aromatic heterocyclic ring obtained by substituting part of carbon atoms constituting the above-described aromatic hydrocarbon ring with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

In Formula (a10-1), $n_{ax1}$ represents an integer of 1 to 3, preferably 1 or 2, and more preferably 1.

Specific examples of the constitutional unit represented by General Formula (a10-1) are shown below.

In the formulae shown below, R$^\alpha$ represents a hydrogen atom, a methyl group, or a trifluoromethyl group.

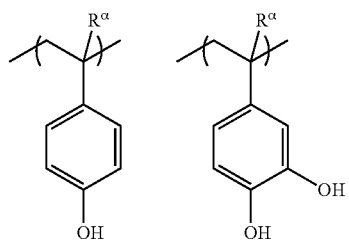

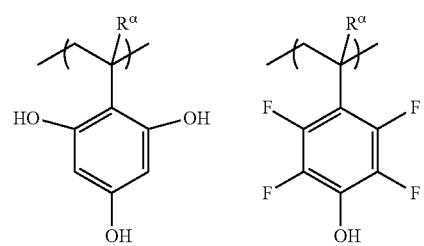

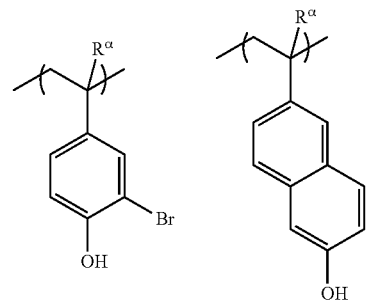

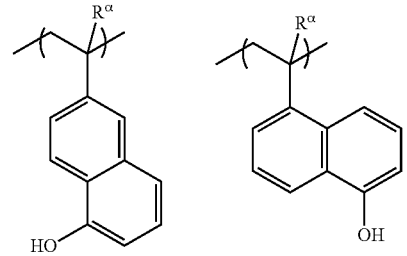

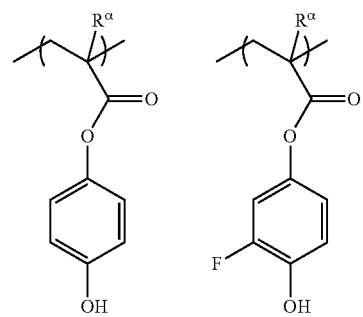

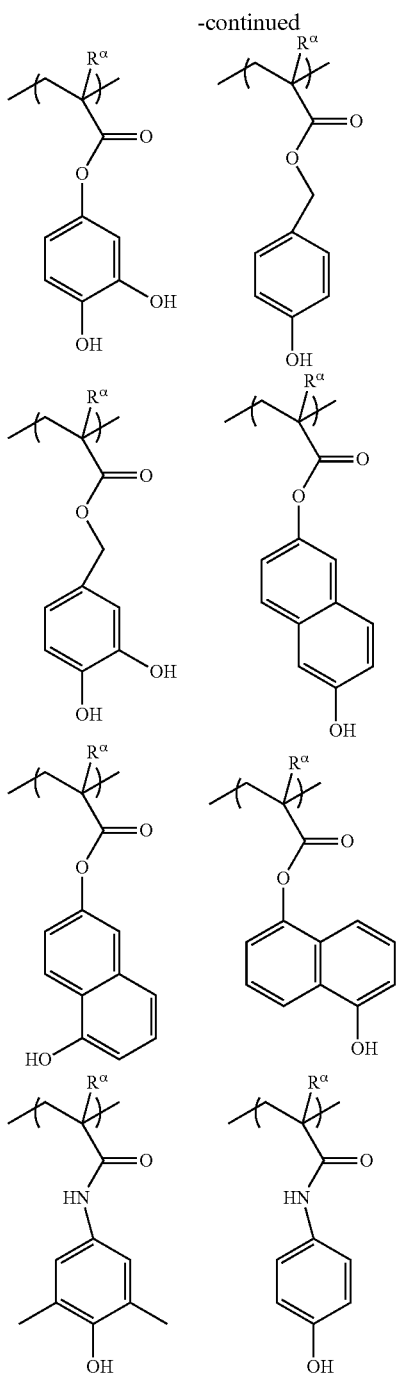

The constitutional unit (a10) contained in the component (A1) may be one kind or may be two or more kinds.

The proportion of the constitutional unit (a10) in the component (A1) is, for example, in a range of 0% to 80% by mole, and is preferably in a range of 10% to 80% by mole, more preferably in a range of 20% to 70% by mole, and particularly preferably in a range of 30% to 60% by mole, with respect to the total (100% by mole) of all constitutional units constituting the component (A1), from the viewpoint of further improving the effects of the present invention.

[Constitutional Unit (a2)]

The component (A1) may further have, as necessary, a constitutional unit (a2) (provided that a group having the constitutional unit (a1) is excluded) containing a lactone-containing cyclic group, a —$SO_2$-containing cyclic group, or a carbonate-containing cyclic group, in addition to the constitutional unit (a1).

In a case where the component (A1) is used for forming a resist film, the lactone-containing cyclic group, the —$SO_2$-containing cyclic group, or the carbonate-containing cyclic group in the constitutional unit (a2) is effective for improving the adhesiveness of the resist film to the substrate. Further, due to having the constitutional unit (a2), lithography characteristics can be improved, for example, due to the effects obtained by suitably adjusting the acid diffusion length, increasing the adhesiveness of the resist film to the substrate, suitably adjusting the solubility during development, and improving etching resistance.

The "lactone-containing cyclic group" indicates a cyclic group that contains a ring (lactone ring) containing a —O—C(=O)— in the ring skeleton. In a case where the lactone ring is counted as the first ring and the group contains only the lactone ring, the group is referred to as a monocyclic group. Further, in a case where the group has other ring structures, the group is referred to as a polycyclic group regardless of the structures. The lactone-containing cyclic group may be a monocyclic group or a polycyclic group.

The lactone-containing cyclic group for the constitutional unit (a2) is not particularly limited, and any lactone-containing cyclic group may be used. Specific examples thereof include groups each represented by General Formulae (a2-r-1) to (a2-r-7) shown below.

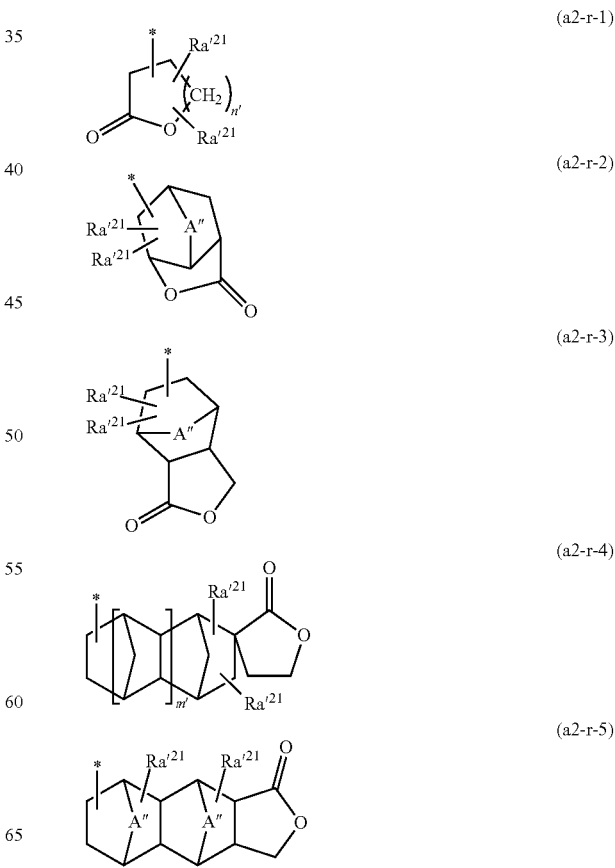

-continued

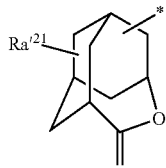
(a2-r-6)

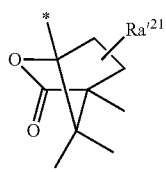
(a2-r-7)

[In the formulae, each Ra'²¹ independently represent a hydrogen atom, an alkyl group, an alkoxy group, a halogen atom, a halogenated alkyl group, a hydroxyl group, —COOR", —OC(═O)R", a hydroxyalkyl group, or a cyano group; R" represents a hydrogen atom, an alkyl group, a lactone-containing cyclic group, a carbonate-containing cyclic group, or a —SO₂-containing cyclic group; A" represents an oxygen atom, a sulfur atom, or an alkylene group having 1 to 5 carbon atoms, which may contain an oxygen atom (—O—) or a sulfur atom (—S—); and n' represents an integer in a range of 0 to 2, and m' is 0 or 1.]

In General Formulae (a2-r-1) to (a2-r-7), the alkyl group as Ra'²¹ is preferably an alkyl group having 1 to 6 carbon atoms. The alkyl group is preferably a linear alkyl group or a branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, and a hexyl group. Among these, a methyl group or ethyl group is preferable, and a methyl group is particularly preferable.

The alkoxy group as Ra'²¹ is preferably an alkoxy group having 1 to 6 carbon atoms. Further, the alkoxy group is preferably a linear or branched alkoxy group. Specific examples of the alkoxy groups include a group formed by linking the above-described alkyl group mentioned as the alkyl group represented by Ra'²¹ to an oxygen atom (—O—).

Examples of the halogen atom as Ra'²¹ include a fluorine atom, a chlorine atom, a bromine atom, and an iodine atom. Among these, a fluorine atom is preferable.

Examples of the halogenated alkyl group as Ra'²¹ include group obtained by substituting part or all hydrogen atoms in the above-described alkyl group as Ra'²¹ with the above-described halogen atoms. The halogenated alkyl group is preferably a fluorinated alkyl group and particularly preferably a perfluoroalkyl group.

In —COOR" and —OC(═O)R" as Ra'²¹, R" represents a hydrogen atom, an alkyl group, a lactone-containing cyclic group, a carbonate-containing cyclic group, or a —SO₂-containing cyclic group.

The alkyl group as R" may be linear, branched, or cyclic, and preferably has 1 to 15 carbon atoms.

In a case where R" represents a linear or branched alkyl group, it is preferably an alkyl group having 1 to 10 carbon atoms, more preferably an alkyl group having 1 to 5 carbon atoms, and particularly preferably a methyl group or an ethyl group.

In a case where R" represents a cyclic alkyl group, the cyclic alkyl group preferably has 3 to 15 carbon atoms, more preferably 4 to 12 carbon atoms, and particularly preferably 5 to 10 carbon atoms. Specific examples thereof include a group obtained by removing one or more hydrogen atoms from a monocycloalkane, which may be or may not be substituted with a fluorine atom or a fluorinated alkyl group; and a group obtained by removing one or more hydrogen atoms from a polycycloalkane such as bicycloalkane, tricycloalkane, or tetracycloalkane More specific examples thereof include a group obtained by removing one or more hydrogen atoms from a monocycloalkane such as cyclopentane or cyclohexane; and a group obtained by removing one or more hydrogen atoms from a polycycloalkane such as adamantane, norbornane, isobornane, tricyclodecane, or tetracyclododecane.

Examples of the lactone-containing cyclic group as R" include the same ones as the groups each represented by General Formulae (a2-r-1) to (a2-r-7).

The carbonate-containing cyclic group as R" is the same as the carbonate-containing cyclic group described below. Specific examples thereof include groups each represented by General Formulae (ax3-r-1) to (ax3-r-3).

The —SO₂-containing cyclic group as R" is the same as —SO₂-containing cyclic group described below. Specific examples thereof include groups each represented by General Formulae (a5-r-1) to (a5-r-4).

The hydroxyalkyl group as Ra'²¹ preferably has 1 to 6 carbon atoms, and specific examples thereof include a group obtained by substituting at least one hydrogen atom in the alkyl group as Ra'²¹ with a hydroxyl group.

In General Formulae (a2-r-2), (a2-r-3) and (a2-r-5), as the alkylene group having 1 to 5 carbon atoms as A", a linear or branched alkylene group is preferable, and examples thereof include a methylene group, an ethylene group, an n-propylene group, and an isopropylene group. Specific examples of the alkylene groups that contain an oxygen atom or a sulfur atom include a group obtained by interposing —O— or —S— in the terminal of the alkylene group or between the carbon atoms of the alkylene group, and examples thereof include —O—CH₂—, —CH₂—O—CH₂—, —S—CH₂—, and —CH₂—S—CH₂—. A" is preferably an alkylene group having 1 to 5 carbon atoms or —O—, more preferably an alkylene group having 1 to 5 carbon atoms, and most preferably a methylene group.

Specific examples of the groups each represented by General Formulae (a2-r-1) to (a2-r-7) are shown below.

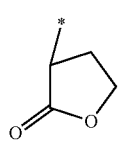
(r-Ic-1-1)

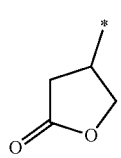
(r-Ic-1-2)

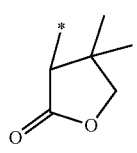
(r-Ic-1-3)

(r-Ic-1-4)
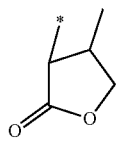
(r-Ic-1-5)
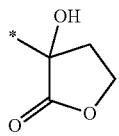
(r-Ic-1-6)
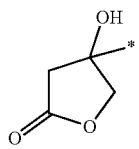
(r-Ic-1-7)
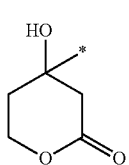
(r-Ic-2-1)
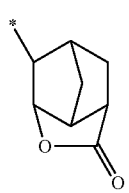
(r-Ic-2-2)
(r-Ic-2-3)
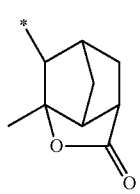
(r-Ic-2-4)
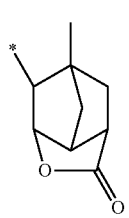
(r-Ic-2-5)
(r-Ic-2-6)
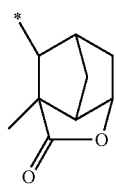
(r-Ic-2-7)
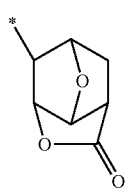
(r-Ic-2-8)
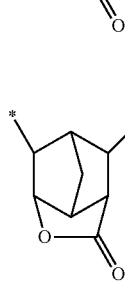
(r-Ic-2-9)
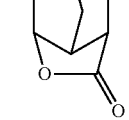
(r-Ic-2-10)
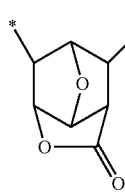
(r-Ic-2-11)
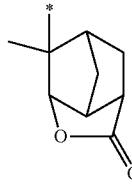
(r-Ic-2-12)
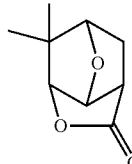
(r-Ic-2-13)
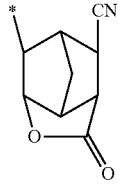
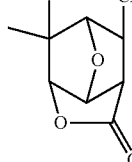

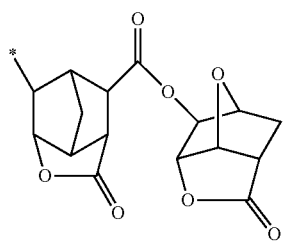 (r-Ic-2-14)
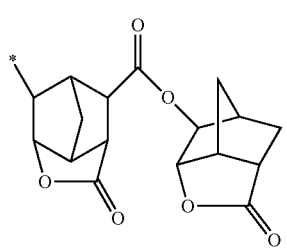 (r-Ic-2-15)
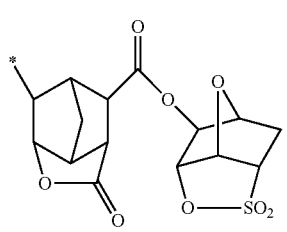 (r-Ic-2-16)
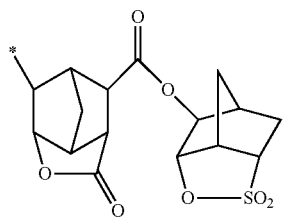 (r-Ic-2-17)
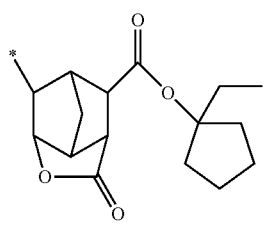 (r-Ic-2-18)
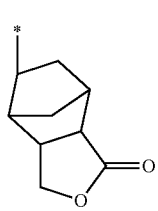 (r-Ic-3-1)
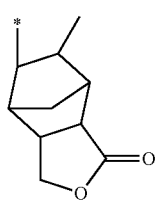 (r-Ic-3-2)
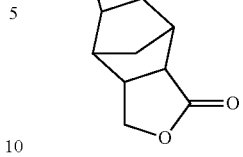 (r-Ic-3-3)
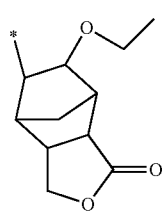 (r-Ic-3-4)
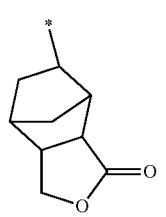 (r-Ic-3-5)
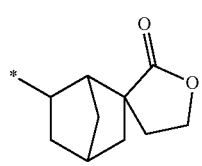 (r-Ic-4-1)
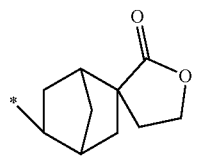 (r-Ic-4-2)
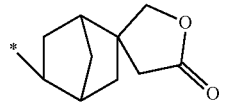 (r-Ic-4-3)
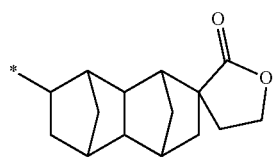 (r-Ic-4-4)
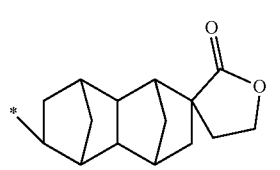 (r-Ic-4-5)
(r-Ic-4-6)

(r-Ic-4-7)
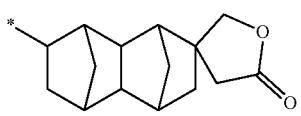

(r-Ic-4-8)
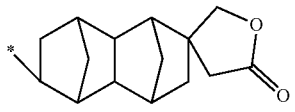

(r-Ic-4-9)
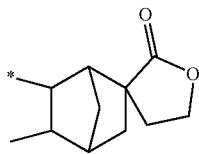

(r-Ic-5-1)
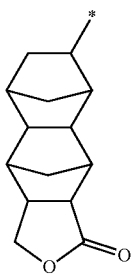

(r-Ic-5-2)
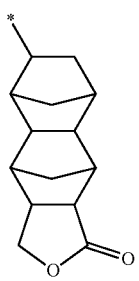

(r-Ic-5-3)
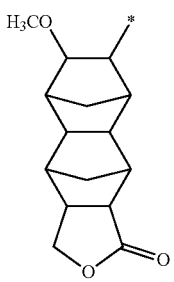

(r-Ic-5-4)
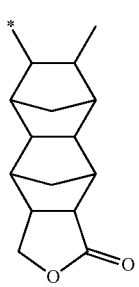

(r-Ic-6-1)
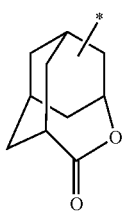

(r-Ic-7-1)
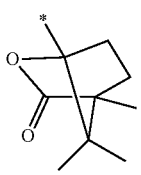

The "—SO$_2$-containing cyclic group" indicates a cyclic group having a ring containing —SO$_2$— in the ring skeleton thereof. Specifically, it is a cyclic group in which the sulfur atom (S) in —SO$_2$— forms a part of the ring skeleton of the cyclic group. In a case where the ring containing —SO$_2$— in the ring skeleton thereof is counted as the first ring and the group contains only the ring, the group is referred to as a monocyclic group. In a case where the group further has other ring structures, the group is referred to as a polycyclic group regardless of the ring structures. The —SO$_2$-containing cyclic group may be a monocyclic group or a polycyclic group. The —SO$_2$-containing cyclic group is particularly preferably a cyclic group containing —O—SO$_2$— in the ring skeleton thereof, in other words, a cyclic group containing a sultone ring in which —O—S— in the —O—SO$_2$— group forms a part of the ring skeleton thereof.

More specific examples of the —SO$_2$-containing cyclic group include groups each represented by General Formulae (a5-r-1) to (a5-r-4) shown below.

(a5-r-1)
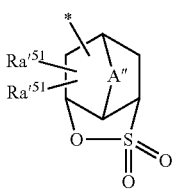

(a5-r-2)
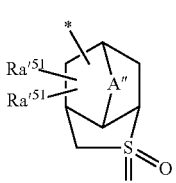

(a5-r-3)
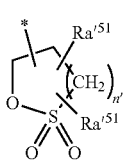

(a5-r-4)

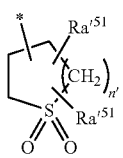

[In the formulae, Ra'⁵¹s each independently represent a hydrogen atom, an alkyl group, an alkoxy group, a halogen atom, a halogenated alkyl group, a hydroxyl group, —COOR", —OC(=O)R", a hydroxyalkyl group, or a cyano group; R" represents a hydrogen atom, an alkyl group, a lactone-containing cyclic group, a carbonate-containing cyclic group, or a —SO$_2$-containing cyclic group; A" represents an oxygen atom, a sulfur atom, or an alkylene group having 1 to 5 carbon atoms, which may contain an oxygen atom or a sulfur atom; and n' represents an integer in a range of 0 to 2.]

In General Formulae (a5-r-1) and (a5-r-2), A" has the same definition as that for A" in General Formulae (a2-r-2), (a2-r-3) and (a2-r-5).

Examples of the alkyl group, the alkoxy group, the halogen atom, the halogenated alkyl group, —COOR", —OC(=O)R", and the hydroxyalkyl group as Ra'⁵¹ each include the same ones as those mentioned in the explanation of Ra'²¹ in General Formulae (a2-r-1) to (a2-r-7).

Specific examples of the groups each represented by General Formulae (a5-r-1) to (a5-r-4) are shown below. In the formulae shown below, "Ac" represents an acetyl group.

(r-s1-1-1)

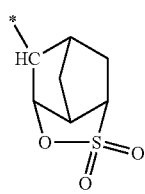

(r-s1-1-2)

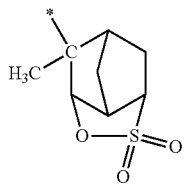

(r-s1-1-3)

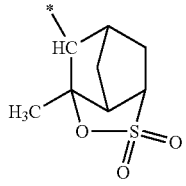

(r-s1-1-4)

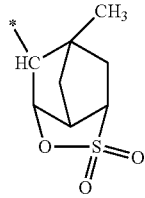

(r-s1-1-5)

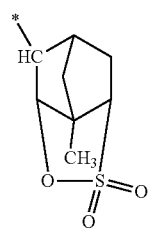

(r-s1-1-6)

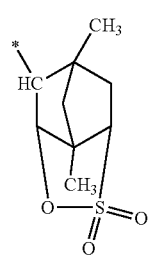

(r-s1-1-7)

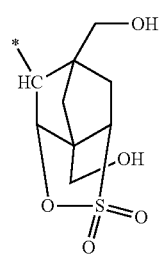

(r-s1-1-8)

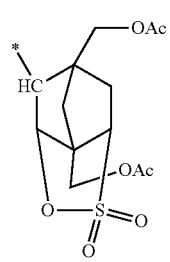

(r-s1-1-9)

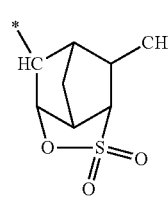

(r-s1-1-10)

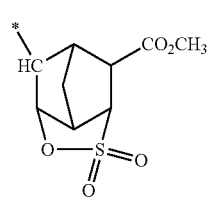

(r-s1-1-11)

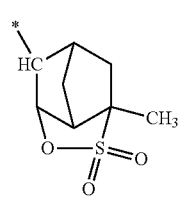

(r-s1-1-12)
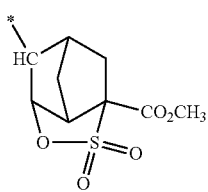
(r-s1-1-13)
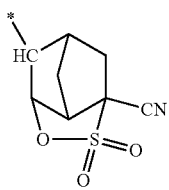
(r-s1-1-14)
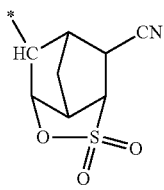
(r-s1-1-15)
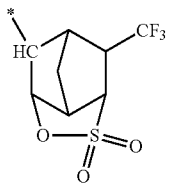
(r-s1-1-16)
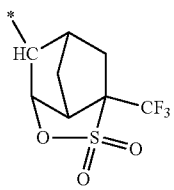
(r-s1-1-17)
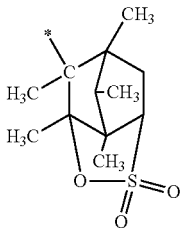
(r-s1-1-18)
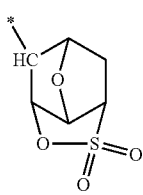
(r-s1-1-19)
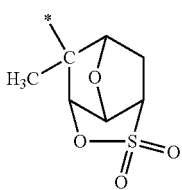
(r-s1-1-20)
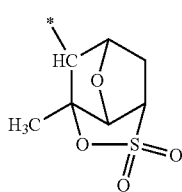
(r-s1-1-21)
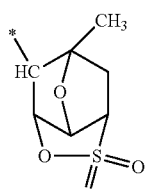
(r-s1-1-22)
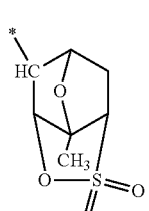
(r-s1-1-23)
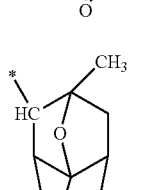
(r-s1-1-24)
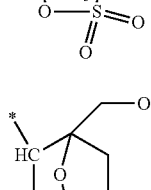
(r-s1-1-25)
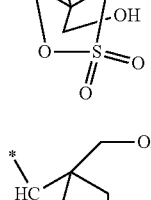
(r-s1-1-26)
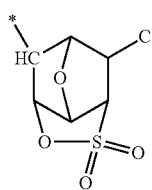

-continued (r-s1-1-27)
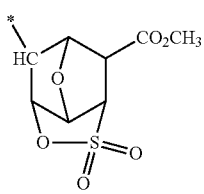

(r-s1-1-28)
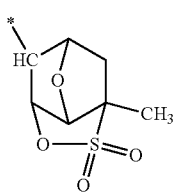

(r-s1-1-29)
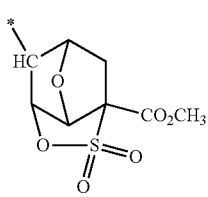

(r-s1-1-30)
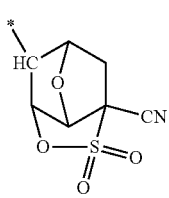

(r-s1-1-31)
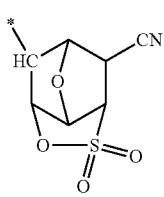

(r-s1-1-32)
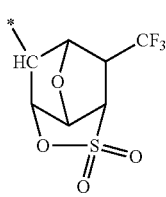

(r-s1-1-33)
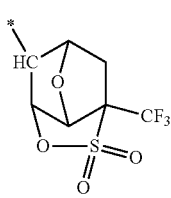

(r-s1-2-1)
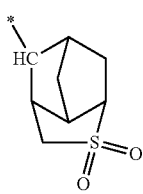

-continued (r-s1-2-2)
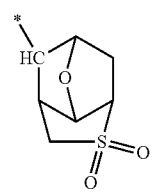

(r-s1-3-1)
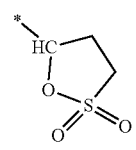

(r-s1-4-1)
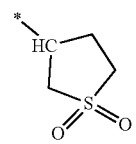

The "carbonate-containing cyclic group" indicates a cyclic group having a ring (a carbonate ring) containing —O—C(=O)—O— in the ring skeleton thereof. In a case where the carbonate ring is counted as the first ring and the group contains only the carbonate ring, the group is referred to as a monocyclic group. Further, in a case where the group has other ring structures, the group is referred to as a polycyclic group regardless of the structures. The carbonate-containing cyclic group may be a monocyclic group or a polycyclic group.

The carbonate ring-containing cyclic group is not particularly limited, and any carbonate ring-containing cyclic group may be used. Specific examples thereof include groups each represented by General Formulae (ax3-r-1) to (ax3-r-3) shown below.

(ax3-r-1)
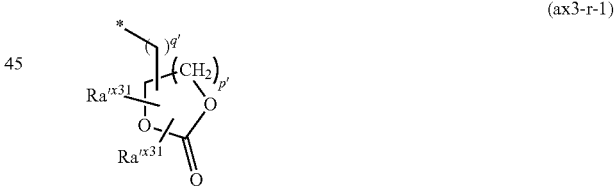

(ax3-r-2)

-continued (ax3-r-3)

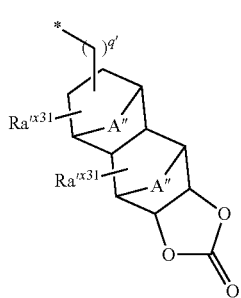

[In the formulae, $Ra'^{x31}$s independently represent a hydrogen atom, an alkyl group, an alkoxy group, a halogen atom, a halogenated alkyl group, a hydroxyl group, —COOR", —OC(=O)R", a hydroxyalkyl group, or a cyano group; R" represents a hydrogen atom, an alkyl group, a lactone-containing cyclic group, a carbonate-containing cyclic group, or a —SO$_2$-containing cyclic group; A" represents an oxygen atom, a sulfur atom, or an alkylene group having 1 to 5 carbon atoms, which may contain an oxygen atom or a sulfur atom; and p' represents an integer in a range of 0 to 3, and q' is 0 or 1.]

In General Formulae (ax3-r-2) and (ax3-r-3), A" has the same definition as that for A" in General Formulae (a2-r-2), (a2-r-3) and (a2-r-5).

Examples of the alkyl group, the alkoxy group, the halogen atom, the halogenated alkyl group, —COOR", —OC(=O)R", and the hydroxyalkyl group as $Ra'^{31}$ each include the same ones as those mentioned in the explanation of $Ra'^{21}$ in General Formulae (a2-r-1) to (a2-r-7).

Specific examples of the groups each represented by General Formulae (ax3-r-1) to (ax3-r-3) are shown below.

(r-cr-1-1)

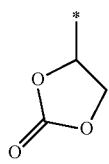

(r-cr-1-2)

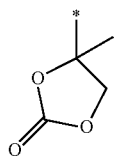

(r-cr-1-3)

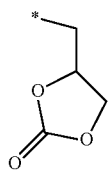

(r-cr-1-4)

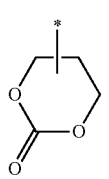

(r-cr-1-5)

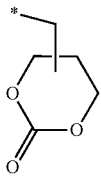

(r-cr-1-6)

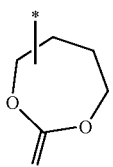

(r-cr-1-7)

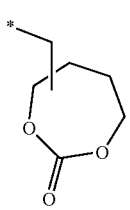

(r-cr-2-1)

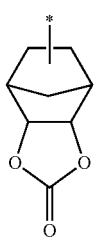

(r-cr-2-2)

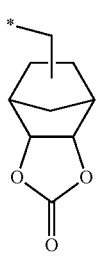

(r-cr-2-3)

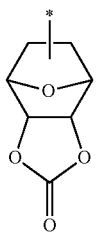

(r-cr-2-4)

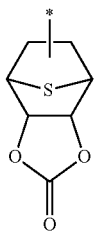

-continued (r-cr-3-1)

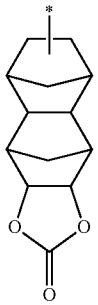

(r-cr-3-2)

(r-cr-3-3)

(r-cr-3-4)

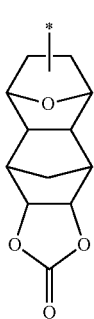

(r-cr-3-5)

Among them, the constitutional unit (a2) is preferably a constitutional unit derived from acrylic acid ester in which the hydrogen atom bonded to the carbon atom at the α-position may be substituted with a substituent.

The constitutional unit (a2) is preferably a constitutional unit represented by General Formula (a2-1).

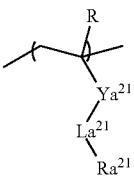

(a2-1)

[In the formula, R represents a hydrogen atom, an alkyl group having 1 to 5 carbon atoms, or a halogenated alkyl group having 1 to 5 carbon atoms. $Ya^{21}$ represents a single bond or a divalent linking group. $La^{21}$ represents —O—, —COO—, —CON(R')—, —OCO—, —CONHCO— or —CONHCS—, and R' represents a hydrogen atom or a methyl group. However, in a case where $La^{21}$ represents —O—, $Ya^{21}$ does not represent —CO—. $Ra^{21}$ represents a lactone-containing cyclic group, a carbonate-containing cyclic group, or a —SO$_2$-containing cyclic group.]

In General Formula (a2-1), R has the same definition as described above. R is preferably a hydrogen atom, an alkyl group having 1 to 5 carbon atoms, or a fluorinated alkyl group having 1 to 5 carbon atoms, and particularly preferably a hydrogen atom or a methyl group in terms of industrial availability.

In General Formula (a2-1), the divalent linking group as $Ya^{21}$ is not particularly limited, and suitable examples thereof include a divalent hydrocarbon group which may have a substituent and a divalent linking group having a hetero atom. The descriptions for the divalent hydrocarbon group which may have a substituent and the divalent linking group containing a hetero atom, as $Ya^{21}$, are each the same as the descriptions for the divalent hydrocarbon group which may have a substituent and the divalent linking group containing a hetero atom, as Ye', in General Formula (a10-1) described above.

$Ya^{21}$ is preferably a single bond, an ester bond [—C(=O)—O—], an ether bond (—O—), a linear or branched alkylene group, or a combination thereof.

In General Formula (a2-1), $Ra^{21}$ represents a lactone-containing cyclic group, a —SO$_2$-containing cyclic group, or a carbonate-containing cyclic group.

Suitable examples of the lactone-containing cyclic group, the —SO$_2$-containing cyclic group, and the carbonate-containing cyclic group as $Ra^{21}$ include groups each represented by General Formulae (a2-r-1) to (a2-r-7), groups each represented by General Formulae (a5-r-1) to (a5-r-4), and groups each represented by General Formulae (ax3-r-1) to (ax3-r-3) described above.

Among them, a lactone-containing cyclic group or a —SO$_2$-containing cyclic group is preferable, and groups each represented by General Formula (a2-r-1), (a2-r-2), (a2-r-6), to (a5-r-1) are more preferable. Specifically, groups each represented by Chemical Formulae (r-lc-1-1) to (r-lc-1-7), (r-lc-2-1) to (r-lc-2-18), (r-lc-6-1), (r-sl-1-1), and (r-sl-1-18) are more preferable.

The constitutional unit (a2) contained in the component (A1) may be one kind or may be two or more kinds.

In a case where the component (A1) has the constitutional unit (a2), the proportion of the constitutional unit (a2) in the component (A1) is preferably in a range of 0% to 50% by mole, more preferably in a range of 5% to 45% by mole, still more preferably in a range of 10% to 40% by mole, and particularly preferably in a range of 10% to 30% by mole with respect to the total (100% by mole) of all constitutional units constituting the component (A1).

In a case where the proportion of the constitutional unit (a2) is set to be equal to or larger than the lower limit value of the preferred range, the effect obtained by allowing the component (A1) to contain the constitutional unit (a2) can be sufficiently achieved. In a case where it is equal to or smaller than the upper limit value thereof, the balance with other constitutional units can be obtained, and thus various lithography characteristics are improved.

• Constitutional Unit (a3)

In addition to the constitutional unit (a1), the component (A1) may further have, as necessary, a constitutional unit (a3) (provided that a constitutional unit corresponding to the constitutional unit (a1) or the constitutional unit (a2) is excluded) containing a polar group-containing aliphatic hydrocarbon group. In a case where the component (A1) has the constitutional unit (a3), lithography characteristics can be improved, for example, due to the effects obtained by suitably adjusting the acid diffusion length, increasing the adhesiveness of the resist film to the substrate, suitably adjusting the solubility during development, and improving etching resistance.

Examples of the polar group include a hydroxyl group, a cyano group, a carboxy group, or a hydroxyalkyl group obtained by substituting part of hydrogen atoms of the alkyl group with a fluorine atom, and the polar group is particularly preferably a hydroxyl group.

Examples of the aliphatic hydrocarbon group include a linear or branched hydrocarbon group (preferably an alkylene group) having 1 to 10 carbon atoms, and a cyclic aliphatic hydrocarbon group (a cyclic group). The cyclic group may be a monocyclic group or a polycyclic group. For example, these cyclic groups can be appropriately selected and used from a large number of groups that have been proposed in resins for a resist composition for an ArF excimer laser. The cyclic group is preferably a polycyclic group and more preferably has 7 to 30 carbon atoms.

Among them, a constitutional unit derived from an acrylic acid ester that includes an aliphatic polycyclic group containing a hydroxyl group, cyano group, carboxy group, or a hydroxyalkyl group obtained by substituting part of hydrogen atoms of the alkyl group with a fluorine atom is particularly preferable. Examples of the polycyclic group include groups obtained by removing two or more hydrogen atoms from a bicycloalkane, tricycloalkane, tetracycloalkane, or the like. Specific examples thereof include a group obtained by removing two or more hydrogen atoms from a polycycloalkane such as adamantane, norbornane, isobornane, tricyclodecane, or tetracyclododecane. Among these polycyclic groups, a group obtained by removing two or more hydrogen atoms from adamantane, a group obtained by removing two or more hydrogen atoms from norbornane, or a group obtained by removing two or more hydrogen atoms from tetracyclododecane are industrially preferable.

The constitutional unit (a3) is not particularly limited, and any constitutional unit may be used as long as the constitutional unit contains a polar group-containing aliphatic hydrocarbon group.

The constitutional unit (a3) is preferably a constitutional unit derived from an acrylic acid ester in which the hydrogen atom bonded to the carbon atom at the α-position may be substituted with a substituent, where the constitutional unit contains a polar group-containing aliphatic hydrocarbon group.

In a case where the hydrocarbon group in the polar group-containing aliphatic hydrocarbon group is a linear or branched hydrocarbon group having 1 to 10 carbon atoms, the constitutional unit (a3) is preferably a constitutional unit derived from a hydroxyethyl ester of acrylic acid.

In addition, in a case where the hydrocarbon group in the polar group-containing aliphatic hydrocarbon group is a polycyclic group, preferred examples of the constitutional unit (a3) include a constitutional unit represented by General Formula (a3-1), a constitutional unit represented by General Formula (a3-2), and a constitutional unit represented by General Formula (a3-3) shown below.

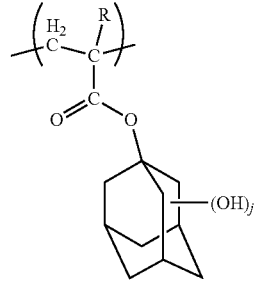

(a3-1)

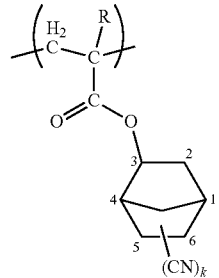

(a3-2)

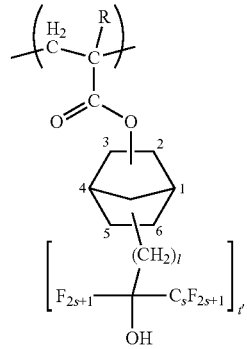

(a3-3)

[In the formulae, R has the same definition as described above, j represents an integer in a range of 1 to 3, k represents an integer in a range of 1 to 3, t' represents an integer in a range of 1 to 3, 1 represents an integer in a range of 1 to 5, and s represents an integer in a range of 1 to 3.]

In General Formula (a3-1), j is preferably 1 or 2 and more preferably 1. In a case where j represents 2, it is preferable that the hydroxyl groups is bonded to the 3-position and the 5-position of the adamantyl group. In a case where j represents 1, it is preferable that the hydroxyl group is bonded to the 3-position of the adamantyl group. It is preferable that j represents 1, and it is particularly preferable that the hydroxyl group is bonded to the 3-position of the adamantyl group.

In General Formula (a3-2), k is preferably 1. The cyano group is preferably bonded to the 5-position or the 6-position of the norbornyl group.

In General Formula (a3-3), it is preferable that t' represents 1. It is preferable that 1 represents 1. It is preferable that s represents 1. Further, it is preferable that a 2-norbornyl group or 3-norbornyl group is bonded to the terminal of the carboxy group of the acrylic acid. It is preferable that the fluorinated alkyl alcohol is bonded to the 5-position or the 6-position of the norbornyl group.

The constitutional unit (a3) contained in the component (A1) may be one kind or may be two or more kinds.

In a case where the component (A1) has the constitutional unit (a3), the constitutional unit (a3) is preferably in a range of 0% to 40% by mole, more preferably in a range of 2% to 30% by mole, still more preferably in a range of 5% to 25% by mole, and particularly preferably in a range of 5% to 20% by mole, with respect to the total of all constitutional units constituting the component (A1).

In a case where the proportion of the constitutional unit (a3) is set to be equal to or larger than the lower limit value of the preferred range, the effect obtained by allowing the constitutional unit (a3) to be contained can be sufficiently achieved. In a case where it is equal to or smaller than the upper limit value thereof, the balance with other constitutional units can be obtained, and thus various lithography characteristics are improved.

[Constitutional Unit (a6)]

In addition to the constitutional unit (a1), the component (A1) may further have a constitutional unit (a6) that generates acid upon exposure.

The constitutional unit (a6) is not particularly limited as long as it generates acid upon exposure, and for example, a constitutional unit which can be copolymerized with the constitutional unit (a1) or the like and into which a structure proposed as an acid generator for a chemically amplified resist in the related art is introduced can be used.

Examples of the suitable constitutional unit that can be copolymerized with the constitutional unit (a1) and the like include a constitutional unit derived from a (meth)acrylic acid ester and a constitutional unit derived from hydroxystyrene.

Suitable examples of the constitutional unit into which a structure proposed as an acid generator for a chemically amplified resist in the related art is introduced include a constitutional unit into which a structure of the component (B) described later is introduced.

Examples of the constitutional unit (a6) include a constitutional unit (a6a) having an anion group that generates acid upon exposure in the side chain, and a constitutional unit (a6c) having a cation group that is decomposed upon exposure in the side chain.

• In Regard to Constitutional Unit (a6a)

The constitutional unit (a6a) is a constitutional unit having an anion group that generates acid upon exposure in the side chain.

The anion group that generates acid upon exposure is not particularly limited; however, a sulfonic acid anion, an amide anion, or a methide anion is preferable. Among the above, the constitutional unit (a6a) is preferably a constitutional unit having an anion group represented by General Formula (a6a-r-11).

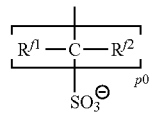

(a6a-r-11)

[In the formula, $R^{f1}$ and $R^{f2}$ each independently represent a hydrogen atom, an alkyl group, a fluorine atom, or a fluorinated alkyl group, where at least one of $R^{f1}$ and $R^{f2}$ represents a fluorine atom or a fluorinated alkyl group, and p0 represents an integer in a range of 1 to 8.]

In General Formula (a6a-r-11), $R^{f1}$ and $R^{f2}$ each independently represent a hydrogen atom, an alkyl group, a fluorine atom, or a fluorinated alkyl group, where at least one of $R^{f1}$ and $R^{f2}$ represents a fluorine atom or a fluorinated alkyl group.

The alkyl group as $R^{f1}$ and $R^{f2}$ is preferably an alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group.

The fluorinated alkyl group as $R^{f1}$ and $R^{f2}$ is preferably a group obtained by substituting part or all hydrogen atoms of the alkyl group as $R^{f1}$ and $R^{f2}$ with a fluorine atom.

$R^{f1}$ and $R^{f2}$ are each independently preferably a fluorine atom or a fluorinated alkyl group.

In General Formula (aha-r-11), p0 represents an integer in a range of 1 to 8 and is preferably an integer in a range of 1 to 4 and more preferably 1 or 2.

Examples of the cation that may form a salt together with the anion group of the constitutional unit (aha) include an organic cation. The organic cation is not particularly limited, and among the above, an onium cation is preferable, and among the above, a sulfonium cation or an iodonium cation is more preferable. Organic cations each represented by General Formula (ca-1) to (ca-4) described later are particularly preferable.

Hereinafter, specific examples of the constitutional unit having the anion group represented by General Formula (aha-r-11) will be shown. In the following formulae, $R^{\alpha}$ represents a hydrogen atom, a methyl group, or a trifluoromethyl group. In the following formulae, $(M^{m+})_{1/m}$ represents an m-valent organic cation that forms a salt together with an anion group.

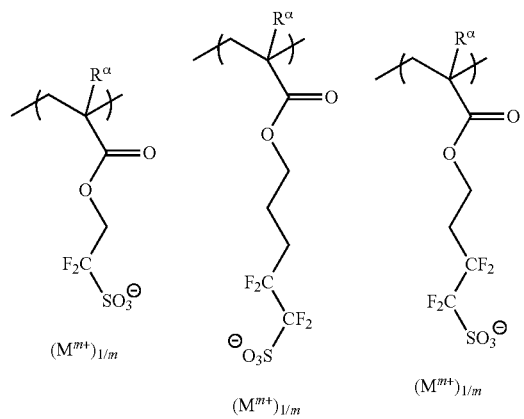

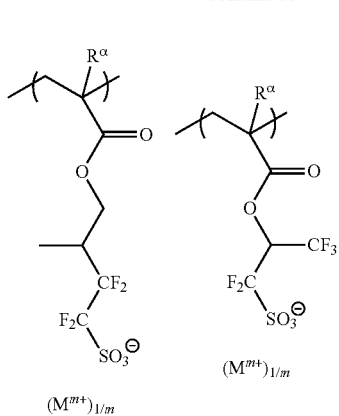
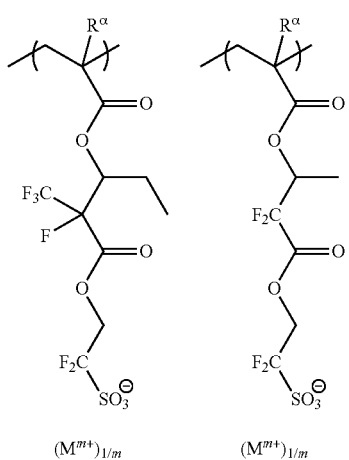
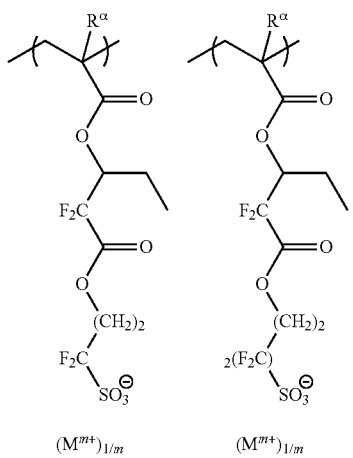
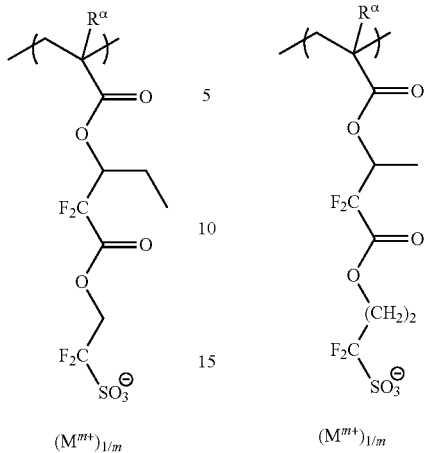
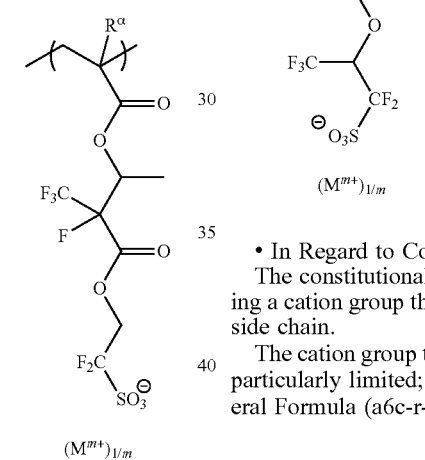
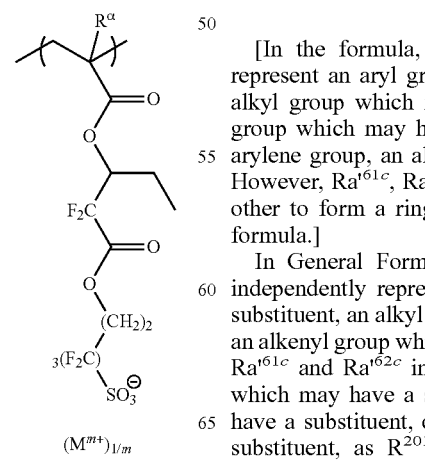
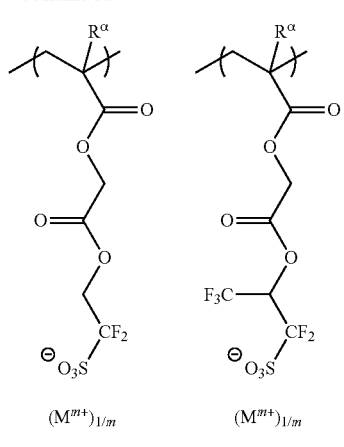
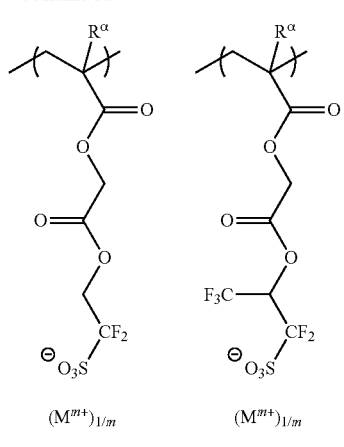
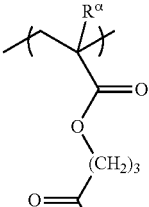
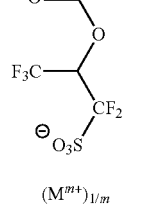

• In Regard to Constitutional Unit (a6c)

The constitutional unit (a6c) is a constitutional unit having a cation group that is decomposed upon exposure, in the side chain.

The cation group that is decomposed upon exposure is not particularly limited; however, a group represented by General Formula (a6c-r-1) is preferable.

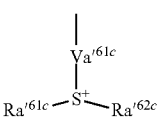

(a6c-r-1)

[In the formula, $Ra'^{61c}$ and $R'^{62c}$ each independently represent an aryl group which may have a substituent, an alkyl group which may have a substituent, or an alkenyl group which may have a substituent. $Va'^{61c}$ represents an arylene group, an alkylene group, or an alkenylene group. However, $Ra'^{61c}$, $Ra'^{62c}$, and $Va'^{61c}$ may be bonded to each other to form a ring together with the sulfur atom in the formula.]

In General Formula (a6c-r-1), $Ra'^{61c}$ and $Ra'^{62c}$ each independently represent an aryl group which may have a substituent, an alkyl group which may have a substituent, or an alkenyl group which may have a substituent. Examples of $Ra'^{61c}$ and $Ra'^{62c}$ include the same one as the aryl group which may have a substituent, an alkyl group which may have a substituent, or an alkenyl group which may have a substituent, as $R^{201}$ to $R^{203}$ in General Formula (ca-1) described later.

Va'$^{61c}$ represents an arylene group, an alkylene group, or an alkenylene group, and examples thereof include a group obtained by removing one hydrogen atom from the aryl group, the alkyl group, or the alkenyl group, as Ra'$^{61c}$ and Ra'$^{62c}$.

However, Ra'$^{61c}$, Ra'$^{62c}$, and Va'$^{61c}$ may be bonded to each other to form a ring together with the sulfur atom in the formula. Examples of the ring structure that is formed here include a group obtained by removing one hydrogen atom from a ring that is formed by bonding R$^{201}$ to R$^{203}$ in General Formula (ca-1) described later to each other together with the sulfur atom in the formula.

The anion which may form a salt with the cation moiety of the constitutional unit (a6c) is not particularly limited, and examples thereof include an anion moiety of an onium salt-based acid generator represented by General Formula (b-1), (b-2), or (b-3), which is exemplified in the description of the component (B) described later. It is particularly preferably an anion moiety of an onium salt-based acid generator represented by General Formula (b-1), and among the above, it is preferably a fluorinated alkyl sulfonic acid ion having 1 to 8 carbon atoms (preferably having 1 to 4 carbon atoms) or at least one selected from anions each represented by General Formulae (an-1) to (an-3) described later, respectively.

Hereinafter, specific examples of the constitutional unit having the cation group represented by General Formula (a6c-r-1) will be shown. In the following formulae, R$^\alpha$ represents a hydrogen atom, a methyl group, or a trifluoromethyl group. In the following formula, A$^-$ represents a counter anion that forms a salt with a cation group.

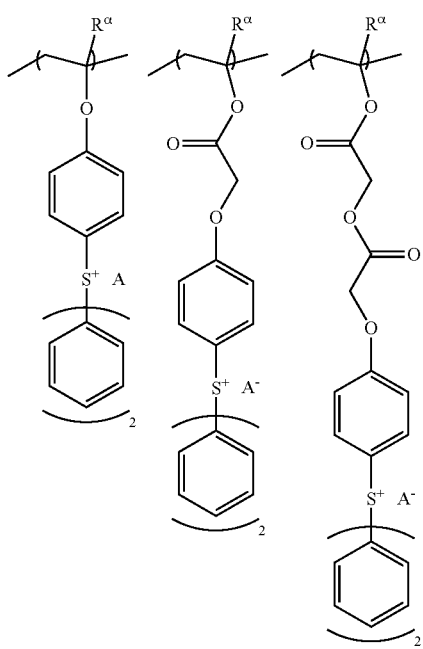

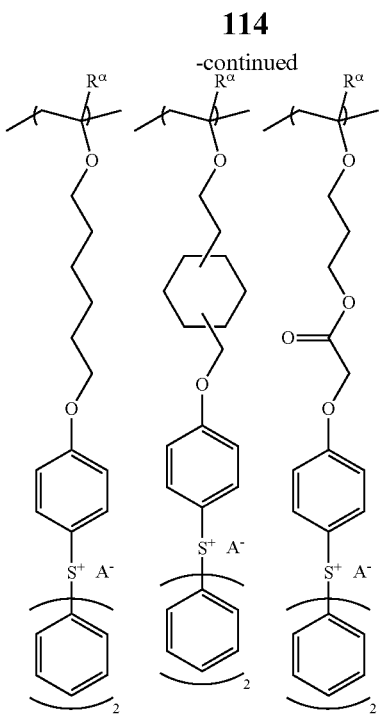

The constitutional unit (a6) contained in the component (A1) may be one kind or may be two or more kinds.

In the component (A1), the proportion of the constitutional unit (a6) is preferably in a range of 0% to 30% by mole, more preferably in a range of 1% to 20% by mole, and particularly preferably in a range of 1.5% to 15% by mole, with respect to the total of all constitutional units constituting the component (A1).

In a case where the proportion of the constitutional unit (a6) is set to be equal to or larger than the lower limit value, roughness is reduced and thus a good resist pattern shape is easily obtained. In a case where it is set to be equal to or smaller than the upper limit value, the balance with other constitutional units can be achieved, and thus lithography characteristics are further improved.

[Other Constitutional Units]

The component (A1) may have other constitutional units other than the constitutional unit (a1), the constitutional unit (a10), the constitutional unit (a2), the constitutional unit (a3), and the constitutional unit (a6), which are described above.

Examples of the other constitutional units include a constitutional unit (a9) represented by General Formula (a9-1) described later, a constitutional unit derived from styrene, a constitutional unit derived from a styrene derivative (provided that a constitutional unit corresponding to the constitutional unit (a10) is excluded), and a constitutional unit containing an acid non-dissociable aliphatic cyclic group.

Constitutional Unit (a9):

The constitutional unit (a9) is a constitutional unit represented by General Formula (a9-1).

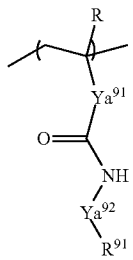

(a9-1)

[In the formula, R represents a hydrogen atom, an alkyl group having 1 to 5 carbon atoms, or a halogenated alkyl group having 1 to 5 carbon atoms. $Ya^{91}$ represents a single bond or a divalent linking group. $Ya^{92}$ represents a divalent linking group. $R^{91}$ represents a hydrocarbon group which may have a substituent.]

In General Formula (a9-1), R has the same definition as described above.

R is preferably a hydrogen atom, an alkyl group having 1 to 5 carbon atoms, or a fluorinated alkyl group having 1 to 5 carbon atoms, and particularly preferably a hydrogen atom or a methyl group in terms of industrial availability.

In General Formula (a9-1), examples of the divalent linking group as $Ya^{91}$ include the same one as the divalent linking group as $Ya^{x1}$ in General Formula (a10-1). Above them, the $Ya^{91}$ is preferably a single bond.

In General Formula (a9-1), examples of the divalent linking group as $Ya^{92}$ include the same one as the divalent linking group as $Ya^{x1}$ in General Formula (a10-1).

In the divalent linking group as $Ya^{92}$, the divalent hydrocarbon group which may have a substituent is preferably a linear or branched aliphatic hydrocarbon group.

In addition, in the divalent linking group as $Ya^{92}$, examples of the divalent linking group containing a hetero atom include —O—, —C(=O)—O—, —C(=O)—, —O—C(=O)—O—, —C(=O)—NH—, —NH—, —NH—C(=NH)—(H may be substituted with a substituent such as an alkyl group, an acyl group, or the like), —S—, —S(=O)$_2$—, —S(=O)$_2$—O—, —C(=S)—, and a group represented by General Formula —$Y^{21}$—O—$Y^{22}$—, —$Y^{21}$—O—, —$Y^{21}$—C(=O)—O—, —C(=O)—O—$Y^{21}$, [$Y^{21}$—C(=O)—O]$_{m'}$—$Y^{22}$—, or —$Y^{21}$—O—C(=O)—$Y^{22}$— [in the formulae, $Y^{21}$ and $Y^{22}$ each independently represent a divalent hydrocarbon group which may have a substituent, 0 represents an oxygen atom, and m' represents an integer in a range of 0 to 3]. Among them, —C(=O)— or —C(=S)— is preferable.

In General Formula (a9-1), examples of the hydrocarbon group as $R^{91}$ include an alkyl group, a monovalent alicyclic hydrocarbon group, an aryl group, and an aralkyl group.

The alkyl group as $R^{91}$ preferably has 1 to 8 carbon atoms, more preferably 1 to 6 carbon atoms, and still more preferably 1 to 4 carbon atoms, and it may be linear or may be branched. Specific preferred examples thereof include a methyl group, an ethyl group, a propyl group, a butyl group, a hexyl group, and an octyl group.

The monovalent alicyclic hydrocarbon group as $R^{91}$ preferably has 3 to 20 carbon atoms and more preferably 3 to 12 carbon atoms, and it may be polycyclic or may be monocyclic. The monocyclic alicyclic hydrocarbon group is preferably a group obtained by removing one or more hydrogen atoms from a monocycloalkane. The monocycloalkane preferably has 3 to 6 carbon atoms, and specific examples thereof include cyclobutane, cyclopentane, and cyclohexane. The polycyclic alicyclic hydrocarbon group is preferably a group obtained by removing one or more hydrogen atoms from a polycycloalkane, where the polycycloalkane is preferably a group having 7 to 12 carbon atoms. Specific examples thereof include adamantane, norbornane, isobornane, tricyclodecane, and tetracyclododecane.

The aryl group as $R^{91}$ preferably has 6 to 18 carbon atoms, more preferably 6 to 10 carbon atoms, and particularly preferably a phenyl group.

The aralkyl group as $R^{91}$ is preferably an aralkyl group obtained by bonding an alkylene group having 1 to 8 carbon atoms to the above-described "aryl group as $R^{91}$", more preferably an aralkyl group obtained by bonding an alkylene group having 1 to 6 carbon atoms to the above-described "aryl group as $R^{91}$", and particularly preferably an aralkyl group obtained by bonding an alkylene group having 1 to 4 carbon atoms to the above-described "aryl group as $R^{91}$".

In the hydrocarbon group as $R^{91}$, it is preferable that part or all hydrogen atoms of the hydrocarbon group are substituted with a fluorine atom, and it is more preferable that 30% to 100% of hydrogen atoms of the hydrocarbon group is substituted with a fluorine atom. Among the above, a perfluoroalkyl group obtained by substituting all hydrogen atoms of the above-described alkyl group with a fluorine atom is particularly preferable.

The hydrocarbon group as $R^{91}$ may have a substituent. Examples of the substituent include a halogen atom, an oxo group (=O), a hydroxyl group (—OH), an amino group (—NH$_2$), and —SO$_2$—NH$_2$. Further, part of carbon atoms constituting the hydrocarbon group may be substituted with a substituent containing a hetero atom. Examples of the substituent containing a hetero atom include —O—, —NH—, —N=, —C(=O)—O—, —S—, —S(=O)$_2$—, and —S(=O)$_2$—O—.

As $R^{91}$, examples of the hydrocarbon group having a substituent include lactone-containing cyclic groups each represented by General Formulae (a2-r-1) to (a2-r-7).

Further, as $R^{91}$, examples of the hydrocarbon group having a substituent include —SO$_2$-containing cyclic groups each represented by General Formulae (a5-r-1) to (a5-r-4); and substituted aryl groups and monovalent heterocyclic groups represented by the following chemical formulae.

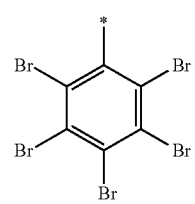

(r-ar-1)

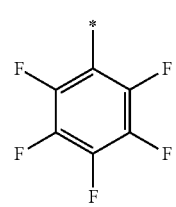

(r-ar-2)

-continued
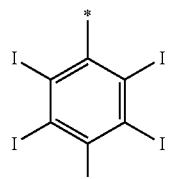 (r-ar-3)
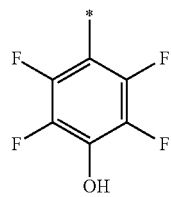 (r-ar-4)
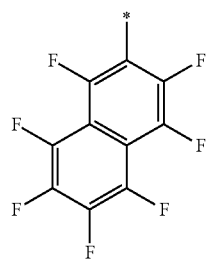 (r-ar-5)
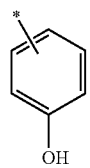 (r-ar-6)
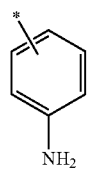 (r-ar-7)
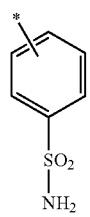 (r-ar-8)
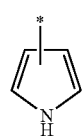 (r-hr-1)
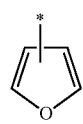 (r-hr-2)
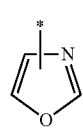 (r-hr-3)
-continued
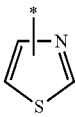 (r-hr-4)
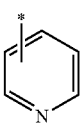 (r-hr-5)
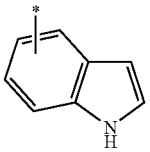 (r-hr-6)
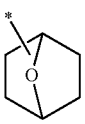 (r-hr-7)
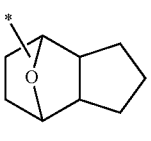 (r-hr-8)
 (r-hr-9)
 (r-hr-10)
 (r-hr-11)
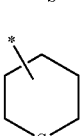 (r-hr-12)
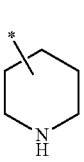 (r-hr-13)
(r-hr-14)
(r-hr-15)

(r-hr-16)

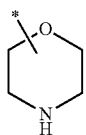

Among the constitutional units (a9), a constitutional unit represented by General Formula (a9-1-1) is preferable.

(a9-1-1)

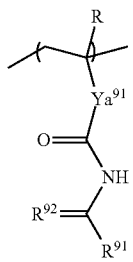

[In the formula, R has the same definition as described above, $Ya^{91}$ represents a single bond or a divalent linking group, $R^{91}$ represents a hydrocarbon group which may have a substituent, and $R^{92}$ represents an oxygen atom or a sulfur atom.]

The description for $Ya^{91}$, $R^{91}$, and R in General Formula (a9-1-1) is the same as described above. In addition, $R^{92}$ represents an oxygen atom or a sulfur atom.

Specific examples of the constitutional unit represented by General Formula (a9-1) or General Formula (a9-1-1) are shown below. In the following formulae, $R^{\alpha}$ represents a hydrogen atom, a methyl group, or a trifluoromethyl group.

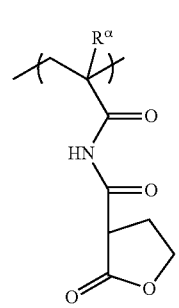
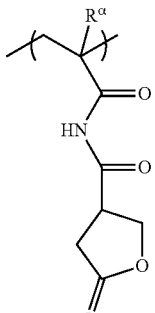
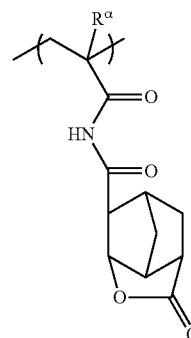
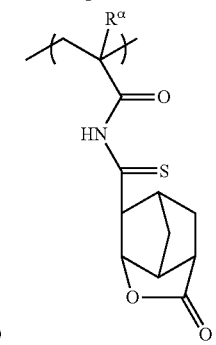

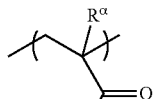
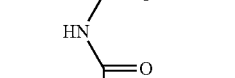
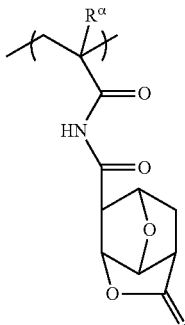
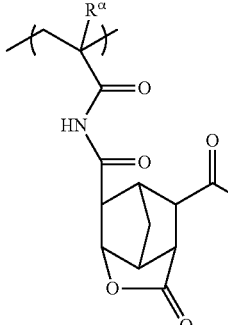
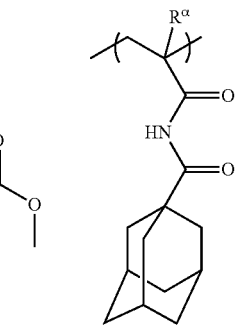
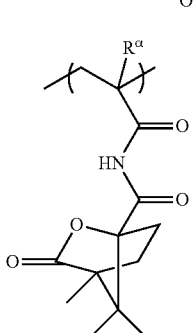
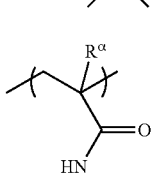
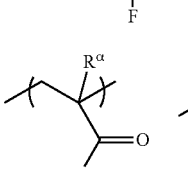
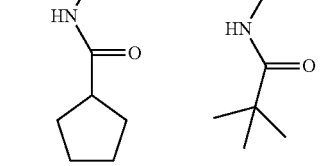
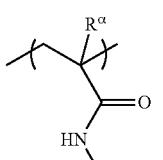
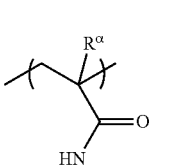
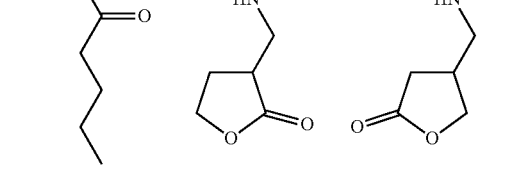

-continued

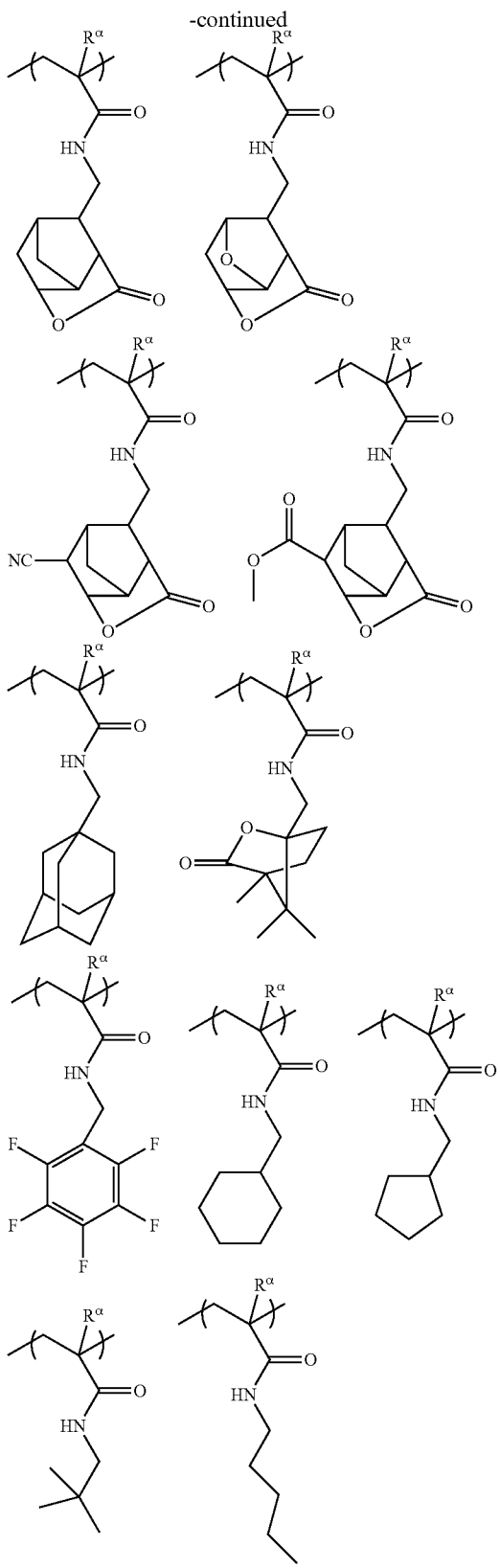

The constitutional unit (a9) contained in the component (A1) may be one kind or may be two or more kinds.

In a case where the component (A1) has the constitutional unit (a9), the proportion of the constitutional unit (a9) is preferably in a range of 0% to 40% by mole, more preferably in a range of 3% to 30% by mole, still more preferably in a range of 5% to 25% by mole, and particularly preferably in a range of 10% to 20% by mole, with respect to the total (100% by mole) of all constitutional units constituting the component (A1).

In a case where the proportion of the constitutional unit (a9) is set to be equal to or larger than the lower limit value thereof, for example, the effects of suitably adjusting the acid diffusion length, increasing the adhesiveness of the resist film to the substrate, suitably adjusting the solubility during development, and improving etching resistance are obtained. In a case where it is equal to or smaller than the upper limit value thereof, balance with other constitutional units can be obtained, and thus various lithography characteristics are improved.

Constitutional unit (a4): The constitutional unit (a4) is a constitutional unit containing an acid non-dissociable aliphatic cyclic group.

The "acid non-dissociable cyclic group" in the constitutional unit (a4) is a cyclic group that remains in the constitutional unit without being dissociated even in a case where acid acts when the acid is generated in the resist composition upon exposure (for example, when acid is generated from the component (B) described later).

Examples of the constitutional unit (a4) preferably include a constitutional unit derived from an acrylic acid ester including an acid non-dissociable aliphatic cyclic group. As the cyclic group, a large number of known ones in the related art as cyclic groups used as the resin component of a resist composition for ArF excimer laser, KrF excimer laser (preferably ArF excimer laser), or the like can be used.

It is preferable to be at least one selected from a tricyclodecyl group, an adamantyl group, a tetracyclododecyl group, an isobornyl group, and a norbornyl group, from the viewpoint of industrial availability and the like. These polycyclic groups may have, as a substituent, a linear or branched alkyl group having 1 to 5 carbon atoms.

Specific examples of the constitutional unit (a4) include constitutional units each represented by General Formulae (a4-1) to (a4-7).

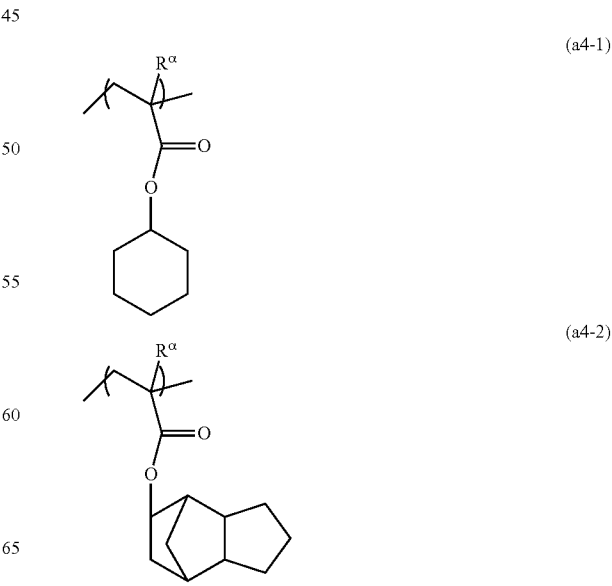

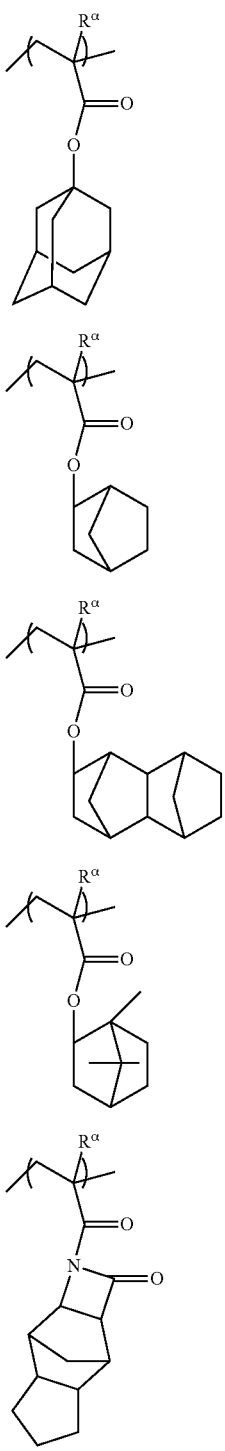

[In the formula, $R^\alpha$ has the same definition as described above.]

The component (A1) contained in the resist composition may be used alone or a combination of two or more kinds thereof may be used.

The component (A1) preferably contains a polymeric compound (A1-1) (hereinafter, also referred to as a "component (A1-1)") having a constitutional unit (a1).

Examples of the preferred component (A1-1) include a polymeric compound having a repeating structure of the constitutional unit (a1) and the constitutional unit (a10); a polymeric compound having a repeating structure of the constitutional unit (a1) and the constitutional unit (a3); a polymeric compound having a repeating structure of the constitutional unit (a1) and the constitutional unit (a2); and a polymeric compound having a repeating structure of the constitutional unit (a1) and the constitutional unit (a6).

In addition to the combination of the above two constitutional units, the constitutional units described above may be appropriately combined as a third constitutional unit or three or more constitutional units in accordance with the desired effect. Examples of the combination of three or more constitutional units include a combination of the constitutional unit (a1), the constitutional unit (a10), and the constitutional unit (a3); a combination of the constitutional unit (a1), the constitutional unit (a10), and the constitutional unit (a2); a combination of the constitutional unit (a1), the constitutional unit (a10), the constitutional unit (a2), and the constitutional unit (a3); and a combination of the constitutional unit (a1), the constitutional unit (a2), the constitutional unit (a3), and the constitutional unit (a6).

The constitutional unit (a6) is preferably a constitutional unit (a6a) or a constitutional unit (a6c). In a case where the component (A1) contains at least one of the constitutional unit (a6a) and the constitutional unit (a6c), the component (A1) is not only the base material component (A) but also an onium salt.

The component (A1) can be produced by dissolving, in a polymerization solvent, each monomer from which the constitutional unit is derived, adding thereto a radical polymerization initiator such as azobisisobutyronitrile (AIBN) or dimethyl azobisisobutyrate (for example, V-601) to carry out polymerization. Alternatively, the component (A1) can be produced by dissolving, in a polymerization solvent, a monomer from which the constitutional unit (a1) is derived and, as necessary, a precursor (a monomer in which the functional group of the following monomer is protected) of a monomer from which a constitutional unit other than the constitutional unit (a1) is derived, and adding thereto a radical polymerization initiator as described above to carry out polymerization and then carrying out a deprotection reaction. Here, a —C(CF$_3$)$_2$—OH group may be introduced into the terminal of the component (A1) during the polymerization using a chain transfer agent such as HS—CH$_2$—CH$_2$—CH$_2$—C(CF$_3$)$_2$—OH in combination. As described above, a copolymer into which a hydroxyalkyl group, formed by substitution of part of hydrogen atoms in the alkyl group with fluorine atoms, has been introduced is effective for reducing development defects and reducing line edge roughness (LER: uneven irregularities of a line side wall).

The mass average molecular weight (Mw) (based on the polystyrene equivalent value determined by gel permeation chromatography (GPC)) of the component (A1), which is not particularly limited, is preferably in a range of 1,000 to 50,000, more preferably in a range of 2,000 to 30,000, and still more preferably in a range of 3,000 to 20,000.

In a case where Mw of the component (A1) is equal to or smaller than the upper limit value of this preferred range, a resist solvent solubility sufficient to be used as a resist is exhibited. On the other hand, in a case where it is equal to or larger than the lower limit value of this preferred range, dry etching resistance and the cross-sectional shape of the resist pattern become excellent.

Further, the dispersity (Mw/Mn) of the component (A1) is not particularly limited; however, is preferably in a range of 1.0 to 4.0, more preferably in a range of 1.0 to 3.0, and particularly preferably in a range of 1.1 to 2.0. Mn represents the number average molecular weight.

• In Regard to Component (A2)

In the resist composition, a base material component (hereinafter, referred to as a "component (A2)") exhibiting changed solubility in a developing solution under action of acid, which does not correspond to the component (A1), may be used in combination as the component (A).

The component (A2) is not particularly limited and may be freely selected and used from a large number of known base material components for the chemically amplified resist composition in the related art.

As the component (A2), one kind of a polymeric compound or low molecular weight compound may be used alone, or a combination of two or more kinds thereof may be used.

The proportion of the component (A1) in the component (A) is preferably 25% by mass or more, more preferably 50% by mass or more, still more preferably 75% by mass or more, and may be 100% by mass with respect to the total mass of the component (A). In a case where the proportion is 25% by mass or more, a resist pattern having various excellent lithography characteristics such as high sensitivity, resolution, and roughness amelioration can be easily formed. Such effects are particularly remarkable in the lithography using an electron beam or EUV.

The content of the component (A) in the resist composition may be adjusted depending on the resist film thickness to be formed and the like.

«Component (B)»

The component (B) is an acid generator component that generates acid upon exposure.

The component (B) is not particularly limited, and those which have been proposed so far as an acid generator for a chemically amplified resist composition in the related art can be used.

Examples of such an acid generator are numerous and include onium salt-based acid generators such as an iodonium salt and a sulfonium salt; an oxime sulfonate-based acid generator; diazomethane-based acid generators such as bisalkyl or bisaryl sulfonyl diazomethanes and poly(bissulfonyl)diazomethanes; nitrobenzylsulfonate-based acid generators; iminosulfonate-based acid generators; and disulfone-based acid generators.

Examples of the onium salt-based acid generator include a compound represented by General Formula (b-1) (hereinafter, also referred to as a "component (b-1)"), a compound represented by General Formula (b-2) (hereinafter, also referred to as a "component (b-2)"), and a compound represented by General Formula (b-3) (hereinafter, also referred to as a "component (b-3)").

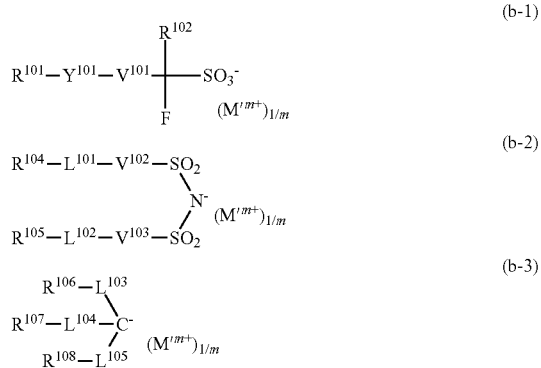

[In the formulae, $R^{101}$ and $R^{104}$ to $R^{108}$ each independently represent a cyclic group which may have a substituent, a chain-like alkyl group which may have a substituent, or a chain-like alkenyl group which may have a substituent. $R^{104}$ and $R^{105}$ may be bonded to each other to form a ring. $R^{102}$ represents a fluorine atom or a fluorinated alkyl group having 1 to 5 carbon atoms. $Y^{101}$ represents a single bond or a divalent linking group containing an oxygen atom. $V^{101}$ to $V^{103}$ each independently represents a single bond, an alkylene group, or a fluorinated alkylene group. $L^{101}$ and $L^{102}$ each independently represent a single bond or an oxygen atom. $L^{103}$ to $L^{105}$ each independently represents a single bond, —CO— or —SO$_2$—. m represents an integer of 1 or more, and $M'^{m+}$ represents an m-valent onium cation.]

{Anion Moiety}

• Anion Moiety of Component (b-1)

[In General Formula (b-1), $R^{101}$ represents a cyclic group which may have a substituent, a chain-like alkyl group which may have a substituent, or a chain-like alkenyl group which may have a substituent.

Cyclic Group which May have Substituent:

The cyclic group is preferably a cyclic hydrocarbon group, and the cyclic hydrocarbon group may be an aromatic hydrocarbon group or an aliphatic hydrocarbon group. The aliphatic hydrocarbon group indicates a hydrocarbon group that has no aromaticity. The aliphatic hydrocarbon group may be saturated or unsaturated. In general, it is preferable that the aliphatic hydrocarbon group is saturated.

The aromatic hydrocarbon group as $R^{101}$ represents a hydrocarbon group having an aromatic ring. The aromatic hydrocarbon group preferably has 3 to 30 carbon atoms, more preferably 5 to 30, still more preferably 5 to 20, particularly preferably 6 to 15, and most preferably 6 to 10. Here, the number of carbon atoms in a substituent is not included in the number of carbon atoms.

Specific examples of the aromatic ring contained in the aromatic hydrocarbon group as $R^{101}$ include benzene, fluorene, naphthalene, anthracene, phenanthrene, biphenyl, and an aromatic heterocyclic ring obtained by substituting part of carbon atoms constituting one of these aromatic rings with a hetero atom. Examples of the hetero atom in the aromatic heterocyclic rings include an oxygen atom, a sulfur atom, and a nitrogen atom.

Specific examples of the aromatic hydrocarbon group as $R^{101}$ include a group (an aryl group such as a phenyl group or a naphthyl group) obtained by removing one hydrogen atom from the above-described aromatic ring and a group (an arylalkyl group such as a benzyl group, a phenethyl group, a 1-naphthylmethyl group, a 2-naphthylmethyl group, 1-naphthylethyl group, or a 2-naphthylethyl group) obtained by substituting one hydrogen atom in the aromatic ring with an alkylene group. The alkylene group (an alkyl chain in the arylalkyl group) preferably has 1 to 4 carbon atoms, more preferably 1 or 2 carbon atoms, and particularly preferably 1 carbon atom.

Examples of the cyclic aliphatic hydrocarbon group as $R^{101}$ include aliphatic hydrocarbon groups containing a ring in the structure thereof.

Examples of the aliphatic hydrocarbon group containing a ring in the structure thereof include an alicyclic hydrocarbon group (a group obtained by removing one hydrogen atom from an aliphatic hydrocarbon ring), a group obtained by bonding the alicyclic hydrocarbon group to the terminal of a linear or branched aliphatic hydrocarbon group, and a group obtained by interposing the alicyclic hydrocarbon group is in a linear or branched aliphatic hydrocarbon group.

The alicyclic hydrocarbon group preferably has 3 to 20 carbon atoms and more preferably 3 to 12 carbon atoms.

The alicyclic hydrocarbon group may be a polycyclic group or a monocyclic group. The monocyclic alicyclic hydrocarbon group is preferably a group obtained by removing one or more hydrogen atoms from a monocycloalkane. The monocycloalkane preferably has 3 to 6 carbon atoms, and specific examples thereof include cyclopentane and cyclohexane. The polycyclic alicyclic hydrocarbon group is preferably a group obtained by removing one or more hydrogen atoms from a polycycloalkane, and the polycycloalkane preferably has 7 to 30 carbon atoms. Among the above, a polycycloalkane having a bridged ring-based polycyclic skeleton, such as adamantane, norbornane, isobornane, tricyclodecane, or tetracyclododecane, and a polycycloalkane having a condensed ring-based polycyclic skeleton, such as a cyclic group having a steroid skeleton is more preferable.

Among them, the cyclic aliphatic hydrocarbon group as $R^{101}$ is preferably a group obtained by removing one or more hydrogen atoms from a monocycloalkane or a polycycloalkane, more preferably a group obtained by removing one hydrogen atom from a polycycloalkane, particularly preferably an adamantyl group or a norbornyl group, and most preferably an adamantyl group.

The linear or branched aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and most preferably 1 to 3 carbon atoms.

The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group is preferably a branched alkylene group, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. The alkyl group in the alkylalkylene group is preferably a linear alkyl group having 1 to 5 carbon atoms.

The cyclic hydrocarbon group as $R^{101}$ may contain a hetero atom such as a heterocyclic ring. Specific examples thereof include lactone-containing cyclic groups each represented by General Formulae (a02-r1-1), (a02-r1-2), and (a2-r-2) to (a2-r-7) described above, —$SO_2$-containing cyclic groups each represented by General Formulae (a5-r-1) to (a5-r-4), and other heterocyclic groups each represented by Chemical Formulae (r-hr-1) to (r-hr-16).

Examples of the substituent of the cyclic group as $R^{101}$ include an alkyl group, an alkoxy group, a halogen atom, a halogenated alkyl group, a hydroxy group, a carbonyl group, and a nitro group.

The alkyl group as the substituent is preferably an alkyl group having 1 to 12 carbon atoms, and a methyl group, an ethyl group, a propyl group, an n-butyl group, or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom for the substituent include a fluorine atom, a chlorine atom, a bromine atom, and an iodine atom, and a fluorine atom is preferable.

Examples of the above-described halogenated alkyl group as the substituent include a group obtained by substituting part or all hydrogen atoms in an alkyl group having 1 to 5 carbon atoms such as a methyl group, an ethyl group, a propyl group, an n-butyl group, or a tert-butyl group, with the above-described halogen atom.

The carbonyl group as the substituent is a group that substitutes a methylene group (—$CH_2$—) constituting the cyclic hydrocarbon group.

Chain-Like Alkyl Group which May have Substituent:

The chain-like alkyl group as $R^{101}$ may be linear or branched.

The linear alkyl group preferably has 1 to 20 carbon atoms, more preferably 1 to 15 carbon atoms, and most preferably 1 to 10 carbon atoms. Specific examples thereof include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecil group, an icosyl group, a henicosyl group, and a docosyl group.

The branched alkyl group preferably has 3 to 20 carbon atoms, more preferably 3 to 15 carbon atoms, and most preferably 3 to 10 carbon atoms. Specific examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Chain-Like Alkenyl Group which May have Substituent:

A chain-like alkenyl group as $R^{101}$ may be linear or branched, and the chain-like alkenyl group preferably has 2 to 10 carbon atoms, more preferably 2 to 5 carbon atoms, still more preferably 2 to 4 carbon atoms, and particularly preferably 3 carbon atoms. Examples of the linear alkenyl group include a vinyl group, a propenyl group (an allyl group), and a butynyl group. Examples of the branched alkenyl group include a 1-methylvinyl group, a 2-methylvinyl group, a 1-methylpropenyl group, and a 2-methylpropenyl group.

Among the above, the chain-like alkenyl group is preferably a linear alkenyl group, more preferably a vinyl group or a propenyl group, and particularly preferably a vinyl group.

Examples of the substituent in the chain-like alkyl group or alkenyl group as $R^{101}$, an alkoxy group, a halogen atom, a halogenated alkyl group, a hydroxy group, a carbonyl group, a nitro group, an amino group, a cyclic group as $R^{101}$ or the like may be used.

Among the above examples, $R^{101}$ is preferably a cyclic group which may have a substituent and more preferably a cyclic hydrocarbon group which may have a substituent. The substituent is preferably a hydroxy group, a carbonyl group, a nitro group, or an amino group, and among the above, a hydroxy group is more preferable since it is easily distributed on the substrate side in the resist film.

More specifically, the cyclic hydrocarbon group is preferably a phenyl group; a naphthyl group; a group obtained by removing one or more hydrogen atoms from a polycycloalkane; lactone-containing cyclic groups each represented by General Formulae (a02-r1-1), (a02-r1-2), and (a2-r-2) to (a2-r-7) described above; and —SO$_2$-containing cyclic groups each represented by General Formulae (a5-r-1) to (a5-r-4).

In General Formula (b-1), $Y^{101}$ represents a single bond or a divalent linking group containing an oxygen atom.

In a case where $Y^{101}$ represents a divalent linking group containing an oxygen atom, $Y^{101}$ may contain an atom other than the oxygen atom. Examples of the atom other than the oxygen atom include a carbon atom, a hydrogen atom, a sulfur atom, and a nitrogen atom.

Examples of divalent linking groups containing an oxygen atom include non-hydrocarbon-based oxygen atom-containing linking groups such as an oxygen atom (an ether bond; —O—), an ester bond (—C(=O)—O—), an oxycarbonyl group (—O—C(=O)—), an amide bond (—C(=O)—NH—), a carbonyl group (—C(=O)—), or a carbonate bond (—O—C(=O)—O—); and combinations of the above-described non-hydrocarbon-based oxygen atom-containing linking groups with an alkylene group. Furthermore, a sulfonyl group (—SO$_2$—) may be linked to the combination. Examples of such a divalent linking group containing an oxygen atom include linking groups each represented by General Formulae (y-al-1) to (y-al-7) shown below.

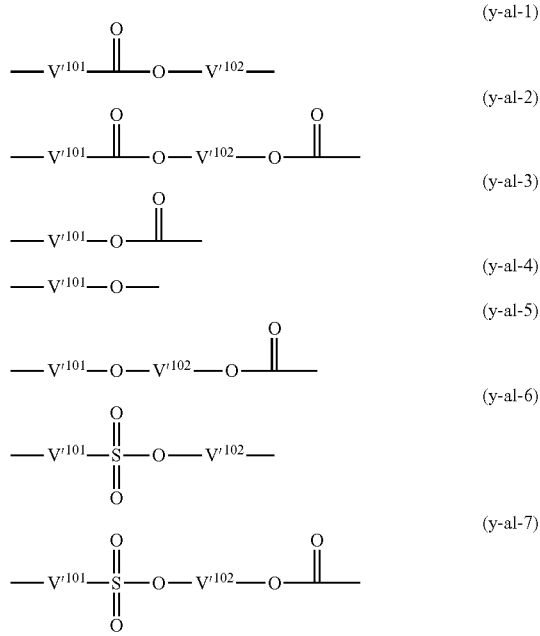

[In the formulae, $V'^{101}$ represents a single bond or an alkylene group having 1 to 5 carbon atoms, and $V'^{102}$ represents a divalent saturated hydrocarbon group having 1 to 30 carbon atoms.]

The divalent saturated hydrocarbon group as $V'^{102}$ is preferably an alkylene group having 1 to 30 carbon atoms, more preferably an alkylene group having 1 to 10 carbon atoms, and still more preferably an alkylene group having 1 to 5 carbon atoms.

The alkylene group as $V'^{101}$ and $V'^{102}$ may be a linear alkylene group or a branched alkylene group, and a linear alkylene group is preferable.

Specific examples of the alkylene group as $V'^{101}$ and $V'^{102}$ include a methylene group [—CH$_2$—]; an alkylmethylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, or —C(CH$_2$CH$_3$)$_2$—; an ethylene group [—CH$_2$CH$_2$—]; an alkylethylene group such as —CH(CH$_3$)CH$_2$—, —CH(CH$_3$)CH(CH$_3$)—, —C(CH$_3$)$_2$CH$_2$—, or —CH(CH$_2$CH$_3$)CH$_2$—; a trimethylene group (n-propylene group) [—CH$_2$CH$_2$CH$_2$—]; an alkyltrimethylene group such as —CH(CH$_3$)CH$_2$CH$_2$— or —CH$_2$CH(CH$_3$)CH$_2$—; a tetramethylene group [—CH$_2$CH$_2$CH$_2$CH$_2$—]; an alkyltetramethylene group such as —CH(CH$_3$)CH$_2$CH$_2$CH$_2$—, or —CH$_2$CH(CH$_3$)CH$_2$CH$_2$—; and a pentamethylene group [—CH$_2$CH$_2$CH$_2$CH$_2$CH$_2$—].

Further, part of methylene groups in the alkylene group as $V'^{101}$ and $V'^{102}$ may be substituted with a divalent aliphatic cyclic group having 5 to 10 carbon atoms. The aliphatic cyclic group is preferably a divalent group in which one hydrogen atom has been removed from the cyclic aliphatic hydrocarbon group (a monocyclic aliphatic hydrocarbon group or a polycyclic aliphatic hydrocarbon group) as $Ra'^3$ in General Formula (a1-r-1), and a cyclohexylene group, a 1,5-adamantylene group, or a 2,6-adamantylene group is more preferable.

$Y^{101}$ preferably represents a divalent linking group containing an ester bond or a divalent linking group containing an ether bond and more preferably linking groups each represented by General Formulae (y-al-1) to (y-al-5).

In General Formula (b-1), $V^{101}$ represents a single bond, an alkylene group, or a fluorinated alkylene group. The alkylene group and the fluorinated alkylene group as $V^{101}$ preferably have 1 to 4 carbon atoms. Examples of the fluorinated alkylene group as $V^{101}$ include a group obtained by substituting part or all hydrogen atoms in the alkylene group as $V^{101}$ with a fluorine atom. Among them, $V^{101}$ is preferably a single bond or a fluorinated alkylene group having 1 to 4 carbon atoms.

In General Formula (b-1), $R^{102}$ represents a fluorine atom or a fluorinated alkyl group having 1 to 5 carbon atoms. $R^{102}$ is preferably a fluorine atom or a perfluoroalkyl group having 1 to 5 carbon atoms and more preferably a fluorine atom.

In a case where $Y^{101}$ represents a single bond, specific examples of the anion moiety of the component (b-1) include a fluorinated alkylsulfonate anion such as a trifluoromethanesulfonate anion or a perfluorobutanesulfonate anion; and in a case where $Y^{101}$ represents a divalent linking group containing an oxygen atom, specific examples thereof include an anion represented by any one of General Formulae (an-1) to (an-3) shown below.

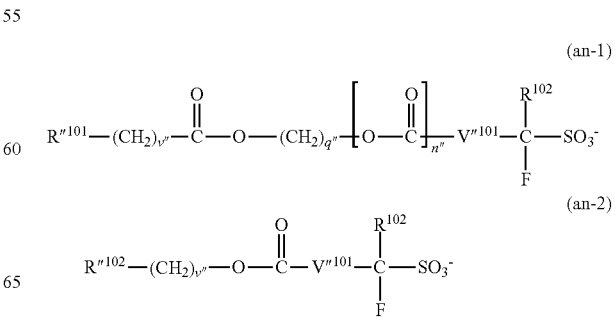

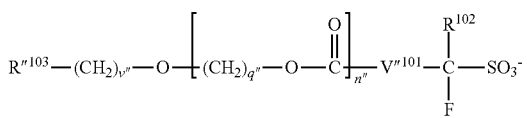

(an-3)

[In the formula, $R'''^{101}$ represents an aliphatic cyclic group which may have a substituent, groups each represented by General Formula (r-hr-1) to (r-hr-6), or a chain-like alkyl group which may have a substituent. $R'''^{102}$ is an aliphatic cyclic group which may have a substituent, lactone-containing cyclic groups each represented by General Formulae (a02-r1-1), (a02-r1-2), and (a2-r-2) to (a2-r-7) described above, or —SO$_2$-containing cyclic groups each represented by General Formulae (a5-r-1) to (a5-r-4). $R'''^{103}$ represents an aromatic cyclic group which may have a substituent, an aliphatic cyclic group which may have a substituent, or a chain-like alkenyl group which may have a substituent. $V'''^{101}$ represents a single bond, an alkylene group having 1 to 4 carbon atoms, or a fluorinated alkylene group having 1 to 4 carbon atoms. $R^{102}$ represents a fluorine atom or a fluorinated alkyl group having 1 to 5 carbon atoms. Each v" independently represents an integer in a range of 0 to 3, each q" independently represents an integer in a range of 1 to 20, and n" represents 0 or 1.]

As the aliphatic cyclic group as $R'''^{101}$ and $R'''^{103}$ which may have a substituent, the same groups as the cyclic aliphatic hydrocarbon group as $R^{101}$ described above are preferable. Examples of the substituent include the same one as the substituent which may be substituted for a cyclic aliphatic hydrocarbon group as $R^{101}$. Among these, the substituent is preferably a hydroxy group, a carbonyl group, a nitro group, or an amino group, and among the above, a hydroxy group is more preferable since it is easily distributed on the substrate side in the resist film.

The aromatic cyclic group which may have a substituent, as $R'''^{103}$, is preferably the group exemplified as the aromatic hydrocarbon group for the cyclic hydrocarbon group, as $R^{101}$. Examples of the substituent include the same one as the substituent which may be substituted for the aromatic hydrocarbon group as $R^{101}$.

As the chain-like alkyl group as $R'''^{101}$ which may have a substituent, the same groups exemplified as the chain-like alkyl groups represented by $R^{101}$ are preferable. As the chain-like alkenyl group as $R'''^{103}$ which may have a substituent, the same groups exemplified as the chain-like alkenyl groups represented by $R^{101}$ are preferable.

In General Formulae (an-1) to (an-3), $V'''^{101}$ represents a single bond, an alkylene group having 1 to 4 carbon atoms, or a fluorinated alkylene group having 1 to 4 carbon atoms. $V'''^{101}$ is preferably a single bond, an alkylene group (a methylene group) having 1 carbon atom, or a fluorinated alkylene group having 1 to 3 carbon atoms.

In General Formulae (an-1) to (an-3), $R^{102}$ represents a fluorine atom or a fluorinated alkyl group having 1 to 5 carbon atoms. $R^{102}$ is preferably a perfluoroalkyl group having 1 to 5 carbon atoms or a fluorine atom and more preferably a fluorine atom.

In General Formulae (an-1) to (an-3), v" represents an integer of 0 to 3 and preferably represents 0 or 1. q" represents an integer of 1 to 20, preferably represents an integer of 1 to 10, more preferably an integer of 1 to 5, still more preferably 1, 2, or 3, and particularly preferably 1 or 2. n" represents 0 or 1.

• Anion Moiety of Component (b-2)

In General Formula (b-2), $R^{104}$ and $R^{105}$ each independently represent a cyclic group which may have a substituent, a chain-like alkyl group which may have a substituent or a chain-like alkenyl group which may have a substituent, and examples of each of them include the same one as $R^{101}$ in General Formula (b-1). However, $R^{104}$ and $R^{105}$ may be bonded to each other to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. It is preferable that the number of carbon atoms in the chain-like alkyl group as $R^{104}$ and $R^{105}$ is small since the solubility in a resist solvent is also excellent in this range of the number of carbon atoms. Further, in the chain-like alkyl group as $R^{104}$ and $R^{105}$, it is preferable that the number of hydrogen atoms substituted with a fluorine atom is large since the acid strength increases and the transparency to high energy radiation of 200 nm or less or an electron beam is improved. The proportion of fluorine atoms in the chain-like alkyl group, that is, the fluorination rate is preferably in a range of 70% to 100% and more preferably in a range of 90% to 100%, and it is most preferable that the chain-like alkyl group is a perfluoroalkyl group in which all hydrogen atoms is substituted with a fluorine atom.

In General Formula (b-2), $V^{102}$ and $V^{103}$ each independently represent a single bond, an alkylene group, or a fluorinated alkylene group, and examples thereof include the same one as $V^{101}$ in General Formula (b-1).

In General Formula (b-2), $L^{101}$ and $L^{102}$ each independently represent a single bond or an oxygen atom.

• Anion Moiety of Component (b-3)

In General Formula (b-3), $R^{106}$ to $R^{108}$ each independently represents a cyclic group which may have a substituent or a chain-like alkyl group which may have a substituent or a chain-like alkenyl group which may have a substituent, and examples each of them include the same one as $R^{101}$ in General Formula (b-1).

$L^{103}$ to $L^{105}$ each independently represents a single bond, —CO—, or —SO$_2$—.

{Cation Moiety}

In Formulae (b-1), (b-2), and (b-3), m represents an integer of 1 or more. $M^{m+}$ represents an m-valent onium cation and suitably includes a sulfonium cation and an iodonium cation. Examples thereof include organic cations each represented by General Formulae (ca-1) to (ca-4).

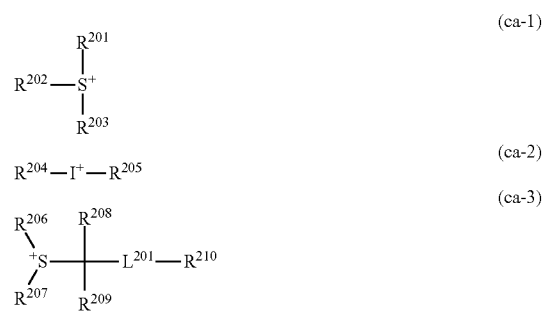

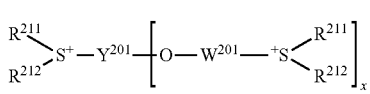

(ca-4)

[In the formula, $R^{201}$ to $R^{207}$, $R^{211}$, and $R^{212}$ each independently represents an aryl group which may have a substituent, an alkyl group which may have a substituent, or an alkenyl group which may have a substituent. $R^{201}$ to $R^{203}$, $R^{206}$ and $R^{207}$, and $R^{211}$ and $R^{212}$ may each be bonded to each other to form a ring together with the sulfur atoms in the formulae. $R^{208}$ to $R^{209}$ may each independently represent a hydrogen atom or an alkyl group having 1 to 5 carbon atoms or may be bonded to each other to form a ring together with a sulfur atom in the formula. $R^{210}$ represents an aryl group which may have a substituent, an alkyl group which may have a substituent, an alkenyl group which may have a substituent, or a —$SO_2$-containing cyclic group which may have a substituent. $L^{201}$ represents —C(=O)— or —C(=O)—O—. A plurality of $Y^{201}$'s each independently represent an arylene group, an alkylene group, or an alkenylene group. x represents 1 or 2. $W^{201}$ represents an (x+1)-valent linking group.

Examples of the aryl group as $R^{201}$ to $R^{207}$, $R^{211}$, and $R^{212}$ include an aryl group having 6 to 20 carbon atoms, and a phenyl group or a naphthyl group is preferable.

The alkyl group as $R^{201}$ to $R^{207}$, $R^{211}$, and $R^{212}$ is preferably a chain-like or cyclic alkyl group having 1 to 30 carbon atoms.

The alkenyl group as $R^{201}$ to $R^{207}$, $R^{211}$, and $R^{212}$ preferably has 2 to 10 carbon atoms.

Examples of the substituent which may be contained in $R^{201}$ to $R^{207}$, $R^{211}$, and $R^{212}$ include an alkyl group, a halogen atom, a halogenated alkyl group, a carbonyl group, a cyano group, an amino group, an aryl group, and groups each represented by General Formulae (ca-r-1) to (ca-r-7) shown above.

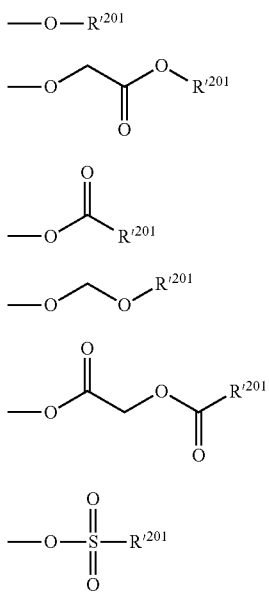

[ca-r-1]
[ca-r-2]
[ca-r-3]
[ca-r-4]
[ca-r-5]
[ca-r-6]

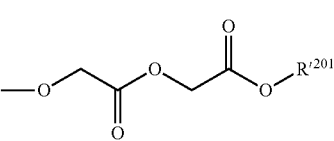

[ca-r-7]

[In the formulae, each $R'^{201}$ independently represents a hydrogen atom, a cyclic group which may have a substituent, a chain-like alkyl group which may have a substituent, or a chain-like alkenyl group which may have a substituent.]

Examples of the cyclic group which may have a substituent, the chain-like alkyl group which may have a substituent, and the chain-like alkenyl group which may have a substituent as $R'^{201}$ are the same as those represented by $R^{101}$ in Formula (b-1) described later, and examples of the cyclic group which may have a substituent and the chain-like alkyl group which may have a substituent include the same one as the acid dissociable group represented by Formula (a1-r-2) described above.

$R^{201}$ to $R^{203}$, $R^{206}$ and $R^{207}$, and $R^{211}$ and $R^{212}$ are bonded to each other to form a ring with a sulfur atom in the formula, these groups may be bonded to each other via a hetero atom such as a sulfur atom, an oxygen atom or a nitrogen atom, or a functional group such as a carbonyl group, —SO—, —$SO_2$—, —$SO_3$—, —COO—, —CONH— or —N($R_N$)- (here, $R_N$ represents an alkyl group having 1 to 5 carbon atoms). Regarding the ring to be formed, a ring containing a sulfur atom in a formula in the ring skeleton thereof is preferably a 3-membered to 10-membered ring and particularly preferably a 5-membered to 7-membered ring containing a sulfur atom. Specific examples of the ring to be formed include a thiophene ring, a thiazole ring, a benzothiophene ring, a benzothiophene ring, a thianthrene ring, a dibenzothiophene ring, a 9H-thioxanthene ring, a thioxanthone ring, a thianthrene ring, a phenoxathiin ring, a tetrahydrothiophenium ring, and a tetrahydrothiopyranium ring.

$R^{208}$ and $R^{209}$ each independently represent a hydrogen atom or an alkyl group having 1 to 5 carbon atoms and are preferably a hydrogen atom or an alkyl group having 1 to 3 carbon atoms. In a case where $R^{208}$ and $R^{209}$ each independently represent an alkyl group, $R^{208}$ and $R^{209}$ may be bonded to each other to form a ring.

$R^{210}$ represents an aryl group which may have a substituent, an alkyl group which may have a substituent, an alkenyl group which may have a substituent, or a —$SO_2$-containing cyclic group which may have a substituent.

Examples of the aryl group as $R^{210}$ include an unsubstituted aryl group having 6 to 20 carbon atoms, and a phenyl group or a naphthyl group is preferable.

The alkyl group as $R^{210}$, a chain-like or cyclic alkyl group having 1 to 30 carbon atoms is preferable.

The alkenyl group as $R^{210}$ preferably has 2 to 10 carbon atoms. The —$SO_2$-containing cyclic group which may have a substituent, as $R^{210}$, is preferably a "—$SO_2$-containing polycyclic group", and more preferably a group represented by General Formula (a5-r-1).

Each $Y^{201}$ independently represents an arylene group, an alkylene group, or an alkenylene group.

Examples of the arylene group as $Y^{201}$ include groups obtained by removing one hydrogen atom from an aryl group mentioned as the aromatic hydrocarbon group represented by $R^{101}$ in General Formula (b-1) described later.

Examples of the alkylene group and alkenylene group as $Y^{201}$ include groups obtained by removing one hydrogen atom from the chain-like alkyl group or the chain-like alkenyl group as $R^{101}$ in General Formula (b-1) described later.

In General Formula (ca-4), x represents 1 or 2.

$W^{201}$ represents an (x+1)-valent linking group, that is, a divalent or trivalent linking group.

The divalent linking group as $W^{201}$ is preferably a divalent hydrocarbon group which may have a substituent, and as examples thereof include the same divalent hydrocarbon group, which may have a substituent, as $Ya^{21}$ in General Formula (a2-1) described above. The divalent linking group as $W^{201}$ may be linear, branched, or cyclic and is preferably cyclic. Among these, a group obtained by combining two carbonyl groups at both terminals of an arylene group is preferable. Examples of the arylene group include a phenylene group and a naphthylene group, and a phenylene group is particularly preferable.

Examples of the trivalent linking group as $W^{201}$ include a group obtained by removing one hydrogen atom from the above-described divalent linking group as $W^{201}$ and a group obtained by bonding the divalent linking group to another divalent linking group. The trivalent linking group as W is preferably a group obtained by bonding two carbonyl groups to an arylene group.

Specific examples of the suitable cation represented by General Formula (ca-1) include cations each represented by Chemical Formulae (ca-1-1) to (ca-1-78) and (ca-1-101) to (ca-1-149) shown below.

In the following chemical formulae, g1 indicates the number of repetitions, and g1 can be an integer in a range of 1 to 5. g2 indicates the number of repetitions, and g2 represents an integer in a range of 0 to 20. g3 indicates the number of repetitions, and g3 represents an integer in a range of 0 to 20.

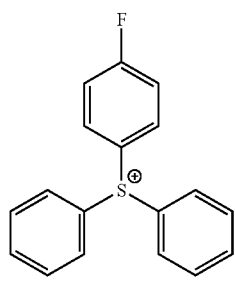
(ca-1-1)

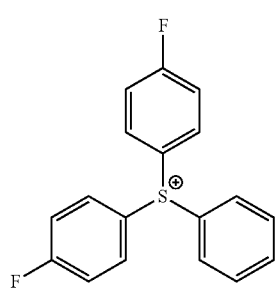
(ca-1-2)

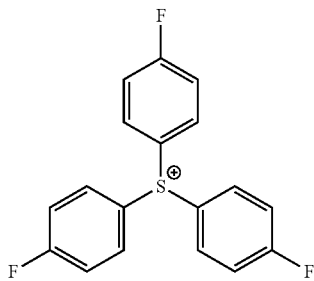
(ca-1-3)

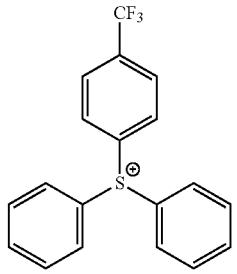
(ca-1-4)

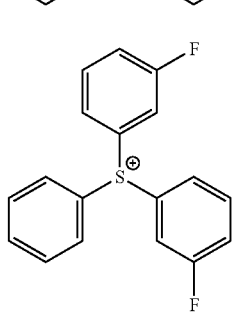
(ca-1-5)

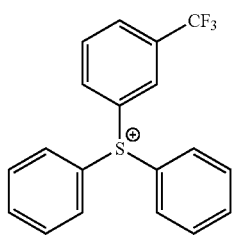
(ca-1-6)

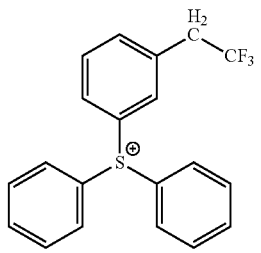
(ca-1-7)

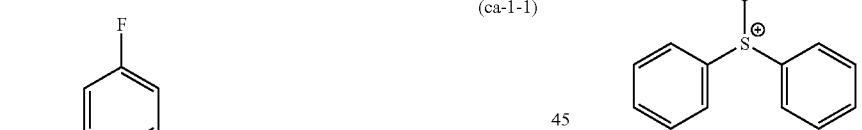
(ca-1-8)

-continued
(ca-1-9)
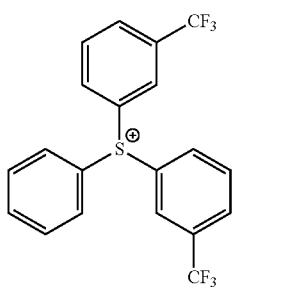
(ca-1-10)
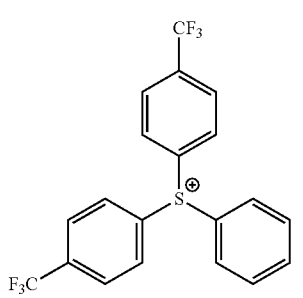
(ca-1-11)
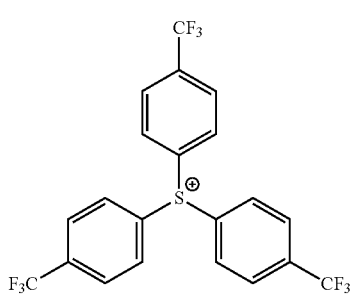
(ca-1-12)
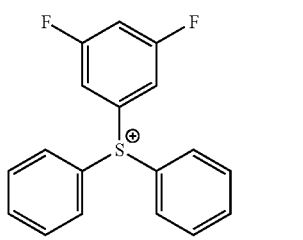
(ca-1-13)
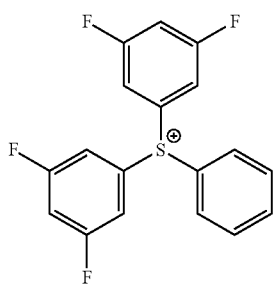
-continued
(ca-1-14)
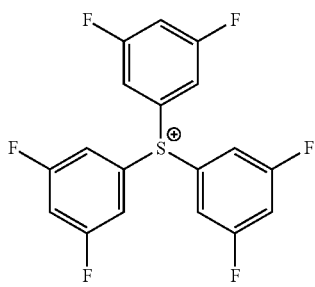
(ca-1-15)
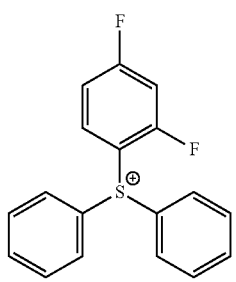
(ca-1-16)
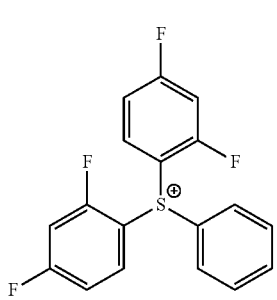
(ca-1-17)
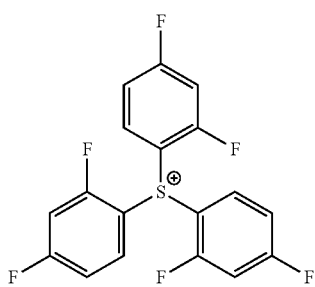
(ca-1-18)
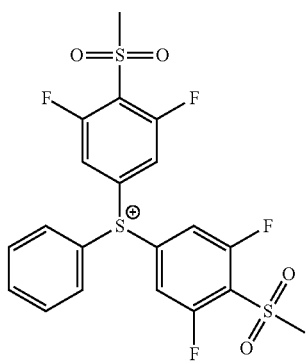

-continued
(ca-1-19)
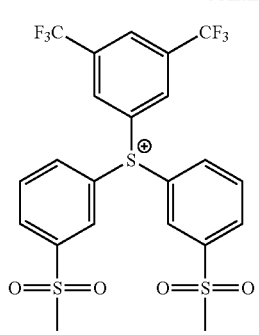
(ca-1-20)
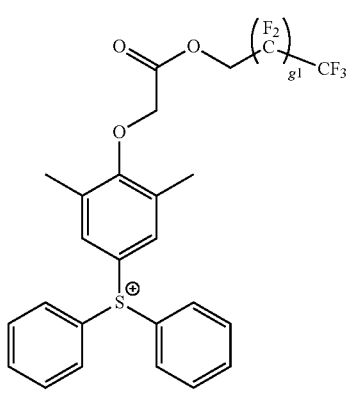
(ca-1-21)
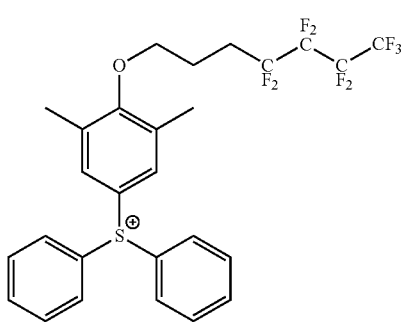
(ca-1-22)
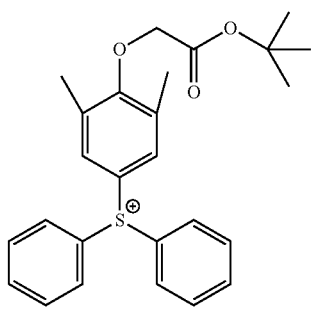
-continued
(ca-1-23)
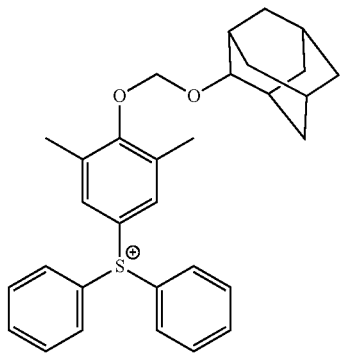
(ca-1-24)
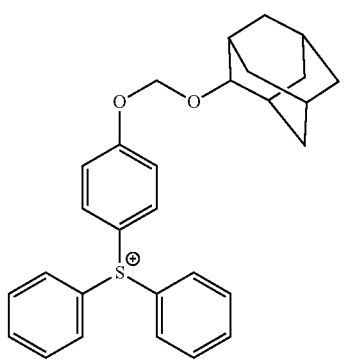
(ca-1-25)
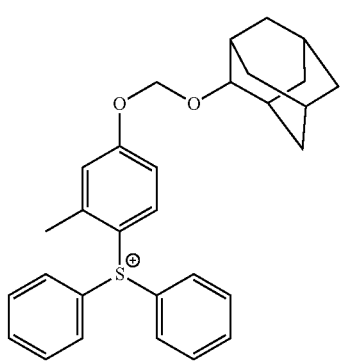
(ca-1-26)

(ca-1-27)
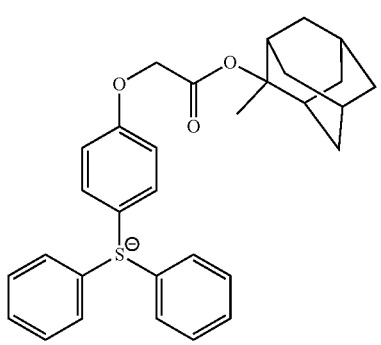
(ca-1-28)
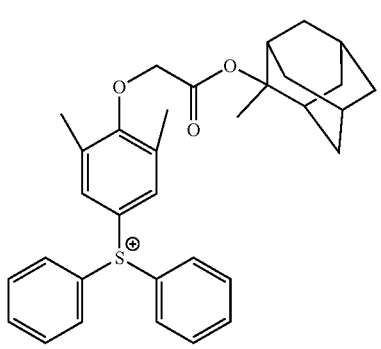
(ca-1-29)
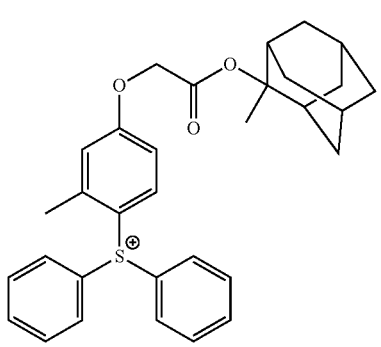
(ca-1-30)
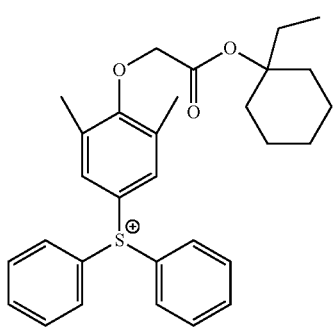
(c1-1-31)
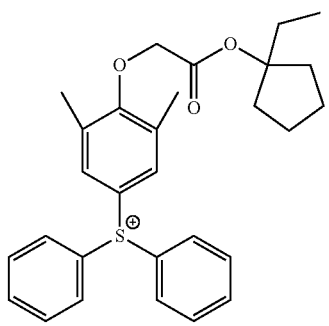
(ca-1-32)
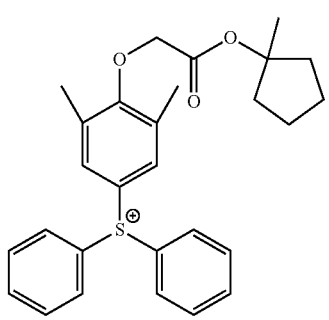
(ca-1-33)
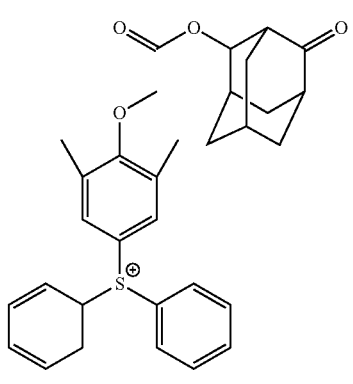
(ca-1-34)
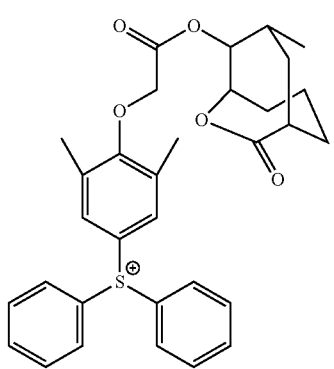

(ca-1-35)
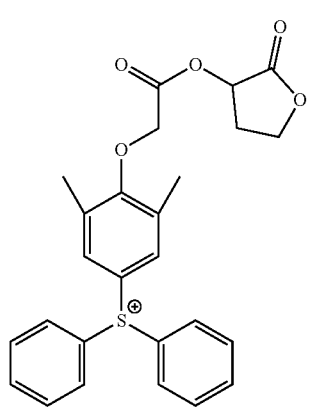
(ca-1-39)
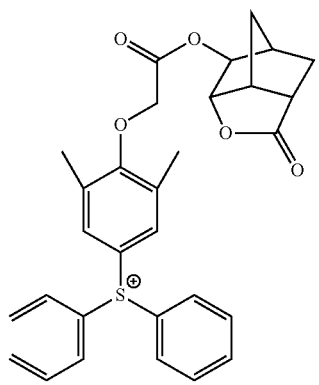
(ca-1-36)
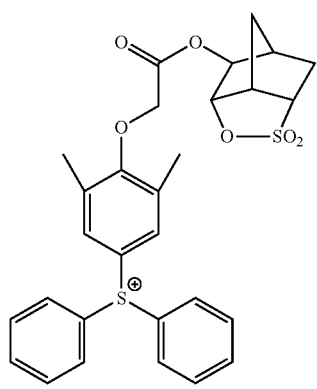
(ca-1-40)
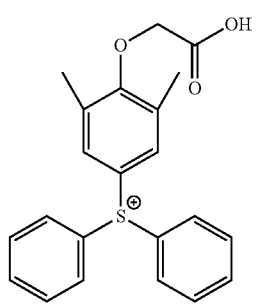
(ca-1-37)
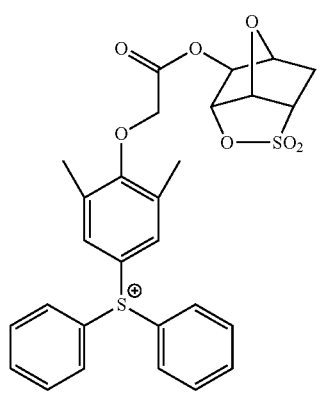
(ca-1-41)
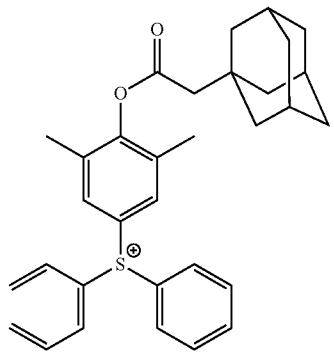
(ca-1-38)
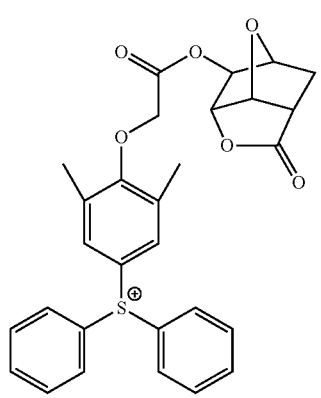
(ca-1-42)
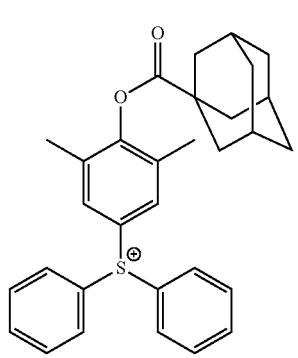

-continued
(ca-1-43)
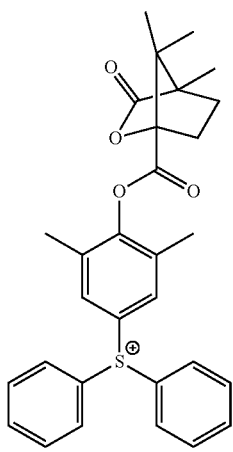
(ca-1-44)
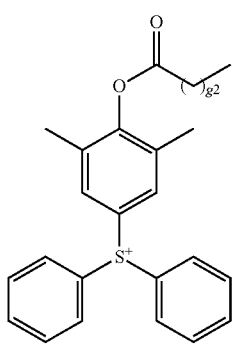
(ca-1-45)
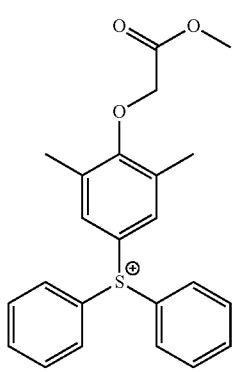
(ca-1-46)
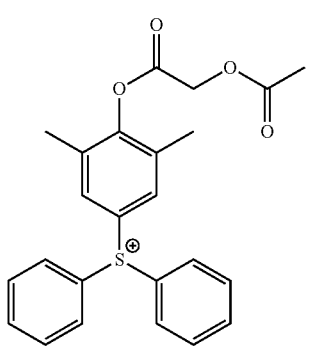
-continued
(ca-1-47)
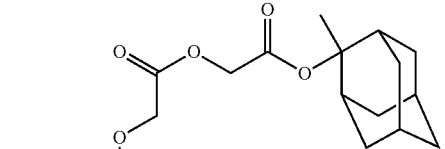
(ca-1-48)
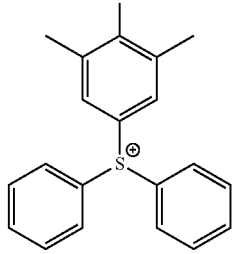
(ca-1-49)
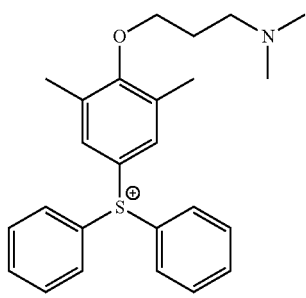
(ca-1-50)
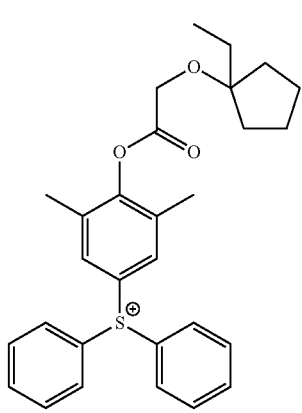

(ca-1-51)
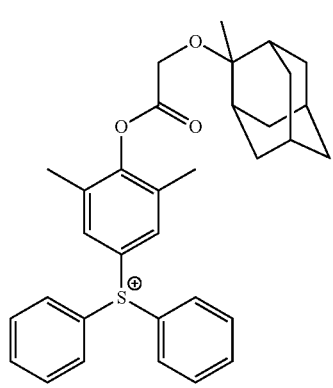
(ca-1-52)
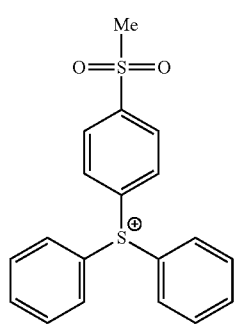
(ca-1-53)
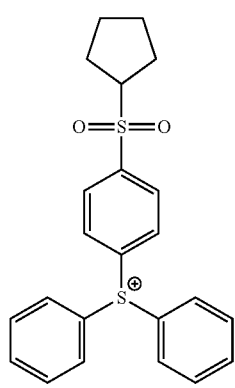
(ca-1-54)
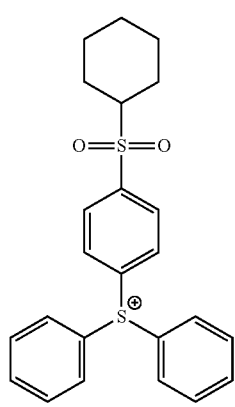
(ca-1-55)
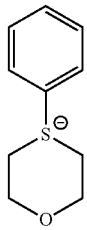
(ca-1-56)
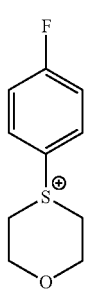
(ca-1-57)
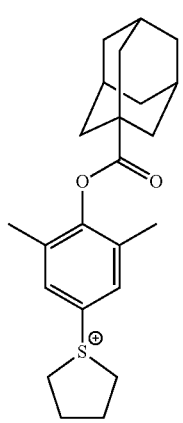
(ca-1-58)
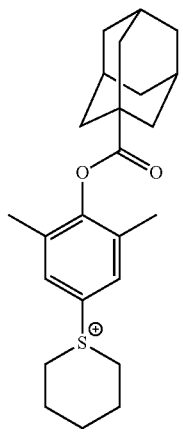

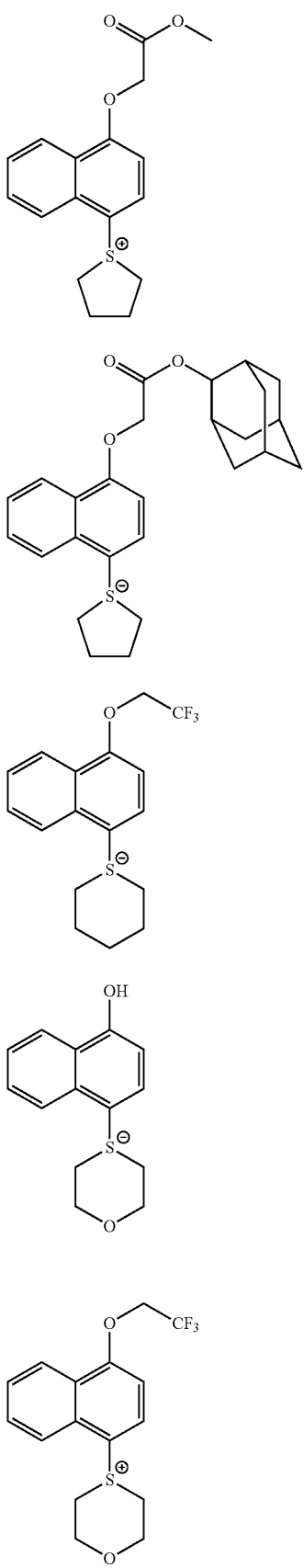
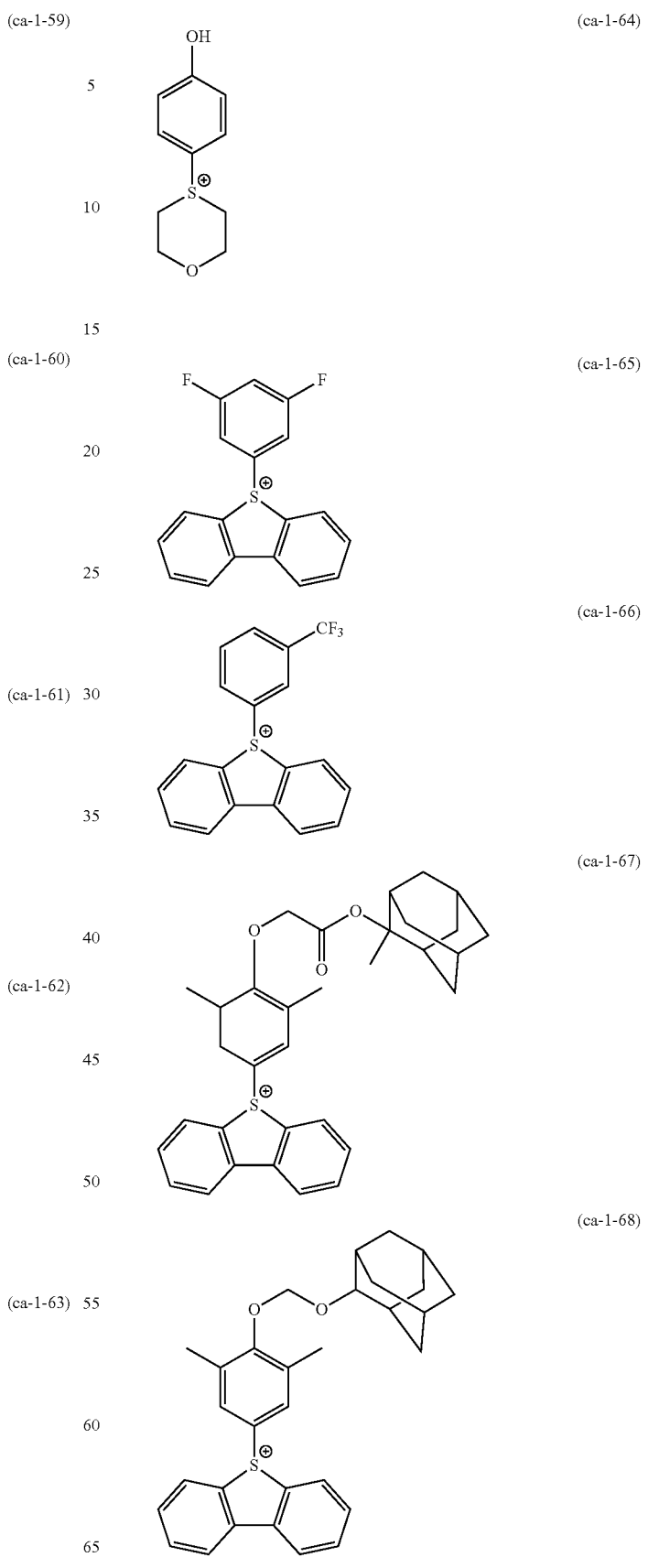

(ca-1-69) 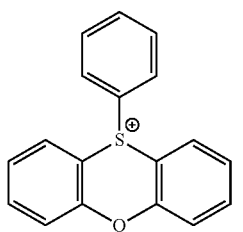
(ca-1-70) 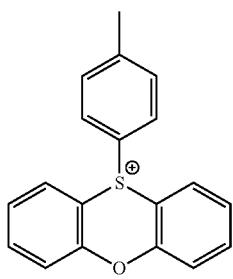
(ca-1-71) 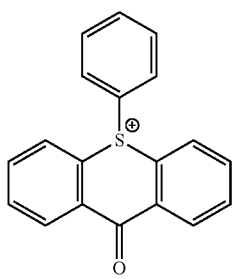
(ca-1-72) 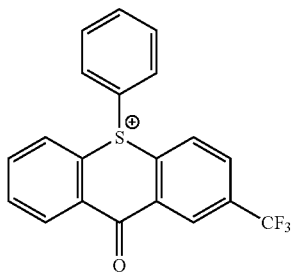
(ca-1-73) 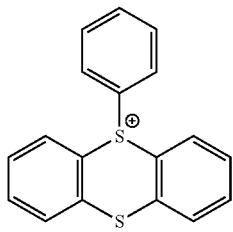
(ca-1-74) 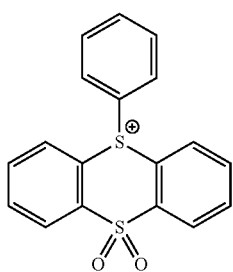
(ca-1-75) 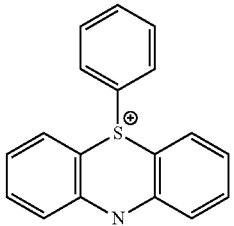
(ca-1-76) 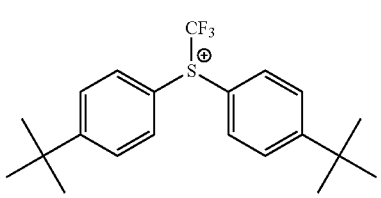
(ca-1-77) 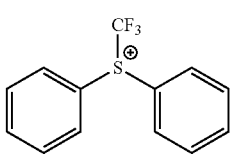
(ca-1-78) 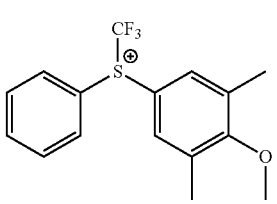
(ca-1-101) 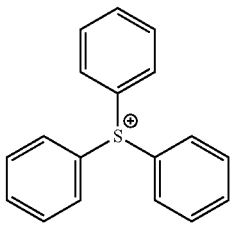
(ca-1-102) 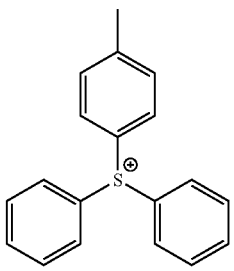
(ca-1-103) 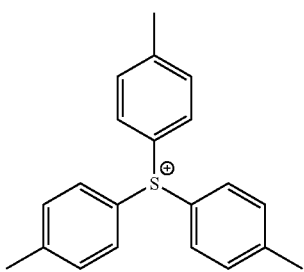

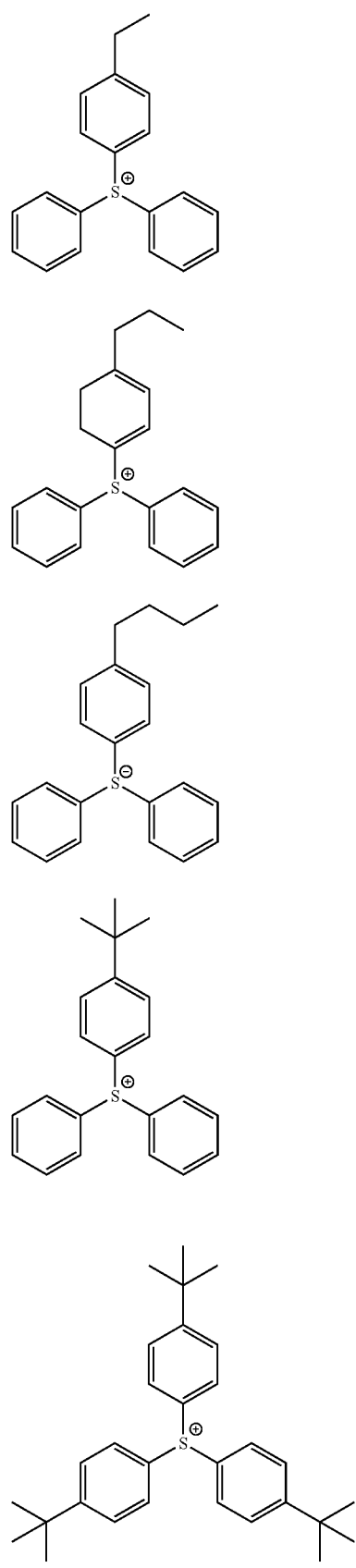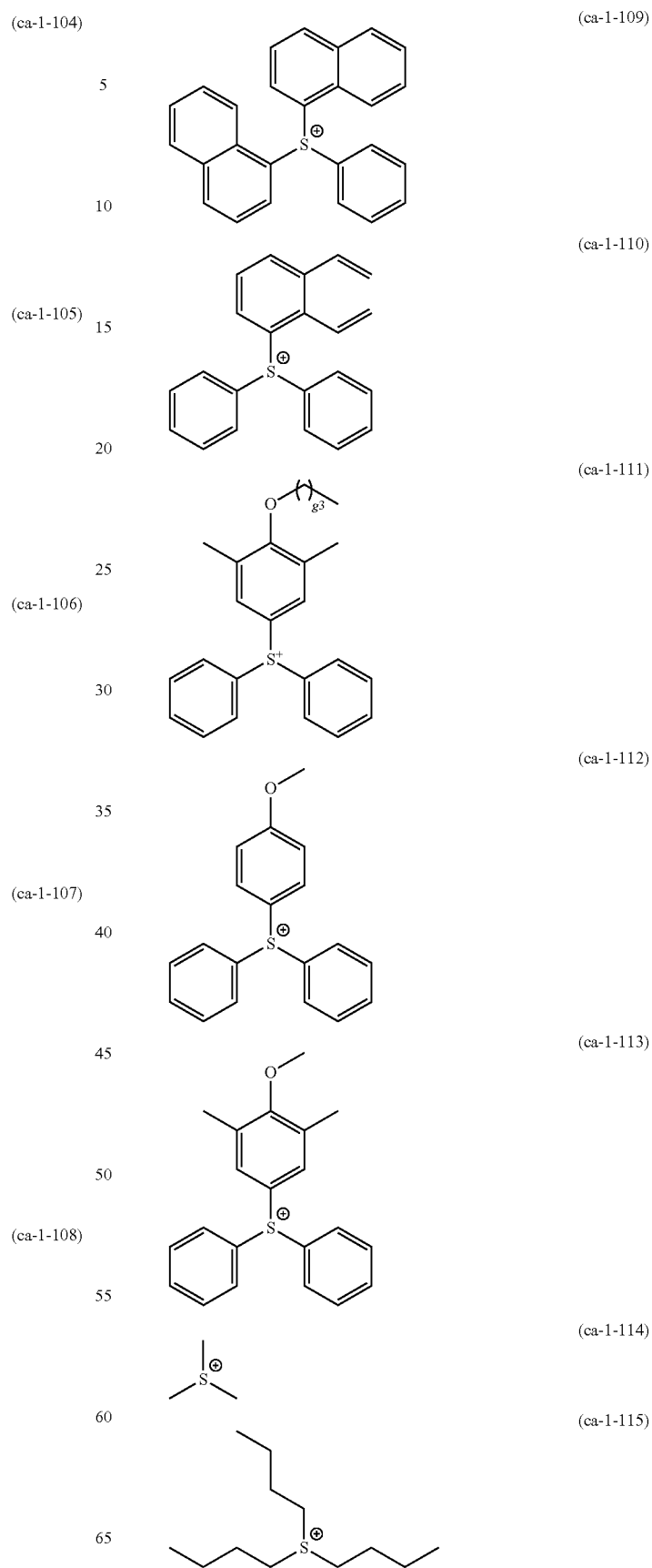

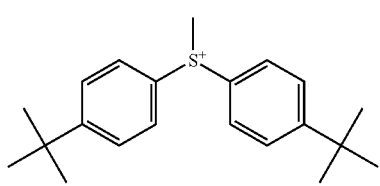
(ca-1-116)
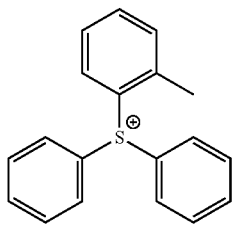
(ca-1-117)
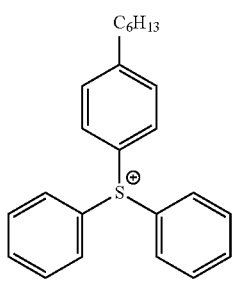
(ca-1-118)
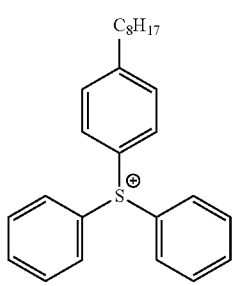
(ca-1-119)
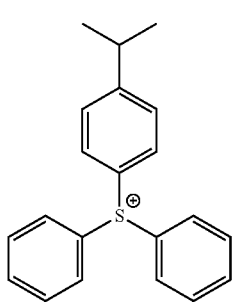
(ca-1-120)
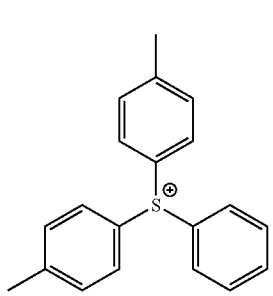
(ca-1-121)
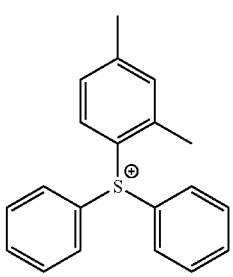
(ca-1-122)
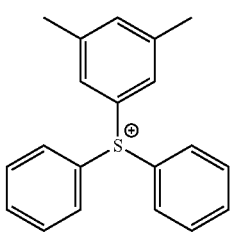
(ca-1-123)
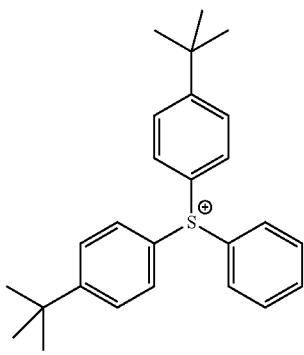
(ca-1-124)
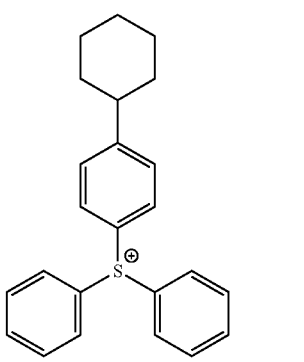
(ca-1-125)
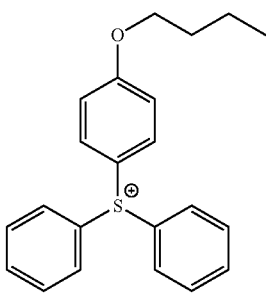
(ca-1-126)

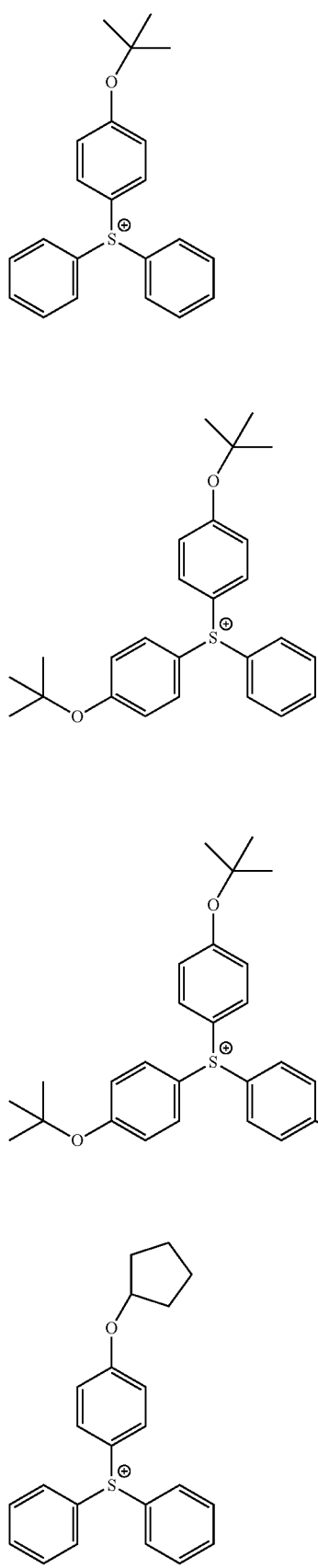
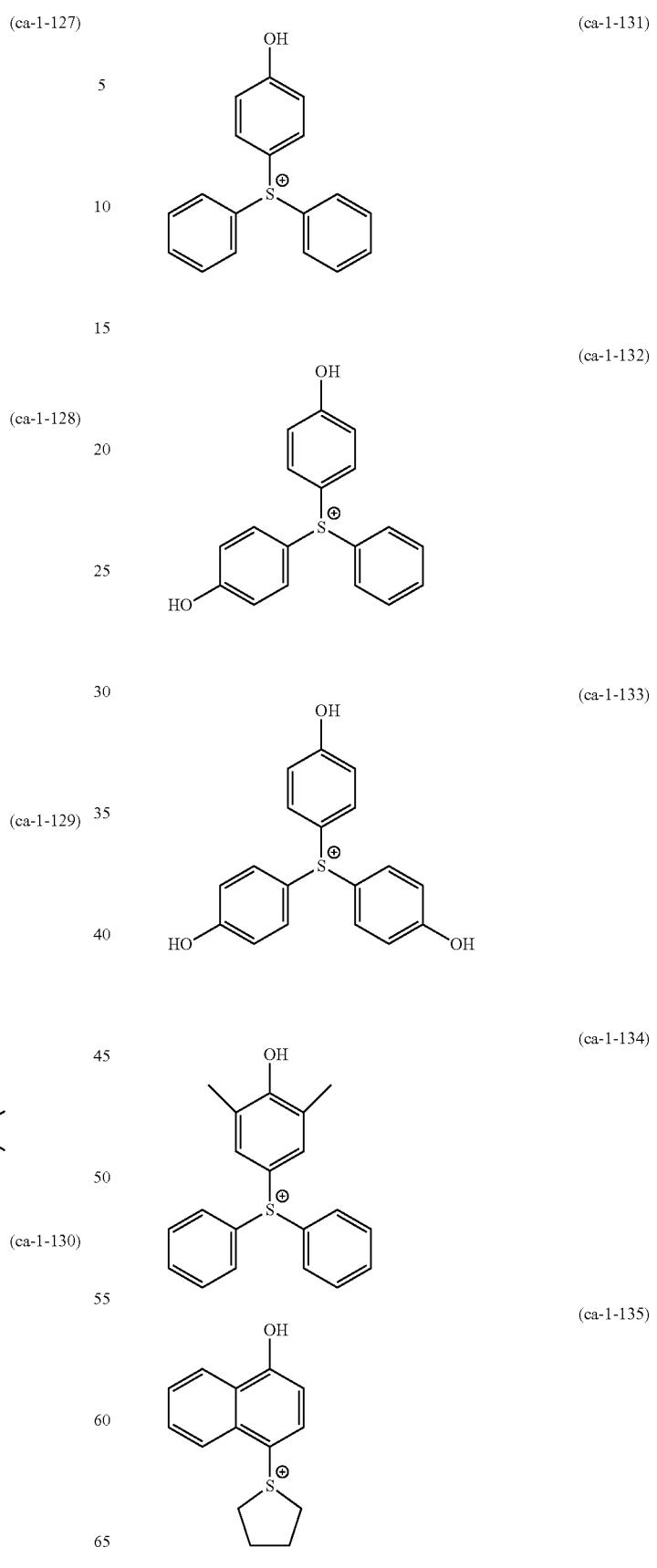

(ca-1-136)
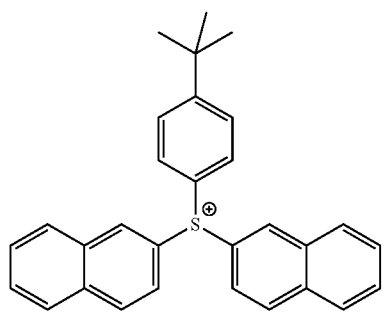
(ca-1-137)
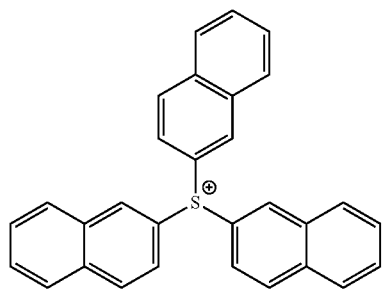
(ca-1-138)
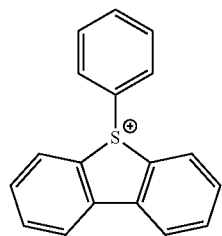
(ca-1-139)
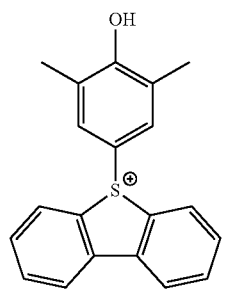
(ca-1-140)
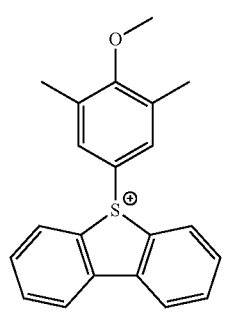
(ca-1-141)
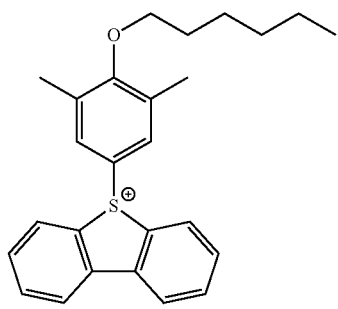
(ca-1-142)
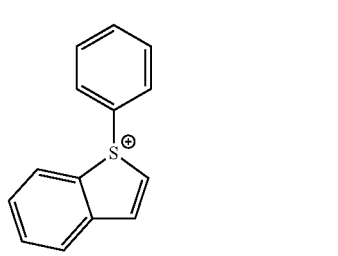
(ca-1-143)
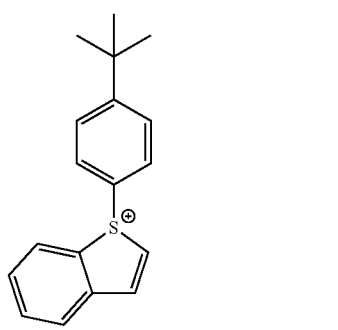
(ca-1-144)
(ca-1-145)
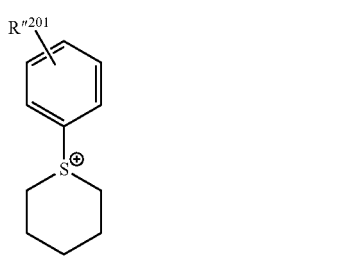
(ca-1-146)
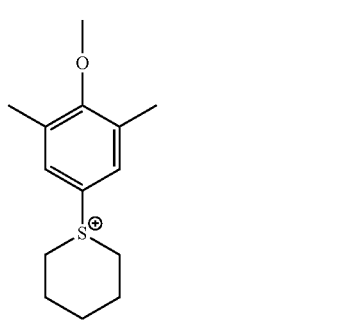

-continued (ca-1-147)
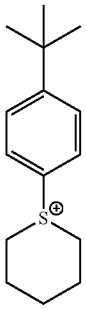

(ca-1-148)
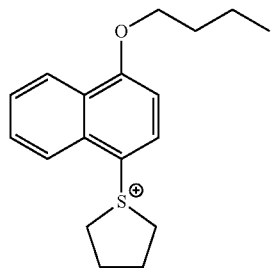

(ca-1-149)
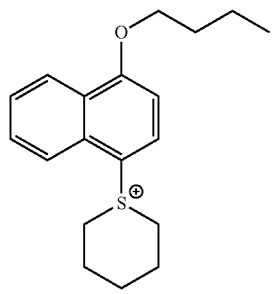

[In the formula, R''$^{201}$ represents a hydrogen atom or a substituent. Examples of the substituent include an alkyl group, a halogen atom, a halogenated alkyl group, a carbonyl group, a cyano group, an amino group, an aryl group, and groups each represented by General Formulae (ca-r-1) to (ca-r-7), which are mentioned as the substituents which may be contained in R$^{201}$ to R$^{207}$, R$^{211}$, and R$^{212}$.

Specific examples of the suitable cation represented by General Formula (ca-2) include cations each represented by General Formulae (ca-2-1) to (ca-2-2), a diphenyliodonium cation, a bis(4-tert-butylphenyl)iodonium cation.

(ca-2-1)
(ca-2-2)
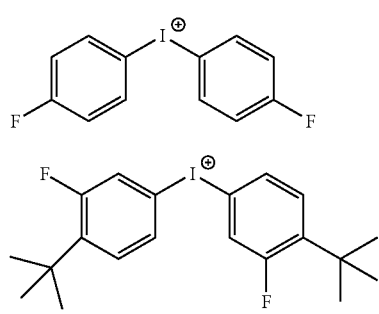

Specific examples of the suitable cation represented by General Formula (ca-3) include cations each represented by General Formulae (ca-3-1) to (ca-3-7).

(ca-3-1)
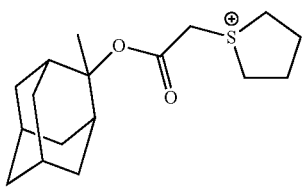

(ca-3-2)
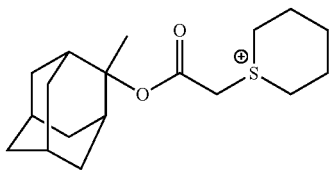

(ca-3-3)
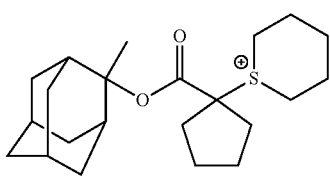

(ca-3-4)
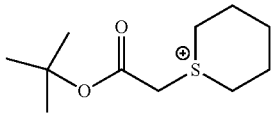

(ca-3-5)
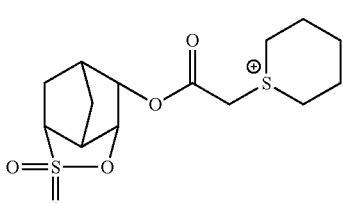

(ca-3-6)
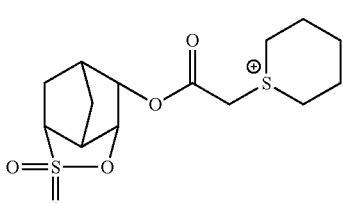

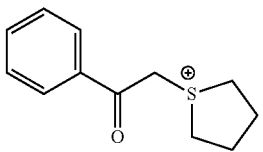

(ca-3-7)
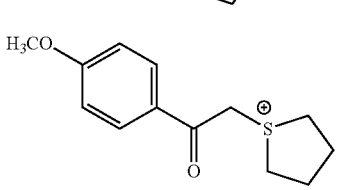

Specific examples of the suitable cation represented by General Formula (ca-4) include cations each represented by General Formulae (ca-4-1) and (ca-4-2).

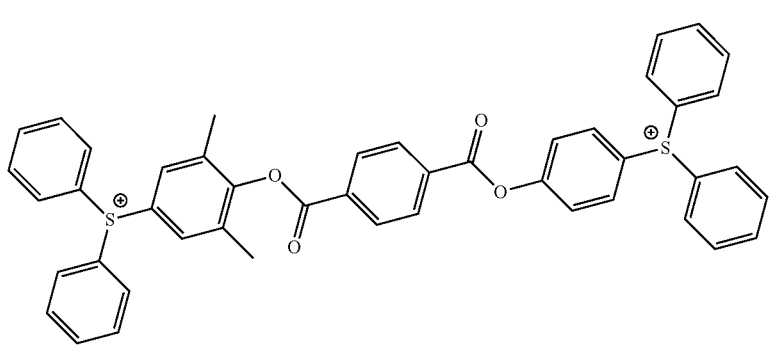

(ca-4-1)

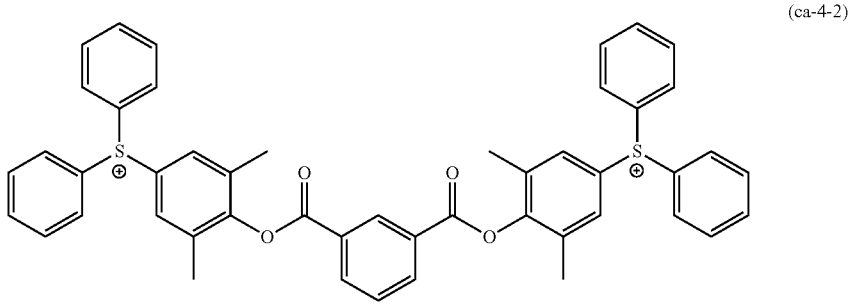

(ca-4-2)

Among the above, the cation moiety $((M^{m+})_{1/m})$ is preferably a cation represented by General Formula (ca-1) and more preferably cations each represented by Chemical Formulae (ca-1-1) to (ca-1-78) and (ca-1-101) to (ca-1-149).

The onium salt-based acid generator in the present invention is particularly preferably the component (b-1) among the components (b-1), (b-2), and (b-3) described above.

In the resist composition, the component (B) may be used alone or a combination of two or more kinds thereof may be used.

In a case where the resist composition contains the component (B), the content of the component (B) in the resist composition is preferably 0 parts by mass or more, more preferably in a range of 20 to 80 parts by mass, and still more preferably in a range of 30 to 70 parts by mass, with respect to 100 parts by mass of the component (A).

In a case where the content of the component (B) is set to be in the above-described range, pattern formation can be satisfactorily carried out.

«Component (D)»

The resist composition in the present embodiment may further contain a base component (hereinafter, referred to as a "component (D)") in addition to the component (A) or the component (A) and the component (B). The component (D) acts as a quencher (an acid diffusion controlling agent) which traps the acid generated in the resist composition upon exposure.

The component (D) may be a photodecomposable base (D1) which lose acid diffusion controllability (hereinafter, referred to as the "component (D1)") by decomposition upon exposure and a nitrogen-containing organic compound (D2) (hereinafter, referred to as a "component (D2)") which does not correspond to the component (D1).

In a case where a resist composition containing the component (D) is obtained, the contrast between the exposed portions and unexposed portions of the resist film can be further improved at the time of forming a resist pattern.

• In Regard to Component (D1)

In a case where a resist composition containing the component (D1) is obtained, the contrast between the exposed portions and unexposed portions of the resist film can be further improved at the time of forming a resist pattern. The component (D1) is not particularly limited as long as it is decomposed upon exposure and loses the acid diffusion controllability. The component (D1) is preferably one or more compounds selected from the group consisting of a compound represented by General Formula (d1-1) (hereinafter, referred to as a "component (d1-1)"), a compound represented by General Formula (d1-2) (hereinafter, referred to as a "component (d1-2)"), and a compound represented by General Formula (d1-3) (hereinafter, referred to as a "component (d1-3)").

In the exposed portions of the resist film, the components (d1-1) to (d1-3) are decomposed and then lose the acid diffusion controllability (basicity), and thus they cannot act as a quencher, while acting as a quencher in the unexposed portions of the resist film.

(d1-1)

(d1-2)

(d1-3)

[In the formulae, $Rd^1$ to $Rd^4$ represent cyclic groups which may have a substituent, chain-like alkyl groups which may have a substituent, or chain-like alkenyl groups which may have a substituent. Here, the carbon atom adjacent to the S atom as $Rd^2$ in General Formula (d1-2) has no fluorine atom bonded thereto. $Yd^1$ represents a single bond or a divalent linking group. m represents an integer of 1 or more, and each $M^{m+}$ independently represents an m-valent organic cation].

{Component (d1-1)}
• Anion Moiety

In General Formula (d1-1), Rd' represents a cyclic group which may have a substituent, a chain-like alkyl group which may have a substituent, or a chain-like alkenyl group which may have a substituent, and examples thereof each include the same one as $R'^{201}$.

Among these, $Rd^1$ is preferably an aromatic hydrocarbon group which may have a substituent, an aliphatic cyclic group which may have a substituent, or a chain-like alkyl group which may have a substituent. Examples of the substituent which may be contained in these groups include a hydroxyl group, an oxo group, an alkyl group, an aryl group, a fluorine atom, a fluorinated alkyl group, lactone-containing cyclic groups each represented by General Formulae (a2-r-1) to (a2-r-7), an ether bond, an ester bond, and a combination thereof. In a case where an ether bond or an ester bond is included as the substituent, the substituent may be bonded via an alkylene group, and the substituent in this case is preferably linking groups each represented by General Formulae (y-al-1) to (y-al-5).

Suitable examples of the aromatic hydrocarbon group include a phenyl group, a naphthyl group, and a polycyclic structure (a polycyclic structure including a bicyclooctane skeleton and a ring structure other than the bicyclooctane skeleton) including a bicyclooctane skeleton.

The aliphatic cyclic group is preferably a group obtained by removing one or more hydrogen atoms from a polycycloalkane such as adamantane, norbornane, isobornane, tricyclodecane, or tetracyclododecane.

The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl group, or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, or a 4-methylpentyl group.

In a case where the chain-like alkyl group is a fluorinated alkyl group having a fluorine atom or a fluorinated alkyl group as a substituent, the fluorinated alkyl group preferably has 1 to 11 carbon atoms, more preferably 1 to 8 carbon atoms, and still more preferably 1 to 4 carbon atoms. The fluorinated alkyl group may contain an atom other than the fluorine atom. Examples of the atom other than the fluorine atom include an oxygen atom, a sulfur atom, and a nitrogen atom.

$Rd^1$ is preferably a fluorinated alkyl group obtained by substituting part or all of hydrogen atoms constituting a linear alkyl group with a fluorine atom and particularly preferably a fluorinated alkyl group obtained by substituting all hydrogen atoms constituting a linear alkyl group with a fluorine atom (a linear perfluoroalkyl group).

Preferred specific examples of the anion moiety of the component (d1-1) are shown below.

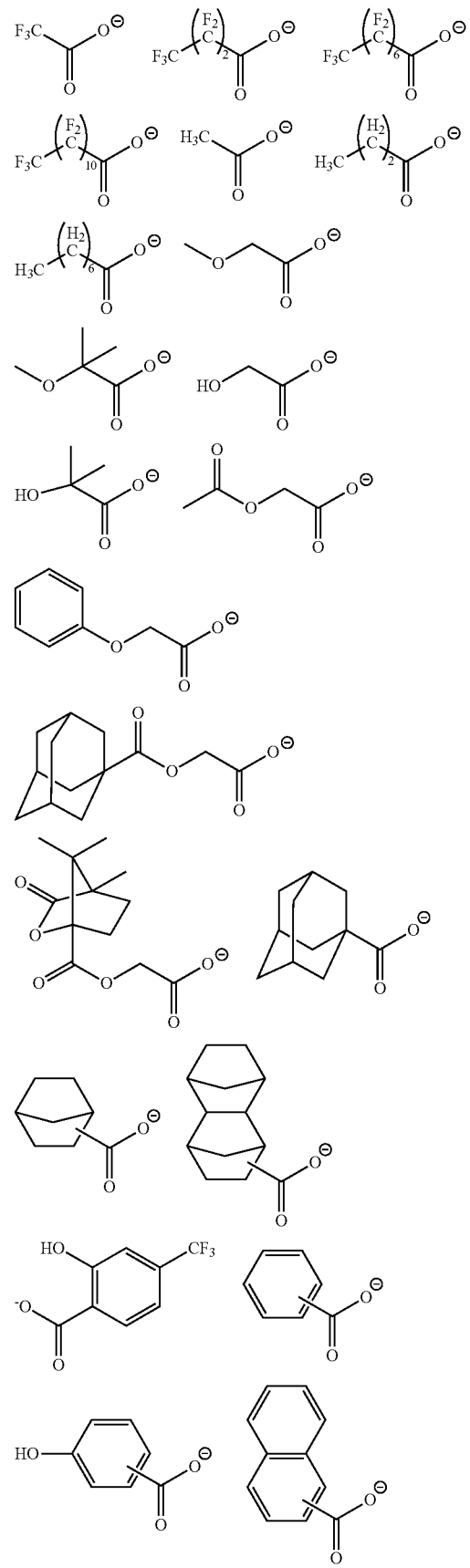

-continued

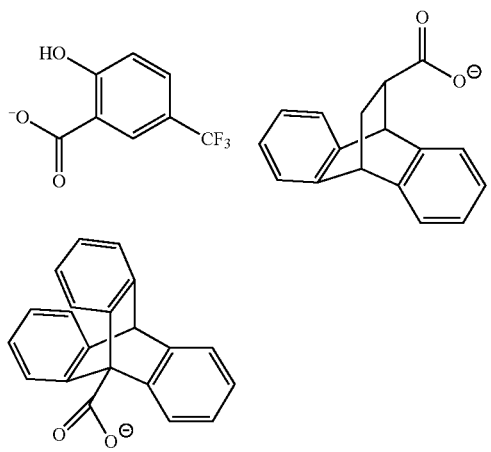

• Cation Moiety

In General Formula (d1-1), $M^{m+}$ represents an m-valent organic cation.

The suitable examples of the organic cation as $M^{m+}$ include the same ones as the cations each represented by General Formulae (ca-1) to (ca-4), the cation represented by General Formula (ca-1) is preferable, and the cations each represented General Formulae (ca-1-1) to (ca-1-78) and (ca-1-101) to (ca-1-149) are still more preferable.

The component (d1-1) may be used alone or a combination of two or more kinds thereof may be used.

{Component (d1-2)}

• Anion Moiety

In General Formula (d1-2), $Rd^2$ represents a cyclic group which may have a substituent, a chain-like alkyl group which may have a substituent, or a chain-like alkenyl group which may have a substituent, and examples thereof include the same one as $R'^{201}$.

Here, the carbon atom adjacent to the S atom in $Rd^2$ has no fluorine atom bonded thereto (the carbon atom adjacent to the S atom in $Rd^2$ is not substituted with a fluorine atom). As a result, the anion of the component (d1-2) becomes an appropriately weak acid anion, thereby improving the quenching ability of the component (D).

$Rd^2$ is preferably a chain-like alkyl group which may have a substituent or an aliphatic cyclic group which may have a substituent. The chain-like alkyl group preferably has 1 to 10 carbon atoms and more preferably 3 to 10 carbon atoms. The aliphatic cyclic group is more preferably a group (which may have a substituent) in which one or more hydrogen atoms have been removed from adamantane, norbornane, isobornane, tricyclodecane, tetracyclododecane, or the like; and a group in which one or more hydrogen atoms have been removed from camphor or the like.

The hydrocarbon group as $Rd^2$ may have a substituent. Examples of the substituent include the same one as the substituent which may be contained in the hydrocarbon group (the aromatic hydrocarbon group, the aliphatic cyclic group, or the chain-like alkyl group) as Rd' in General Formula (d1-1).

Preferred specific examples of the anion moiety of the component (d1-2) are shown below.

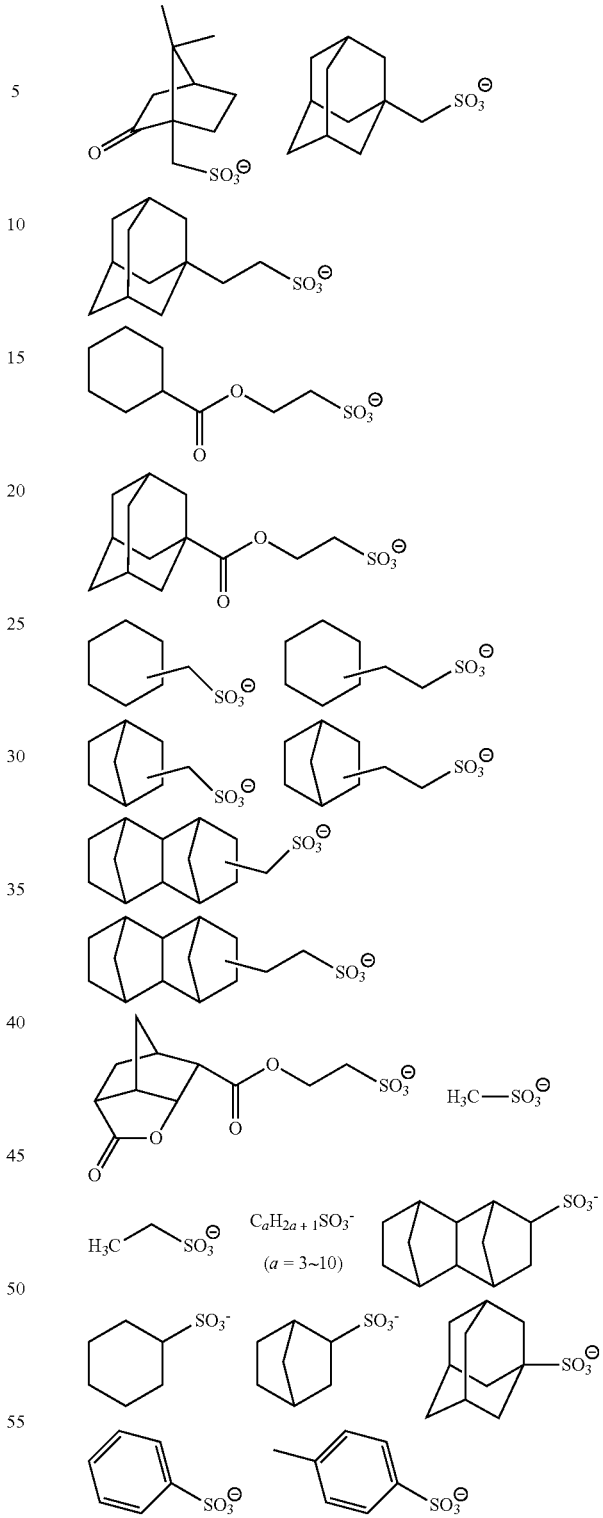

• Cation Moiety

In General Formula (d1-2), $M'^{m+}$ represents an m-valent organic cation and is the same as $M^{m+}$ in General Formula (d1-1).

The component (d1-2) may be used alone or a combination of two or more kinds thereof may be used.

{Component (d1-3)}

• Anion Moiety

In General Formula (d1-3), $Rd^3$ represents a cyclic group which may have a substituent, a chain-like alkyl group which may have a substituent, or a chain-like alkenyl group which may have a substituent, examples thereof include the same one as $R'^{201}$, and a cyclic group containing a fluorine atom, a chain-like alkyl group, or a chain-like alkenyl group is preferable. Among the above, a fluorinated alkyl group is preferable, and the same one as the fluorinated alkyl group as Rd' described above is more preferable.

In General Formula (d1-3), $Rd^4$ represents a cyclic group which may have a substituent, a chain-like alkyl group which may have a substituent, or a chain-like alkenyl group which may have a substituent, and examples thereof include the same one as $R'^{201}$.

Among them, an alkyl group which may have a substituent, an alkoxy group which may have a substituent, an alkenyl group which may have a substituent, or a cyclic group which may have a substituent is preferable.

The alkyl group as $Rd^4$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an iso-pentyl group, and a neopentyl group. Part of hydrogen atoms in the alkyl group as $Rd^4$ may be substituted with a hydroxyl group, a cyano group, or the like.

The alkoxy group as $Rd^4$ is preferably an alkoxy group having 1 to 5 carbon atoms, and specific examples of the alkoxy group having 1 to 5 carbon atoms include a methoxy group, an ethoxy group, an n-propoxy group, an iso-propoxy group, an n-butoxy group, and a tert-butoxy group. Among them, a methoxy group and an ethoxy group are preferable.

Examples of the alkenyl group as $Rd^4$ include the same one as the alkenyl group as $R'^{201}$, and a vinyl group, a propenyl group (an allyl group), a 1-methylpropenyl group, or a 2-methylpropenyl group is preferable. These groups may have an alkyl group having 1 to 5 carbon atoms or a halogenated alkyl group having 1 to 5 carbon atoms as a substituent.

Examples of the cyclic group as $Rd^4$ include the same one as the cyclic group described above as $R'^{201}$, and the cyclic group is preferably an alicyclic group obtained by removing one or more hydrogen atoms from a cycloalkane such as cyclopentane, cyclohexane, adamantane, norbornane, isobornane, tricyclodecane, or tetracyclododecane, or an aromatic group such as a phenyl group or a naphthyl group. In a case where $Rd^4$ represents an alicyclic group, the resist composition can be satisfactorily dissolved in an organic solvent, thereby improving lithography characteristics. In a case where $Rd^4$ is an aromatic group, the resist composition is excellent in light absorption efficiency and thus has good sensitivity and lithography characteristics in the lithography using EUV or the like as a light source for exposure.

In General Formula (d1-3), $Yd^1$ represents a single bond or a divalent linking group.

The divalent linking group as $Yd^1$ is not particularly limited, and examples thereof include a divalent hydrocarbon group (an aliphatic hydrocarbon group or an aromatic hydrocarbon group) which may have a substituent and a divalent linking group containing a hetero atom. Examples of these divalent linking groups each include the same one as the divalent hydrocarbon group which may have a substituent and the divalent linking group containing a hetero atom, which are mentioned in the explanation of the divalent linking group as $Ya^{21}$ in General Formula (a2-1).

$Yd^1$ is preferably a carbonyl group, an ester bond, an amide bond, an alkylene group, or a combination of these. The alkylene group is more preferably a linear or branched alkylene group and still more preferably a methylene group or an ethylene group.

Preferred specific examples of the anion moiety for the component (d1-3) are shown below.

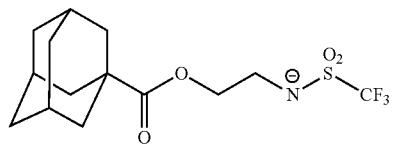

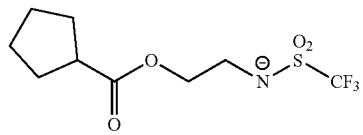

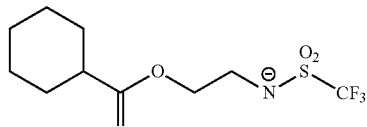

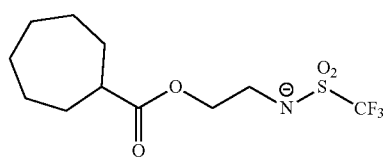

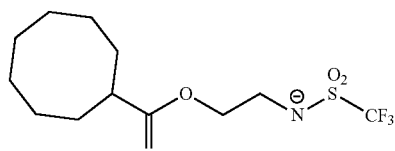

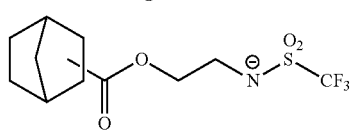

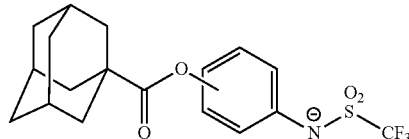

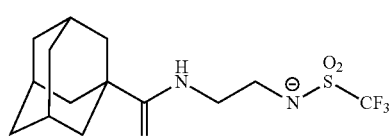

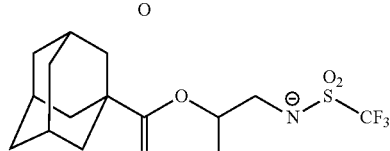

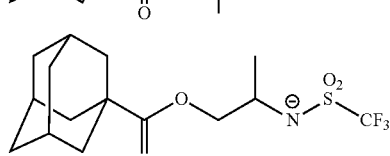

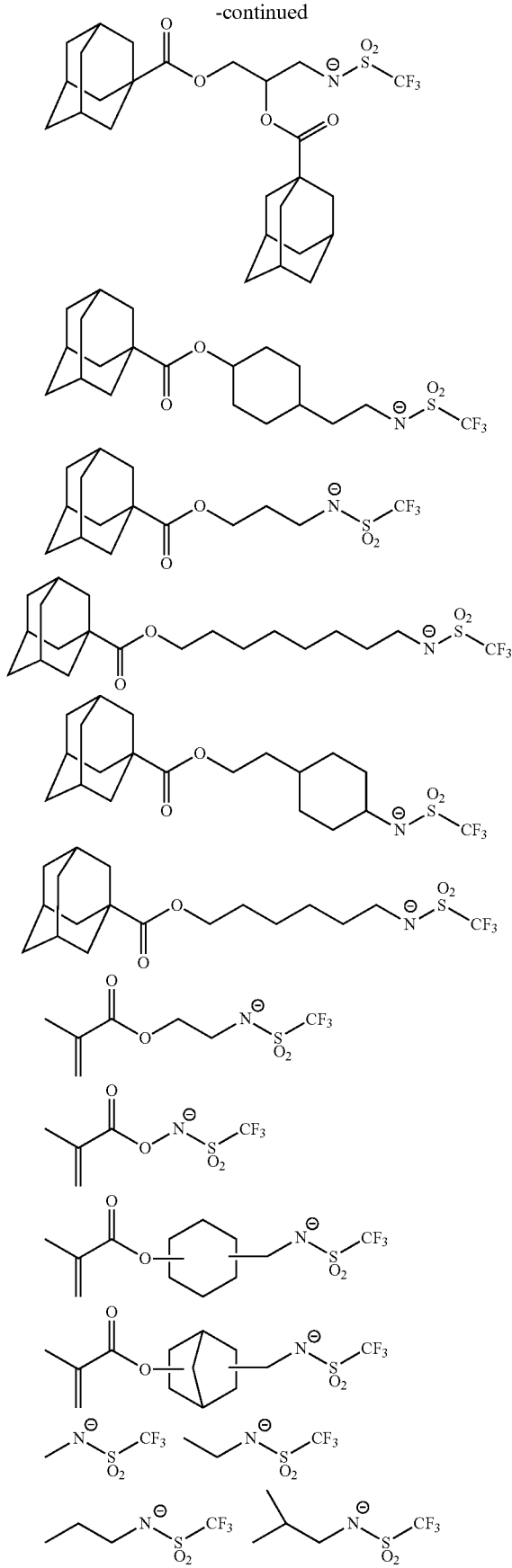

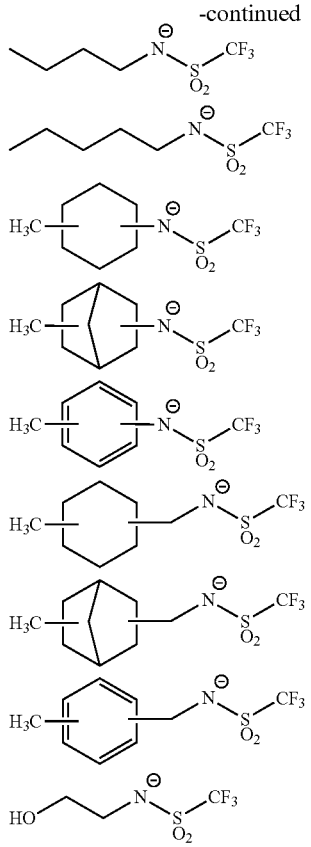

• Cation Moiety

In General Formula (d1-3), $M^{m+}$ represents an m-valent organic cation and is the same as $M^{m+}$ in General Formula (d1-1).

One kind of the component (d1-3) may be used alone, or a combination of two or more kinds thereof may be used.

As the component (D1), any one of the above components (d1-1) to (d1-3) may be used alone, or a combination of two or more thereof may be used.

In a case where the resist composition contains the component (D1), the content of the component (D1) in the resist composition is preferably in a range of 0 to 40 parts by mass, more preferably in a range of 1 to 30 parts by mass, and still more preferably in a range of 5 to 25 parts by mass with respect to 100 parts by mass of the component (A).

In a case where the content of the component (D1) is equal to or larger than the preferred lower limit value, particularly excellent lithography characteristics and a particularly excellent resist pattern shape are easily obtained.

On the other hand, in a case where the content of the component (D1) is equal to or smaller than the upper limit value, the sensitivity can be maintained satisfactorily, and the throughput is also excellent.

Production Method for Component (D1):

The production method for the components (d1-1) and (d1-2) are not particularly limited, and the components (d1-1) and (d1-2) can be produced by conventionally known technique.

Further, the production method for the component (d1-3) is not particularly limited, and the component (d1-3) can be produced in the same manner as disclosed in United States Patent Application, Publication No. 2012-0149916.

• In Regard to Component (D2)

The acid diffusion controlling agent component may contain a nitrogen-containing organic compound component (hereinafter, referred to as a "component (D2)") which does not correspond to the above-described component (D1).

The component (D2) is not particularly limited as long as it acts as an acid diffusion controlling agent and does not correspond to the component (D1), and any conventionally known compound may be used. Among the above, aliphatic amines are preferable, and among the aliphatic amines, a secondary aliphatic amine or a tertiary aliphatic amine is more preferable.

An aliphatic amine is an amine having one or more aliphatic groups, and the aliphatic groups preferably have 1 to 12 carbon atoms.

Examples of the aliphatic amine include an amine obtained by substituting at least one hydrogen atom of ammonia ($NH_3$) with an alkyl group or hydroxyalkyl group having 12 or fewer carbon atoms (an alkylamine or an alkyl alcohol amine) and a cyclic amine.

Specific examples of alkylamines and alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanol amine, triethanol amine, diisopropanol amine, triisopropanol amine, di-n-octanol amine, and tri-n-octanol amine. Among these, a trialkylamine having 5 to 10 carbon atoms is preferable, and tri-n-pentylamine or tri-n-octylamine is particularly preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine. The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

In addition, as the component (D2), an aromatic amine may be used.

Examples of aromatic amines include 4-dimethylaminopyridine, pyrrole, indole, pyrazole, imidazole, and derivatives thereof, tribenzylamine, 2,6-diisopropylaniline, and N-tert-butoxycarbonylpyrrolidine.

The component (D2) may be used alone or be combination of two or more kinds thereof may e used. In a case where the resist composition contains the component (D2), the amount of the component (D2) in the resist composition is typically in a range of 0 to 5 parts by mass with respect to 100 parts by mass of the component (A). By setting the content within the above range, the resist pattern shape, the post-exposure temporal stability, and the like are improved.

«Component (E): At Least One Compound Selected from Group Consisting of Organic Carboxylic Acid, Phosphorus Oxo Acid, and Derivatives Thereof»

For the intended purpose of preventing any deterioration in sensitivity, and improving the resist pattern shape and the post-exposure temporal stability, the resist composition may contain at least one compound (E) (hereinafter, referred to as a component (E)) selected from the group consisting of an organic carboxylic acid, and a phosphorus oxo acid and a derivative thereof, as an optional component.

The organic carboxylic acid is suitably, for example, acetic acid, malonic acid, citric acid, malic acid, succinic acid, benzoic acid, hydroxybenzoic acid, salicylic acid, phthalic acid, terephthalic acid, or isophthalic acid.

Examples of the phosphorus oxo acid include phosphoric acid, phosphonic acid, and phosphinic acid. Among these, phosphonic acid is particularly preferable.

Examples of the phosphorus oxo acid derivative include an ester obtained by substituting a hydrogen atom in the above-described oxo acid with a hydrocarbon group. Examples of the hydrocarbon group include an alkyl group having 1 to 5 carbon atoms and an aryl group having 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate, and dibenzyl phosphonate.

Examples of phosphinic acid derivatives include phosphinic acid esters and phenylphosphinic acid.

Among the above, the component (E) is preferably an organic carboxylic acid and more preferably an aromatic carboxylic acid. Specifically, it is preferably benzoic acid, hydroxybenzoic acid, salicylic acid, phthalic acid, terephthalic acid, or isophthalic acid and is more preferably salicylic acid.

In the resist composition, the component (E) may be used alone or be combination of two or more kinds thereof may e used.

In a case where the resist composition contains the component (E), the content of the component (E) is preferably in a range of 0 to 5 parts by mass, more preferably in a range of 0.1 to 5 parts by mass, and still more preferably in a range of 0.1 to 4 parts by mass with respect to 100 parts by mass of the component (A).

«Component (F): Fluorine Additive Component»

The resist composition in the present embodiment may further include a fluorine additive component (hereinafter, referred to as a "component (F)") in order to impart water repellency to the resist film or to improve lithography characteristics.

As the component (F), a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be mentioned.

Specific examples of the component (F) include a polymer having a constitutional unit (f11) represented by General Formula (f1-1) or a constitutional unit (f12) represented by General Formula (f1-2).

The polymer having a constitutional unit (f11) represented by General Formula (f1-1) is preferably a polymer (homopolymer) consisting only of a constitutional unit (f11) represented by General Formula (f1-1); a copolymer of the constitutional unit (f11) and the constitutional unit (a1); and a copolymer of the constitutional unit (f11), a constitutional unit derived from acrylic acid or methacrylic acid, and the constitutional unit (a1). The constitutional unit (a1) to be copolymerized with the constitutional unit (f11) is preferably a constitutional unit derived from 1-methyl-1-adamantyl(meth)acrylate and more preferably a constitutional unit derived from 1-methyl-1-adamantyl(meth)acrylate.

The polymer having a constitutional unit (f12) represented by General Formula (f1-2) is preferably a polymer (homopolymer) consisting only of a constitutional unit (f12) represented by General Formula (f1-2); a copolymer of the constitutional unit (f12) and the constitutional unit (a01); and a copolymer of the constitutional unit (f12) and the constitutional unit (a1). Among them, the copolymer is preferably a copolymer of the constitutional unit (f12) and the constitutional unit (a01).

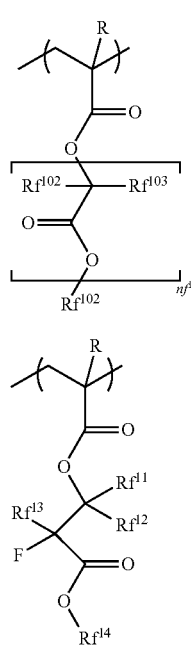

[In the formula, R has the same definition as described above.] $Rf^{102}$ and $Rf^{103}$ each independently represent a hydrogen atom, a halogen atom, an alkyl group having 1 to 5 carbon atoms, or a halogenated alkyl group having 1 to 5 carbon atoms, and $Rf^{102}$ and $Rf^{103}$ may be the same or different from each other. $nf^1$ represents an integer in a range of 0 to 5 and $Rf^{101}$ represents an organic group containing a fluorine atom. $Rf^{11}$ and $Rf^{12}$ each independently represent a hydrogen atom, an alkyl group having 1 to 4 carbon atoms, or a fluorinated alkyl group having 1 to 4 carbon atoms. $Rf^{13}$ represents a fluorine atom or a fluorinated alkyl group having 1 to 4 carbon atoms. $Rf^{14}$ represents a linear or branched alkyl group having 1 to 4 carbon atoms or a linear fluorinated alkyl group having 1 to 4 carbon atoms.]

In General Formula (f1-1), R bonded to the carbon atom at the α-position has the same definition as described above. R is preferably a hydrogen atom or a methyl group.

In General Formula (f1-1), examples of the halogen atom as $Rf^{102}$ and $Rf^{103}$ include a fluorine atom, a chlorine atom, a bromine atom, and an iodine atom, and a fluorine atom is particularly preferable. Examples of the alkyl group having 1 to 5 carbon atoms as $Rf^{102}$ and $Rf^{103}$ include the same one as the alkyl group having 1 to 5 carbon atoms as R, and a methyl group or an ethyl group is preferable. Specific examples of the halogenated alkyl group having 1 to 5 carbon atoms as $Rf^{102}$ and $Rf^{103}$ include a group obtained by substituting part or all hydrogen atoms of an alkyl group having 1 to 5 carbon atoms with a halogen atom. Examples of the halogen atom include a fluorine atom, a chlorine atom, a bromine atom and, an iodine atom, and a fluorine atom is particularly preferable. Among the above, $Rf^{102}$ and $Rf^{103}$ is preferably a hydrogen atom, a fluorine atom, or an alkyl group having 1 to 5 carbon atoms and more preferably a hydrogen atom, a fluorine atom, a methyl group, or an ethyl group.

In General Formula (f1-1), $nf^1$ represents an integer in a range of 1 to 5, preferably an integer in a range of 1 to 3, and more preferably an integer of 1 or 2.

In General Formula (f1-1), $Rf^{101}$ represents an organic group containing a fluorine atom and is preferably a hydrocarbon group containing a fluorine atom.

The hydrocarbon group containing a fluorine atom may be linear, branched, or cyclic, and preferably has 1 to 20 carbon atoms, more preferably 1 to 15 carbon atoms, and particularly preferably 1 to 10 carbon atoms.

In addition, in the hydrocarbon group containing a fluorine atom, 25% or more of the hydrogen atoms in the hydrocarbon group are preferably fluorinated, more preferably 50% or more are fluorinated, and particularly preferably 60% or more are fluorinated since the hydrophobicity of the resist film during immersion exposure increases.

Among the above, $Rf^{101}$ is more preferably a fluorinated hydrocarbon group having 1 to 6 carbon atoms, still more preferably a trifluoromethyl group, —CH$_2$—CF$_3$, —CH$_2$—CF$_2$—CF$_3$, or —CH(CF$_3$)$_2$, —CH$_2$—CH$_2$—CF$_3$, or —CH$_2$—CH$_2$—CF$_2$—CF$_2$—CF$_2$—CF$_3$, and particularly preferably —CH$_2$—CF$_3$.

In General Formula (f1-2), R bonded to the carbon atom at the α-position has the same definition as described above. R is preferably a hydrogen atom or a methyl group.

In General Formula (f1-2), $R^{f11}$ and $R^{f12}$ each independently represent a hydrogen atom, an alkyl group having 1 to 4 carbon atoms, or a fluorinated alkyl group having 1 to 4 carbon atoms.

The alkyl group having 1 to 4 carbon atoms as $R^{f11}$ and $R^{f12}$ may be linear, branched, or cyclic, and is preferably a linear or branched alkyl group. Specific suitable examples thereof include a methyl group and an ethyl group, and an ethyl group is particularly preferable.

The fluorinated alkyl group having 1 to 4 carbon atoms as $R^{f11}$ and $R^{f12}$ is a group obtained by substituting part or all hydrogen atoms in an alkyl group having 1 to 4 carbon atoms with a fluorine atom. In the fluorinated alkyl group, the alkyl group in a state of not being substituted with a fluorine atom may be linear, branched, or cyclic, and examples thereof include the same one as the "alkyl group having 1 to 4 carbon atoms as $R^{f11}$ and $R^{f12}$"

Among the above, it is preferable that $R^{f11}$ and $R^{f12}$ are a hydrogen atom or an alkyl group having 1 to 4 carbon atoms, and it is particularly preferable that one of $R^{f11}$ and $R^{f12}$ is a hydrogen atom and the other is an alkyl group having 1 to 4 carbon atoms.

In General Formula (f1-2), $Rf^{13}$ represents a fluorine atom or a fluorinated alkyl group having 1 to 4 carbon atoms.

Examples of the fluorinated alkyl group having 1 to 4 carbon atoms as $Rf^{13}$ include the same one as the "fluorinated alkyl group having 1 to 4 carbon atoms as $R^{f11}$ and $R^{f12}$", which preferably has 1 to 3 carbon atoms and more preferably 1 or 2 carbon atoms.

In the fluorinated alkyl group as $Rf^{13}$, the proportion (the fluorination rate (%)) of the number of fluorine atoms with respect to the total number of fluorine atoms and hydrogen atoms contained in the fluorinated alkyl group is preferably in a range of 30% to 100% and more preferably in a range of 50% to 100%. The higher the fluorination rate, the higher the hydrophobicity of the resist film.

Among the above, $Rf^{13}$ is preferably a fluorine atom.

In General Formula (f1-2), $Rf^{14}$ represents a linear or branched alkyl group having 1 to 4 carbon atoms or a linear fluorinated alkyl group having 1 to 4 carbon atoms, and it is preferably a linear alkyl group having 1 to 4 carbon atoms or a linear fluorinated alkyl group having 1 to 4 carbon atoms.

Specific examples of the alkyl group as $Rf^{14}$ include a methyl group, an ethyl group, a propyl group, an isopropyl group, an n-butyl group, an isobutyl group, and a tert-butyl group. Among them, a methyl group or an ethyl group is preferable, and a methyl group is most preferable.

Specific suitable examples of the fluorinated alkyl group as $Rf^{14}$ include $-CH_2-CF_3$, $-CH_2-CH_2-CF_3$, $-CH_2-CF_2-CF_3$, and $-CH_2-CF_2-CF_2-CF_3$, and among them, $-CH_2-CH_2-CF_3$ is particularly preferable.

The weight average molecular weight (Mw) (based on the polystyrene-equivalent value determined by gel permeation chromatography) of the component (F) is preferably in a range of 1,000 to 50,000, more preferably in a range of 5,000 to 40,000, and most preferably in a range of 10,000 to 30,000. In a case where the weight average molecular weight is equal to or smaller than the upper limit value of the above-described range, the resist composition exhibits a satisfactory solubility in a resist solvent enough to be used as a resist. On the other hand, in a case where the weight average molecular weight is equal to or larger than the lower limit value of the above-described range, dry etching resistance and the cross-sectional shape of the resist pattern become excellent.

Further, the dispersity (Mw/Mn) of the component (F) is preferably in a range of 1.0 to 5.0, more preferably in a range of 1.0 to 3.0, and most preferably in a range of 1.0 to 2.5.

In the resist composition in the present embodiment, the component (F) may be used alone or a combination of two or more kinds thereof may be used.

In a case where the resist composition contains the component (F), the content of the component (F) to be used is typically at a proportion in a range of 0 to 10 parts by mass, with respect to 100 parts by mass of the component (A).

«Component (S): Organic Solvent Component»

The resist composition in the present embodiment may be produced by dissolving the resist materials in an organic solvent component (hereinafter, referred to as a "component (S)").

The component (S) may be any organic solvent which can dissolve the respective components to be used to obtain a homogeneous solution, and optional organic solvent can be appropriately selected and used from those which are known as solvents for a chemically amplified resist composition in the related art.

Examples of the component (S) include lactones such as γ-butyrolactone; ketones such as acetone, methyl ethyl ketone, cyclohexanone, methyl-n-pentyl ketone, methyl isopentyl ketone, 2-heptanone, ethylene carbonate, and propylene carbonate; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate, polyhydric alcohol derivatives including compounds having an ether bond, such as a monoalkyl ether (such as monomethyl ether, monoethyl ether, monopropyl ether or monobutyl ether) compounds having an ester bond, such as ethylene glycol monoacetate, diethylene glycol monoacetate, propylene glycol monoacetate, and dipropylene glycol monoacetate, polyhydric alcohol derivatives including compounds having an ether bond, such as a monoalkyl ether (such as monomethyl ether, monoethyl ether, monopropyl ether or monobutyl ether) or monophenyl ether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzyl ether, cresylmethyl ether, diphenyl ether, dibenzyl ether, phenetole, butylphenyl ether, ethyl benzene, diethyl benzene, pentyl benzene, isopropyl benzene, toluene, xylene, cymene and mesitylene; and dimethylsulfoxide (DMSO).

In the resist composition in the present embodiment, the component (S) may be used alone or as a mixed solvent of two or more kinds thereof.

Among the above, PGMEA, PGME, γ-butyrolactone, propylene carbonate, EL or cyclohexanone is preferable, and PGMEA, PGME, or γ-butyrolactone is more preferable.

Further, a mixed solvent obtained by mixing PGMEA with a polar solvent is also preferable. The blending ratio (mass ratio) of the mixed solvent can be appropriately determined, taking into consideration the compatibility of the PGMEA with the polar solvent; however, it is preferably in a range of 1:9 to 9:1 and more preferably in a range of 2:8 to 8:2.

More specifically, in a case where EL or cyclohexanone is blended as the polar solvent, the PGMEA:EL or cyclohexanone mass ratio is preferably in a range of 1:9 to 9:1 and more preferably in a range of 2:8 to 8:2. Alternatively, in a case where PGME is blended as the polar solvent, the PGMEA:PGME mass ratio is preferably in a range of 1:9 to 9:1, more preferably in a range of 2:8 to 8:2, and still more preferably in a range of 3:7 to 7:3. Furthermore, a mixed solvent of PGMEA, PGME, and cyclohexanone is also preferable.

In addition, as another example, the component (S) is also preferably a mixed solvent of at least one selected from PGMEA and EL with at least one selected from γ-butyrolactone and propylene carbonate. In this case, regarding the mixing ratio, the mass ratio of the former to the latter is preferably in a range of 60:40 to 99:1 and more preferably in a range of 70:30 to 95:5.

In the resist composition, the content of the component (S) is 97% by mass or more with respect to the total mass (100% by mass) of the resist composition. In a case where the content of the component (S) is set to 97% by mass or more, pattern collapse can be suppressed, and thus the change in pattern size before and after the step (i) can be suppressed. The content of the component (S) is preferably in a range of 97% to 99.95% by mass, more preferably in a range of 97% to 99.9% by mass, and still more preferably in a range of 97% to 98.5% by mass.

As desired, other miscible additives can also be added to the resist composition. For example, for improving the performance of the resist film, an additive resin, a dissolution inhibitor, a plasticizer, a stabilizer, a colorant, a halation prevention agent, and a dye can be appropriately contained therein.

The resist composition contains the component (A) described above, the onium salt, and the organic solvent component (S). The onium salt may be the component (A), the component (B), or the component (D).

Examples of the resist composition include one which contains the component (A) containing an onium salt and an organic solvent component (S); one which contains the component (A) containing an onium salt, the component (D) containing an onium salt, and an organic solvent component (S); one which contains the component (A) containing an onium salt, the component (B) containing an onium salt, the component (D) containing an onium salt, and an organic solvent component (S); one which contains the component (A), the component (B) containing an onium salt, and an organic solvent component (S); and one which contains the component (A), the component (B) containing an onium salt, the component (D) containing an onium salt, and an organic solvent component (S). The resist composition preferably further contains the component (E) in addition to these components.

The resist composition preferably contains two or more kinds of onium salts from the viewpoint of suppressing pattern collapse and the like. Preferred examples thereof include one in which the component (A) and the component (D) contain an onium salt; and one in which the component (B) and the component (D) contain an onium salt.

In the resist composition, the content of the onium salt is preferably in a range of 0.05% to 2.9% by mass with respect to the total mass (100% by mass) of the resist composition. The content of the onium salt is more preferably in a range of 0.1% to 2% by mass and still more preferably in a range of 0.5% to 1.5% by mass. In a case where the content of the onium salt is within the above range, pattern collapse can be suppressed, and thus the change in pattern size before and after the step (i) can be suppressed.

In a case where the resist composition contains two or more kinds of onium salts, the above content of the onium salt is the total value of the contents of the onium salts contained in the resist composition.

For example, in a case where the resist composition contains only the component (A) as an onium salt, the content of the component (A) is preferably in a range of 0.05% to 2.9% by mass and more preferably in a range of 0.1% to 2.8% by mass with respect to the total mass (100% by mass) of the resist composition. In addition, for example, in a case where the resist composition contains only the component (B) as an onium salt, the content of the component (B) is preferably in a range of 0.05% to 1.6% by mass and more preferably in a range of 0.5% to 1.4% by mass with respect to the total mass (100% by mass) of the resist composition. In addition, for example, in a case where the resist composition contains only the component (D) as an onium salt, the content of the component (D) is preferably in a range of 0.05% to 1.6% by mass and more preferably in a range of 0.5% to 1.0% by mass with respect to the total mass (100% by mass) of the resist composition.

In addition, for example, in a case where the resist composition contains the component (A) and the component (D) as an onium salt, the total of the contents of the component (A) and the component (D) is preferably in a range of 0.05% to 2.9% by mass with respect to the total mass (100% by mass) of the resist composition. Among the above, the content of the component (A) is preferably in a range of 0.04% to 2.8% by mass and more preferably in a range of 0.5% to 2.8% by mass. In addition, the content of the component (D) is preferably in a range of 0.01% to 0.2% by mass and more preferably in a range of 0.03% to 0.18% by mass.

In addition, for example, in a case where the resist composition contains the component (A) and the component (B) as an onium salt, the total of the contents of the component (A) and the component (B) is preferably in a range of 0.05% to 2.9% by mass with respect to the total mass (100% by mass) of the resist composition. Among the above, the content of the component (A) is preferably in a range of 0.04% to 2.8% by mass and more preferably in a range of 0.5% to 2.8% by mass. In addition, the content of the component (B) is preferably in a range of 0.01% to 1.6% by mass and more preferably in a range of 0.05% to 1.1% by mass.

In addition, for example, in a case where the resist composition contains the component (B) and the component (D) as an onium salt, the total of the contents of the component (B) and the component (D) is preferably in a range of 0.05% to 1.8% by mass with respect to the total mass (100% by mass) of the resist composition. Among the above, the content of the component (B) is preferably in a range of 0.04% to 1.6% by mass and more preferably in a range of 0.08% to 1.4% by mass. In addition, the content of the component (D) is preferably in a range of 0.01% to 0.5% by mass and more preferably in a range of 0.01% to 0.3% by mass.

In addition, for example, in a case where the resist composition contains the component (A), the component (B), and the component (D) as an onium salt, the total of the contents of the component (A), the component (B), and the component (D) is preferably in a range of 0.05% to 2.9% by mass with respect to the total mass (100% by mass) of the resist composition. Among the above, the content of the component (A) is preferably in a range of 0.04% to 2.8% by mass and more preferably in a range of 0.5% to 2.8% by mass. In addition, the content of the component (B) is preferably in a range of 0.01% to 1.6% by mass and more preferably in a range of 0.01% to 1.4% by mass. In addition, the content of the component (D) is preferably in a range of 0.01% to 0.5% by mass and more preferably in a range of 0.01% to 0.2% by mass.

According to the production method for a resist composition purified product of the present aspect described above, a filtration target (a resist composition) is filtrated in the step (i) by using a filter having a porous membrane that has a porous structure in which adjacent spherical cells are connected to each other and contains at least one resin skeleton selected from the group consisting of polyimide and polyamide imide. As a result, foreign substances such as an organic substance and a metal impurity are removed from the filtration target more than ever. In particular, due to the use of the polyimide-based resin porous membrane, highly polar components and polymers, which have been difficult to be removed in the related art, are sufficiently removed from a filtration target, and among them, the highly polar polymer is specifically removed. In addition, in the step (i), a metal component as an impurity is also sufficiently removed from a filtration target. As described above, various foreign substances are efficiently removed by such a production method, and a high-purity resist composition purified product can be obtained.

Further, according to the production method for a resist composition purified product of the present aspect, a resist composition that contains the component (A), the onium salt, and the component (S) and in which the content of the component (S) is 97% by mass or more is filtered in the step (i). In a case where such a resist composition is used, the pattern collapse of a resist pattern is suppressed in a case where the resist pattern is formed by using the resist composition purified product that undergone the step (i) (or the step (i) and the step (ii)). Further, before and after the step (i) (or the step (i) and the step (ii))), only impurities are removed, and thus the component variation of the resist composition is small. As a result, variation of pattern size before and after the step (i) (or the step (i) and the step (ii))) can be suppressed.

The filter in the present aspect is not limited to the one that includes a porous membrane in which the interconnection pores 5 in which the adjacent spherical cell 1*a* and the spherical cell 1*b* are connected to each other as shown in FIG. 1 is formed, and may include a porous membrane in which, in addition to the interconnection pores 5 in which the spherical cells 1*a* and 1*b* are connected to each other, a cell or interconnection pore having another form is formed.

Examples of the cell (hereinafter, referred to as "another cell") having another form include a cell that differs in shape or pore diameter, and examples thereof include an elliptical cell, a polyhedral cell, a spherical cell having a different pore diameter. Examples of the above-described "interconnection pore having another form" include an interconnection pore in which a spherical cell and another cell are connected to each other.

The shape or pore diameter of another cell may be appropriately determined depending on the kinds of impurities to be removed. The interconnection pore in which a spherical cell and another cell are connected to each other can be formed, for example, by selecting a material of the fine grain material described above or controlling the shape of the fine grains.

According to the filter including a porous membrane in which, in addition to the interconnection pore in which adjacent spherical cells are connected to each other, a cell or interconnection pore having another form is formed, it is possible to efficiently remove various foreign substances from a filtration target.

Further, the filter having a polyimide-based resin porous membrane, which is used in the filtration step, replace a filter cartridge or the like for removing impurities having a fine grain shape, which has been installed in the related art, in the supply line of the resist composition or the point of use (POU) in the semiconductor manufacturing process or can be used in combination with these. As a result, various foreign substances can be efficiently removed from a filtration target using the same device and operation as those in the related art, and a high-purity resist composition purified product can be produced.

(Resist Pattern Forming Method)

The resist pattern forming method according to the second aspect of the present invention includes a step of obtaining a resist composition purified product, by the production method for a resist composition purified product according to the first aspect, a step of forming a resist film on a support using the resist composition purified product, a step of exposing the resist film, and a step of developing the exposed resist film to form a resist pattern.

The resist pattern forming method according to the present aspect can be carried out, for example, as follows. First, a resist composition purified product is obtained by the production method for a resist composition purified product according to the first aspect.

Next, the resist composition purified product is applied onto a support with a spinner or the like, and a baking (post-apply baking (PAB)) treatment is carried out, for example, at a temperature condition in a range of 80° C. to 150° C. for 40 to 120 seconds, preferably for 60 to 90 seconds to form a resist film.

Following the selective exposure carried out on the resist film by, for example, exposure through a mask (mask pattern) having a predetermined pattern formed on the mask by using an exposure apparatus such as an ArF exposure apparatus, an electron beam lithography apparatus, or an EUV exposure apparatus, or direct irradiation of the resist film for drawing with an electron beam without using a mask pattern, baking treatment (post-exposure baking (PEB)) is carried out, for example, under a temperature condition in a range of 80° C. to 150° C. for 40 to 120 seconds and preferably 60 to 90 seconds.

Next, the resist film is subjected to a developing treatment. The developing treatment is carried out using an alkali developing solution in a case of an alkali developing process, and a developing solution containing an organic solvent (organic developing solution) in a case of a solvent developing process.

After the developing treatment, it is preferable to carry out a rinse treatment. As the rinse treatment, water rinsing using pure water is preferable in a case of an alkali developing process, and rinsing using a rinse liquid containing an organic solvent is preferable in a case of a solvent developing process.

In a case of a solvent developing process, after the developing treatment or the rinse treatment, the developing solution or the rinse liquid remaining on the pattern can be removed by a treatment using a supercritical fluid.

After the developing treatment or the rinse treatment, drying is carried out. As desired, baking treatment (post-baking) can be carried out following the developing treatment.

In this manner, a resist pattern can be formed.

The support is not particularly limited, and a known one in the related art can be used. For example, a substrate for an electronic component, and such a substrate having a predetermined wiring pattern formed thereon can be used. Specific examples of the material of the substrate include metals such as silicon wafer, copper, chromium, iron, and aluminum; and glass. As the material for the wiring pattern, copper, aluminum, nickel, gold, or the like can be used.

Further, as the support, any support having the substrate described above, on which an inorganic and/or organic film is provided, may be used. As the inorganic film, an inorganic antireflection film (inorganic BARC) can be used. Examples of the organic film include an organic antireflection film (organic BARC) and an organic film such as a lower-layer organic film used in a multilayer resist method.

The wavelength to be used for exposure is not particularly limited and the exposure can be carried out using radiation such as an ArF excimer laser, a KrF excimer laser, an $F_2$ excimer laser, an extreme ultraviolet ray (EUV), a vacuum ultraviolet ray (VUV), an electron beam (EB), an X ray, or a soft X ray. The resist composition purified product is highly useful for a KrF excimer laser, an ArF excimer laser, EB, or EUV, and is particularly useful for EB or EUV.

The exposure method of the resist film can be a general exposure (dry exposure) carried out in air or an inert gas such as nitrogen, or liquid immersion exposure (liquid immersion lithography).

The liquid immersion lithography is an exposure method in which the region between the resist film and the lens at the lowermost position of the exposure apparatus is pre-filled with a solvent (liquid immersion medium) that has a larger refractive index than the refractive index of air, and the exposure (immersion exposure) is carried out in this state.

The liquid immersion medium is preferably a solvent that exhibits a refractive index larger than the refractive index of air but smaller than the refractive index of the resist film to be exposed. The refractive index of such a solvent is not particularly limited as long as it satisfies the above-described requirements.

Examples of the solvent which exhibits a refractive index that is larger than the refractive index of air but smaller than the refractive index of the resist film include water, fluorine-based inert liquids, silicone-based solvents, and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$, or $C_5H_3F_7$ as the main component, and the boiling point is preferably in a range of 70° to 180° C. and more preferably in a range of 80° to 160° C. A fluorine-based inert liquid having a boiling point in the above-described range is advantageous in that removing the medium used in the liquid immersion after the exposure can be carried out by a simple method.

A fluorine-based inert liquid is particularly preferably a perfluoroalkyl compound obtained by substituting all hydrogen atoms of the alkyl group with a fluorine atom. Examples of the perfluoroalkyl compound include a perfluoroalkyl ether compound and a perfluoroalkylamine compound.

Further, specific examples of the perfluoroalkyl ether compound include perfluoro(2-butyl-tetrahydrofuran) (boiling point: 102° C.), and examples of the perfluoroalkylamine compound include perfluorotributylamine (boiling point: 174° C.).

As the liquid immersion medium, water is preferable in terms of cost, safety, environment, and versatility.

Examples of the alkali developing solution used for a developing treatment in an alkali developing process include an aqueous solution of 0.1% to 10% by mass of tetramethylammonium hydroxide (TMAH).

The organic solvent contained in the organic developing solution, which is used for a developing treatment in a solvent developing process may be any organic solvent capable of dissolving the component (A) (component (A) prior to exposure), and can be appropriately selected from the conventionally known organic solvents. Specific examples of the organic solvent include polar solvents such as a ketone-based solvent, an ester-based solvent, an alcohol-based solvent, a nitrile-based solvent, an amide-based solvent, and an ether-based solvent, and hydrocarbon-based solvents.

A ketone-based solvent is an organic solvent containing C—C(=O)—C in the structure thereof. An ester-based solvent is an organic solvent containing C—C(=O)—O—C in the structure thereof. An alcohol-based solvent is an organic solvent containing an alcoholic hydroxyl group in the structure thereof. The "alcoholic hydroxyl group" indicates a hydroxyl group bonded to a carbon atom of an aliphatic hydrocarbon group. A nitrile-based solvent is an organic solvent containing a nitrile group in the structure thereof. An amide-based solvent is an organic solvent containing an amide group in the structure thereof. An ether-based solvent is an organic solvent containing C—O—C in the structure thereof.

Some organic solvents have a plurality of the functional groups which characterize the above-described solvents in the structure thereof. In such a case, the organic solvent can be classified as any type of solvent having a characteristic functional group. For example, diethylene glycol monomethyl ether can be classified as an alcohol-based solvent or an ether-based solvent.

A hydrocarbon-based solvent consists of a hydrocarbon which may be halogenated and does not have any substituent other than the halogen atom. Examples of the halogen atom include a fluorine atom, a chlorine atom, a bromine atom and, an iodine atom, and a fluorine atom is preferable.

Among the above, the organic solvent contained in the organic developing solution is preferably a polar solvent and more preferably a ketone-based solvent, an ester-based solvent, or a nitrile-based solvent.

As desired, the organic developing solution may have a conventionally known additive blended. Examples of the additive include surfactants. The surfactant is not particularly limited, and for example, an ionic or non-ionic fluorine-based and/or a silicone-based surfactant can be used. The surfactant is preferably a non-ionic surfactant and more preferably a non-ionic fluorine surfactant or a non-ionic silicone-based surfactant.

In a case where a surfactant is blended, the amount of the surfactant to be blended is typically in a range of 0.001% to 5% by mass, preferably in a range of 0.005% to 2% by mass, and more preferably in a range of 0.01% to 0.5% by mass with respect to the total amount of the organic developing solution.

The developing treatment can be carried out by a conventionally known developing method. Examples thereof include a method in which the support is dipped in the developing solution for a predetermined time (a dip method), a method in which the developing solution is cast upon the surface of the support by surface tension and maintained for a predetermined time (a puddle method), a method in which the developing solution is sprayed onto the surface of the support (spray method), and a method in which a developing solution is continuously ejected from a developing solution ejecting nozzle and applied to a support which is scanned at a constant rate while being rotated at a constant rate (dynamic dispense method).

As the organic solvent contained in the rinse liquid used in the rinse treatment after the developing treatment in a case of a solvent developing process, an organic solvent hardly dissolving the resist pattern can be appropriately selected and used, among the organic solvents mentioned as organic solvents that are used for the organic developing solution. In general, at least one kind of solvent selected from the group consisting of a hydrocarbon-based solvent, a ketone-based solvent, an ester-based solvent, an alcohol-based solvent, an amide-based solvent, and an ether-based solvent is used. Among these, at least one kind of solvent selected from the group consisting of a hydrocarbon-based solvent, a ketone-based solvent, an ester-based solvent, an alcohol-based solvent, and an amide-based solvent is preferable, at least one kind of solvent selected from the group consisting of an alcohol-based solvent and an ester-based solvent is more preferable, and an alcohol-based solvent is particularly preferable.

As the organic solvent, one kind of solvent may be used alone, or two or more kinds of solvents may be used in combination. Further, an organic solvent other than the above-described examples or water may be mixed thereto. However, in consideration of the development characteristics, the amount of water to be blended in the rinse liquid is preferably 30% by mass or less, more preferably 10% by mass or less, still more preferably 5% by mass or less, and particularly preferably 3% by mass or less with respect to the total amount of the rinse liquid.

A conventionally known additive can be blended with the rinse liquid as necessary. Examples of the additive include surfactants. Examples of the surfactant include the same ones as those described above, the surfactant is preferably a non-ionic surfactant and more preferably a non-ionic fluorine surfactant or a non-ionic silicone-based surfactant.

In a case where a surfactant is blended, the amount of the surfactant to be blended is typically in a range of 0.001% to 5% by mass, preferably in a range of 0.005% to 2% by mass, and more preferably in a range of 0.01% to 0.5% by mass with respect to the total amount of the rinse liquid.

The rinse treatment (the washing treatment) using a rinse liquid can be carried out by a conventionally known rinse method. Examples of the rinse treatment method include a method (a rotational coating method) in which the rinse liquid is continuously applied to the support while rotating it at a constant rate, a method (dip method) in which the support is dipped in the rinse liquid for a predetermined time, and a method (spray method) in which the rinse liquid is sprayed onto the surface of the support.

According to the resist pattern forming method of the present aspect described above, since the resist composition purified product obtained by the production method for a resist composition purified product according to the first aspect is used, it is possible to form a resist pattern having a good shape, in which the occurrence of defects is further suppressed and defects such as the generation of scum or microbridge are reduced. Further, it is possible to form a resist pattern in which pattern collapse is suppressed and the difference in pattern size is small as compared with the case where a resist composition before filtration is used.

The defect count for the resist pattern is determined by measuring the number of total defects (the total number of defects, unit: number) in the support using a surface defect observation device (manufactured by KLA Corporation or the like).

(Resist Composition Purified Product)

The resist composition purified product according to the third aspect of the present invention is a resist composition purified product containing a base material component (A) that exhibits changed solubility in a developing solution under action of acid, an onium salt, and an organic solvent component (S). The resist composition purified product is characterized in that the number of counting target objects having a size of 0.135 µm or more, which are counted by a light scattering-type liquid-borne grain counter, is less than 1 piece/mL.

The resist composition purified product according to the present aspect can be obtained by the production method for a resist composition purified product according to the first aspect described above. The resist composition purified product obtained by the production method according to the first aspect is a composition subjected to filtration through a filter having a polyimide-based resin porous membrane to remove foreign substances. As a result, in the resist composition purified product according to the present aspect, the number of counting target objects having a size of 0.135 µm or more, which are counted by a light scattering-type liquid-borne grain counter, is less than 1 piece/mL, and thus it is possible to realize a resist composition formulation product having a very small number of foreign substances.

In the resist composition purified product according to the present aspect, the number of counting target objects having a size of 0.135 µm or more, which are counted by a light scattering-type liquid-borne grain counter, is preferably 0.8 pieces/mL or less, more preferably 0.5 pieces/mL or less, and still more preferably 0.3 pieces/mL or less.

Using the resist composition purified product according to the present aspect, it is possible to form a resist pattern having a small number of defects due to a very small number of foreign substances as described above.

As the light scattering-type liquid-borne grain counter, for example, KS-41 manufactured by RION Co., Ltd. can be used.

In the resist composition purified product according to the present aspect, the content of the metal component (M) is less than 1.1 ppb, more preferably 1 ppb or less, still more preferably 0.9 ppb or less, and even still more preferably 0.85 ppb or less, where the metal component (M) is selected from the group consisting of Li, Na, Mg, Al, K, Ca, Ti, V, Cr, Mn, Fe, Co, Ni, Cu, Zn, As, Ag, Cd, Sn, Ba, W, Au, and Pb.

The resist composition purified product according to the fourth aspect of the present invention is a resist composition purified product containing a base material component (A) that exhibits changed solubility in a developing solution under action of acid, an onium salt, and an organic solvent component (S). In the resist composition purified product, the content of the metal component (M) is less than 1.1 ppb, where the metal component (M) is selected from the group consisting of Li, Na, Mg, Al, K, Ca, Ti, V, Cr, Mn, Fe, Co, Ni, Cu, Zn, As, Ag, Cd, Sn, Ba, W, Au, and Pb.

The resist composition purified product according to the present aspect can be obtained by the production method for a resist composition purified product according to the first aspect described above. The resist composition purified product obtained by the production method according to the first aspect is a composition subjected to filtration through a filter having a polyimide-based resin porous membrane to remove metal impurities. As a result, in the resist composition purified product according to the present aspect, the content of the metal component (M) is less than 1.1 ppb, where the metal component (M) is selected from the group consisting of Li, Na, Mg, Al, K, Ca, Ti, V, Cr, Mn, Fe, Co, Ni, Cu, Zn, As, Ag, Cd, Sn, Ba, W, Au, and Pb, and thus it is possible to realize a resist composition formulation product having a very small number of metal impurities.

Various base material components, acid generators, acid diffusion controlling agents, organic solvents, and the like, which are blended in a resist composition, contain metal components such as trace amounts of metal ion impurities. This metal component may be originally contained in the blending component; however, it may also be mixed from a chemical liquid transfer path such as a pipe or a joint of a producing device. In the production method for a resist composition purified product according to the first aspect, these metal components can be effectively removed.

In the resist composition purified product according to the present aspect, the content of the metal component (M) is preferably 1 ppb or less, more preferably 0.9 ppb or less, and still more preferably 0.85 ppb or less.

Using the resist composition purified product according to the present aspect, it is possible to form a resist pattern having a small number of defects due to the fact the content of the metal component (M) is very small as described above.

The content of the metal component (M) is the total content of Li, Na, Mg, Al, K, Ca, Ti, V, Cr, Mn, Fe, Co, Ni, Cu, Zn, As, Ag, Cd, Sn, Ba, W, Au, and Pb. The content of the metal component (M) in the resist composition purified product can be measured using an inductively coupled plasma-mass spectrometer (ICP-MS 8900, manufactured by Agilent Technologies, Inc.).

In the preferred aspect, in the resist composition purified product, the number of counting target objects having a size of 0.135 μm or more, which are counted by a light scattering-type liquid-borne grain counter, is less than 1 piece/mL, and the content of the metal component (M) is less than 1.1 ppb, where the metal component (M) is selected from the group consisting of Li, Na, Mg, Al, K, Ca, Ti, V, Cr, Mn, Fe, Co, Ni, Cu, Zn, As, Ag, Cd, Sn, Ba, W, Au, and Pb.

The resist composition purified product according to the third aspect or the fourth aspect preferably has the same formulation as the resist composition that is used in the production method for a resist composition purified product according to the first aspect described above, except that foreign substances and metal components are removed.

The resist composition purified product according to the third aspect or the third aspect can be produced, for example, by a production method having the following steps (a) to (c).

The step (a): A step of filtering a resin solution prepared by dissolving a resin component for resist (a component (A)) in an organic solvent component (S) with a filter having a polyimide-based resin porous membrane to obtain a resin solution purified product The step (b): A step of mixing the resin solution purified product with another component (the component (B), the component (D), the component (E), the component (F) described above, or the like) to obtain a resist composition The step (c): A step of filtering the resist composition with a filter having a polyimide-based resin porous membrane «Resist Pattern Forming Method»

The resist pattern forming method according to the fifth aspect of the present invention includes a step of forming a resist film on a support using the resist composition formulation product according to the third aspect or the fourth aspect, a step of exposing the resist film, and a step of developing the exposed resist film to form a resist pattern.

The resist pattern forming method according to the present aspect can be carried out in the same manner as the resist pattern forming method according to the second aspect described above.

EXAMPLES

Hereinafter, the present invention will be described in more detail based on Examples, but the present invention is not limited to these Examples.

<Preparation of Resist Composition>

(Resist Compositions 1 to 13)

Resist compositions 1 to 13 were prepared by mixing and dissolving each component shown in Table 1.

TABLE 1

|  | Component (A) | Component (B) | Component (D) | Component (E) | Component (S) |
| --- | --- | --- | --- | --- | --- |
| Resist composition 1 | (A)-1 [2] | (B)-1 [0.8] | (D)-1 [0.15] | (E)-1 [0.05] | (S)-1 [97] |
| Resist composition 2 | (A)-1 [1.15] | (B)-1 [0.7] | (D)-1 [0.1] | (E)-1 [0.05] | (S)-1 [98] |
| Resist composition 3 | (A)-1 [1.6] | (B)-1 [1] | (D)-1 [0.35] | (E)-1 [0.05] | (S)-1 [97] |
| Resist composition 4 | (A)-1 [2] | (B)-2 [0.8] | (D)-1 [0.15] | (E)-1 [0.05] | (S)-1 [97] |
| Resist composition 5 | (A)-2 [2] | (B)-1 [0.8] | (D)-1 [0.15] | (E)-1 [0.05] | (S)-1 [97] |
| Resist composition 6 | (A)-3 [2] | (B)-1 [0.8] | (D)-1 [0.15] | (E)-1 [0.05] | (S)-1 [97] |
| Resist composition 7 | (A)-4 [2] | (B)-1 [0.8] | (D)-1 [0.15] | (E)-1 [0.05] | (S)-1 [97] |
| Resist composition 8 | (A)-1 [2] | (B)-1 [0.8] | (D)-1 [0.15] | (E)-1 [0.05] | (S)-1 [97] |
| Resist composition 9 | (A)-5 [2.75] | — | (D)-1 [0.15] | (E)-1 [0.05] | (S)-1 [97] |
| Resist composition 10 | (A)-1 [2] | (B)-1 [0.8] | (D)-1 [0.15] | (E)-1 [0.05] | (S)-1 [97] |
| Resist composition 11 | (A)-1 [14.15] | (B)-1 [0.65] | (D)-1 [0.15] | (E)-1 [0.05] | (S)-1 [85] |
| Resist composition 12 | (A)-1 [7] | (B)-1 [0.3] | (D)-1 [0.15] | (E)-1 [0.05] | (S)-1 [92.5] |
| Resist composition 13 | (A)-1 [2] | (B)-1 [0.8] | (D)-1 [0.15] | (E)-1 [0.05] | (S)-1 [97] |

In Table 1, each abbreviation has the following meaning. The numerical values in the brackets are blending amounts (% by mass). The mass average molecular weight (Mw) and the polydispersity (Mw/Mn) of (A)-1 to (A) 5 were determined by a GPC measurement (in terms of polystyrene equivalent value), and the copolymer composition ratio (the proportion (the molar ratio) of each constitutional unit in the structural formula) was determined from a carbon 13 nuclear magnetic resonance spectrum (600 MHz $^{13}$C-NMR).

(A)-1: a polymeric compound represented by Chemical Formula (A)-1. (Mw): 5,000, (Mw/Mn): 1.6, (molar ratio): l/m=50/50.

(A)-1

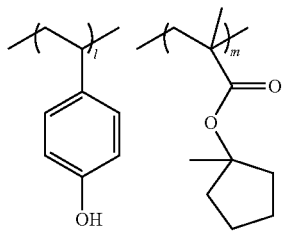

(A)-2: a polymeric compound represented by Chemical Formula (A)-2.

(Mw): 5,500, (Mw/Mn): 1.6, (molar ratio): l/m=50/50.

(A)-2

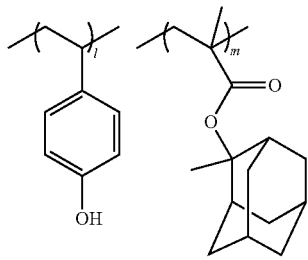

(A)-3: a polymeric compound represented by Chemical Formula (A)-3.

(Mw): 7,000, (Mw/Mn): 1.7, (molar ratio): l/m/n=40/50/10.

(A)-3

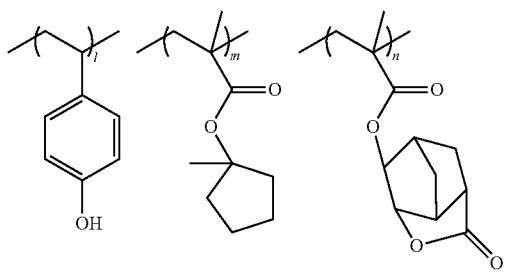

(A)-4: a polymeric compound represented by Chemical Formula (A)-4.

(Mw): 6,000, (Mw/Mn): 1.6, (molar ratio): l/m/n=30/55/15.

(A)-4

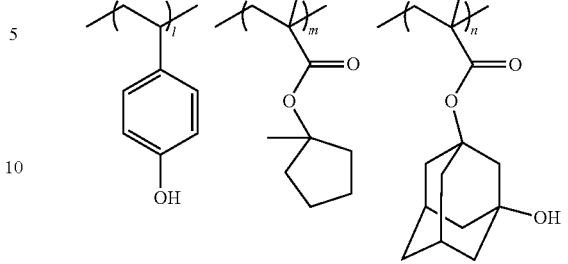

(A)-5: a polymeric compound represented by Chemical Formula (A)-5.

(Mw): 6,500, (Mw/Mn): 1.7, (molar ratio): l/m/n/o=35/35/20/10.

(A)-5

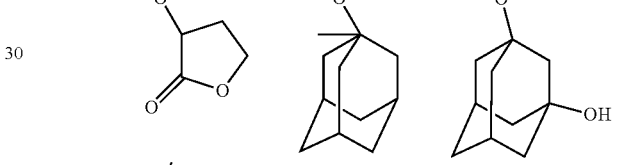

(B)-1: an acid generator consisting of a compound represented by Chemical Formula (B)-1.

(B)-2: an acid generator consisting of a compound represented by Chemical Formula (B)-2.

(B)-1

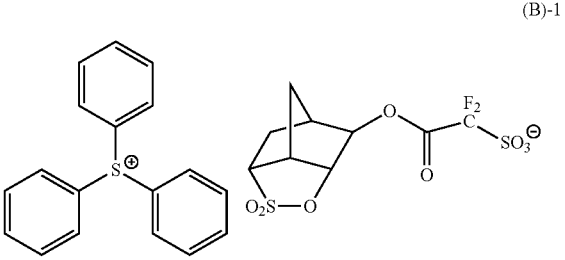

-continued (B)-2

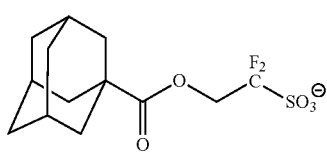

(D)-1: an acid diffusion suppressing agent consisting of a compound represented by Chemical Formula (D)-1.

(D)-1

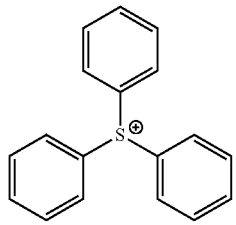

(E)-1: salicylic acid.
(S)-1: a mixed solvent of propylene glycol monomethyl ether acetate/propylene glycol monomethyl ether=20/80 (mass ratio)

<Production of Resist Composition Purified Product (1)>

Examples 1 to 9 and Comparative Examples 1 to 3

The resist compositions 1 to 13 were each filtered using filters and filtration conditions shown in Table 3 to produce resist composition purified products. The kind of each filter (1-1), (1-2), (2), and (3) is shown in Table 2. The porous membrane in the filters (1) and (1-2) can be obtained according to the production method described in Japanese Unexamined Patent Application, First Publication No. 2017-68262. In the filters (1-1), (1-2), and (2), the average pore diameters of the interconnection pores measured by the BET method were each about 8 nm (specific surface area: about 35 m$^2$/g), about 10 nm (specific surface area: about 96 m$^2$/g), and about 18 nm (specific surface area: about 14 m$^2$/g). Regarding the micropore diameter distribution (%) obtained by the porometer, the filters (1-1) and (1-2) were 45% or more, and the filter (2) was 40% or less. The average pore diameters were each about 8 nm, about 10 nm, and about 18 nm. The pore diameter (the pore diameter A), at which the micropore diameter distribution (%) was maximal, was 90 nm or less. The ratios (the maximum pore diameter/the pore diameter A) of the maximum pore diameter in the pore diameter distribution width relative to the pore diameter A were each about 1.23, about 1.16, and about 1.60 in the filters (1-1), (1-2), and (2).

TABLE 2

Filter (1-1) A 10 inch filter including a porous membrane having a polyimide resin structure in which interconnection pores in which adjacent spherical cells are connected to each other are formed. Average pore diameter of spherical cells: 300 nm.

TABLE 2-continued

Filter (1-2) A 10 inch filter including a porous membrane having a polyimide resin structure in which interconnection pores in which adjacent spherical cells are connected to each other are formed. Average pore diameter of spherical cells: 100 nm.
(2) A 10 inch filter including a porous membrane made of polyamide (nylon). Pore size: 5 nm, manufactured by Pall Corporation
(3) A 10 inch filter including a porous membrane made of polyethylene. Pore size: 1 nm, manufactured by Entegris, Inc.

TABLE 3

| | | Filtering condition | | |
|---|---|---|---|---|
| | Resist composition | Filter | | Filtering pressure (Mpa) | Filtering temperature (° C.) |
| Example 1 | Resist composition 1 | (1-1) | (3) | 0.1 | 23 |
| Example 2 | Resist composition 2 | (1-1) | (3) | 0.1 | 23 |
| Example 3 | Resist composition 3 | (1-1) | (3) | 0.1 | 23 |
| Example 4 | Resist composition 4 | (1-1) | (3) | 0.1 | 23 |
| Example 5 | Resist composition 5 | (1-1) | (3) | 0.1 | 23 |
| Example 6 | Resist composition 6 | (1-1) | (3) | 0.1 | 23 |
| Example 7 | Resist composition 7 | (1-1) | (3) | 0.1 | 23 |
| Example 8 | Resist composition 8 | (1-1) | | 0.2 | 23 |
| Example 9 | Resist composition 9 | (1-1) | (3) | 0.1 | 23 |
| Example 10 | Resist composition 10 | (1-2) | | 0.2 | 23 |
| Comparative Example 1 | Resist composition 11 | (1-1) | (3) | 0.1 | 23 |
| Comparative Example 2 | Resist composition 12 | (1-1) | (3) | 0.1 | 23 |
| Comparative Example 3 | Resist composition 13 | (2) | (3) | 0.1 | 23 |

《Evaluation of Resist Composition Purified Products》

A resist pattern was formed using the resist composition produced by the production method of each example, and the following evaluation was carried out.

[Evaluation of Resist Pattern Collapse]

The resist composition purified product produced by the production method of each example was applied onto an 8-inch silicon substrate which had been subjected to a hexamethyldisilazane (HMDS) treatment using a spinner, subjected to a pre-baking (PAB) treatment on a hot plate at a temperature of 110° C. for 60 seconds, and dried to form a resist film having a film thickness of 50 nm.

Next, drawing (exposure) was carried out on the resist film by using an electron beam lithography apparatus JEOL-JBX-9300FS (manufactured by JEOL Ltd.), with the target size being set to a 1:1 line and space pattern (hereinafter, referred to as an "LS pattern") of a line width of 30 nm, at an acceleration voltage of 100 kV.

Next, post-exposure baking (PEB) treatment was carried out at 110° C. for 60 seconds, further alkali developing was carried out at 23° C. for 60 seconds using an aqueous solution of 2.38% by mass of tetramethylammonium hydroxide (TMAH), and then water rinsing was carried out for 15 seconds with pure water.

The obtained LS pattern was observed using a scanning electron microscope (product name: S-9380) manufactured by Hitachi High-Tech Corporation, and the presence or absence of pattern collapse was evaluated based on the following evaluation criteria. The obtained results are shown in Table 4 as "Pattern collapse".

Evaluation Criteria
  ○: Pattern collapse is absent
  x: Pattern collapse is present.
[Evaluation of Size Change Rate of Resist Pattern]

An LS pattern was formed using the resist composition purified product of each example and the resist composition (each of the resist compositions 1 to 13) before purification of each example by the same method as the above except that an LS pattern having a line width of 65 nm and a pitch of 225 nm was formed on a resist film having a film thickness of 60 nm. The obtained LS pattern was observed from above the LS pattern with a scanning electron microscope (product name: S-9380) manufactured by Hitachi High-Tech Corporation, and the line width (nm) was measured.

From the measurement results of the above observation, the LS pattern formed by using the resist composition purified product of each example was compared with the LS pattern formed by using the resist composition before being subjected to filter filtration (before purification), and the amount of change in pattern size due to filtration was determined. The amount of change in the pattern size was evaluated based on the following evaluation criteria, and the obtained results are shown in Table 4 as "Pattern size change".

Evaluation Criteria
  ○: The amount of change in pattern size is 1 nm or less.
  x: The amount of change in pattern size is more than 1 nm.
[Evaluation of Defects (Number of Defects)]

In [Evaluation of resist pattern collapse] described above, the resist composition purified product evaluated as "○" was used to form an LS pattern in the same manner as in [Evaluation of resist pattern collapse]. With respect to the obtained LS pattern, the number of total defects (the total number of defects) in the wafer was measured using a surface defect observation device (manufactured by KLA Corporation, product name: KLA2371). The obtained results of the above are shown in Table 4 as "Number of defects". The number of wafers used for such measurement was two for each example, and the average value therefrom was adopted.

TABLE 4

| | Pattern collapse | Pattern size change | Number of defects (relative value in case where Example 1 is set to 1) |
|---|---|---|---|
| Example 1 | ○ | ○ | 1 |
| Example 2 | ○ | ○ | 1 |
| Example 3 | ○ | ○ | 1 |
| Example 4 | ○ | ○ | 1 |
| Example 5 | ○ | ○ | 1 |
| Example 6 | ○ | ○ | 1 |
| Example 7 | ○ | ○ | 1 |
| Example 8 | ○ | ○ | 10 |
| Example 9 | ○ | ○ | 1 |
| Example 10 | ○ | ○ | 6 |
| Comparative Example 1 | X | — | — |
| Comparative Example 2 | X | — | — |
| Comparative Example 3 | ○ | X | 15 or more |

From the results shown in Table 4, it can be confirmed that in a case where the present invention is applied, pattern collapse, change in pattern size due to filtration, and occurrence of defects are further suppressed.

[Evaluation of Grain Amount]

In [Evaluation of resist pattern collapse] described above, using a light scattering type liquid-borne grain counter [manufactured by Rion Co., Ltd., model number: KS-41, light source: semiconductor laser excited solid-state laser (wavelength: 830 nm, rated output: 0.2 W), flow amount: 10 mL/min], counting target objects having a size of 0.135 μm or more in the resist composition purified product evaluated as "○" were counted based on the dynamic light scattering method. The counting was carried out three times, and the average value thereof was used as the counted value. The light scattering-type liquid-borne grain counter was used after calibration with a polystyrene latex (PSL) standard grain solution. The results are shown in Table 5 as "Grain amount".

[Evaluation of Metal Component Content]

The metal ion amount (the mass in terms of ppb) of the resist composition purified product evaluated as "○" in [Evaluation of resist pattern collapse] described above were measured by using an inductively coupled plasma-mass spectrometer (ICP-MS 8900, manufactured by Agilent Technologies, Inc.). The metal ion amount was determined as the total ion amount of Li, Na, Mg, Al, K, Ca, Ti, V, Cr, Mn, Fe, Co, Ni, Cu, Zn, As, Ag, Cd, Sn, Ba, W, Au, and Pb. The results are shown in Table 5 as "Metal component content".

TABLE 5

| | Grain amount (particles/mL) | Metal component content (ppb) |
|---|---|---|
| Example 1 | 0.1 | 0.8 |
| Example 2 | 0.1 | 0.8 |
| Example 3 | 0.1 | 0.8 |
| Example 4 | 0.1 | 0.8 |
| Example 5 | 0.1 | 0.8 |
| Example 6 | 0.1 | 0.8 |
| Example 7 | 0.1 | 0.8 |
| Example 8 | 0.6 | 0.8 |
| Example 9 | 0.1 | 0.8 |
| Example 10 | 0.3 | 0.8 |
| Comparative Example 3 | 1.0 | 1.1 |

From the results shown in Table 5, it can be confirmed that in a case where the present invention is applied, the grain amount and the metal component content are further reduced.

REFERENCE SIGNS LIST

1a: Spherical cell
1b: Spherical cell
5: Interconnection pore

What is claimed is:

1. A production method for a resist composition purified product, comprising:
  (i) filtering a resist composition with a filter having a porous structure in which adjacent spherical cells are connected to each other,
  wherein the filter has a porous membrane containing at least one resin selected from the group consisting of polyimide and polyamide imide,
  wherein the resist composition contains a base material component (A) that exhibits changed solubility in a developing solution under action of acid, an onium salt, and an organic solvent component(S), where a content of the organic solvent component(S) is 97% by mass or more, and wherein the onium salt contains a compound represented by General Formula (d1-1), (d1-2) or (d1-3):

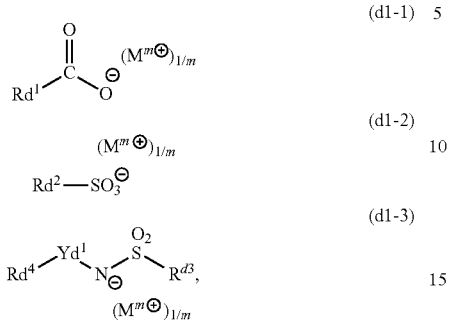

wherein $Rd^1$ to $Rd^4$ represent cyclic groups which may have a substituent, chain-like alkyl groups which may have a substituent, or chain-like alkenyl groups which may have a substituent, the carbon atom adjacent to the S atom as $Rd^2$ in General Formula (d1-2) has no fluorine atom bonded thereto; $Yd^1$ represents a single bond or a divalent linking group; m represents an integer of 1 or more, and each $M^{m+}$ independently represents an m-valent organic cation.

2. The production method for a resist composition purified product according to claim 1,
wherein a content of the onium salt in the resist composition is in a range of 0.05% to 2.9% by mass.

3. The production method for a resist composition purified product according to claim 1,
wherein the resist composition contains two or more onium salts.

4. The production method for a resist composition purified product according to claim 1,
wherein the base material component (A) contains a polymeric compound having a constitutional unit containing a hydroxystyrene skeleton.

5. The production method for a resist composition purified product according to claim 1,
wherein an average sphere diameter of the spherical cells is in a range of 10 to 500 nm.

6. The production method for a resist composition purified product according to claim 1,
wherein the porous structure includes interconnection pores having an average pore diameter in a range of 1 to 50 nm, where the average pore diameter is determined by a BET method.

7. The production method for a resist composition purified product according to claim 1,
wherein the filter has a polyimide porous membrane.

8. The production method for a resist composition purified product according to claim 1, further comprising:
(ii) filtering the resist composition after the step (i) with a filter having a porous membrane containing a polyethylene resin.

9. A resist pattern forming method comprising:
obtaining a resist composition purified product, by the production method for a resist composition purified product according to claim 1;
forming a resist film on a support using the resist composition purified product;
exposing the resist film; and
developing the exposed resist film to form a resist pattern.

10. A resist composition purified product comprising:
a base material component (A) that exhibits changed solubility in a developing solution under action of acid;
an onium salt that contains a compound represented by General Formula (d1-1), (d1-2) or (d1-3):

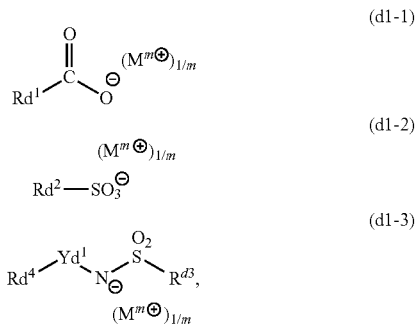

wherein $Rd^1$ to $Rd^4$ represent cyclic groups which may have a substituent, chain-like alkyl groups which may have a substituent, or chain-like alkenyl groups which may have a substituent, the carbon atom adjacent to the S atom as $Rd^2$ in General Formula (d1-2) has no fluorine atom bonded thereto; $Yd^1$ represents a single bond or a divalent linking group; m represents an integer of 1 or more, and each $M^{m+}$ independently represents an m-valent organic cation; and
an organic solvent component(S), where a content of the organic solvent component(S) is 97% by mass or more,
wherein the number of counting target objects having a size of 0.135 μm or more is less than 1 piece/mL, where the counting target objects are counted by a light scattering-type liquid-borne grain counter.

11. A The resist composition purified product according to claim 10,
wherein a content of a metal component (M) is less than 1.1 ppb, where the metal component (M) is selected from the group consisting of Li, Na, Mg, Al, K, Ca, Ti, V, Cr, Mn, Fe, Co, Ni, Cu, Zn, As, Ag, Cd, Sn, Ba, W, Au, and Pb.

12. A resist pattern forming method comprising:
a step of forming a resist film on a support using the resist composition purified product according to claim 10;
a step of exposing the resist film; and
a step of developing the exposed resist film to form a resist pattern.

13. A resist pattern forming method comprising:
a step of forming a resist film on a support using the resist composition purified product according to claim 11;
a step of exposing the resist film; and
a step of developing the exposed resist film to form a resist pattern.

* * * * *